US010100092B2

(12) United States Patent
Atkinson et al.

(10) Patent No.: US 10,100,092 B2
(45) Date of Patent: Oct. 16, 2018

(54) COMPOSITIONS AND METHODS TO DETECT VARIOUS INFECTIOUS ORGANISMS

(71) Applicant: VCA Antech, Inc., Lake Success, NY (US)

(72) Inventors: Brett Atkinson, Fowler, IN (US); Scott Moroff, New York, NY (US); Irina Sokolchik, West Lafayette, IN (US); Todd A. Woodring, Trabuco Canyon, CA (US); Colby Woodruff, Brownsburg, IN (US)

(73) Assignee: VCA, Inc., Los Angeles, CA (US)

( * ) Notice: Subject to any disclaimer, the term of this patent is extended or adjusted under 35 U.S.C. 154(b) by 302 days.

(21) Appl. No.: 13/668,171

(22) Filed: Nov. 2, 2012

(65) Prior Publication Data

US 2013/0129764 A1 May 23, 2013

Related U.S. Application Data

(60) Provisional application No. 61/555,399, filed on Nov. 3, 2011, provisional application No. 61/650,386, filed on May 22, 2012.

(51) Int. Cl.

| | |
|---|---|
| ***C07K 14/195*** | (2006.01) |
| ***C07K 7/08*** | (2006.01) |
| ***G01N 33/53*** | (2006.01) |
| ***G01N 33/569*** | (2006.01) |

(52) U.S. Cl.

CPC .............. *C07K 14/195* (2013.01); *C07K 7/08* (2013.01); *G01N 33/5308* (2013.01); *G01N 33/569* (2013.01); *Y02A 50/57* (2018.01)

(58) Field of Classification Search

None

See application file for complete search history.

(56) References Cited

U.S. PATENT DOCUMENTS

| | | | |
|---|---|---|---|
| 4,569,794 | A | 2/1986 | Smith et al. |
| 5,143,854 | A | 9/1992 | Pirrung et al. |
| 5,215,882 | A | 6/1993 | Bahl et al. |
| 5,308,753 | A | 5/1994 | Dorward et al. |
| 5,618,533 | A | 4/1997 | Flavell et al. |
| 5,643,733 | A | 7/1997 | Robinson et al. |
| 5,643,751 | A | 7/1997 | Robinson et al. |
| 5,707,807 | A | 1/1998 | Kato |
| 5,780,041 | A | 7/1998 | Simpson et al. |
| 5,807,522 | A | 9/1998 | Brown et al. |
| 5,837,832 | A | 11/1998 | Chee et al. |
| 5,958,342 | A | 9/1999 | Gamble et al. |
| 5,965,702 | A | 10/1999 | Robinson et al. |
| 5,994,076 | A | 11/1999 | Chenchik et al. |
| 6,004,755 | A | 12/1999 | Wang |
| 6,040,138 | A | 3/2000 | Lockhart et al. |
| 6,048,695 | A | 4/2000 | Bradley et al. |
| 6,060,240 | A | 5/2000 | Kamb et al. |
| 6,087,112 | A | 7/2000 | Dale |
| 6,090,556 | A | 7/2000 | Kato |
| 6,229,000 | B1 | 5/2001 | Franz et al. |
| 6,436,399 | B1 | 8/2002 | Rikihisa et al. |
| 6,437,116 | B1 | 8/2002 | Norris et al. |
| 6,475,492 | B1 | 11/2002 | Philipp et al. |
| 6,486,130 | B1 | 11/2002 | Livey et al. |
| 6,660,274 | B2 | 12/2003 | Philipp |
| 6,685,885 | B2 | 2/2004 | Nolte et al. |
| 6,716,591 | B1 | 4/2004 | Flavell et al. |
| 6,719,983 | B2 | 4/2004 | Norris et al. |
| 6,740,744 | B2 | 5/2004 | Norris et al. |
| 6,878,816 | B2 | 4/2005 | Norris et al. |
| 7,008,625 | B2 | 3/2006 | Dattwyler et al. |
| 7,060,281 | B1 | 6/2006 | Dattwyler et al. |
| 7,135,176 | B2 | 11/2006 | Norris et al. |
| 7,405,831 | B2 | 7/2008 | Nolte et al. |
| 7,552,282 | B1 | 6/2009 | Bermingham et al. |
| 7,659,968 | B2 | 2/2010 | Wang et al. |
| 7,663,092 | B2 | 2/2010 | Nolte et al. |
| 7,785,597 | B2 | 8/2010 | Norris et al. |
| 7,787,126 | B2 | 8/2010 | Nolte et al. |
| 7,863,434 | B2 | 1/2011 | Murphy et al. |
| 7,887,815 | B2 | 2/2011 | Dattwyler et al. |
| 7,910,356 | B2 | 3/2011 | Nolte et al. |
| 2003/0099639 | A1 | 5/2003 | Rikihisa et al. |
| 2003/0129680 | A1 | 7/2003 | O'Connor |
| 2004/0067517 | A1 | 4/2004 | Philipp |

(Continued)

FOREIGN PATENT DOCUMENTS

| | | |
|---|---|---|
| CA | 2072008 | 1/2003 |
| CA | 2681722 | 10/2008 |

(Continued)

OTHER PUBLICATIONS

Bowie et al (Science, 1990, 257:1306-1310).*

Burgess et al (J. of Cell Bio. 111:2129-2138, 1990).*

Lazar et al. (Molecular and Cellular Biology, 1988, 8:1247-1252).*

Bork (Genome Research, 2000,10:398-400).*

Cardenas et al., "Enzyme-Linked Immunosorbent Assay with Conserved Immunoreactive Glycoproteins gp36 and gp19 Has Enhanced Sensitivity and Provides Species-Specific Immunodiagnosis of Ehrlichia canis Infection," Clin. Vaccine Immunol. (2007) 14(2):123-128.

De La Fuente et al., "Sequence analysis of the msp4 gene of Anaplasma phagocytophilum strains," J. Clin. Microbiol. (2005) 43(3):1309-1317.

(Continued)

*Primary Examiner* — Robert A Zeman

(74) *Attorney, Agent, or Firm* — Rimon P.C.

(57) ABSTRACT

The invention relates to compositions and methods for the detection of various infectious organisms, including heartworm (*Dirofilaria immitis*), *Ehrlichia Canis, Anaplasma phagocytophilum*, and *Borrelia burgdorferi*. More particularly, this invention relates to antibodies that bind to a heartworm antigen, the *E. Canis* gp36 polypeptide, the *A. phagocytophilum* p44 polypeptide, the *B. burgdorferi* OspA, OspC, OspF, p39, p41 and VlsE polypeptides, and uses thereof.

26 Claims, 13 Drawing Sheets

Specification includes a Sequence Listing.

(56) References Cited

U.S. PATENT DOCUMENTS

| | | | |
|---|---|---|---|
| 2004/0166593 | A1 | 8/2004 | Nolte et al. |
| 2006/0256676 | A1 | 11/2006 | Nolte et al. |
| 2007/0023643 | A1 | 2/2007 | Nolte et al. |
| 2007/0212257 | A1 | 9/2007 | Nolte et al. |
| 2007/0259366 | A1 | 11/2007 | Lawrence et al. |
| 2008/0175755 | A1 | 7/2008 | Nolte et al. |
| 2008/0248497 | A1 | 10/2008 | Beall et al. |
| 2009/0002716 | A1 | 1/2009 | Nolte et al. |
| 2009/0263913 | A1 | 10/2009 | Nolte et al. |
| 2010/0136039 | A1 | 6/2010 | Lundberg et al. |
| 2010/0145627 | A1 | 6/2010 | Wang et al. |
| 2010/0317026 | A1 | 12/2010 | Barbour et al. |
| 2013/0129764 | A1 | 5/2013 | Atkinson et al. |

FOREIGN PATENT DOCUMENTS

| | | |
|---|---|---|
| WO | WO-93/04175 | 3/1993 |
| WO | WO-99/52370 | 10/1999 |
| WO | WO-02/16421 | 2/2002 |
| WO | WO-2005/044989 | 5/2005 |
| WO | WO 2006138509 A2 * | 12/2006 |
| WO | WO-2012/135701 | 10/2012 |

OTHER PUBLICATIONS

Dumler et al., "Human granulocytic anaplasmosis and Anaplasma phagocytophilum," Emerging Infect. Dis. (2005) 11(12):1828-1834.

Ijdo et al. "Serodiagnosis of human granulocytic ehrlichiosis by a recombinant HGE-44-based enzyme-linked immunosorbent assay," J. Clin. Microbiol. (1999) 37:3540-3544.

Magnarelli et al. "Recombinant protein-44-based class-specific enzyme-linked immunosorbent assays for serologic diagnosis of human granulocytic ehrlichiosis," Eur. J. Clin. Microbiol. & Infect. Dis. (2001) 20:482-485.

Magnarelli et al. "Reactivity of dog sera to whole-cell or recombinant antigens of Borrelia burgdorferi by ELISA and immunoblot analysis," J. Med. Microbiol. (2001) 50:889-895.

Magnarelli et al. "Reactivity of serum samples of dogs and horses tested by use of class-specific recombinant-based enzyme-linked immunosorbent assays for detection of granulocytic ehrlichiosis," Am. J. Vet. Res. (2001) 62(9):1365-1369.

Magnarelli et al., "Antibodies to granulocytic ehrlichiae in cattle from Connecticut," J. Med. Microbiol. (2002) 51:326-331.

Magnarelli et al., "Comparative reactivity of human sera to recombinant VlsE and other Borrelia burgdorferi antigens in class-specific enzyme-linked immunosorbent assays for Lyme borreliosis," J. Med. Microbiol. (2002) 51:649-655.

Magnarellii et al., "Use of recombinant antigens of Borrelia burgdorferi and Anaplasma phagocytophilum in enzyme-linked immunosorbent assays to detect antibodies in white-tailed deer," J. Wildlife Dis. (2004) 40(2):249-258.

Field et al., "Purification of a RAS-responsive adenylyl cyclase complex from *Saccharomyces cerevisiae* by use of an epitope addition method," Mol. Cell. Biol. (1988) 8:2159-2165.

Evan et al., "Isolation of monoclonal antibodies specific for human c-myc proto-oncogene product," Mol. Cell. Biol. (1985) 5:3610-3616.

Paborsky et al., "Mammalian cell transient expression of tissue factor for the production of antigen," (1990) Protein Engineering 3:547-553.

Kanehisa, "Use of statistical criteria for screening potential homologies in nucleic acid sequences," Nucleic Acids Res. (1984) 12:203-215.

Kozak, "Structural features in eukaryotic mRNAs that modulate the initiation of translation," J. Biol. Chem. (1991) 266:19867-19870.

Kyte and Doolittle, "A simple method for displaying the hydropathic character of a protein," J. Mol. Biol. (1982) 157:105-132.

Lafleur et al., "Bacterin that induces anti-OspA and anti-OspC borreliacidal antibodies provides a high level of protection against canine Lyme disease," Clin. Vacc. Immunol. (2009) 16:253-259.

Lafleur et al., "One-year duration of immunity induced by vaccination with a canine Lyme disease bacterin," Clin. Vacc. Immunol. (2010) 17:870-874.

Dumler et al., "Reorganization of genera in the families Rickettsiaceae and Anaplasmataceae in the order Rickettsiales: unification of some species of *Ehrlichia* with *Anaplasma*, *Cowdria* with *Ehrlichia* and *Ehrlichia* with *Neorickettsia*, descriptions of six new species combinations and designation of *Ehrlichia equi* and 'HGE agent' as subjective synonyms of *Ehrlichia phagocytophila*," Int J Syst Evol Microbiol (2001) 51:2145.

Chen et al., "Identification of a granulocytotropic *Ehrlichia* species as the etiologic agent of human disease," J Clin Microbiol 32:589 (1994).

Foley et al., "Association between polyarthritis and thrombocytopenia and increased prevalence of vectorborne pathogens in Californian dogs," Vet Rec (2007) 160:159.

Lappin et al., "Molecular and serologic evidence of Anaplasma phagocytophilum infection in cats in North America," J Am Vet Med Assoc (2004) 225:893-896.

Rejmanek et al., "Molecular characterization reveals distinct genospecies of *Anaplasma phagocytophilum* from diverse North American hosts," J. Med. Microbiol. (2012) 61:204-212.

Kirtz et al., "Anaplasma phagocytophilum infection in a dog: identifying the causative agent using PCR," J Small Anim Pract (2005) 46:300.

Ravnik et al., "Anaplasmosis in dogs: the relation of haematological, biochemical and clinical alterations to antibody titre and PCR confirmed infection," Vet Microbiol. (2011) 149:172-176.

Beall et al., "Serological and molecular prevalence of *Borrelia burgdorferi*,*Anaplasma phagocytophilum*, and *Ehrlichia* species in dogs from Minnesota," Vector Borne Zoonotic Dis. (2008) 8:455-464.

Chandrashekar et al., "Performance of a commercially available in-clinic ELISA for the detection of antibodies against Anaplasma phagocytophilum, Ehrlichia canis, and Borrelia burgdorferi and Dirofilaria immitis antigen in dogs," Am J Vet Res. (2010) 71:1443-1450.

Ge et al., "Identification of novel surface proteins of Anaplasma phagocytophilum by affinity purification and proteomics," J Bacteriol. (2007) 189:7819-7828.

Zhao et al., "Differential phase-contrast BioCD biosensor," Appl Opt. (2007) 46:6196-6209.

Original claim 1 of U.S. Appl. No. 09/996,056, filed Nov. 27, 2001.

Amendment in Reply to Final Action for U.S. Appl. No. 09/996,056, filed Jan. 7, 2005.

Declaration by Onderdonk, filed Jan. 7, 2005.

Notice of Allowance for U.S. Appl. No. 12/614,895, dated Apr. 14, 2011.

Amendment and Reply for U.S. Appl. No. 12/614,895, filed Oct. 13, 2010.

Notice of Abandonment for U.S. Appl. No. 10/280,884, dated Mar. 7, 2008.

Notice of Abandonment for U.S. Appl. No. 11/510,727, dated Oct. 28, 2008.

Description of Protein A and G from Wikipedia, May 31, 2011.

Wilske et al., "Immunological and molecular polymorphisms of OspC, an immunodominant major outer surface protein of Borrelia burgdorferi," Infection & Immunity (1993) 61(5):2182-2191.

Wikipedia Definition of Immunologic Adjuvant, Jun. 21, 2011.

Original sequence listing for U.S. Appl. No. 09/982,259, filed Feb. 25, 2002.

Original claims for U.S. Appl. No. 09/982,259, filed Oct. 16, 2001.

Amendment and Response for U.S. Appl. No. 09/982,259, filed May 18, 2004.

Revised sequence listing for U.S. Appl. No. 09/982,259, filed May 18, 2004.

Second revised sequence listing for U.S. Appl. No. 09/982,259, filed Aug. 27, 2004.

Claims for U.S. Appl. No. 09/288,339, filed Apr. 8, 1999.

Office Action for U.S. Appl. No. 09/288,339, dated Sep. 8, 2000.

Office Action for U.S. Appl. No. 09/288,339, dated Mar. 14, 2001.

Final Office Action for U.S. Appl. No. 09/288,339, dated Sep. 7, 2001.

(56) References Cited

OTHER PUBLICATIONS

Amendment after Final Office Action for U.S. Appl. No. 09/288,339, filed Dec. 4, 2001.
Amendment after Final Office Action for U.S. Appl. No. 09/288,339, filed Mar. 1, 2002.
Notice of Allowability for U.S. Appl. No. 09/288,339, dated Mar. 7, 2002.
Amendment and Response for U.S. Appl. No. 09/066,046, filed May 4, 2000.
Certificate of Correction for U.S. Pat. No. 6,204,242, issued Aug. 14, 2001.
Palmer et al., "The immunoprotective Anaplasma marginale major surface protein 2 is encoded by a polymorphic multigene family," Infection and Immunity (1994) 62(9):3808-3816.
Information from BIOS, patentlens.net, Jun. 6, 2011.
Sambrook et al., Molecular Cloning: A Laboratory Manual, 3rd ed., Cold Spring Press, Plainview, NY (2001) p. 6.58.
Claims for U.S. Appl. No. 09/295,028, filed Apr. 20, 1999.
Office Action for U.S. Appl. No. 09/295,028, dated Jun. 29, 2000.
Amendment for U.S. Appl. No. 09/295,028, filed Aug. 31, 2000.
Final Office Action for U.S. Appl. No. 09/295,028, dated Nov. 17, 2000.
Asanovich et al., "Partial Characterization of Cloned Genes Encoding Immunoreactive Proteins of Ehrlichia equi and the Agent of Human Granulocytic Ehrlichiosis," Abstracts of the General Meeting of the American Society for Microbiology: Abstract No. D-22 (1996).
MeSH Descriptor Data for Anaplasma phagocytophilum, National Library of Medicine, Jun. 7, 2011.
Dumler et al., "Serologic cross-reactions among Ehrlichia equi, Ehrlichia phagocytophila, and human granulocytic Ehrlichia," Journal of Clinical Microbiology (1995) 33(5):1098-1103.
Nyindo et al., "Antigenic analysis of four species of the genus *Ehrlichia* by use of protein immunoblot," Am J Vet Res. (1991) 52(8):1225-1230.
Original claims for U.S. Appl. No. 08/158,353, filed Nov. 24, 1993.
Office Action for U.S. Appl. No. 08/158,353, dated Jul. 15, 1994.
Amendment for U.S. Appl. No. 08/158,353, filed Feb. 3, 1995.
Office Action for U.S. Appl. No. 08/158,353, dated May 3, 1995.
Final Office Action for U.S. Appl. No. 08/158,353, dated Jan. 23, 1996.
Amendment after Final Office Action for U.S. Appl. No. 08/158,353, filed Jul. 29, 1996.
Second Amendment after Final Office Action for U.S. Appl. No. 08/158,353, filed Oct. 23, 1996.
Wagner et al., "A fluorescent bead-based multiplex assay for the simultaneous detection of antibodies to B. burgdorferi outer surface proteins in canine serum," Vet Immunol Immunopathol. (2011) 140(3-4):190-198.
Magnarelli et al., "Serologic diagnosis of canine and equine borreliosis: use of recombinant antigens in enzyme-linked immunosorbent assays," J Clin Microbiol. (1997) 35(1):169-173.
Straubinger et al., "Status of Borrelia burgdorferi infection after antibiotic treatment and the effects of corticosteroids: An experimental study," J Infect Dis. (2000) 181(3):1069-1081.
Preac-Mursic et al., "Active immunization with pC protein of Borrelia burgdorferi protects gerbils against B. burgdorferi infection," Infection (1992) 20:342-348.
Krupka and Straubinger, "Lyme borreliosis in dogs and cats: background, diagnosis, treatment and prevention of infections with Borrelia burgdorferi sensu stricto," Vet Clin North Am Small Anim Pract. (2010) 40(6):1103-1109.
Wang et al., "Disease severity in a murine model of lyme borreliosis is associated with the genotype of the infecting Borrelia burgdorferi sensu stricto strain," J Infect Dis. (2002) 186(6):782-791.
Casjens et al., "A bacterial genome in flux: the twelve linear and nine circular extrachromosomal DNAs in an infectious isolate of the Lyme disease spirochete Borrelia burgdorferi," Molecular Microbiology (2000) 35(3):490-516.
Package insert for the Lyme western blot assay from Zeus Scientific, issued Oct. 11, 2006.
Bagby et al., "Direct electrochemistry of two genetically distinct flavodoxins isolated from Azotobacter chroococcum grown under nitrogen-fixing conditions," Biochem. J. (1991) 277:313-319.
Original claims for U.S. Appl. No. 09/792,957, filed Feb. 26, 2001.
Response to Restriction Requirement with Amendment for U.S. Appl. No. 09/792,957, filed Apr. 25, 2006.
Amendment for U.S. Appl. No. 09/792,957, filed Oct. 13, 2006.
Office Action for U.S. Appl. No. 09/792,957, dated Mar. 24, 2008.
Amendment for U.S. Appl. No. 09/792,957, filed Jul. 8, 2008.
Office Action for U.S. Appl. No. 09/792,957, dated Sep. 25, 2008.
Amendment for U.S. Appl. No. 09/792,957, filed Dec. 18, 2008.
Final Office Action for U.S. Appl. No. 09/792,957, dated Mar. 17, 2009.
Amendment for U.S. Appl. No. 09/792,957, filed Sep. 16, 2009.
Notice of Allowance for U.S. Appl. No. 09/792,957, dated Dec. 7, 2009.
Ross et al., "Molecular cloning of a highly repeated DNA element from *Mycobacterium tuberculosis* and its use as an epidemiological tool," J. Clin. Microbiol. (1992) 30(4):942-946.
Thepot et al., "Complete sequence of the rabbit whey acidic protein gene," Nucleic Acids Res. (1990) 18(12):3641.
Diaz et al., "Role of the major pneumococcal autolysin in the atypical response of a clinical isolate of *Streptococcus pneumoniae*," Journal of Bacteriology (1992) 174(17):5508-5515.
Setiady et al., "Tobacco mitotic cyclins: cloning, characterization, gene expression and functional assay," The Plant Journal (1995) 8(6):949-957.
Fu et al., "Carboxy-terminal-extended variant of the human fibrinogen alpha subunit: a novel exon conferring marked homology to beta and gamma subunits," Biochemistry (1992) 31(48):11968-11972.
Zuerner et al., "Nucleotide sequence analysis of a gene cloned from Leptospira biflexa serovar patoc which complements an argE defect in *Escherichia coli*," J. Bacteriol. (1988) 170(10):4548-4554.
Lewin, Genes V, Oxford University Press Inc., NY (1994) , p. 179.
Storey et al., "Molecular cloning and sequencing of three granulocytic Ehrlichia genes encoding high-molecular-weight immunoreactive proteins," Infection and Immunity (1998) 66(4):1356-1363.
Interview Summary initiated by Applicant for U.S. Appl. No. 13/346,088, dated Sep. 10, 2012.
Response to Non-Final Office Action for U.S. Appl. No. 13/346,088, filed Oct. 1, 2012.
Information from BIOS, "Hybridisation Language in Patent Claims," dated Oct. 29, 2012.
Hybridization probe from Wikipedia, dated Oct. 12, 2012.
Nagase et al., "Prediction of the coding sequences of unidentified human genes. IV. The coding sequences of 40 new genes (KIAA0121-KIAA0160) deduced by analysis of cDNA clones from human cell line KG-1," DNA Research (1995) 2:167-174.
Preliminary Amendment for U.S. Appl. No. 11/053,711, filed Jan. 29, 2007.
Zhi et al., "Multiple p44 genes encoding major outer membrane proteins are expressed in the human granulocytic ehrlichiosis agent," The Journal of Biological Chemistry (1999) 274(25):17828-17836.
Gen Bank Accesion No. AF135254, Jun. 30, 1999.
Svinarich et al., "Characterization of the Human Lysyl Oxidase Gene Locus," The Journal of Biological Chemistry (1992) 267(20):14382-14387.
Final Office Action for U.S. Appl. No. 13/346,088, dated Oct. 17, 2012.
Hengen, "Purification of His-Tag fusion proteins from *Escherichia coli*," Trends Biochem. Sci. (1995) 20(7):285-286.
Response to Restriction Requirement for U.S. Appl. No. 11/004,678, filed Oct. 12, 2012.
Lux et al., "Analysis of cDNA for human erythrocyte ankyrin indicates a repeated structure with homology to tissue-differentiation and cell-cycle control proteins," Nature (1990) 344(6261):36-42.

(56) References Cited

OTHER PUBLICATIONS

Van Vliet et al., "Molecular cloning, sequence analysis, and expression of the gene encoding the immunodominant 32-kilodalton protein of Cowdria ruminantium," Infection and Immunity (1994) 62(4):1451-1456.
Notice of Patent Expiration for U.S. Pat. No. 5,618,533, issued May 4, 2009.
Original claims for U.S. Pat. No. 5,618,533, filed Dec. 10, 1993.
Preliminary Amendment for U.S. Appl. No. 08/166,160, filed Dec. 10, 1993.
Preliminary Amendment for U.S. Appl. No. 10/222,566, filed Aug. 16, 2002.
Amendment and Supplemental Response for U.S. Appl. No. 10/222,566, filed Aug. 29, 2003.
Amendment and Response to Office Action for U.S. Appl. No. 12/853,019, filed May 17, 2011.
Second Preliminary Amendment for U.S. Appl. No. 09/445,803, filed Dec. 13, 1999.
Office Action for U.S. Appl. No. 09/445,803, dated Mar. 7, 2002.
Office Action for U.S. Appl. No. 09/445,803, dated Sep. 18, 2002.
Response and Amendment for U.S. Appl. No. 09/445,803, filed Dec. 10, 2002.
Final Office Action for U.S. Appl. No. 09/445,803, dated Feb. 21, 2003.
Response and Amendment for U.S. Appl. No. 09/445,803, filed Apr. 2, 2003.
Notice of Allowability for U.S. Appl. No. 09/445,803, dated Apr. 16, 2003.
Notice of Abandonment for U.S. Appl. No. 10/632,780, dated Sep. 17, 2008.
Original claims for U.S. Appl. No. 09/300,971, filed Apr. 28, 1999.
Response for U.S. Appl. No. 09/300,971, filed Jun. 23, 2000.
Office Action for U.S. Appl. No. 09/300,971, dated Aug. 23, 2000.
Amendment and Response for U.S. Appl. No. 09/300,971, filed Dec. 22, 2000.
Office Action for U.S. Appl. No. 09/300,971, dated Mar. 23, 2001.
Amendment and Response for U.S. Appl. No. 09/300,971, filed Jun. 25, 2001.
Office Action for U.S. Appl. No. 09/300,971, dated Sep. 28, 2001.
Amendment and Response for U.S. Appl. No. 09/300,971, filed Jan. 25, 2002.
Wallich et al., "The Borrelia burgdorferi flagellum-associated 41-kilodalton antigen (flagellin): molecular cloning, expression, and amplification of the gene," Infection and Immunity (1990) 58(6):1711-1719.
Gherna and Woese, "A Partial Phylogenetic Analysis of the "Flavobacter-Bacteroides" Phylum: Basis for Taxonomic Restructuring," System. Appl. Microbiol. (1992) 15:513521.
Embley et al., "A group I intron in the small subunit ribosomal RNA gene from *Naegleria andersoni* ssp. andersoni strain PPMFB-6," Nucleic Acids Research (1992) 20(23):6411.
Kamoda et al., "Cloning of a lignostilbene-alpha,beta-dioxygenase isozyme gene from Pseudomonas paucimobilis TMY1009," Biosci. Biotechnol. Biochem. (1995) 59(10):1866-1868.
Garciadeblas et al., "Differential expression of two genes encoding isoforms of the ATPase involved in sodium efflux in *Saccharomyces cerevisiae*," Mol. Gen. Genet. (1993) 236(2-3):363-368.
Karasawa et al., "The human homolog of the glomerulosclerosis gene Mpv17: structure and genomic organization," Hum. Mol. Genet. (1993) 2(11):1829-1834.
Maruyama et al., "A novel domain sequence of connectin localized at the I band of skeletal muscle sarcomeres: homology ro neurofilament subunits," Biolchem. Biophsy. Res. Comm. (1993) 194:1288-1291.
Shibuya et al., "Nucleotide sequence of alpha-galactosidase cDNA from Mortierella vinacea," Biosci. Biotechnol. Biochem. (1995) 59(7):1345-1348.
Boyd et al., "Molecular genetic basis of allelic polymorphism in malate dehydrogenase (mdh) in natural populations of *Escherichia coli* and *Salmonella enterica*," Proc. Natl. Acad. Sci. U.S.A. (1994) 91(4):1280-1284.
Saito et al., "Entire nucleotide sequence for Bacillus brevis Nagano Grs2 gene encoding gramicidin S synthetase 2: a multifunctional peptide synthetase," J. Biochem. (1994) 116(2):357-367.
Smith et al., "In trypanosomes the homolog of the largest subunit of RNA polymerase II is encoded by two genes and has a highly unusual C-terminal domain structure," Cell (1989) 56(5):815-827.
Scott-Craig et al., "The cyclic peptide synthetase catalyzing HC-toxin production in the filamentous fungus Cochliobolus carbonum is encoded by a 15.7-kilobase open reading frame," J. Biol. Chem. (1992) 267(36):26044-26049.
Schwecke et al., "The biosynthetic gene cluster for the polyketide immunosuppressant rapamycin," Proc. Natl. Acad. Sci. U.S.A. (1995) 92(17):7839-7843.
Amendment for U.S. Appl. No. 12/859,236, filed Sep. 1, 2011.
Notice of Allowance for U.S. Appl. No. 12/859,236, dated Sep. 19, 2011.
Amendment and Request for Interview with SPE for U.S. Appl. No. 08/375,993, filed Feb. 22, 1996.
Final Office Action for U.S. Appl. No. 08/375,993, dated May 30, 1996.
Amendment after Final for U.S. Appl. No. 08/375,993, filed Oct. 25, 1996.
Preliminary Amendment for U.S. Appl. No. 07/422,881, dated Jan. 24, 1990.
Office Action for U.S. Appl. No. 07/422,881, dated Jun. 5, 1991.
Amendment for U.S. Appl. No. 07/422,881, filed Oct. 16, 1991.
Office Action for U.S. Appl. No. 07/422,881, dated Mar. 26, 1993.
Notice of Abandonment for U.S. Appl. No. 07/422,881, dated Oct. 16, 1993.
Howe et al., "Organization of genes encoding two outer membrane proteins of the Lyme disease agent Borrelia burgdorferi within a single transcriptional unit," Infection and Immunity (1986) 54(1):207-212.
Notice of Allowance for U.S. Appl. No. 08/375,993, dated Dec. 11, 1996.
Bajwa et al., "Structural analysis of the two tandemly repeated acid phosphatase genes in yeast," Nucleic Acids Research (1984) 12(20):7721-7739.
Amendment with Terminal Disclaimer for U.S. Appl. No. 08/479,017, filed Aug. 17, 1998.
Notice of Allowability for U.S. Appl. No. 08/479,017, dated Jan. 5, 2000.
Information from BIOS, "Hybridisation Language in Patent Claims," dated Jun. 6, 2011.
U.S. Appl. No. 08/479,017, filed Jun. 6, 1995.
Amendment for U.S. Appl. No. 08/479,017, filed May 5, 1992.
Office Action for U.S. Appl. No. 08/479,017, dated Jun. 23, 1997.
Amendment and Request for Interview for U.S. Appl. No. 08/479,017, filed Dec. 29, 1997.
Second Amendment with Terminal Disclaimer and Notice of Appeal for U.S. Appl. No. 08/466,393, filed Aug. 3, 1998.
U.S. Appl. No. 08/466,393, filed Jun. 6, 1995.
Amendment and Petition for U.S. Appl. No. 08/466,393, filed Mar. 21, 1997.
Office Action for U.S. Appl. No. 08/466,393, dated May 2, 1997.
Office Action for U.S. Appl. No. 08/466,393, dated Feb. 2, 1998.
Amendment after Final for U.S. Appl. No. 08/466,393, filed Jul. 20, 1998.
Hochuli et al., "Genetic approach to facilitate purification of recombinant proteins with a novel metal chelate adsorbent," Nature Biotechnology (1988) 6:1321-1325.
Amendment with Terminal Disclaimer for U.S. Appl. No. 08/470,627, filed Mar. 24, 2000.
Amendment for U.S. Appl. No. 08/470,627, filed May 19, 1997.
Office Action for U.S. Appl. No. 08/470,627, dated May 13, 1999.
Amendment for U.S. Appl. No. 08/470,627, filed Nov. 8, 1999.
Office Action for U.S. Appl. No. 08/470,627, dated Feb. 4, 2000.
Akin et al., "The immunoglobulin (IgG) antibody response to OspA and OspB correlates with severe and prolonged Lyme arthritis and

(56) References Cited

OTHER PUBLICATIONS the IgG response to P35 correlates with mild and brief arthritis," Infect. Immun. (1999) 67(1):173-181.
Schutzer et al., "Early and specific antibody response to OspA in Lyme Disease," J. Clin. Invest. (1994) 94:454-457.
International Search Report for WO 2012/047607, dated May 21, 2012.
De Voer et al., "Development of a fluorescent-bead-based multiplex immunoassay to determine immunoglobulin G subclass responses to Neisseria meningitidis serogroup A and C polysaccharides," Clin. & Vaccine Immunol. (2008) 15(8):1188-1193.
GenBank accession No. AAN37936.1, Mar. 1, 2003.
GenBank accession No. NP_05128, locus NC_000950, Jul. 22, 2013.
Amendment for U.S. Appl. No. 13/107,787, filed Feb. 18, 2013.
Dykhuizen et al., "Borrelia burgdorferi is clonal: implications for taxonomy and vaccine development," Proc. Natl. Acad. Sci. USA (1993) 90:10163-10167.
Office Action for U.S. Appl. No. 13/107,787, dated Nov. 30, 2012.
Amendment for U.S. Appl. No. 13/107,796, filed Feb. 18, 2013.
International Search Report and Written Opinion for PCT/US2012/063446, dated Nov. 7, 2013, 16 pages.
Invitation to Pay Additional Fees for PCT/US2012/063446, dated Sep. 5, 2013, 8 pages.
Wang et al., "Two Monoclonal Antibodies with Defined Epitopes of P44 Major Surface Proteins Neutralize Anaplasma phagocytophilum by Distinct Mechanisms", Infection and Immunity (2006) 74(3):1873-1882.
International Preliminary Report and Patentability for PCT/US12/63446, dated May 1, 2014, 8 pages.

* cited by examiner

Figure 1A

MMSMAIVMAGNDVRAHDDVSALENGGAGYFYVGLDYSPAFSKIRDFSIRESNGETKAVYPYLKDGKSVKL
ESHKFDWNTPDPRIGFKDNMLVAMEGSVGYGIGGARVELEIGYERFKTKGIRDSGSKEDEADTVYLLAKE
LAYDVVTGQTDKLTAALAKTSGKDIVQFANAVKISSSAIDGKVCTGSHADLAPGTNAGKKFVVNPEASGS
TDGDTSQCSGLGHSSGVTQNPKLFSTFVDTVKIAEDKNWPTGRAKSNTSLKTGDTNSNAKAVATDLVQEL
TPEEKTIVAGLLAKTIEGGEVVEIRAVSSTSVMVNACYDLLSEGLCVVPYACVGLGGNFVGVVDGHITPK
LAYRLKAGLSYQLSPVISAFAGGFYHRVVGDGVYDDLPAQRLVDDTSPAGRTKDTAIANFSMAYVGGEFG
VRFAF

Figure 1B

ATGATGTCAATGGCTATAGTCATGGCTGGGAATGATGTCAGGGCTCATGATGACGTTAGCGCTTTGGAGA
ATGGTGGTGCGGGATATTTCTATGTTGGTTTGGATTACAGTCCAGCGTTTAGCAAGATAAGAGATTTTAG
TATAAGGGAGAGTAACGGAGAGACAAAGGCAGTATATCCATACTTAAAGGATGGAAAGAGTGTAAAGCTT
GAGTCGCACAAGTTTGACTGGAACACACCTGATCCTCGGATTGGGTTTAAGGACAACATGCTTGTAGCTA
TGGAAGGCAGTGTTGGTTATGGTATTGGTGGTGCCAGGGTTGAGCTTGAGATTGGTTACGAGCGCTTCAA
GACCAAGGGTATTAGAGATAGTGGTAGTAAGGAAGATGAAGCTGATACAGTATATCTACTAGCTAAGGAG
TTAGCTTATGATGTTGTTACTGGACAGACTGATAAGCTTACCGCTGCTCTTGCCAAGACCTCCGGTAAAG
ATATCGTTCAGTTTGCGAATGCTGTGAAAATTTCTAGCTCTGCCATCGATGGGAAGGTTTGTACTGGTAG
CCATGCTGACCTAGCGCCTGGTACGAATGCGGGGAAAAAGTTCGTTGTGAACCCGGAAGCCAGCGGGAGT
ACTGATGGGGATACGTCACAGTGTAGTGGTTTAGGGCATAGTAGTGGTGTTACACAGAATCCGAAGTTAT
TTAGTACTTTTGTGGACACTGTGAAGATTGCTGAGGATAAAAACTGGCCGACGGGCAGGGCAAAATCGAA
CACATCACTGAAGACGGGTGATACTAATAGTAACGCCAAAGCCGTGGCTACAGACCTAGTACAGGAGCTA
ACCCCTGAAGAAAAAACCATAGTAGCAGGGTTACTAGCTAAGACTATTGAAGGGGGTGAAGTTGTTGAGA
TCAGGGCGGTTTCTTCTACTTCCGTAATGGTCAATGCTTGTTATGATCTTCTTAGTGAAGGTTTATGTGT
TGTTCCTTATGCTTGTGTTGGTCTTGGCGGTAACTTCGTGGGCGTGGTTGATGGCCATATCACTCCTAAG
CTTGCTTATAGATTAAAGGCTGGGTTGAGTTATCAGCTCTCTCCTGTAATCTCCGCTTTTGCGGGTGGAT
TCTACCATCGCGTTGTGGGAGATGGCGTTTATGATGATCTGCCGGCTCAACGTCTTGTAGATGATACTAG
TCCGGCGGGCCGTACTAAGGATACTGCTATTGCTAACTTCTCCATGGCTTATGTCGGTGGGGAATTTGGT
GTTAGGTTCGCTTTTTAA

Figure 1C

GHTSGVSQNPKVFSSFVDSVKIADDKK

Figure 1D

GHTSGVTNNPKLFTTFVDSVKVAEDKK

Figure 1E

GHSSGATQNPKTLSTFVDSVKIANKK

Figure 1F

NTTGASQNPKTLSTFVDSVKIAEEK

Figure 1G

MGGNTTGASQNPKTLSTFVDSVKIAEEKGGGHTSGVSQNPKVFSSFVDSVKIADDKGGGHSSGATQNPKTLSTFVDS
VKIANKGGGHSSGATQNPKTLSTFVDSVKIANKPGGGHTSGVSQNPKVFSSFVDSVKIADDKGGGHTSGVSQNPKVF
SSFVDSVKIADDKGGGNTTGASQNPKTLSTFVDSVKIAEEKGGGNTTGASQNPKTLSTFVDSVKIAEEKGGGHSSGA
TQNPKTLSTFVDSVKIANK

Figure 1H

ATGGGCGGCAATACCACCGGCGCAAGCCAAAACCCGAAAACCCTGAGCACGTTCGTTGACAGCGTTAAAATCGCAGA
AGAAAAAGGCGGCGGTCATACCAGCGGCGTCTCTCAGAACCCGAAAGTTTTTAGCTCTTTCGTGGATAGCGTTAAAA
TTGCAGATGACAAAGGCGGTGGCCATAGTTCCGGTGCTACCCAGAATCCGAAAACGCTGTCTACGTTTGTCGATTCT
GTGAAAATTGCGAACAAAGGTGGCGGTCACTCATCGGGCGCCACCCAAAATCCGAAAACCCTGAGTACGTTCGTTGA
CTCCGTCAAAATCGCGAACAAACCGGGCGGTGGCCATACGAGTGGTGTGTCCCAGAATCCGAAAGTTTTTAGCAGCT
TCGTGGATTCCGTTAAAATTGCCGATGACAAAGGTGGCGGTCACACCTCAGGCGTGTCGCAAAACCCGAAAGTGTTT
AGTTCCTTCGTCGACAGTGTGAAAATCGCGGACGATAAAGGCGGTGGCAACACCACCGGTGCAAGCCAGAATCCGAA
AACCCTGTCAACGTTTGTTGATTCGGTCAAAATTGCAGAAGAAAAAGGTGGCGGTAACACCACGGGCGCTTCTCAAA
ACCCGAAAACGCTGTCTACCTTCGTGGATTCTGTTAAAATCGCGGAAGAAAAAGGCGGTGGCCACTCATCGGGTGCG
ACCCAGAACCCGAAAACGCTGAGCACCTTTGTGGACTCCGTGAAAATTGCGAATAAA

Figure 1I

MGGHTSGVSQNPKVFSSFVDSVKIADDKGGHTSGVSQNPKVFSSFVDSVKIADDKGGGHT
SGVSQNPKVFSSFVDSVKIADDKGGHTSGVSQNPKVFSSFVDSVKIADDKGPGHTSGVSQ
NPKVFSSFVDSVKIADDKGGGHTSGVSQNPKVFSSFVDSVKIADDKGHTSGVSQNPKVFS
SFVDSVKIADDKPGGGHTSGVSQNPKVFSSFVDSVKIADDKGGGHTSGVSQNPKVFSSFV
DSVKIADDK

Figure 1J

ATGGGCGGTCACACCTCAGGCGTCTCACAGAACCCGAAAGTCTTCAGCTCGTTTGTTGATAGCGTTAAAATCGCAGA
TGATAAAGGCGGCCATACCAGTGGCGTCTCCCAGAACCCGAAAGTGTTTAGCTCTTTCGTGGATAGCGTTAAAATTG
CGGATGACAAAGGCGGTGGCCATACCTCAGGCGTTTCGCAGAACCCGAAAGTCTTTAGTTCCTTCGTCGATAGTGTG
AAAATTGCAGATGACAAAGGTGGCCACACGAGCGGTGTGTCTCAAAATCCGAAAGTGTTTAGCTCGTTCGTTGATTC
TGTCAAAATCGCTGATGACAAAGGCCCGGGTCACACGAGTGGCGTCTCCCAGAATCCTAAGGTGTTTAGCAGCTTTG
TGGATAGCGTTAAAATCGCCGATGACAAAGGTGGCGGTCATACCTCAGGTGTGAGCCAAAATCCGAAAGTCTTTAGT
AGCTTCGTCGATAGCGTGAAAATCGCTGACGACAAAGGTCATACCTCTGGCGTTAGCCAGAATCCTAAAGTGTTTAG
CAGCTTTGTTGACTCTGTCAAAATTGCTGATGACAAACCGGGCGGTGGCCATACCAGTGGTGTGTCCCAGAACCCGA
AAGTTTTTAGCAGCTTTGTTGATTCAGTGAAAATCGCGGACGATAAAGGTGGCGGTCACACGTCGGGTGTGTCCCAG
AACCCGAAAGTCTTCTCGTCGTTTGTGGATAGCGTGAAAATCGCAGATGATAAA

Figure 1K

MGGHSSGATQNPKTLSTFVDSVKIANKGGGHSSGATQNPKTLSTFVDSVKIANKGGGHSS
GATQNPKTLSTFVDSVKIANKGGHSSGATQNPKTLSTFVDSVKIANKGGGHSSGATQNPK
TLSTFVDSVKIANKPGGGHSSGATQNPKTLSTFVDSVKIANKGHSSGATQNPKTLSTFVD
SVKIANKPGGGHSSGATQNPKTLSTFVDSVKIANKGGGHSSGATQNPKTLSTFVDSVKIA
NK

Figure 1L

ATGGGCGGTCACTCCAGCGGCGCAACCCAAAACCCGAAAACCCTGAGCACGTTCGTCGATAGCGTCAAAATCGCAAA
TAAAGGCGGCGGCCATAGCTCTGGTGCGACCCAGAATCCGAAAACGCTGTCAACGTTTGTGGATTCGGTTAAAATTG
CGAACAAAGGCGGTGGCCATAGTTCCGGTGCCACCCAGAATCCGAAAACCCTGTCTACCTTTGTCGATTCTGTGAAA
ATTGCAAACAAAGGTGGCCACTCATCGGGCGCTACGCAAAATCCGAAAACCCTGAGTACGTTCGTTGACTCCGTCAA
AATCGCAAACAAAGGTGGCGGTCACAGCTCTGGTGCTACCCAAAATCCGAAAACGCTGAGCACGTTCGTGGACTCGG
TTAAAATCGCGAACAAACCGGGCGGTGGCCACAGCTCCGGTGCAACGCAAAACCCGAAAACGCTGTCTACCTTCGTT
GATTCTGTGAAAATTGCGAACAAAGGTCACTCATCGGGCGCCACCCAAAACCCTAAGACGCTGAGCACCTTCGTTGA
CTCTGTTAAAATCGCAAACAAACCGGGTGGCGGTCATTCTAGCGGCGCGACGCAAAACCCTAAGACCCTGTCCACGT
TCGTGGATTCTGTTAAAATCGCCAACAAAGGCGGTGGCCACAGTTCCGGCGCAACGCAGAACCCGAAAACCCTGAGC
ACCTTTGTGGACTCCGTGAAAATCGCAAATAAA

Figure 1M

MGNTTGASQNPKTLSTFVDSVKIAEEKGGGNTTGASQNPKTLSTFVDSVKIAEEKGGNTT
GASQNPKTLSTFVDSVKIAEEKGGGNTTGASQNPKTLSTFVDSVKIAEEKGPGNTTGASQ
NPKTLSTFVDSVKIAEEKGGGNTTGASQNPKTLSTFVDSVKIAEEKNTTGASQNPKTLST
FVDSVKIAEEKGPGNTTGASQNPKTLSTFVDSVKIAEEKGGGNTTGASQNPKTLSTFVDS
VKIAEEK

Figure 1N

ATGGGCAATACCACGGGCGCAAGCCAGAATCCGAAAACCCTGTCTACGTTTGTCGATAGCGTTAAAATCGCAGAAGA
AAAAGGCGGCGGTAACACCACGGGTGCGTCACAAAACCCGAAAACGCTGTCTACGTTTGTGGATTCTGTTAAAATTG
CAGAAGAAAAAGGCGGTAACACCACGGGCGCTTCGCAAAATCCGAAAACCCTGAGTACGTTCGTCGACTCCGTGAAA
ATCGCGGAAGAAAAAGGCGGTGGCAACACCACCGGTGCATCTCAAAACCCTAAGACCCTGAGCACGTTTGTTGATTC
GGTCAAAATCGCCGAAGAAAAAGGTCCGGGCAACACCACGGGCGCTAGCCAAAACCCGAAAACGCTGAGCACGTTCG
TGGACTCTGTTAAAATTGCCGAAGAAAAAGGTGGCGGTAACACCACGGGTGCCAGTCAGAACCCTAAGACGCTGAGC
ACCTTTGTCGATTCCGTGAAAATTGCGGAAGAGAAAAACACCACGGGCGCCTCCCAAAACCCGAAAACCCTGTCAAC
CTTCGTTGACTCGGTCAAAATTGCGGAAGAAAAAGGCCCGGGTAACACCACGGGTGCGTCTCAGAATCCGAAAACGC
TGAGCACCTTCGTTGATTCTGTTAAAATCGCTGAGGAGAAAGGCGGTGGCAATACGACGGGCGCCTCGCAGAACCCG
AAAACCCTGAGCACCTTTGTTGATAGCGTGAAAATCGCAGAAGAAAAA

Figure 2A

MKKNTLSAILMTLFLFISCNNSGKDGNTSANSADESVKGPNLTEISKKITESNAVVLAVK
EVETLLASIDEVAKKAIGNLIAQNGLNAGANQNGSLLAGAYVISTLIAEKLDGLKNSEEL
KEKIEDAKKCNKAFTDKLKSSHAELGIANGAATDANAKAAILKTNGTKDKGAQELEKLFE
SVKNLSKAAQETLNNSVKELTSPVVAESPKKP

Figure 2B

ATGAAAAAGAATACATTAAGTGCAATATTAATGACTTTATTTTTATTTATATCTTGTAATAATTCAGGGA
AAGATGGGAATACATCTGCAAATTCTGCTGATGAGTCTGTTAAAGGGCCTAATCTTACAGAAATAAGTAA
AAAAATTACAGAATCTAACGCAGTTGTTCTCGCCGTGAAAGAAGTTGAAACTCTGCTTGCATCTATAGAT
GAAGTTGCTAAGAAAGCTATTGGGAATTTGATAGCCCAAAATGGTTTAAATGCCGGCGCAAATCAAAACG
GATCATTGTTAGCGGGAGCCTACGTAATATCAACCCTAATAGCAGAAAAATTAGATGGATTGAAAAATTC
AGAAGAATTAAAGGAAAAAATTGAAGATGCTAAAAAATGTAACAAAGCATTTACTGATAAACTAAAAAGT
AGTCATGCGGAACTCGGTATAGCGAATGGAGCTGCTACTGATGCTAATGCAAAAGCGGCTATTTTAAAAA
CAAATGGTACTAAAGATAAGGGTGCTCAAGAGCTTGAAAAGTTATTTGAATCAGTAAAAAACTTGTCAAA
AGCAGCTCAAGAAACACTAAATAATTCAGTTAAAGAACTTACAAGTCCTGTTGTGGCAGAAAGTCCAAAA
AAACCTTAA

Figure 2C

ATGAAAAAAAAATACGCTGTCTGCGATTCTGATGACGCTGTTCCTGTTCATTAGCTGCAATAATTCGGGCAAAGATGG
CAATACCTCGGCGAACAGTGCGGATGAATCCGTGAAAGGCCCGAATCTGACCGAAATTAGCAAGAAAATTACGGAAT
CTAACGCAGTGGTTCTGGCTGTCAAAGAAGTGGAAACCCTGCTGGCAAGCATTGACGAAGTTGCGAAAAAAGCCATT
GGCAATCTGATCGCCCAGAACGGCCTGAATGCAGGTGCTAACCAAAATGGCAGTCTGCTGGCGGGTGCCTATGTCAT
TTCCACCCTGATCGCGGAAAAACTGGATGGTCTGAAAAACAGCGAAGAACTGAAAGAAAAAATCGAAGATGCGAAAA
AATGCAACAAAGCTTTCACGGACAAACTGAAAAGCTCTCATGCGGAACTGGGCATTGCCAACGGTGCGGCCACCGAT
GCAAATGCTAAAGCAGCTATCCTGAAAACCAACGGCACGAAAGACAAAGGTGCCCAGGAACTGGAAAAACTGTTCGA
ATCAGTTAAAAACCTGTCGAAAGCGGCCCAAGAAACGCTGAATAATAGCGTGAAAGAACTGACCTCGCCGGTGGTGG
CTGAAAGTCCGAAAAAACCG

Figure 3A

MSKDLEGAVKDLESSEQNVKKTEQEIKKQVEGFLEILETKDLNTLDTKEIEKQIQELKNKIEKLDSKKTSIETYSGY
EEKINKIKEKLNGKGLEDKLNELSESLKKKKEERKKALQEAKKKFEEYKNQAESATGVTHGSQVQRQGGVGLQAWQC
ANSLGFKNMTSGNNTSDMTNEVITNSLKKIEEELKNIGETVEGKKE

Figure 3B

TAGGAGACAATCTTTATGAATAAAAAAATAAAAATGTTTATTATTTGTGCTATTTTTATGCTGATAAGTTCTTGTAA
GAATGATGTAACTAGTAAAGATTTAGAAGGGGCGGTGAAAGATTTAGAAAGTTCAGAACAAAATGTAAAAAAAACAG
AACAAGAGATAAAAAAACAAGTTGAAGGATTTTTAGAAATTTTAGAGACAAAAGATTTAAACACATTAGATACAAAA
GAAATTGAAAAACAAATTCAAGAATTAAAGAATAAGATAGAAAAATTAGACTCTAAAAAAACTTCTATTGAAACATA
TTCTGGGTATGAAGAAAAAATAAACAAAATAAAAGAAAAATTAAACGGAAAAGGACTTGAAGATAAATTAAATGAAC
TTTCAGAGAGCTTAAAAAAGAAAAAAGAGGAGAGAAAAAAAGCTTTACAAGAGGCTAAAAAGAAATTTGAAGAGTAT
AAAAACCAAGCTGAATCTGCAACTGGAGTAACGCATGGTTCTCAAGTCCAAAGACAAGGTGGTGTTGGATTACAAGC
TTGGCAGTGTGCTAATAGTTTGGGGTTTAAAAATATGACTAGTGGTAATAATACTAGCGATATGACCAATGAAGTTA
TAACTAATTCGCTTAAAAAGATTGAAGAAGAACTTAAAAATATTGGAGAAACTGTAGAAGGTAAAAAAGAATAA

Figure 3C

ATGTCTAAAGATCTTGAAGGTGCGGTTAAAGATCTGGAAAGCTCTGAACAGAACGTGAAGAAAACCGAACAGGAAAT
CAAAAAACAGGTTGAAGGCTTTCTGGAAATTCTGGAAACCAAAGATCTGAACACCCTGGATACGAAAGAAATTGAAA
AACAGATCCAGGAACTGAAAAACAAAATCGAAAAACTGGATAGCAAGAAAACCAGTATTGAAACGTACAGCGGTTAC
GAAGAAAAAATCAACAAAATCAAAGAAAAACTGAATGGCAAAGGTCTGGAAGATAAACTGAACGAACTGAGTGAAAG
CCTGAAAAAGAAAAAAGAAGAACGTAAAAAAGCACTGCAGGAAGCGAAGAAAAAATTCGAAGAATACAAAAACCAGG
CGGAAAGTGCCACCGGCGTGACGCATGGTAGCCAGGTTCAGCGTCAGGGCGGTGTGGGTCTGCAGGCATGGCAGTGC
GCAAACTCTCTGGGCTTCAAAAATATGACCAGCGGTAACAATACCTCTGATATGACGAACGAAGTGATTACGAATAG
CCTGAAGAAAATTGAAGAAGAACTGAAAAATATTGGTGAAACTGTTGAAGGTAAGAAGGAATAA

Figure 4A

MNKILLLILLESIVFLSCSGKGSLGSEIPKVSLIIDGTFDDKSFNESALNGVKKVKEEFKIELVLKESSSNSYLSDL
EGLKDAGSDLIWLIGYRFSDVAKVAALQNPDMKYAIIDPIYSNDPIPANLVGMTFRAQEGAFLTGYIAAKLSKTGKI
GFLGGIEGEIVDAFRYGYEAGAKYANKDIKISTQYIGSFADLEAGRSVATRMYSDEIDIIHHAAGLGGIGAIEVAKE
LGSGHYIIGVDEDQAYLAPDNVITSTTKDVGRALNIFTSNHLKTNTFEGGKLINYGLKEGVVGFVRNPKMISFELEK
EIDNLSSKIINKEIIVPSNKESYEKFLKEFI

Figure 4B

TCCTGATAGTGAATATGCATTTGATTTATTTAAATCAAAGTTATAAACTACTAAATATAGCTTTGTTTGT
AAAGGGGAAATAGTTTATGAATAAAATATTGTTGTTGATTTTGCTTGAGAGTATTGTTTTTTTATCTTGT
AGTGGTAAAGGTAGTCTTGGGAGCGAAATTCCTAAGGTATCTTTAATAATTGATGGAACTTTTGATGATA
AATCTTTTAATGAGAGTGCTTTAAATGGCGTAAAAAAAGTTAAAGAAGAATTTAAAATTGAGCTTGTTTT
AAAAGAATCCTCATCAAATTCTTATTTATCTGATCTTGAAGGGCTTAAGGATGCGGGCTCAGATTTAATT
TGGCTTATTGGGTATAGATTTAGCGATGTGGCCAAGGTTGCGGCTCTTCAAAATCCCGATATGAAATATG
CAATTATTGATCCTATTTATTCTAACGATCCTATTCCTGCAAATTTGGTGGGCATGACCTTTAGAGCTCA
AGAGGGTGCATTTTTAACGGGTTATATTGCTGCAAAACTTTCTAAAACAGGTAAAATTGGATTTTTAGGG
GGAATAGAAGGCGAGATAGTAGATGCTTTTAGGTATGGGTATGAAGCTGGTGCTAAGTATGCTAATAAAG
ATATAAAGATATCTACTCAGTATATTGGTAGTTTTGCTGACCTTGAAGCTGGTAGAAGCGTTGCAACTAG
AATGTATTCTGATGAGATAGACATTATTCATCATGCTGCAGGCCTTGGAGGAATTGGGGCTATTGAGGTT
GCAAAAGAACTTGGTTCTGGGCATTACATTATTGGAGTTGATGAAGATCAAGCATATCTTGCTCCTGACA
ATGTAATAACATCTACAACTAAAGATGTTGGTAGAGCTTTAAATATTTTTACATCTAACCATTTAAAAAC
TAATACTTTCGAAGGTGGCAAATTAATAAATTATGGCCTTAAAGAAGGAGTTGTGGGGTTTGTAAGAAAT
CCTAAAATGATTTCCTTTGAACTTGAAAAAGAAATTGACAATCTTTCTAGCAAAATAATCAACAAAGAAA
TTATTGTTCCATCTAATAAAGAAAGTTATGAGAAGTTTCTTAAAGAATTTATTTAA

Figure 4C

ATGAATAAAATCCTGCTGCTGATCCTGCTGGAATCTATCGTGTTCCTGAGTTGTAGTGGCAAAGGCTCTC
TGGGTAGTGAAATCCCGAAAGTTAGCCTGATTATCGATGGCACCTTTGATGACAAATCTTTCAACGAAAG
TGCCCTGAATGGTGTCAAAAAAGTGAAAGAAGAATTCAAAATCGAACTGGTCCTGAAAGAAAGCTCTAGT
AATTCGTATCTGAGCGATCTGGAAGGCCTGAAAGATGCGGGTTCTGACCTGATTTGGCTGATCGGCTACC
GTTTCAGTGATGTTGCAAAAGTCGCGGCCCTGCAGAACCCGGACATGAAATATGCTATTATCGATCCGAT
TTACTCGAATGACCCGATCCCGGCAAACCTGGTGGGCATGACCTTTCGTGCACAAGAAGGCGCTTTCCTG
ACGGGTTATATTGCAGCTAAACTGAGCAAAACCGGCAAAATCGGTTTTCTGGGCGGTATTGAAGGTGAAA
TCGTTGATGCGTTCCGCTATGGCTACGAAGCAGGTGCTAAATACGCCAACAAAGATATCAAAATCTCCAC
GCAGTACATTGGCTCATTTGCAGACCTGGAAGCAGGTCGTTCGGTGGCAACCCGCATGTACAGCGATGAA
ATCGACATTATCCATCACGCAGCAGGTCTGGGCGGTATTGGTGCAATCGAAGTCGCTAAAGAACTGGGCT
CTGGTCATTATATTATCGGCGTGGATGAAGACCAAGCGTACCTGGCCCCGGATAACGTGATTACGTCCAC
CACGAAAGACGTTGGTCGTGCGCTGAACATCTTTACCTCAAATCACCTGAAAACCAACACGTTCGAAGGC
GGTAAACTGATTAATTATGGTCTGAAAGAAGGCGTGGTTGGTTTTGTTCGCAACCCGAAAATGATTAGCT
TCGAACTGGAAAAAGAAATCGATAACCTGTCCTCAAAAATCATCAACAAAGAAATCATTGTTCCGTCAAA
TAAAGAAAGTTACGAAAAATTCCTGAAAGAATTCATT

Figure 5A

MKKCVQEGVQQEGAQQPGGGMKKNDQIGAAIALRGVACVQEGVQQEGAQQPGGGMKKNDQIGAAIALRGVACVQEGV
QQEGAQQPGGGMKKNDQIGAAIALRGVAGCVQEGVQQEGAQQPGGGMKKNDQIGAAIALRGVAGCVQEGVQQEGAQQ
PGGGMKKNDQIGAAIALRGVAGCVQEGVQQEGAQQPGGGMKKNDQIGAAIALRGVACVQEGVQQEGAQQPGGGMKKN
DQIGAAIALRGVA

Figure 5B

ATGAAAAAATGTGTCCAGGAAGGTGTGCAACAGGAAGGTGCCCAGCAGCCGGGTGGCGGTATGAAAAAAAACGACCA
GATTGGCGCAGCGATTGCACTGCGTGGCGTGGCTTGCGTTCAGGAAGGCGTGCAGCAAGAAGGCGCACAGCAACCGG
GCGGTGGCATGAAGAAAAACGATCAGATTGGTGCCGCAATTGCCCTGCGTGGTGTTGCATGTGTGCAGGAAGGTGTG
CAGCAAGAAGGCGCTCAGCAACCGGGTGGCGGTATGAAGAAAAACGACCAGATTGGTGCAGCTATCGCACTGCGTGG
TGTGGCTGGCTGCGTTCAGGAAGGTGTCCAGCAAGAAGGCGCACAGCAGCCGGGCGGTGGCATGAAGAAAAACGACC
AAATCGGTGCCGCCATTGCCCTGCGTGGTGTGGCAGGTTGTGTGCAGGAAGGTGTCCAGCAAGAAGGCGCCCAGCAA
CCGGGTGGCGGTATGAAGAAAAACGATCAAATCGGCGCCGCCATTGCGCTGCGCGGCGTTGCCGGTTGTGTCCAGGA
AGGTGTCCAGCAAGAAGGCGCGCAGCAACCGGGCGGTGGCATGAAGAAAAACGATCAGATCGGCGCCGCGATTGCCC
TGCGTGGCGTGGCATGTGTCCAGGAAGGCGTGCAGCAAGAAGGCGCCCAGCAACCGGGCGGCGGCATGAAAAAAAAT
GACCAAATCGGTGCGGCTATCGCTCTGCGTGGCGTGGCG

Figure 6A

MLFILMGYCMLHLTTEITNIDFAHDFHIHQGERFGVSSGDLELDIANHPGHGYHILFKNNGHVISDLHGVKAEDFNF
NMKDHSLNVSFLIDPMAPFHELDVNNHPNFFISMHAYQDGCDNCVHGNPSRPAIVNQAQVLLPSGVTEDSVSAPATE
DSVSAPATEDSVSAPATEDSVSAPATEDSVSAPATEDSVSAPATEDSVSAPATEDSVSAPATEDSVSAPATEDSVSA
PATEDSVSAPATEDSVSAPATEDSVSAPATEDSVSAPATEDSVSAPATEDSVSAPATEDSVSAPATEDSVSAPATAA
TGSTTSYNHNTELEFLDSGILNMLY

Figure 6B

ATGCTATTTATACTAATGGGTTATTGTATGCTTCATTTAACAACAGAAATCACAAACATT
GATTTTGCTCATGATTTTCATATACATCAAGGTGAAAGATTTGGTGTTTCAAGTGGTGAT
CTAGAACTTGATATTGCAAACCATCCTGGACATGGTTATCATATTTTATTTAAGAACAAT
GGCCATGTAATATCAGATTTACATGGTGTTAAAGCTGAAGACTTTAACTTTAATATGAAG
GATCATAGTTTGAATGTTTCTTTCTTAATTGATCCAATGGCTCCTTTTCATGAGTTAGAT
GTTAATAACCATCCTAACTTCTTTATTTCTATGCATGCTTATCAAGATGGTTGTGATAAT
TGTGTACATGGAAATCCATCACGTCCTGCTATAGTAAATCAAGCTCAAGTTTTATTACCA
AGTGGAGTTACTGAAGATTCTGTTTCTGCTCCAGCTACTGAAGATTCTGTTTCTGCTCCA
GCTACTGAAGATTCTGTTTCTGCTCCAGCTACTGAAGATTCTGTTTCTGCTCCAGCTACT
GAAGATTCTGTTTCTGCTCCAGCTACTGAAGATTCTGTTTCTGCTCCAGCTACTGAAGAT
TCTGTTTCTGCTCCAGCTACTGAAGATTCTGTTTCTGCTCCAGCTACTGAAGATTCTGTT
TCTGCTCCAGCTACTGAAGATTCTGTTTCTGCTCCAGCTACTGAAGATTCTGTTTCTGCT
CCAGCTACTGAAGATTCTGTTTCTGCTCCAGCTACTGAAGATTCTGTTTCTGCTCCAGCT
ACTGAAGATTCTGTTTCTGCTCCAGCTACTGAAGATTCTGTTTCTGCTCCAGCTACTGAA
GATTCTGTTTCTGCTCCAGCTACTGAAGATTCTGTTTCTGCTCCAGCTACTGAAGATTCT
GTTTCTGCTCCAGCTACTGCAGCAACAGGTTCAACAACATCATATAATCACAACACTGAA
CTTGAGTTTTTAGATTCTGGTATTCTTAACATGTTGTACTAA

Figure 7A

ATGGCACATCACCACCACCATCACGTGGATGACGACGACAAG

Figure 7B

MAHHHHHHVDDDDK

Figure 8A

ATGCACCATCATCATCATCATCATCATGGTGTTGATCTGGGTACCGAGAACCTGTACTTCCAATCCAATGCC

Figure 8B

MHHHHHHHHGVDLGTENLYFQSNA

SEQUENCE LISTING

```
<160> NUMBER OF SEQ ID NOS: 36

<210> SEQ ID NO 1
<211> LENGTH: 425
<212> TYPE: PRT
<213> ORGANISM: A. phagocytophilum
<220> FEATURE:
<221> NAME/KEY: misc_feature
<222> LOCATION: (1)...(425)
<223> OTHER INFORMATION: amino acid sequence of p44 polypeptide

<400> SEQUENCE: 1

Met Met Ser Met Ala Ile Val Met Ala Gly Asn Asp Val Arg Ala His
1               5                   10                  15

Asp Asp Val Ser Ala Leu Glu Asn Gly Gly Ala Gly Tyr Phe Tyr Val
            20                  25                  30

Gly Leu Asp Tyr Ser Pro Ala Phe Ser Lys Ile Arg Asp Phe Ser Ile
        35                  40                  45

Arg Glu Ser Asn Gly Glu Thr Lys Ala Val Tyr Pro Tyr Leu Lys Asp
    50                  55                  60

Gly Lys Ser Val Lys Leu Glu Ser His Lys Phe Asp Trp Asn Thr Pro
65                  70                  75                  80

Asp Pro Arg Ile Gly Phe Lys Asp Asn Met Leu Val Ala Met Glu Gly
                85                  90                  95

Ser Val Gly Tyr Gly Ile Gly Gly Ala Arg Val Glu Leu Glu Ile Gly
            100                 105                 110

Tyr Glu Arg Phe Lys Thr Lys Gly Ile Arg Asp Ser Gly Ser Lys Glu
        115                 120                 125

Asp Glu Ala Asp Thr Val Tyr Leu Leu Ala Lys Glu Leu Ala Tyr Asp
    130                 135                 140

Val Val Thr Gly Gln Thr Asp Lys Leu Thr Ala Ala Leu Ala Lys Thr
145                 150                 155                 160

Ser Gly Lys Asp Ile Val Gln Phe Ala Asn Ala Val Lys Ile Ser Ser
                165                 170                 175

Ser Ala Ile Asp Gly Lys Val Cys Thr Gly Ser His Ala Asp Leu Ala
            180                 185                 190

Pro Gly Thr Asn Ala Gly Lys Lys Phe Val Val Asn Pro Glu Ala Ser
        195                 200                 205

Gly Ser Thr Asp Gly Asp Thr Ser Gln Cys Ser Gly Leu Gly His Ser
    210                 215                 220

Ser Gly Val Thr Gln Asn Pro Lys Leu Phe Ser Thr Phe Val Asp Thr
225                 230                 235                 240

Val Lys Ile Ala Glu Asp Lys Asn Trp Pro Thr Gly Arg Ala Lys Ser
                245                 250                 255

Asn Thr Ser Leu Lys Thr Gly Asp Thr Asn Ser Asn Ala Lys Ala Val
            260                 265                 270

Ala Thr Asp Leu Val Gln Glu Leu Thr Pro Glu Glu Lys Thr Ile Val
        275                 280                 285
```

Ala Gly Leu Leu Ala Lys Thr Ile Glu Gly Gly Glu Val Val Glu Ile
    290                 295                 300

Arg Ala Val Ser Ser Thr Ser Val Met Val Asn Ala Cys Tyr Asp Leu
305                 310                 315                 320

Leu Ser Glu Gly Leu Cys Val Val Pro Tyr Ala Cys Val Gly Leu Gly
                325                 330                 335

Gly Asn Phe Val Gly Val Val Asp Gly His Ile Thr Pro Lys Leu Ala
            340                 345                 350

Tyr Arg Leu Lys Ala Gly Leu Ser Tyr Gln Leu Ser Pro Val Ile Ser
        355                 360                 365

Ala Phe Ala Gly Gly Phe Tyr His Arg Val Val Gly Asp Gly Val Tyr
    370                 375                 380

Asp Asp Leu Pro Ala Gln Arg Leu Val Asp Asp Thr Ser Pro Ala Gly
385                 390                 395                 400

Arg Thr Lys Asp Thr Ala Ile Ala Asn Phe Ser Met Ala Tyr Val Gly
                405                 410                 415

Gly Glu Phe Gly Val Arg Phe Ala Phe
            420                 425

<210> SEQ ID NO 2
<211> LENGTH: 1278
<212> TYPE: DNA
<213> ORGANISM: A. phagocytophilum
<220> FEATURE:
<221> NAME/KEY: misc_feature
<222> LOCATION: (1)...(1278)
<223> OTHER INFORMATION: nucleotide sequence of p44 polypeptide

<400> SEQUENCE: 2
atgatgtcaa tggctatagt catggctggg aatgatgtca gggctcatga tgacgttagc 60
gctttggaga atggtggtgc gggatatttc tatgttggtt tggattacag tccagcgttt 120
agcaagataa gagattttag tataagggag agtaacggag agacaaaggc agtatatcca 180
tacttaaagg atggaaagag tgtaaagctt gagtcgcaca agtttgactg gaacacacct 240
gatcctcgga ttgggtttaa ggacaacatg cttgtagcta tggaaggcag tgttggttat 300
ggtattggtg gtgccagggt tgagcttgag attggttacg agcgcttcaa gaccaagggt 360
attagagata gtggtagtaa ggaagatgaa gctgatacag tatatctact agctaaggag 420
ttagcttatg atgttgttac tggacagact gataagctta ccgctgctct tgccaagacc 480
tccggtaaag atatcgttca gtttgcgaat gctgtgaaaa tttctagctc tgccatcgat 540
gggaaggttt gtactggtag ccatgctgac ctagcgcctg gtacgaatgc ggggaaaaag 600
ttcgttgtga acccggaagc cagcgggagt actgatgggg atacgtcaca gtgtagtggt 660
ttagggcata gtagtggtgt tacacagaat ccgaagttat ttagtacttt tgtggacact 720
gtgaagattg ctgaggataa aaactggccg acgggcaggg caaaatcgaa cacatcactg 780
aagacgggtg atactaatag taacgccaaa gccgtggcta cagacctagt acaggagcta 840
acccctgaag aaaaaaccat agtagcaggg ttactagcta agactattga agggggtgaa 900
gttgttgaga tcagggcggt ttcttctact tccgtaatgg tcaatgcttg ttatgatctt 960
cttagtgaag gtttatgtgt tgttccttat gcttgtgttg gtcttggcgg taacttcgtg 1020
ggcgtggttg atggccatat cactcctaag cttgcttata gattaaaggc tgggttgagt 1080
tatcagctct ctcctgtaat ctccgctttt gcgggtggat tctaccatcg cgttgtggga 1140
gatggcgttt atgatgatct gccggctcaa cgtcttgtag atgatactag tccggcgggc 1200
cgtactaagg atactgctat tgctaacttc tccatggctt atgtcggtgg ggaatttggt 1260
gttaggttcg ctttttaa 1278

<210> SEQ ID NO 3
<211> LENGTH: 27
<212> TYPE: PRT
<213> ORGANISM: A. phagocytophilum
<220> FEATURE:
<221> NAME/KEY: misc_feature
<222> LOCATION: (1)...(27)
<223> OTHER INFORMATION: amino acid sequence of mutant p44 polypeptide

<400> SEQUENCE: 3

Gly His Thr Ser Gly Val Ser Gln Asn Pro Lys Val Phe Ser Ser Phe
1 5 10 15

Val Asp Ser Val Lys Ile Ala Asp Asp Lys Lys
20 25

<210> SEQ ID NO 4
<211> LENGTH: 27
<212> TYPE: PRT
<213> ORGANISM: A. phagocytophilum
<220> FEATURE:
<221> NAME/KEY: misc_feature
<222> LOCATION: (1)...(27)
<223> OTHER INFORMATION: amino acid sequence of mutant p44 polypeptide

<400> SEQUENCE: 4

Gly His Thr Ser Gly Val Thr Asn Asn Pro Lys Leu Phe Thr Thr Phe
1 5 10 15

Val Asp Ser Val Lys Val Ala Glu Asp Lys Lys
20 25

<210> SEQ ID NO 5
<211> LENGTH: 26
<212> TYPE: PRT
<213> ORGANISM: A. phagocytophilum
<220> FEATURE:
<221> NAME/KEY: misc_feature
<222> LOCATION: (1)...(26)
<223> OTHER INFORMATION: amino acid sequence of mutant p44 polypeptide

<400> SEQUENCE: 5

Gly His Ser Ser Gly Ala Thr Gln Asn Pro Lys Thr Leu Ser Thr Phe
1 5 10 15

Val Asp Ser Val Lys Ile Ala Asn Lys Lys
20 25

<210> SEQ ID NO 6
<211> LENGTH: 25
<212> TYPE: PRT
<213> ORGANISM: A. phagocytophilum
<220> FEATURE:
<221> NAME/KEY: misc_feature
<222> LOCATION: (1)...(25)
<223> OTHER INFORMATION: aminmo acid sequence of mutant p44 polypeptide

<400> SEQUENCE: 6

Asn Thr Thr Gly Ala Ser Gln Asn Pro Lys Thr Leu Ser Thr Phe Val
1 5 10 15

Asp Ser Val Lys Ile Ala Glu Glu Lys 20 25

<210> SEQ ID NO 7
<211> LENGTH: 250
<212> TYPE: PRT
<213> ORGANISM: A. phagocytophilum
<220> FEATURE:
<221> NAME/KEY: misc_feature
<222> LOCATION: (1)...(250)
<223> OTHER INFORMATION: amino acid sequence of multimer of mutant p44 polypeptide

<400> SEQUENCE: 7

```
Met Gly Gly Asn Thr Thr Gly Ala Ser Gln Asn Pro Lys Thr Leu Ser
 1               5                  10                  15

Thr Phe Val Asp Ser Val Lys Ile Ala Glu Glu Lys Gly Gly Gly His
            20                  25                  30

Thr Ser Gly Val Ser Gln Asn Pro Lys Val Phe Ser Ser Phe Val Asp
        35                  40                  45

Ser Val Lys Ile Ala Asp Asp Lys Gly Gly Gly His Ser Ser Gly Ala
    50                  55                  60

Thr Gln Asn Pro Lys Thr Leu Ser Thr Phe Val Asp Ser Val Lys Ile
65                  70                  75                  80

Ala Asn Lys Gly Gly Gly His Ser Ser Gly Ala Thr Gln Asn Pro Lys
                85                  90                  95

Thr Leu Ser Thr Phe Val Asp Ser Val Lys Ile Ala Asn Lys Pro Gly
            100                 105                 110

Gly Gly His Thr Ser Gly Val Ser Gln Asn Pro Lys Val Phe Ser Ser
        115                 120                 125

Phe Val Asp Ser Val Lys Ile Ala Asp Asp Lys Gly Gly Gly His Thr
    130                 135                 140

Ser Gly Val Ser Gln Asn Pro Lys Val Phe Ser Ser Phe Val Asp Ser
145                 150                 155                 160

Val Lys Ile Ala Asp Asp Lys Gly Gly Gly Asn Thr Thr Gly Ala Ser
                165                 170                 175

Gln Asn Pro Lys Thr Leu Ser Thr Phe Val Asp Ser Val Lys Ile Ala
            180                 185                 190

Glu Glu Lys Gly Gly Gly Asn Thr Thr Gly Ala Ser Gln Asn Pro Lys
        195                 200                 205

Thr Leu Ser Thr Phe Val Asp Ser Val Lys Ile Ala Glu Glu Lys Gly
    210                 215                 220

Gly Gly His Ser Ser Gly Ala Thr Gln Asn Pro Lys Thr Leu Ser Thr
225                 230                 235                 240

Phe Val Asp Ser Val Lys Ile Ala Asn Lys
                245                 250
```

<210> SEQ ID NO 8
<211> LENGTH: 750
<212> TYPE: DNA
<213> ORGANISM: A. phagocytophilum
<220> FEATURE:
<221> NAME/KEY: misc_feature
<222> LOCATION: (1)...(750)
<223> OTHER INFORMATION: nucleotide sequence of multimer of mutant p44 polypeptide

<400> SEQUENCE: 8

```
atgggcggca ataccaccgg cgcaagccaa aacccgaaaa ccctgagcac gttcgttgac      60

agcgttaaaa tcgcagaaga aaaaggcggc ggtcatacca gcggcgtctc tcagaacccg     120
```

```
aaagtttta gctctttcgt ggatagcgtt aaaattgcag atgacaaagg cggtggccat    180

agttccggtg ctacccagaa tccgaaaacg ctgtctacgt ttgtcgattc tgtgaaaatt    240

gcgaacaaag gtggcggtca ctcatcgggc gccacccaaa atccgaaaac cctgagtacg    300

ttcgttgact ccgtcaaaat cgcgaacaaa ccgggcggtg gccatacgag tggtgtgtcc    360

cagaatccga aagtttttag cagcttcgtg gattccgtta aaattgccga tgacaaaggt    420

ggcggtcaca cctcaggcgt gtcgcaaaac ccgaaagtgt ttagttcctt cgtcgacagt    480

gtgaaaatcg cggacgataa aggcggtggc aacaccaccg gtgcaagcca gaatccgaaa    540

accctgtcaa cgtttgttga ttcggtcaaa attgcagaag aaaaaggtgg cggtaacacc    600

acgggcgctt ctcaaaaccc gaaaacgctg tctaccttcg tggattctgt taaaatcgcg    660

gaagaaaaag gcggtggcca ctcatcgggt gcgacccaga acccgaaaac gctgagcacc    720

tttgtggact ccgtgaaaat tgcgaataaa                                    750
```

```
<210> SEQ ID NO 9
<211> LENGTH: 249
<212> TYPE: PRT
<213> ORGANISM: A. phagocytophilum
<220> FEATURE:
<221> NAME/KEY: misc_feature
<222> LOCATION: (1)...(249)
<223> OTHER INFORMATION: amino acid sequence of multimer of mutant
      p44 polypeptide

<400> SEQUENCE: 9

Met Gly Gly His Thr Ser Gly Val Ser Gln Asn Pro Lys Val Phe Ser
 1               5                   10                  15

Ser Phe Val Asp Ser Val Lys Ile Ala Asp Asp Lys Gly Gly His Thr
            20                  25                  30

Ser Gly Val Ser Gln Asn Pro Lys Val Phe Ser Ser Phe Val Asp Ser
        35                  40                  45

Val Lys Ile Ala Asp Asp Lys Gly Gly Gly His Thr Ser Gly Val Ser
    50                  55                  60

Gln Asn Pro Lys Val Phe Ser Ser Phe Val Asp Ser Val Lys Ile Ala
65                  70                  75                  80

Asp Asp Lys Gly Gly His Thr Ser Gly Val Ser Gln Asn Pro Lys Val
                85                  90                  95

Phe Ser Ser Phe Val Asp Ser Val Lys Ile Ala Asp Asp Lys Gly Pro
            100                 105                 110

Gly His Thr Ser Gly Val Ser Gln Asn Pro Lys Val Phe Ser Ser Phe
        115                 120                 125

Val Asp Ser Val Lys Ile Ala Asp Asp Lys Gly Gly Gly His Thr Ser
    130                 135                 140

Gly Val Ser Gln Asn Pro Lys Val Phe Ser Ser Phe Val Asp Ser Val
145                 150                 155                 160

Lys Ile Ala Asp Asp Lys Gly His Thr Ser Gly Val Ser Gln Asn Pro
                165                 170                 175

Lys Val Phe Ser Ser Phe Val Asp Ser Val Lys Ile Ala Asp Asp Lys
            180                 185                 190

Pro Gly Gly Gly His Thr Ser Gly Val Ser Gln Asn Pro Lys Val Phe
        195                 200                 205

Ser Ser Phe Val Asp Ser Val Lys Ile Ala Asp Asp Lys Gly Gly Gly
    210                 215                 220

His Thr Ser Gly Val Ser Gln Asn Pro Lys Val Phe Ser Ser Phe Val
```

```
225                 230                 235                 240

Asp Ser Val Lys Ile Ala Asp Asp Lys
                245


<210> SEQ ID NO 10
<211> LENGTH: 747
<212> TYPE: DNA
<213> ORGANISM: A. phagocytophilum
<220> FEATURE:
<221> NAME/KEY: misc_feature
<222> LOCATION: (1)...(747)
<223> OTHER INFORMATION: nucleotide sequence of multimer of mutant
      p44 polypeptide

<400> SEQUENCE: 10

atgggcggtc acacctcagg cgtctcacag aacccgaaag tcttcagctc gtttgttgat     60

agcgttaaaa tcgcagatga taaaggcggc cataccagtg gcgtctccca gaacccgaaa    120

gtgtttagct ctttcgtgga tagcgttaaa attgcggatg acaaaggcgg tggccatacc    180

tcaggcgttt cgcagaaccc gaaagtcttt agttccttcg tcgatagtgt gaaaattgca    240

gatgacaaag gtggccacac gagcggtgtg tctcaaaatc cgaaagtgtt tagctcgttc    300

gttgattctg tcaaaatcgc tgatgacaaa ggcccgggtc acacgagtgg cgtctcccag    360

aatcctaagg tgtttagcag ctttgtggat agcgttaaaa tcgccgatga caaaggtggc    420

ggtcatacct caggtgtgag ccaaaatccg aaagtcttta gtagcttcgt cgatagcgtg    480

aaaatcgctg acgacaaagg tcatacctct ggcgttagcc agaatcctaa agtgtttagc    540

agctttgttg actctgtcaa aattgctgat gacaaaccgg gcggtggcca taccagtggt    600

gtgtcccaga acccgaaagt ttttagcagc tttgttgatt cagtgaaaat cgcggacgat    660

aaaggtggcg gtcacacgtc gggtgtgtcc cagaacccga aagtcttctc gtcgtttgtg    720

gatagcgtga aaatcgcaga tgataaa                                        747


<210> SEQ ID NO 11
<211> LENGTH: 242
<212> TYPE: PRT
<213> ORGANISM: A. phagocytophilum
<220> FEATURE:
<221> NAME/KEY: misc_feature
<222> LOCATION: (1)...(242)
<223> OTHER INFORMATION: amino acid sequence of multimer of mutant
      p44 polypeptide

<400> SEQUENCE: 11

Met Gly Gly His Ser Ser Gly Ala Thr Gln Asn Pro Lys Thr Leu Ser
 1               5                  10                  15

Thr Phe Val Asp Ser Val Lys Ile Ala Asn Lys Gly Gly Gly His Ser
            20                  25                  30

Ser Gly Ala Thr Gln Asn Pro Lys Thr Leu Ser Thr Phe Val Asp Ser
        35                  40                  45

Val Lys Ile Ala Asn Lys Gly Gly Gly His Ser Ser Gly Ala Thr Gln
    50                  55                  60

Asn Pro Lys Thr Leu Ser Thr Phe Val Asp Ser Val Lys Ile Ala Asn
65                  70                  75                  80

Lys Gly Gly His Ser Ser Gly Ala Thr Gln Asn Pro Lys Thr Leu Ser
                85                  90                  95

Thr Phe Val Asp Ser Val Lys Ile Ala Asn Lys Gly Gly Gly His Ser
            100                 105                 110

Ser Gly Ala Thr Gln Asn Pro Lys Thr Leu Ser Thr Phe Val Asp Ser
```

```
        115                 120                 125

Val Lys Ile Ala Asn Lys Pro Gly Gly Gly His Ser Ser Gly Ala Thr
    130                 135                 140

Gln Asn Pro Lys Thr Leu Ser Thr Phe Val Asp Ser Val Lys Ile Ala
145                 150                 155                 160

Asn Lys Gly His Ser Ser Gly Ala Thr Gln Asn Pro Lys Thr Leu Ser
                165                 170                 175

Thr Phe Val Asp Ser Val Lys Ile Ala Asn Lys Pro Gly Gly Gly His
            180                 185                 190

Ser Ser Gly Ala Thr Gln Asn Pro Lys Thr Leu Ser Thr Phe Val Asp
        195                 200                 205

Ser Val Lys Ile Ala Asn Lys Gly Gly Gly His Ser Ser Gly Ala Thr
    210                 215                 220

Gln Asn Pro Lys Thr Leu Ser Thr Phe Val Asp Ser Val Lys Ile Ala
225                 230                 235                 240

Asn Lys


<210> SEQ ID NO 12
<211> LENGTH: 726
<212> TYPE: DNA
<213> ORGANISM: A. phagocytophilum
<220> FEATURE:
<221> NAME/KEY: misc_feature
<222> LOCATION: (1)...(726)
<223> OTHER INFORMATION: nucleotide sequence of multimer of mutant
      p44 polypeptide

<400> SEQUENCE: 12

atgggcggtc actccagcgg cgcaacccaa aacccgaaaa ccctgagcac gttcgtcgat     60

agcgtcaaaa tcgcaaataa aggcggcggc catagctctg gtgcgaccca gaatccgaaa    120

acgctgtcaa cgtttgtgga ttcggttaaa attgcgaaca aaggcggtgg ccatagttcc    180

ggtgccaccc agaatccgaa aaccctgtct acctttgtcg attctgtgaa aattgcaaac    240

aaaggtggcc actcatcggg cgctacgcaa aatccgaaaa ccctgagtac gttcgttgac    300

tccgtcaaaa tcgcaaacaa aggtggcggt cacagctctg gtgctaccca aaatccgaaa    360

acgctgagca cgttcgtgga ctcggttaaa atcgcgaaca aaccgggcgg tggccacagc    420

tccggtgcaa cgcaaaaccc gaaaacgctg tctaccttcg ttgattctgt gaaaattgcg    480

aacaaaggtc actcatcggg cgccacccaa aaccctaaga cgctgagcac cttcgttgac    540

tctgttaaaa tcgcaaacaa accgggtggc ggtcattcta gcggcgcgac gcaaaaccct    600

aagaccctgt ccacgttcgt ggattctgtt aaaatcgcca acaaaggcgg tggccacagt    660

tccggcgcaa cgcagaaccc gaaaaccctg agcacctttg tggactccgt gaaaatcgca    720

aataaa                                                               726


<210> SEQ ID NO 13
<211> LENGTH: 247
<212> TYPE: PRT
<213> ORGANISM: A. phagocytophilum
<220> FEATURE:
<221> NAME/KEY: misc_feature
<222> LOCATION: (1)...(247)
<223> OTHER INFORMATION: amino acid sequence of multimer of mutant
      p44 polypeptide

<400> SEQUENCE: 13

Met Gly Asn Thr Thr Gly Ala Ser Gln Asn Pro Lys Thr Leu Ser Thr
 1               5                  10                  15
```

Phe Val Asp Ser Val Lys Ile Ala Glu Glu Lys Gly Gly Gly Asn Thr
20 25 30

Thr Gly Ala Ser Gln Asn Pro Lys Thr Leu Ser Thr Phe Val Asp Ser
35 40 45

Val Lys Ile Ala Glu Glu Lys Gly Gly Asn Thr Thr Gly Ala Ser Gln
50 55 60

Asn Pro Lys Thr Leu Ser Thr Phe Val Asp Ser Val Lys Ile Ala Glu
65 70 75 80

Glu Lys Gly Gly Gly Asn Thr Thr Gly Ala Ser Gln Asn Pro Lys Thr
85 90 95

Leu Ser Thr Phe Val Asp Ser Val Lys Ile Ala Glu Glu Lys Gly Pro
100 105 110

Gly Asn Thr Thr Gly Ala Ser Gln Asn Pro Lys Thr Leu Ser Thr Phe
115 120 125

Val Asp Ser Val Lys Ile Ala Glu Glu Lys Gly Gly Gly Asn Thr Thr
130 135 140

Gly Ala Ser Gln Asn Pro Lys Thr Leu Ser Thr Phe Val Asp Ser Val
145 150 155 160

Lys Ile Ala Glu Glu Lys Asn Thr Thr Gly Ala Ser Gln Asn Pro Lys
165 170 175

Thr Leu Ser Thr Phe Val Asp Ser Val Lys Ile Ala Glu Glu Lys Gly
180 185 190

Pro Gly Asn Thr Thr Gly Ala Ser Gln Asn Pro Lys Thr Leu Ser Thr
195 200 205

Phe Val Asp Ser Val Lys Ile Ala Glu Glu Lys Gly Gly Gly Asn Thr
210 215 220

Thr Gly Ala Ser Gln Asn Pro Lys Thr Leu Ser Thr Phe Val Asp Ser
225 230 235 240

Val Lys Ile Ala Glu Glu Lys
245

<210> SEQ ID NO 14
<211> LENGTH: 741
<212> TYPE: DNA
<213> ORGANISM: A. phagocytophilum
<220> FEATURE:
<221> NAME/KEY: misc_feature
<222> LOCATION: (1)...(741)
<223> OTHER INFORMATION: nucleotide sequence of multimer of mutant p44
polypeptide

<400> SEQUENCE: 14
atgggcaata ccacgggcgc aagccagaat ccgaaaaccc tgtctacgtt tgtcgatagc 60
gttaaaatcg cagaagaaaa aggcggcggt aacaccacgg gtgcgtcaca aaaccccgaaa 120 acgctgtcta cgtttgtgga ttctgttaaa attgcagaag aaaaaggcgg taacaccacg 180
ggcgcttcgc aaaatccgaa aaccctgagt acgttcgtcg actccgtgaa aatcgcggaa 240
gaaaaaggcg gtggcaacac caccggtgca tctcaaaacc ctaagaccct gagcacgttt 300
gttgattcgg tcaaaatcgc cgaagaaaaa ggtccgggca acaccacggg cgctagccaa 360
aacccgaaaa cgctgagcac gttcgtggac tctgttaaaa ttgccgaaga aaaaggtggc 420
ggtaacacca cgggtgccag tcagaaccct aagacgctga gcacctttgt cgattccgtg 480
aaaattgcgg aagagaaaaa caccacgggc gcctcccaaa acccgaaaac cctgtcaacc 540
ttcgttgact cggtcaaaat tgcggaagaa aaaggcccgg gtaacaccac gggtgcgtct 600

```
cagaatccga aaacgctgag caccttcgtt gattctgtta aaatcgctga ggagaaaggc    660

ggtggcaata cgacgggcgc ctcgcagaac ccgaaaaccc tgagcacctt tgttgatagc    720

gtgaaaatcg cagaagaaaa a                                              741


<210> SEQ ID NO 15
<211> LENGTH: 212
<212> TYPE: PRT
<213> ORGANISM: B. burgdorferi
<220> FEATURE:
<221> NAME/KEY: misc_feature
<222> LOCATION: (1)...(212)
<223> OTHER INFORMATION: amino acid sequence of OspC polypeptide

<400> SEQUENCE: 15

Met Lys Lys Asn Thr Leu Ser Ala Ile Leu Met Thr Leu Phe Leu Phe
 1               5                  10                  15

Ile Ser Cys Asn Asn Ser Gly Lys Asp Gly Asn Thr Ser Ala Asn Ser
            20                  25                  30

Ala Asp Glu Ser Val Lys Gly Pro Asn Leu Thr Glu Ile Ser Lys Lys
        35                  40                  45

Ile Thr Glu Ser Asn Ala Val Val Leu Ala Val Lys Glu Val Glu Thr
    50                  55                  60

Leu Leu Ala Ser Ile Asp Glu Val Ala Lys Lys Ala Ile Gly Asn Leu
65                  70                  75                  80

Ile Ala Gln Asn Gly Leu Asn Ala Gly Ala Asn Gln Asn Gly Ser Leu
                85                  90                  95

Leu Ala Gly Ala Tyr Val Ile Ser Thr Leu Ile Ala Glu Lys Leu Asp
            100                 105                 110

Gly Leu Lys Asn Ser Glu Glu Leu Lys Glu Lys Ile Glu Asp Ala Lys
        115                 120                 125

Lys Cys Asn Lys Ala Phe Thr Asp Lys Leu Lys Ser Ser His Ala Glu
    130                 135                 140

Leu Gly Ile Ala Asn Gly Ala Ala Thr Asp Ala Asn Ala Lys Ala Ala
145                 150                 155                 160

Ile Leu Lys Thr Asn Gly Thr Lys Asp Lys Gly Ala Gln Glu Leu Glu
                165                 170                 175

Lys Leu Phe Glu Ser Val Lys Asn Leu Ser Lys Ala Ala Gln Glu Thr
            180                 185                 190

Leu Asn Asn Ser Val Lys Glu Leu Thr Ser Pro Val Val Ala Glu Ser
        195                 200                 205

Pro Lys Lys Pro
    210


<210> SEQ ID NO 16
<211> LENGTH: 639
<212> TYPE: DNA
<213> ORGANISM: B. burgdorferi
<220> FEATURE:
<221> NAME/KEY: misc_feature
<222> LOCATION: (1)...(639)
<223> OTHER INFORMATION: nucleotide sequence of OspC polypeptide

<400> SEQUENCE: 16

atgaaaaaga atacattaag tgcaatatta atgactttat ttttatttat atcttgtaat     60

aattcaggga aagatgggaa tacatctgca aattctgctg atgagtctgt taaagggcct    120

aatcttacag aaataagtaa aaaaattaca gaatctaacg cagttgttct cgccgtgaaa    180

gaagttgaaa ctctgcttgc atctatagat gaagttgcta agaaagctat tgggaatttg    240
```

```
atagcccaaa atggtttaaa tgccggcgca aatcaaaacg gatcattgtt agcgggagcc    300

tacgtaatat caaccctaat agcagaaaaa ttagatggat tgaaaaattc agaagaatta    360

aaggaaaaaa ttgaagatgc taaaaaatgt aacaaagcat ttactgataa actaaaaagt    420

agtcatgcgg aactcggtat agcgaatgga gctgctactg atgctaatgc aaaagcggct    480

attttaaaaa caaatggtac taaagataag ggtgctcaag agcttgaaaa gttatttgaa    540

tcagtaaaaa acttgtcaaa agcagctcaa gaaacactaa ataattcagt taaagaactt    600

acaagtcctg ttgtggcaga aagtccaaaa aaaccttaa                           639


<210> SEQ ID NO 17
<211> LENGTH: 636
<212> TYPE: DNA
<213> ORGANISM: B. burgdorferi
<220> FEATURE:
<221> NAME/KEY: misc_feature
<222> LOCATION: (1)...(636)
<223> OTHER INFORMATION: nucleotide sequence of OspC polypeptide

<400> SEQUENCE: 17

atgaaaaaaa atacgctgtc tgcgattctg atgacgctgt tcctgttcat tagctgcaat     60

aattcgggca aagatggcaa tacctcggcg aacagtgcgg atgaatccgt gaaaggcccg    120

aatctgaccg aaattagcaa gaaaattacg gaatctaacg cagtggttct ggctgtcaaa    180

gaagtggaaa ccctgctggc aagcattgac gaagttgcga aaaaagccat tggcaatctg    240

atcgcccaga acggcctgaa tgcaggtgct aaccaaaatg gcagtctgct ggcgggtgcc    300

tatgtcattt ccaccctgat cgcggaaaaa ctggatggtc tgaaaaacag cgaagaactg    360

aaagaaaaaa tcgaagatgc gaaaaaatgc aacaaagctt tcacggacaa actgaaaagc    420

tctcatgcgg aactgggcat tgccaacggt gcggccaccg atgcaaatgc taaagcagct    480

atcctgaaaa ccaacggcac gaaagacaaa ggtgcccagg aactggaaaa actgttcgaa    540

tcagttaaaa acctgtcgaa agcggcccaa gaaacgctga ataatagcgt gaaagaactg    600

acctcgccgg tggtggctga aagtccgaaa aaaccg                              636


<210> SEQ ID NO 18
<211> LENGTH: 200
<212> TYPE: PRT
<213> ORGANISM: B. burgdorferi
<220> FEATURE:
<221> NAME/KEY: misc_feature
<222> LOCATION: (1)...(200)
<223> OTHER INFORMATION: amino acid sequence of OspF polypeptide

<400> SEQUENCE: 18

Met Ser Lys Asp Leu Glu Gly Ala Val Lys Asp Leu Glu Ser Ser Glu
 1               5                  10                  15

Gln Asn Val Lys Lys Thr Glu Gln Glu Ile Lys Lys Gln Val Glu Gly
            20                  25                  30

Phe Leu Glu Ile Leu Glu Thr Lys Asp Leu Asn Thr Leu Asp Thr Lys
        35                  40                  45

Glu Ile Glu Lys Gln Ile Gln Glu Leu Lys Asn Lys Ile Glu Lys Leu
    50                  55                  60

Asp Ser Lys Lys Thr Ser Ile Glu Thr Tyr Ser Gly Tyr Glu Glu Lys
65                  70                  75                  80

Ile Asn Lys Ile Lys Glu Lys Leu Asn Gly Lys Gly Leu Glu Asp Lys
                85                  90                  95
```

```
Leu Asn Glu Leu Ser Glu Ser Leu Lys Lys Lys Lys Glu Glu Arg Lys
            100                 105                 110

Lys Ala Leu Gln Glu Ala Lys Lys Lys Phe Glu Glu Tyr Lys Asn Gln
        115                 120                 125

Ala Glu Ser Ala Thr Gly Val Thr His Gly Ser Gln Val Gln Arg Gln
    130                 135                 140

Gly Gly Val Gly Leu Gln Ala Trp Gln Cys Ala Asn Ser Leu Gly Phe
145                 150                 155                 160

Lys Asn Met Thr Ser Gly Asn Asn Thr Ser Asp Met Thr Asn Glu Val
                165                 170                 175

Ile Thr Asn Ser Leu Lys Lys Ile Glu Glu Glu Leu Lys Asn Ile Gly
            180                 185                 190

Glu Thr Val Glu Gly Lys Lys Glu
        195                 200


<210> SEQ ID NO 19
<211> LENGTH: 690
<212> TYPE: DNA
<213> ORGANISM: B. burgdorferi
<220> FEATURE:
<221> NAME/KEY: misc_feature
<222> LOCATION: (1)...(690)
<223> OTHER INFORMATION: nucleotide sequence of OspF polypeptide

<400> SEQUENCE: 19

taggagacaa tctttatgaa taaaaaaata aaaatgttta ttatttgtgc tatttttatg     60

ctgataagtt cttgtaagaa tgatgtaact agtaaagatt tagaaggggc ggtgaaagat    120

ttagaaagtt cagaacaaaa tgtaaaaaaa acagaacaag agataaaaaa acaagttgaa    180

ggatttttag aaattttaga gacaaaagat ttaaacacat tagatacaaa agaaattgaa    240

aaacaaattc aagaattaaa gaataagata gaaaaattag actctaaaaa aacttctatt    300

gaaacatatt ctgggtatga agaaaaaata aacaaaataa aagaaaaatt aaacggaaaa    360

ggacttgaag ataaattaaa tgaactttca gagagcttaa aaaagaaaaa agaggagaga    420

aaaaaagctt tacaagaggc taaaaagaaa tttgaagagt ataaaaacca agctgaatct    480

gcaactggag taacgcatgg ttctcaagtc caaagacaag gtggtgttgg attacaagct    540

tggcagtgtg ctaatagttt ggggtttaaa aatatgacta gtggtaataa tactagcgat    600

atgaccaatg aagttataac taattcgctt aaaaagattg aagaagaact taaaaatatt    660

ggagaaactg tagaaggtaa aaaagaataa                                     690


<210> SEQ ID NO 20
<211> LENGTH: 603
<212> TYPE: DNA
<213> ORGANISM: B. burgdorferi
<220> FEATURE:
<221> NAME/KEY: misc_feature
<222> LOCATION: (1)...(603)
<223> OTHER INFORMATION: nucleotide sequence of OspF polypeptide

<400> SEQUENCE: 20

atgtctaaag atcttgaagg tgcggttaaa gatctggaaa gctctgaaca gaacgtgaag     60

aaaaccgaac aggaaatcaa aaaacaggtt gaaggctttc tggaaattct ggaaaccaaa    120

gatctgaaca ccctggatac gaaagaaatt gaaaaacaga tccaggaact gaaaaacaaa    180

atcgaaaaac tggatagcaa gaaaaccagt attgaaacgt acagcggtta cgaagaaaaa    240

atcaacaaaa tcaaagaaaa actgaatggc aaaggtctgg aagataaact gaacgaactg    300
```

-continued

```
agtgaaagcc tgaaaaagaa aaaagaagaa cgtaaaaaag cactgcagga agcgaagaaa    360

aaattcgaag aatacaaaaa ccaggcggaa agtgccaccg gcgtgacgca tggtagccag    420

gttcagcgtc agggcggtgt gggtctgcag gcatggcagt gcgcaaactc tctgggcttc    480

aaaaatatga ccagcggtaa caatacctct gatatgacga acgaagtgat tacgaatagc    540

ctgaagaaaa ttgaagaaga actgaaaaat attggtgaaa ctgttgaagg taagaaggaa    600

taa                                                                  603


<210> SEQ ID NO 21
<211> LENGTH: 339
<212> TYPE: PRT
<213> ORGANISM: B. burgdorferi
<220> FEATURE:
<221> NAME/KEY: misc_feature
<222> LOCATION: (1)...(339)
<223> OTHER INFORMATION: amino acid sequence of p39 polypeptide

<400> SEQUENCE: 21

Met Asn Lys Ile Leu Leu Leu Ile Leu Leu Glu Ser Ile Val Phe Leu
 1               5                  10                  15

Ser Cys Ser Gly Lys Gly Ser Leu Gly Ser Glu Ile Pro Lys Val Ser
            20                  25                  30

Leu Ile Ile Asp Gly Thr Phe Asp Asp Lys Ser Phe Asn Glu Ser Ala
        35                  40                  45

Leu Asn Gly Val Lys Lys Val Lys Glu Glu Phe Lys Ile Glu Leu Val
    50                  55                  60

Leu Lys Glu Ser Ser Ser Asn Ser Tyr Leu Ser Asp Leu Glu Gly Leu
65                  70                  75                  80

Lys Asp Ala Gly Ser Asp Leu Ile Trp Leu Ile Gly Tyr Arg Phe Ser
                85                  90                  95

Asp Val Ala Lys Val Ala Ala Leu Gln Asn Pro Asp Met Lys Tyr Ala
            100                 105                 110

Ile Ile Asp Pro Ile Tyr Ser Asn Asp Pro Ile Pro Ala Asn Leu Val
        115                 120                 125

Gly Met Thr Phe Arg Ala Gln Glu Gly Ala Phe Leu Thr Gly Tyr Ile
    130                 135                 140

Ala Ala Lys Leu Ser Lys Thr Gly Lys Ile Gly Phe Leu Gly Gly Ile
145                 150                 155                 160

Glu Gly Glu Ile Val Asp Ala Phe Arg Tyr Gly Tyr Glu Ala Gly Ala
                165                 170                 175

Lys Tyr Ala Asn Lys Asp Ile Lys Ile Ser Thr Gln Tyr Ile Gly Ser
            180                 185                 190

Phe Ala Asp Leu Glu Ala Gly Arg Ser Val Ala Thr Arg Met Tyr Ser
        195                 200                 205

Asp Glu Ile Asp Ile Ile His His Ala Ala Gly Leu Gly Gly Ile Gly
    210                 215                 220

Ala Ile Glu Val Ala Lys Glu Leu Gly Ser Gly His Tyr Ile Ile Gly
225                 230                 235                 240

Val Asp Glu Asp Gln Ala Tyr Leu Ala Pro Asp Asn Val Ile Thr Ser
                245                 250                 255

Thr Thr Lys Asp Val Gly Arg Ala Leu Asn Ile Phe Thr Ser Asn His
            260                 265                 270

Leu Lys Thr Asn Thr Phe Glu Gly Gly Lys Leu Ile Asn Tyr Gly Leu
        275                 280                 285

Lys Glu Gly Val Val Gly Phe Val Arg Asn Pro Lys Met Ile Ser Phe
```

```
    290                 295                 300

Glu Leu Glu Lys Glu Ile Asp Asn Leu Ser Ser Lys Ile Ile Asn Lys
305                 310                 315                 320

Glu Ile Ile Val Pro Ser Asn Lys Glu Ser Tyr Glu Lys Phe Leu Lys
                325                 330                 335

Glu Phe Ile


<210> SEQ ID NO 22
<211> LENGTH: 1106
<212> TYPE: DNA
<213> ORGANISM: B. burgdorferi
<220> FEATURE:
<221> NAME/KEY: misc_feature
<222> LOCATION: (1)...(1106)
<223> OTHER INFORMATION: nucleotide sequence of p39 polypeptide

<400> SEQUENCE: 22

tcctgatagt gaatatgcat ttgatttatt taaatcaaag ttataaacta ctaaatatag     60

ctttgtttgt aaaggggaaa tagtttatga ataaaatatt gttgttgatt ttgcttgaga    120

gtattgtttt tttatcttgt agtggtaaag gtagtcttgg gagcgaaatt cctaaggtat    180

ctttaataat tgatggaact tttgatgata aatcttttaa tgagagtgct ttaaatggcg    240

taaaaaaagt taaagaagaa tttaaaattg agcttgtttt aaaagaatcc tcatcaaatt    300

cttatttatc tgatcttgaa gggcttaagg atgcgggctc agatttaatt tggcttattg    360

ggtatagatt tagcgatgtg gccaaggttg cggctcttca aaatcccgat atgaaatatg    420

caattattga tcctatttat tctaacgatc ctattcctgc aaatttggtg ggcatgacct    480

ttagagctca agagggtgca tttttaacgg gttatattgc tgcaaaactt tctaaaacag    540

gtaaaattgg atttttaggg ggaatagaag gcgagatagt agatgctttt aggtatgggt    600

atgaagctgg tgctaagtat gctaataaag atataaagat atctactcag tatattggta    660

gttttgctga ccttgaagct ggtagaagcg ttgcaactag aatgtattct gatgagatag    720

acattattca tcatgctgca ggccttggag gaattggggc tattgaggtt gcaaaagaac    780

ttggttctgg gcattacatt attggagttg atgaagatca agcatatctt gctcctgaca    840

atgtaataac atctacaact aaagatgttg gtagagcttt aaatattttt acatctaacc    900

atttaaaaac taatactttc gaaggtggca aattaataaa ttatggcctt aaagaaggag    960

ttgtggggtt tgtaagaaat cctaaaatga tttcctttga acttgaaaaa gaaattgaca   1020

atctttctag caaaataatc aacaaagaaa ttattgttcc atctaataaa gaaagttatg   1080

agaagtttct taaagaattt atttaa                                        1106


<210> SEQ ID NO 23
<211> LENGTH: 1017
<212> TYPE: DNA
<213> ORGANISM: B. burgdorferi
<220> FEATURE:
<221> NAME/KEY: misc_feature
<222> LOCATION: (1)...(1017)
<223> OTHER INFORMATION: nucleotide sequence of p39 polypeptide

<400> SEQUENCE: 23

atgaataaaa tcctgctgct gatcctgctg gaatctatcg tgttcctgag ttgtagtggc     60

aaaggctctc tgggtagtga aatcccgaaa gttagcctga ttatcgatgg cacctttgat    120

gacaaatctt tcaacgaaag tgccctgaat ggtgtcaaaa aagtgaaaga agaattcaaa    180

atcgaactgg tcctgaaaga aagctctagt aattcgtatc tgagcgatct ggaaggcctg    240
```

-continued

```
aaagatgcgg gttctgacct gatttggctg atcggctacc gtttcagtga tgttgcaaaa    300

gtcgcggccc tgcagaaccc ggacatgaaa tatgctatta tcgatccgat ttactcgaat    360

gacccgatcc cggcaaacct ggtgggcatg acctttcgtg cacaagaagg cgctttcctg    420

acgggttata ttgcagctaa actgagcaaa accggcaaaa tcggttttct gggcggtatt    480

gaaggtgaaa tcgttgatgc gttccgctat ggctacgaag caggtgctaa atacgccaac    540

aaagatatca aaatctccac gcagtacatt ggctcatttg cagacctgga agcaggtcgt    600

tcggtggcaa cccgcatgta cagcgatgaa atcgacatta tccatcacgc agcaggtctg    660

ggcggtattg gtgcaatcga agtcgctaaa gaactgggct ctggtcatta tattatcggc    720

gtggatgaag accaagcgta cctggccccg gataacgtga ttacgtccac cacgaaagac    780

gttggtcgtg cgctgaacat ctttacctca aatcacctga aaaccaacac gttcgaaggc    840

ggtaaactga ttaattatgg tctgaaagaa ggcgtggttg gttttgttcg caacccgaaa    900

atgattagct tcgaactgga aaaagaaatc gataacctgt cctcaaaaat catcaacaaa    960

gaaatcattg ttccgtcaaa taaagaaagt tacgaaaaat tcctgaaaga attcatt      1017
```

<210> SEQ ID NO 24
<211> LENGTH: 244
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(244)
<223> OTHER INFORMATION: amino acid sequence of fusion peptide of
      B. burgdorferi p41 and VLsE proteins

<400> SEQUENCE: 24

```
Met Lys Lys Cys Val Gln Glu Gly Val Gln Gln Glu Gly Ala Gln Gln
 1               5                  10                  15

Pro Gly Gly Gly Met Lys Lys Asn Asp Gln Ile Gly Ala Ala Ile Ala
            20                  25                  30

Leu Arg Gly Val Ala Cys Val Gln Glu Gly Val Gln Gln Glu Gly Ala
        35                  40                  45

Gln Gln Pro Gly Gly Gly Met Lys Lys Asn Asp Gln Ile Gly Ala Ala
    50                  55                  60

Ile Ala Leu Arg Gly Val Ala Cys Val Gln Glu Gly Val Gln Gln Glu
65                  70                  75                  80

Gly Ala Gln Gln Pro Gly Gly Gly Met Lys Lys Asn Asp Gln Ile Gly
                85                  90                  95

Ala Ala Ile Ala Leu Arg Gly Val Ala Gly Cys Val Gln Glu Gly Val
            100                 105                 110

Gln Gln Glu Gly Ala Gln Gln Pro Gly Gly Gly Met Lys Lys Asn Asp
        115                 120                 125

Gln Ile Gly Ala Ala Ile Ala Leu Arg Gly Val Ala Gly Cys Val Gln
    130                 135                 140

Glu Gly Val Gln Gln Glu Gly Ala Gln Gln Pro Gly Gly Gly Met Lys
145                 150                 155                 160

Lys Asn Asp Gln Ile Gly Ala Ala Ile Ala Leu Arg Gly Val Ala Gly
                165                 170                 175

Cys Val Gln Glu Gly Val Gln Gln Glu Gly Ala Gln Gln Pro Gly Gly
            180                 185                 190

Gly Met Lys Lys Asn Asp Gln Ile Gly Ala Ala Ile Ala Leu Arg Gly
```

```
        195                 200                 205

Val Ala Cys Val Gln Glu Gly Val Gln Gln Glu Gly Ala Gln Gln Pro
    210                 215                 220

Gly Gly Gly Met Lys Lys Asn Asp Gln Ile Gly Ala Ala Ile Ala Leu
225                 230                 235                 240

Arg Gly Val Ala


<210> SEQ ID NO 25
<211> LENGTH: 732
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(732)
<223> OTHER INFORMATION: nucleotide sequence of fusion peptide of
      B. burgdorferi p41 and VLsE proteins

<400> SEQUENCE: 25

atgaaaaaat gtgtccagga aggtgtgcaa caggaaggtg cccagcagcc gggtggcggt      60

atgaaaaaaa acgaccagat tggcgcagcg attgcactgc gtggcgtggc ttgcgttcag     120

gaaggcgtgc agcaagaagg cgcacagcaa ccgggcggtg gcatgaagaa aaacgatcag     180

attggtgccg caattgccct gcgtggtgtt gcatgtgtgc aggaaggtgt gcagcaagaa     240

ggcgctcagc aaccgggtgg cggtatgaag aaaaacgacc agattggtgc agctatcgca     300

ctgcgtggtg tggctggctg cgttcaggaa ggtgtccagc aagaaggcgc acagcagccg     360

ggcggtggca tgaagaaaaa cgaccaaatc ggtgccgcca ttgccctgcg tggtgtggca     420

ggttgtgtgc aggaaggtgt ccagcaagaa ggcgcccagc aaccgggtgg cggtatgaag     480

aaaaacgatc aaatcggcgc cgccattgcg ctgcgcggcg ttgccggttg tgtccaggaa     540

ggtgtccagc aagaaggcgc gcagcaaccg ggcggtggca tgaagaaaaa cgatcagatc     600

ggcgccgcga ttgccctgcg tggcgtggca tgtgtccagg aaggcgtgca gcaagaaggc     660

gcccagcaac cgggcggcgg catgaaaaaa aatgaccaaa tcggtgcggc tatcgctctg     720

cgtggcgtgg cg                                                         732


<210> SEQ ID NO 26
<211> LENGTH: 333
<212> TYPE: PRT
<213> ORGANISM: E. canis
<220> FEATURE:
<221> NAME/KEY: misc_feature
<222> LOCATION: (1)...(333)
<223> OTHER INFORMATION: amino acid sequence of gp36 polypeptide

<400> SEQUENCE: 26

Met Leu Phe Ile Leu Met Gly Tyr Cys Met Leu His Leu Thr Thr Glu
 1               5                  10                  15

Ile Thr Asn Ile Asp Phe Ala His Asp Phe His Ile His Gln Gly Glu
            20                  25                  30

Arg Phe Gly Val Ser Ser Gly Asp Leu Glu Leu Asp Ile Ala Asn His
        35                  40                  45

Pro Gly His Gly Tyr His Ile Leu Phe Lys Asn Asn Gly His Val Ile
    50                  55                  60

Ser Asp Leu His Gly Val Lys Ala Glu Asp Phe Asn Phe Asn Met Lys
65                  70                  75                  80

Asp His Ser Leu Asn Val Ser Phe Leu Ile Asp Pro Met Ala Pro Phe
```

-continued

```
                85                  90                  95

His Glu Leu Asp Val Asn Asn His Pro Asn Phe Phe Ile Ser Met His
            100                 105                 110

Ala Tyr Gln Asp Gly Cys Asp Asn Cys Val His Gly Asn Pro Ser Arg
        115                 120                 125

Pro Ala Ile Val Asn Gln Ala Gln Val Leu Leu Pro Ser Gly Val Thr
    130                 135                 140

Glu Asp Ser Val Ser Ala Pro Ala Thr Glu Asp Ser Val Ser Ala Pro
145                 150                 155                 160

Ala Thr Glu Asp Ser Val Ser Ala Pro Ala Thr Glu Asp Ser Val Ser
                165                 170                 175

Ala Pro Ala Thr Glu Asp Ser Val Ser Ala Pro Ala Thr Glu Asp Ser
            180                 185                 190

Val Ser Ala Pro Ala Thr Glu Asp Ser Val Ser Ala Pro Ala Thr Glu
        195                 200                 205

Asp Ser Val Ser Ala Pro Ala Thr Glu Asp Ser Val Ser Ala Pro Ala
    210                 215                 220

Thr Glu Asp Ser Val Ser Ala Pro Ala Thr Glu Asp Ser Val Ser Ala
225                 230                 235                 240

Pro Ala Thr Glu Asp Ser Val Ser Ala Pro Ala Thr Glu Asp Ser Val
                245                 250                 255

Ser Ala Pro Ala Thr Glu Asp Ser Val Ser Ala Pro Ala Thr Glu Asp
            260                 265                 270

Ser Val Ser Ala Pro Ala Thr Glu Asp Ser Val Ser Ala Pro Ala Thr
        275                 280                 285

Glu Asp Ser Val Ser Ala Pro Ala Thr Glu Asp Ser Val Ser Ala Pro
    290                 295                 300

Ala Thr Ala Ala Thr Gly Ser Thr Thr Ser Tyr Asn His Asn Thr Glu
305                 310                 315                 320

Leu Glu Phe Leu Asp Ser Gly Ile Leu Asn Met Leu Tyr
                325                 330
```

<210> SEQ ID NO 27
<211> LENGTH: 1002
<212> TYPE: DNA
<213> ORGANISM: E. canis
<220> FEATURE:
<221> NAME/KEY: misc_feature
<222> LOCATION: (1)...(1002)
<223> OTHER INFORMATION: nucleotide sequence of gp36 polypeptide

<400> SEQUENCE: 27

```
atgctattta tactaatggg ttattgtatg cttcatttaa caacagaaat cacaaacatt      60

gattttgctc atgattttca tatacatcaa ggtgaaagat ttggtgtttc aagtggtgat     120

ctagaacttg atattgcaaa ccatcctgga catggttatc atattttatt taagaacaat     180

ggccatgtaa tatcagattt acatggtgtt aaagctgaag actttaactt taatatgaag     240

gatcatagtt tgaatgtttc tttcttaatt gatccaatgg ctccttttca tgagttagat     300

gttaataacc atcctaactt ctttatttct atgcatgctt atcaagatgg ttgtgataat     360

tgtgtacatg gaaatccatc acgtcctgct atagtaaatc aagctcaagt tttattacca     420

agtggagtta ctgaagattc tgtttctgct ccagctactg aagattctgt ttctgctcca     480

gctactgaag attctgtttc tgctccagct actgaagatt ctgtttctgc tccagctact     540

gaagattctg tttctgctcc agctactgaa gattctgttt ctgctccagc tactgaagat     600
```

tctgtttctg ctccagctac tgaagattct gtttctgctc cagctactga agattctgtt 660
tctgctccag ctactgaaga ttctgtttct gctccagcta ctgaagattc tgtttctgct 720
ccagctactg aagattctgt ttctgctcca gctactgaag attctgtttc tgctccagct 780
actgaagatt ctgtttctgc tccagctact gaagattctg tttctgctcc agctactgaa 840
gattctgttt ctgctccagc tactgaagat tctgtttctg ctccagctac tgaagattct 900
gtttctgctc cagctactgc agcaacaggt tcaacaacat catataatca caacactgaa 960
cttgagtttt tagattctgg tattcttaac atgttgtact aa 1002

<210> SEQ ID NO 28
<211> LENGTH: 42
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(42)
<223> OTHER INFORMATION: nucleotide sequence of a Tag from
the pET46 Ek/LIC vector

<400> SEQUENCE: 28
atggcacatc accaccacca tcacgtggat gacgacgaca ag 42

<210> SEQ ID NO 29
<211> LENGTH: 14
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(14)
<223> OTHER INFORMATION: amino acid sequence of a Tag from
the pET46 Ek/LIC vector

<400> SEQUENCE: 29

Met Ala His His His His His His Val Asp Asp Asp Asp Lys
1 5 10

<210> SEQ ID NO 30
<211> LENGTH: 72
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(72)
<223> OTHER INFORMATION: nucleotide sequence of a Tag from
the pEV-L8: His8-TEV-LIC vector

<400> SEQUENCE: 30
atgcaccatc atcatcatca tcatcatggt gttgatctgg gtaccgagaa cctgtacttc 60
caatccaatg cc 72

<210> SEQ ID NO 31
<211> LENGTH: 24
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(24)
<223> OTHER INFORMATION: amino acid sequence of a Tag from the pEV-L8: His8-TEV-LIC vector

<400> SEQUENCE: 31

```
Met His His His His His His His His Gly Val Asp Leu Gly Thr Glu
 1               5                  10                  15

Asn Leu Tyr Phe Gln Ser Asn Ala
            20
```

<210> SEQ ID NO 32
<211> LENGTH: 8
<212> TYPE: PRT
<213> ORGANISM: Artificial Sequence
<220> FEATURE:
<223> OTHER INFORMATION: synthetically constructed epitope

<400> SEQUENCE: 32

```
Asp Tyr Lys Asp Asp Asp Asp Lys
 1               5
```

<210> SEQ ID NO 33
<211> LENGTH: 78
<212> TYPE: DNA
<213> ORGANISM: A. phagocytophilum
<220> FEATURE:
<221> NAME/KEY: misc_feature
<222> LOCATION: (1)...(78)
<223> OTHER INFORMATION: codon-optimized polynucleotide that encodes
p44 polypeptide

<400> SEQUENCE: 33

```
ggtcactcca gcggcgttac ccagaatccg aaactgttca gtacctttgt tgataccgtt     60

aaaatcgcag aagataaa                                                   78
```

<210> SEQ ID NO 34
<211> LENGTH: 26
<212> TYPE: PRT
<213> ORGANISM: A. phagocytophilum
<220> FEATURE:
<221> NAME/KEY: PEPTIDE
<222> LOCATION: (1)...(26)
<223> OTHER INFORMATION: P20C peptide

<400> SEQUENCE: 34

```
Gly His Ser Ser Gly Val Thr Gln Asn Pro Lys Leu Phe Ser Thr Phe
 1               5                  10                  15

Val Asp Thr Val Lys Ile Ala Glu Asp Lys
            20                  25
```

<210> SEQ ID NO 35
<211> LENGTH: 252
<212> TYPE: PRT
<213> ORGANISM: A. phagocytophilum
<220> FEATURE:
<221> NAME/KEY: PEPTIDE
<222> LOCATION: (1)...(252)
<223> OTHER INFORMATION: P20C polypeptide

<400> SEQUENCE: 35

```
Gly Gly His Ser Ser Gly Val Thr Gln Asn Pro Lys Leu Phe Ser Thr
 1               5                  10                  15

Phe Val Asp Thr Val Lys Ile Ala Glu Asp Lys Gly Gly Gly His Ser
            20                  25                  30

Ser Gly Val Thr Gln Asn Pro Lys Leu Phe Ser Thr Phe Val Asp Thr
        35                  40                  45
```

-continued

```
Val Lys Ile Ala Glu Asp Lys Gly Gly Gly His Ser Ser Gly Val Thr
    50                  55                  60

Gln Asn Pro Lys Leu Phe Ser Thr Phe Val Asp Thr Val Lys Ile Ala
65                  70                  75                  80

Glu Asp Lys Gly Gly Gly His Ser Ser Gly Val Thr Gln Asn Pro Lys
                85                  90                  95

Leu Phe Ser Thr Phe Val Asp Thr Val Lys Ile Ala Glu Asp Lys Gly
            100                 105                 110

Gly Pro Gly His Ser Ser Gly Val Thr Gln Asn Pro Lys Leu Phe Ser
        115                 120                 125

Thr Phe Val Asp Thr Val Lys Ile Ala Glu Asp Lys Gly Gly Gly His
    130                 135                 140

Ser Ser Gly Val Thr Gln Asn Pro Lys Leu Phe Ser Thr Phe Val Asp
145                 150                 155                 160

Thr Val Lys Ile Ala Glu Asp Lys Gly Gly His Ser Ser Gly Val Thr
                165                 170                 175

Gln Asn Pro Lys Leu Phe Ser Thr Phe Val Asp Thr Val Lys Ile Ala
            180                 185                 190

Glu Asp Lys Gly Pro Gly Gly His Ser Ser Gly Val Thr Gln Asn Pro
        195                 200                 205

Lys Leu Phe Ser Thr Phe Val Asp Thr Val Lys Ile Ala Glu Asp Lys
    210                 215                 220

Gly Gly Gly His Ser Ser Gly Val Thr Gln Asn Pro Lys Leu Phe Ser
225                 230                 235                 240

Thr Phe Val Asp Thr Val Lys Ile Ala Glu Asp Lys
                245                 250
```

<210> SEQ ID NO 36
<211> LENGTH: 756
<212> TYPE: DNA
<213> ORGANISM: Artificial Sequence
<220> FEATURE:
<223> OTHER INFORMATION: synthetic construct

<400> SEQUENCE: 36

```
ggtggtcact ccagcggcgt tacccagaat ccgaaactgt tcagtacctt tgttgatacc     60

gttaaaatcg cagaagataa aggcggcggc catagctctg gtgttaccca gaacccgaaa    120

ctgtttagca ccttcgtgga tacggttaaa attgcagaag acaaaggcgg tggccacagt    180

tccggcgtca cgcaaaatcc gaaactgttt tctaccttcg tcgatacggt gaaaatcgct    240

gaagacaaag gtggcggtca ttcatcgggt gtgacgcaaa accctaagct gtttagcacc    300

ttcgttgata cggtcaaaat tgcggaagac aaaggcggtc cgggccacag ctctggtgtt    360

acccaaaacc ctaaactgtt tagcacgttt gtggatacgg ttaaaatcgc cgaagataaa    420

ggcggtggcc atagttccgg cgtcacgcag aaccctaagc tgttttcaac gtttgtcgat    480

acggtgaaaa ttgccgaaga taaaggtggc cacagcagcg gcgttaccca aaacccgaaa    540

ctgttttcga cgtttgttga tacggtcaaa atcgccgaag acaaaggccc gggtggccat    600

tctagcggcg tgacgcaaaa ccctaaactg tttagtacct ttgttgacac ggttaaaatt    660

gcggaagata aaggtggcgg tcatagttcc ggcgtgacgc agaatccgaa actgttcagc    720

acctttgtgg acaccgttaa aatcgcagaa gataaa                              756
```

COMPOSITIONS AND METHODS TO DETECT VARIOUS INFECTIOUS ORGANISMS

CROSS-REFERENCE TO RELATED APPLICATIONS

The present application claims the priority benefit of U.S. provisional application Ser. No. 61/555,399, filed Nov. 3, 2011 and claims the priority benefit of U.S. provisional application Ser. No. 61/650,386, filed May 22, 2012. The contents of these applications are incorporated by reference herein in their entireties.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 655242000200SeqList.txt, date recorded: Jan. 28, 2013, size: 47,601 bytes).

TECHNICAL FIELD

The invention relates to compositions and methods for the detection of various infectious organisms, including heartworm (*Dirofilaria immitis*), *Ehrlichia Canis, Anaplasma phagocytophilum*, and *Borrelia burgdorferi*. More particularly, this invention relates to antibodies that bind to a heartworm antigen, the *E. Canis* gp36 polypeptide, the *A. phagocytophilum* p44 polypeptide, the *B. burgdorferi* OspA, OspC, OspF, p39, p41 and VLsE polypeptides, and uses thereof.

BACKGROUND ART

Infectious diseases that affect dogs, cats and other animals having close interactions with humans are important not only from a veterinary standpoint, but also because of the risk to public health. An infectious disease is caused by the presence of organisms such as viruses, bacteria, fungi, or parasites (either animalian or protozoan). Most of these diseases are spread directly from animal to animal, while others require a vector such as a tick or mosquito. Certain infectious diseases are a concern from a public health standpoint because they are zoonoses (transmittable to humans).

Heartworm is a dog parasitoid. It is hard to eliminate and can be fatal; prevention, however, is easily achieved using medication. As the name suggests, an infected mosquito injects a larva into the dog's skin, where it migrates to the circulatory system and takes up residence in the pulmonary arteries and heart, growing and reproducing to an alarming degree. The effects on the dog are quite predictable, cardiac failure over a year or two, leading to death. Treatment of an infected dog is difficult, involving an attempt to poison the healthy worm with arsenic compounds without killing the weakened dog, and frequently does not succeed. Prevention is much the better course, via heartworm prophylactics which contain a compound which kills the larvae immediately upon infection without harming the dog. Often they are available combined with other parasite preventives. The definitive host for heartworm is dog but it can also infect cats, wolves, coyotes, foxes and other animals, such as ferrets, sea lions and even, under very rare circumstances, humans.

There are several species of *Ehrlichia*, but the one that most commonly affects dogs and causes the most severe clinical signs is *E. canis*. This species infects monocytes in the peripheral blood. Two conserved major immunoreactive antigens, gp36 and gp19, are the first proteins to elicit an *E. canis*-specific antibody response, while gp200 and p28 elicit strong antibody responses later in the acute phase of the infection. Recombinant polypeptides gp36, gp19, and gp200 (N and C termini) exhibited 100% sensitivity and specificity for immunodiagnosis by the recombinant glycoprotein enzyme-linked immunosorbent assay (ELISA) compared with the results obtained by an indirect fluorescent-antibody assay (IFA) for the detection of antibodies in dogs that were naturally infected with *E. canis*. Cárdenas et al. (2007) *Clin. Vacc. Immunol.* 14:123-128.

*A. phagocytophilum* is a Gram negative, obligate bacterium of neutrophils. It is also known as the human granulocytic ehrlichiosis (HGE) agent, *Ehrlichia equi*, and *Ehrlichia phagocytophila*, and is the causative agent of human granulocytic anaplasmosis, tick-borne fever of ruminants, and equine and canine granulocytic anaplasmosis. See la Fuente et al. (2005) *J. Clin. Microbiol.* 43:1309-1317. *A. phagocytophilum* binds to fucosylated and sialylated scaffold proteins on neutrophil and granulocyte surfaces. A type IV secretion apparatus is known to help in the transfer of molecules between the bacterium and the host. The most studied ligand is PSGL-1 (CD162). The bacterium adheres to PSGL-1 (CD162) through 44-kDa major surface protein-2 (Msp2 or P44). After the bacteria enters the cell, the endosome stops maturation and does not accumulate markers of late endosomes or phagolysosomes. Because of this the vacuole does not become acidified or fused to lysosomes. *A. phagocytophilum* then divides until cell lysis or when the bacteria leaves to infect other cells. See Dumler et al. (2005) *Emerging Infec. Dis.* 11.

*B. burgdorferi* is a species of Gram negative bacteria predominant in North America, but also exists in Europe, and is the agent of Lyme disease. Lyme disease clinical features include the characteristic bull's eye rash and erythema chronicum migrans (a rash which spreads peripherally and spares the central part), as well as myocarditis, cardiomyopathy, arrythmias, arthritis, arthralgia, meningitis, neuropathies and facial nerve palsy.

A variety of serologic tests, such as IFA staining methods, Western blot analysis, and ELISAs, have been used to verify past or current infections of *B. burgdorferi* and *A. phagocytophilum* infections. Although sensitivities and specificities of these assays were considered acceptable, there is potential for false positive reactions when whole-cell antigens are used because heatshock, flagellin, or other proteins of these pathogens may be shared with other bacteria. Recent advances in the production and use of purified recombinant antigens (i.e., fusion proteins) in ELISAs to detect antibodies in human, dog, horse, and bovine sera have improved laboratory analyses. See IJdo et al. (1999) *J. Clin. Microbiol.* 37:3540-3544; Magnarelli et al. (2001) *Eur. J. Clin. Microbiol. & Infect. Dis.* 20:482-485; Magnarelli et al. (2001) *J. Med. Microbiol.* 50:889-895; Magnarelli et al. (2001) *Am. J. Vet. Res.* 9:1365-1369; Magnarelli et al. (2002) *J. Med. Microbiol.* 51:326-331; Magnarelli et al. (2002) *J. Med. Microbiol.* 51:649-655. The *B. burgdorferi* OspA, OspC, OspF, p39, p41 and VLsE antigens and *A. phagocytophilum* p44 antigen have been all shown to have some, but not 100%, seropositivity. Magnarelli et al. (2004) *J. Wildlife Dis.* 40:249.

SUMMARY OF THE INVENTION

The current invention is directed to various polypeptide antigens from infectious organisms including heartworm, *E.*

*Canis, A. phagocytophilum*, and *B. burgdorferi*, the polynucleotides encoding them, and the antibodies against them. The current invention is also directed to methods of detecting the various polypeptide antigens and antibodies, and use thereof for the detection of infections by these organisms. Further provided are methods of combination detection which are capable of detecting infections by multiple organisms.

Therefore, in one aspect, provided herein is an *A. phagocytophilum* p44 polypeptide comprising amino acids 222-236 of SEQ ID NO:1 (P44-2 disclosed in U.S. Pat. No. 6,436,399 B1), wherein said polypeptide comprises at least one mutation. Additionally, provided herein is an *A. phagocytophilum* p44 polypeptide that exhibits at least 70%, 75%, 80%, 85%, 90%, 95%, 99%, or 100% identity to amino acid 222-236 of SEQ ID NO:1 or the amino acid sequence of SEQ ID NO:1, wherein said polypeptide is not a wild-type P44 protein, and wherein said polypeptide binds to an antibody that is specific for a wild-type P44 protein. Also provided herein is an *A. phagocytophilum* p44 polypeptide comprising amino acids 222-237, 222-238, 222-239, 222-240, 222-241, 222-242, 222-243, 222-244, 222-245, 222-246, or 222-247 of SEQ ID NO:1 or an *A. phagocytophilum* p44 polypeptide comprising amino acids 222-237, 222-238, 222-239, 222-240, 222-241, 222-242, 222-243, 222-244, 222-245, 222-246, or 222-247 of SEQ ID NO:1 that comprises at least one mutation. Additionally, provided herein is an *A. phagocytophilum* p44 polypeptide that exhibits at least 70%, 75%, 80%, 85%, 90%, 95%, 99%, or 100% identity to amino acids 222-237, 222-238, 222-239, 222-240, 222-241, 222-242, 222-243, 222-244, 222-245, 222-246, or 222-247 of SEQ ID NO:1, wherein said polypeptide is not a wild-type P44 protein, and wherein said polypeptide binds to an antibody that is specific for a wild-type P44 protein.

In some embodiments, the polypeptide may comprise 1 to 10, preferably 3-7, mutations. In some embodiments, the mutations may be selected from the group consisting of a substitution, an insertion and a deletion. Some of the exemplary mutations are: Gly222(Del), His223→Asn, Ser224→Thr, Ser225→Thr, Val227→Ala, Thr228→Ser, Gln229→Asn, Leu233→Val, Leu233→Thr, Phe234→Leu, Ser235→Thr, and Thr236→Ser. In some embodiments, the polypeptide may comprise at least 1, 2, 3, 4, 5, 10 or 12 of the exemplary mutations.

In some embodiments, the polypeptide may further comprise a second polypeptide comprising amino acids 237-247 of SEQ ID NO:1. In some embodiments, the second polypeptide may comprise at least 1, or 1 to 5, preferably 2 to 3, mutations. Some of the exemplary mutations are: Thr240→Ser, Gln229→Asn, Ile243→Val, Glu245→Asp, Glu245→Asn, Asp246→Lys, and Asp246→Glu. In some embodiments, the polypeptide may comprise at least 1, 2, 3, 4, 5 or 7 of the exemplary mutations.

In some embodiments, the polypeptide may comprise the amino acid sequence selected from the group consisting of SEQ ID NOs:3-6, or a multimer, a combination, or a chimera of the polypeptides. In some embodiments, the polypeptide may further comprise a tag sequence. In some embodiments, the polypeptide may further comprise an amino acid linker between the polypeptides. In one embodiment, the polypeptide comprises the amino acid sequence of SEQ ID NO:7, which may further comprise a tag sequence.

Further provided herein is a kit for detecting an antibody that specifically binds to an *A. phagocytophilum* p44 polypeptide, which kit comprises, in a container, the polypeptide disclosed above.

Also provided herein is a polynucleotide which encodes the *A. phagocytophilum* p44 polypeptide disclosed above, or a complimentary strand thereof. In some embodiments, the polynucleotide may be DNA or RNA. In some embodiments, the polynucleotide may be codon-optimized for expression in a non-human organism. An exemplary codon-optimized polynucleotide that encodes an *A. phagocytophilum* p44 polypeptide comprising amino acids 222-247 of SEQ ID NO:1 comprises the sequence GGTCACTCCA-GCGGCGTTACCCAGAATCCGAAACTGTTCAGTAC-CTTTGTTGATACCGT TAAAATCGCAGAAGATAAA (SEQ ID NO:33). In some embodiments, the organism may be a virus, a bacterium, a yeast cell, an insect cell, or a mammalian cell. In one embodiment, the polynucleotide comprises the nucleotide sequence of SEQ ID NO:8.

Further provided herein is polynucleotide which encodes an *A. phagocytophilum* p44 polypeptide having the amino acid sequence of SEQ ID NO:1, or a complimentary strand thereof, wherein said polynucleotide is not a wild-type P44 polynucleotide. In some embodiments, the polynucleotide may exhibit at least 70%, 75%, 80%, 85%, 90%, 95%, 99%, or 100% identity to the nucleotide sequence of SEQ ID NO:2. In some embodiments, the polynucleotide may hybridize to the nucleotide sequence of SEQ ID NO:2 under moderately or highly stringent conditions. Further provided herein is polynucleotide which encodes an *A. phagocytophilum* p44 polypeptide having the amino acid sequence of 222-237, 222-238, 222-239, 222-240, 222-241, 222-242, 222-243, 222-244, 222-245, 222-246, or 222-247 of SEQ ID NO:1, or a complimentary strand thereof. In some embodiments, said polynucleotide is not a wild-type P44 polynucleotide. In some embodiments, the polynucleotide may exhibit at least 70%, 75%, 80%, 85%, 90%, 95%, 99%, or 100% identity to the nucleotide sequence of SEQ ID NO:33 or SEQ ID NO:36. In some embodiments, the polynucleotide may hybridize to the nucleotide sequence of SEQ ID NO:33 or SEQ ID NO:36 under moderately or highly stringent conditions.

Further provided herein is a vector comprising the *A. phagocytophilum* p44 polynucleotide disclosed above. In some embodiments, the polynucleotide may comprise a promoter sequence. In some embodiments, the polynucleotide may comprise a poly-A sequence. In some embodiments, the polynucleotide may comprise a translation termination sequence. In some embodiments, the polynucleotide may further encode a tag sequence.

Further provided herein is a non-human organism transformed with the vector disclosed above. In some embodiments, the organism may be a virus, a bacterium, a yeast cell, an insect or an insect cell, or a non-human mammal or a mammalian cell. In some embodiments, the organism may be used in a method for recombinantly making an *A. phagocytophilum* p44 polypeptide, which method comprises culturing the organism, and recovering said polypeptide from said organism. In some embodiments, the method may further comprise isolating the polypeptide, optionally by chromatography. Additionally, provided herein is a polypeptide produced by the method disclosed above. In some embodiments, the polypeptide may comprise post-translational modifications, e.g., a native glycosylation pattern and/or a native phosphorylation pattern.

Further provided herein is a method for detecting an antibody that specifically binds to an *A. phagocytophilum* p44 polypeptide in a sample, which method comprises contacting the polypeptide disclosed above with said sample and detecting a polypeptide-antibody complex formed. In some embodiments, the sample may be from a subject selected from the group consisting of dog, cat, human and horse. In some embodiments, the method may be used for diagnosis, prognosis, stratification, risk assessment, or treatment monitoring of a disease. In some embodiments, the disease may be granulocytic anaplasmosis. In some embodiments, the sample may be selected from the group consisting of a serum, a plasma and a blood sample. In some embodiments, the sample may be a clinical sample. In some embodiments, the antibody may be a monoclonal or polyclonal antibody or antibody fragment. In some embodiments, the polypeptide-antibody complex may be assessed by a sandwich or competitive assay format, optionally with a binder or antibody. In some embodiments, the binder or antibody may be attached to a surface and functions as a capture binder or antibody. In some embodiments, the capture binder or antibody may be attached to the surface directly or indirectly. In some embodiments, the capture binder or antibody may be attached to the surface via a linker, e.g., a biotin-avidin (or streptavidin) linking pair. In some embodiments, at least one of the binders or antibodies may be labeled. In some embodiments, the polypeptide-antibody complex may be assessed by a format selected from the group consisting of an enzyme-linked immunosorbent assay (ELISA), immunoblotting, immunoprecipitation, radioimmunoassay (RIA), immunostaining, latex agglutination, indirect hemagglutination assay (IHA), complement fixation, indirect immunofluorescent assay (IFA), nephelometry, flow cytometry assay, plasmon resonance assay, chemiluminescence assay, lateral flow immunoassay, u-capture assay, inhibition assay and avidity assay. In some embodiments, the polypeptide-antibody complex may be assessed in a homogeneous or a heterogeneous assay format.

In a second aspect, provided herein is a polynucleotide which encodes a *B. burgdorferi* OspC polypeptide having the amino acid sequence of SEQ ID NO:15, or a complimentary strand thereof, wherein said polynucleotide is not a wild-type OspC polynucleotide. In some embodiments, the polynucleotide may exhibit at least 70%, 75%, 80%, 90%, 95% or 99% identity to the nucleotide sequence of SEQ ID NO:16. In some embodiments, the polynucleotide may hybridize to the nucleotide sequence of SEQ ID NO:16 under moderately or highly stringent conditions. In some embodiments, the polynucleotide may be codon-optimized for expression in a non-human organism. In some embodiments, the organism may be selected from the group consisting of a virus, a bacterium, a yeast cell, an insect, an insect cell, a non-human mammal and a mammalian cell. In some embodiments, the polynucleotide may be DNA or RNA. In some embodiments, the polynucleotide may comprise the nucleotide sequence of SEQ ID NO:17.

Further provided herein is a method for detecting an antibody that specifically binds to a *B. burgdorferi* OspC polypeptide in a sample, which method comprises contacting the polypeptide having the amino acid sequence of SEQ ID NO:15 encoded by the polynucleotide which is not a wild-type OspC polynucleotide with said sample and detecting a polypeptide-antibody complex formed.

In a third aspect, provided herein is a polynucleotide which encodes a *B. burgdorferi* OspF polypeptide having the amino acid sequence of SEQ ID NO:18, or a complimentary strand thereof, wherein said polynucleotide is not a wild-type OspF polynucleotide. In some embodiments, the polynucleotide may exhibit at least 70%, 75%, 80%, 90%, 95% or 99% identity to the nucleotide sequence of SEQ ID NO:19. In some embodiments, the polynucleotide may hybridize to the nucleotide sequence of SEQ ID NO:19 under moderately or highly stringent conditions. In some embodiments, the polynucleotide may be codon-optimized for expression in a non-human organism. In some embodiments, the organism may be selected from the group consisting of a virus, a bacterium, a yeast cell, an insect, an insect cell, a non-human mammal and a mammalian cell. In some embodiments, the polynucleotide may be DNA or RNA. In some embodiments, the polynucleotide may comprise the nucleotide sequence of SEQ ID NO:20.

Further provided herein is a method for detecting an antibody that specifically binds to a *B. burgdorferi* OspF in a sample, which method comprises contacting the polypeptide having the amino acid sequence of SEQ ID NO:18 encoded by the polynucleotide which is not a wild-type OspF polynucleotide with said sample and detecting a polypeptide-antibody complex formed.

In a fourth aspect, provided herein is a polynucleotide which encodes a *B. burgdorferi* p39 polypeptide having the amino acid sequence of SEQ ID NO:21, or a complimentary strand thereof, wherein said polynucleotide is not a wild-type p39 polynucleotide. In some embodiments, the polynucleotide may exhibit at least 70%, 75%, 80%, 90%, 95% or 99% identity to the nucleotide sequence of SEQ ID NO:22. In some embodiments, the polynucleotide may hybridize to the nucleotide sequence of SEQ ID NO:22 under moderately or highly stringent conditions. In some embodiments, the polynucleotide may be codon-optimized for expression in a non-human organism. In some embodiments, the organism may be selected from the group consisting of a virus, a bacterium, a yeast cell, an insect, an insect cell, a non-human mammal and a mammalian cell. In some embodiments, the polynucleotide may be DNA or RNA. In some embodiments, the polynucleotide may comprise the nucleotide sequence of SEQ ID NO:23.

Further provided herein is a method for detecting an antibody that specifically binds to a *B. burgdorferi* p39 polypeptide in a sample, which method comprises contacting the polypeptide having the amino acid sequence of SEQ ID NO:21 encoded by the polynucleotide which is not a wild-type p39 polynucleotide with said sample and detecting a polypeptide-antibody complex formed.

Further provided herein is a vector comprising the *B. burgdorferi* OspC, OspF and p39 polynucleotide disclosed above. In some embodiments, the polynucleotide may comprise a promoter sequence. In some embodiments, the polynucleotide may comprise a poly-A sequence. In some embodiments, the polynucleotide may comprise a translation termination sequence. In some embodiments, the polynucleotide may further encode a tag sequence.

Further provided herein is a non-human organism transformed with the vector comprising the *B. burgdorferi* OspC, OspF and p39 polynucleotide disclosed above. In some embodiments, the organism may be a virus, a bacterium, a yeast cell, an insect, insect cell, a non-human mammal or a mammalian cell. In some embodiments, the organism may be used in a method for recombinantly making a *B. burgdorferi* OspC, OspF and p39 polypeptide, which method may comprise culturing the organism, and recovering said polypeptide from said organism. In some embodiments, the method may further comprise isolating the OspC, OspF and p39 polypeptide, optionally by chromatography. Additionally, provided herein is a *B. burgdorferi* OspC, OspF and p39 polypeptide produced by the method disclosed above. In some embodiments, the polypeptide may comprise a post-translational modification, e.g., a native glycosylation pattern and/or a native phosphorylation pattern.

In a fifth aspect, provided herein is an antigenic composition comprising at least two *B. burgdorferi* polypeptides, wherein each of said polypeptides comprises an amino acid sequence selected from the group consisting of: a) an OspA polypeptide, b) an OspC polypeptide, c) an OspF polypeptide, d) a p39 polypeptide, and e) a fusion peptide of p41 and VLsE. In some embodiments, the antigenic composition does not consist of an OspA polypeptide and an OspC polypeptide. In some embodiments, the antigenic composition does not consist of an OspA polypeptide and an OspF polypeptide. In some embodiments, the antigenic composition does not consist of an OspC polypeptide and an OspF polypeptide. In some embodiments, the antigenic composition does not consist of an OspA polypeptide, an OspC polypeptide and an OspF polypeptide. In some embodiments, the antigenic composition may comprise at least 3, 4, or all 5 of said *B. burgdorferi* polypeptides. In some embodiments, the OspC polypeptide may comprise the polypeptide having the amino acid sequence of SEQ ID NO:15 encoded by the polynucleotide which is not a wild-type OspC polynucleotide. In some embodiments, the OspF polypeptide may comprise the polypeptide having the amino acid sequence of SEQ ID NO:18 encoded by the polynucleotide which is not a wild-type OspF polynucleotide. In some embodiments, the p39 polypeptide may comprise the polypeptide having the amino acid sequence of SEQ ID NO:21 encoded by the polynucleotide which is not a wild-type p39 polynucleotide. In some embodiments, the fusion peptide of p41 and VLsE may comprise an amino acid sequence of SEQ ID NO:24. In some embodiments, the polypeptides may form a fusion molecule.

Also provided herein is a method for detecting an antibody that specifically binds to a *B. burgdorferi* antigen in a sample, which method may comprise contacting the antigenic composition comprising at least two *B. burgdorferi* polypeptides, wherein each of said polypeptides may comprise an amino acid sequence selected from the group consisting of OspA, OspC, OspF, p39 polypeptide and a fusion peptide of p41 and VLsE disclosed above with said sample and detecting a polypeptide-antibody complex formed. In some embodiments, the sample may be from a subject selected from the group consisting of cat, dog, human and horse. In some embodiments, the method may be used for diagnosis, prognosis, stratification, risk assessment, or treatment monitoring of a disease. In some embodiments, the disease may be Lyme disease. In some embodiments, the method may be used to distinguish between infection by a Lyme disease pathogen and exposure to a Lyme disease vaccine. In some embodiments, the method may be used to distinguish between exposure to a Nobivac™ Lyme vaccine and exposure to another vaccine. In some embodiments, the sample may be selected from the group consisting of a serum, a plasma and a blood sample. In some embodiments, the sample may be a clinical sample. In some embodiments, the antibody may be a monoclonal or polyclonal antibody or antibody fragment. In some embodiments, the polypeptide-antibody complex may be assessed by a sandwich or competitive assay format, optionally with a binder or antibody. In some embodiments, the binder or antibody may be attached to a surface and functions as a capture binder or antibody. In some embodiments, the capture binder or antibody may be attached to the surface directly or indirectly. In some embodiments, the capture binder or antibody may be attached to the surface via a linker, e.g., a biotin-avidin (or streptavidin) linking pair. In some embodiments, at least one of the binders or antibodies may be labeled. In some embodiments, the polypeptide-antibody complex may be assessed by a format selected from the group consisting of an enzyme-linked immunosorbent assay (ELISA), immunoblotting, immunoprecipitation, radioimmunoassay (RIA), immunostaining, latex agglutination, indirect hemagglutination assay (IHA), complement fixation, indirect immunofluorescent assay (IFA), nephelometry, flow cytometry assay, plasmon resonance assay, chemiluminescence assay, lateral flow immunoassay, u-capture assay, inhibition assay and avidity assay. In some embodiments, the polypeptide-antibody complex may be assessed in a homogeneous or a heterogeneous assay format.

Further provided herein is a method of classifying *Borrelia burgdorferi* infection of a mammal, e.g., an animal, the method comprising: calculating levels of antibodies that specifically bind to an OspA, OspC, OspF, p39 polypeptide and/or a fusion peptide of p41 and VLsE using a method for detecting an antibody that specifically binds to a *B. burgdorferi* antigen in a sample, which method may comprise contacting the antigenic composition comprising at least two *B. burgdorferi* polypeptides, wherein each of said polypeptides may comprise an amino acid sequence selected from the group consisting of OspA, OspC, OspF, p39 polypeptide and a fusion peptide of p41 and VLsE disclosed above with said sample and detecting a polypeptide-antibody complex formed; calculating reference values of the levels of the antibodies; and determining the type of *Borrelia burgdorferi* infection of the mammal by comparing the levels of the antibodies to the reference values.

Also provided herein is a kit for detecting an antibody that specifically binds to a *B. burgdorferi* polypeptide, which kit comprises, in a container, an antigenic composition comprising at least two *B. burgdorferi* polypeptides, wherein each of said polypeptides comprises an amino acid sequence selected from the group consisting of: a) an OspA polypeptide, b) an OspC polypeptide, c) an OspF polypeptide, d) a p39 polypeptide, and e) a fusion peptide of p41 and VLsE. In some embodiments, the antigenic composition does not consist of an OspA polypeptide and an OspC polypeptide. In some embodiments, the antigenic composition does not consist of an OspA polypeptide and an OspF polypeptide. In some embodiments, the antigenic composition does not consist of an OspC polypeptide and an OspF polypeptide. In some embodiments, the antigenic composition does not consist of an OspA polypeptide, an OspC polypeptide and an OspF polypeptide.

In an sixth aspect, provided herein is a composition for detecting multiple disease antigens and/or antibodies, which composition comprises at least two, preferably three of the following reagents: a) an antibody against a *Dirofilaria immitis* antigen, b) an *E. Canis* gp36 polypeptide, c) an *A. phagocytophilum* p44 polypeptide, and d) an antigenic composition comprising a *B. burgdorferi* polypeptide selected from the group consisting of OspA, OspC, OspF, p39 and a fusion peptide of p41 and VLsE. In some embodiments, the composition may comprise all four of the reagents. In some embodiments, the reagent a) may be a chicken polyclonal antibody. In some embodiments, the chicken polyclonal antibody may be produced by immunizing chickens with a canine heartworm antigen. In some embodiments, the reagent b) may comprise a polypeptide having an amino acid sequence of SEQ ID NO:26, which may further comprise a tag sequence. In some embodiments, the reagent c) may comprise an *A. phagocytophilum* p44 polypeptide comprising amino acids 222-236 of SEQ ID NO:1, wherein said polypeptide comprises at least one mutation. In some embodiments, the reagent d) may comprise an antigenic composition comprising at least two *B. burgdorferi* polypeptides, wherein each of said polypeptides comprises an amino acid sequence selected from the group consisting of:

a) an OspA polypeptide, b) an OspC polypeptide, c) an OspF polypeptide, d) a p39 polypeptide, and e) a fusion peptide of p41 and VLsE.

Also provided herein is a kit for detecting multiple infectious organisms, which kit may comprise, in a container, the composition disclosed above. Further provided herein is a method for detecting multiple disease antigens and/or antibodies in a sample, which method may comprise: a) contacting said sample with the composition for detecting multiple disease antigens and/or antibodies, which composition may comprise at least two, preferably three of the following reagents: an antibody against a *Dirofilaria immitis* antigen, an *E. Canis* gp36 polypeptide, an *A. phagocytophilum* p44 polypeptide, and an antigenic composition comprising a *B. burgdorferi* polypeptide selected from the group consisting of OspA, OspC, OspF, p39 and a fusion peptide of p41 and VLsE; and b) detecting a polypeptide-antibody complex formed. In some embodiments, the method may be used for diagnosis, prognosis, stratification, risk assessment, or treatment monitoring of a disease. In some embodiments, the disease may be selected from the group consisting of a heartworm disease, ehrlichiosis, granulocytic anaplasmosis, and Lyme disease.

In a seventh aspect, provided herein is a computer readable medium containing executable instructions that when executed perform a method of classifying *Borrelia burgdorferi* infection of a mammal, e.g., an animal, the method comprising: calculating levels of antibodies that specifically bind to an OspA, OspC, OspF, p39 polypeptide and/or a fusion peptide of p41 and VLsE using a method for detecting an antibody that specifically binds to a *B. burgdorferi* antigen in a sample, which method may comprise contacting the antigenic composition comprising at least two *B. burgdorferi* polypeptides, wherein each of said polypeptides may comprise an amino acid sequence selected from the group consisting of OspA, OspC, OspF, p39 polypeptide and a fusion peptide of p41 and VLsE disclosed above with said sample and detecting a polypeptide-antibody complex formed; calculating reference values of the levels of the antibodies; and determining the type of *Borrelia burgdorferi* infection of the mammal by comparing the levels of the antibodies to the reference values.

Further provided herein is a system for classifying *Borrelia burgdorferi* infection of a mammal, e.g., an animal comprising the computer readable medium disclosed herein and an antigenic composition comprising at least two *B. burgdorferi* polypeptides, wherein each of said polypeptides may comprise an amino acid sequence selected from the group consisting of: a) an OspA polypeptide, b) an OspC polypeptide, c) an OspF polypeptide, d) a p39 polypeptide, and e) a fusion peptide of p41 and VLsE.

BRIEF DESCRIPTION OF THE DRAWINGS

FIGS. 1A (SEQ ID NO:1) and 1B (SEQ ID NO:2) show the amino acid and nucleotide sequences of an *A. phagocytophilum* p44 polypeptide. FIGS. 1C (SEQ ID NO:3), 1D (SEQ ID NO:4), 1E (SEQ ID NO:5) and 1F (SEQ ID NO:6) show the amino acid sequences of mutant p44 polypeptides. FIGS. 1G (SEQ ID NO:7), 1H (SEQ ID NO:8), 1I (SEQ ID NO:9), 1J (SEQ ID NO:10), 1K (SEQ ID NO:11), 1L (SEQ ID NO:12), 1M (SEQ ID NO:13) and 1N (SEQ ID NO:14) show the amino acid and nucleotide sequences of multimers of mutant p44 polypeptides.

FIGS. 2A (SEQ ID NO:15), 2B (SEQ ID NO:16) and 2C (SEQ ID NO:17) show the amino acid and nucleotide sequences of a *B. burgdorferi* OspC polypeptide.

FIGS. 3A (SEQ ID NO:18), 3B (SEQ ID NO:19) and 3C (SEQ ID NO:20) show the amino acid and nucleotide sequences of a *B. burgdorferi* OspF polypeptide.

FIGS. 4A (SEQ ID NO:21), 4B (SEQ ID NO:22) and 4C (SEQ ID NO:23) show the amino acid and nucleotide sequences of a *B. burgdorferi* p39 polypeptide.

FIGS. 5A (SEQ ID NO:24) and 5B (SEQ ID NO:25) show the amino acid and nucleotide sequences of a fusion peptide of *B. burgdorferi* p41 and VLsE proteins.

FIGS. 6A (SEQ ID NO:26) and 6B (SEQ ID NO:27) show the amino acid and nucleotide sequences of an *E. Canis* gp36 polypeptide.

FIGS. 7A (SEQ ID NO:28) and 7B (SEQ ID NO:29) show the nucleotide and amino acid sequences of a Tag from the pET46 Ek/LIC vector (Novagen).

FIGS. 8A (SEQ ID NO:30) and 8B (SEQ ID NO:31) show the nucleotide and amino acid sequences of a Tag from the pEV-L8: His8-TEV-LIC vector (from Purdue University, IN).

DETAILED DESCRIPTION OF THE INVENTION

A. Definitions

Figure 9:
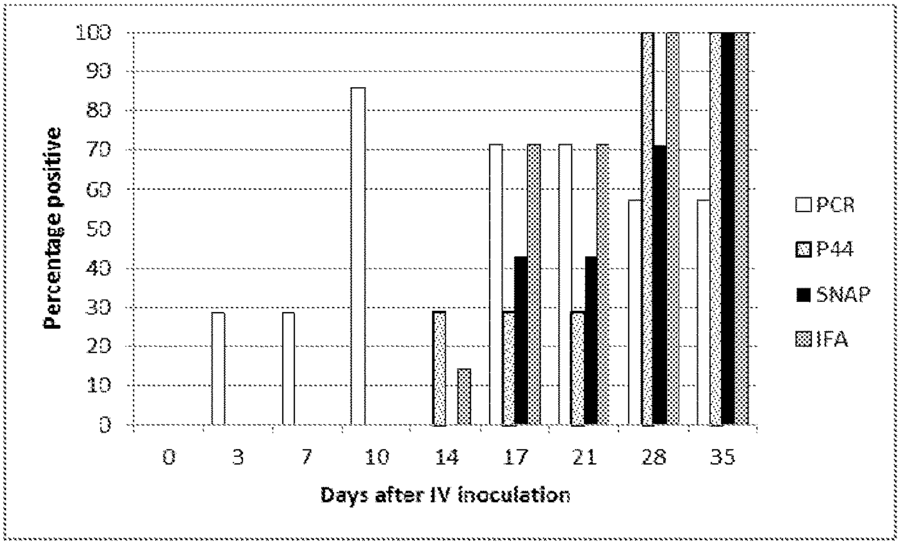
FIG. 9 shows percentages of *A. phagocytophilum* positive assay results in three serological assays and a PCR assay for the first 35 days after IV inoculation of 7 dogs. Blood samples were not available for the PCR assay on Day 14. P44=ACCUPLEX™ BioCD system P44 antibody assay; SNAP=SNAP 4DX, IDEXX Laboratories, Portland, Me.; IFA=Indirect fluorescent antibody assay performed at Antech Laboratories using IFA slides purchased at Prototek Reference Laboratory. The time to first positive result was significantly faster for PCR when compared to each of the 3 serological assays (p=0.0023).

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, the singular forms "a", "an", and "the" include plural references unless indicated otherwise. For example, "a" dimer includes one or more dimers.

The terms "polypeptide", "oligopeptide", "peptide" and "protein" are used interchangeably herein to refer to polymers of amino acids of any length, e.g., at least 5, 6, 7, 8, 9, 10, 20, 30, 40, 50, 100, 200, 300, 400, 500, 1,000 or more amino acids. The polymer may be linear or branched, it may comprise modified amino acids, and it may be interrupted by non-amino acids. The terms also encompass an amino acid polymer that has been modified naturally or by intervention;

for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule, and can be an immunoglobulin of any class, e.g., IgG, IgM, IgA, IgD and IgE. IgY, which is the major antibody type in avian species such as chicken, is also included within the definition. As used herein, the term encompasses not only intact polyclonal or monoclonal antibodies, but also fragments thereof (such as Fab, Fab', F(ab')2, Fv), single chain (ScFv), mutants thereof, naturally occurring variants, fusion proteins comprising an antibody portion with an antigen recognition site of the required specificity, humanized antibodies, chimeric antibodies, and any other modified configuration of the immunoglobulin molecule that comprises an antigen recognition site of the required specificity.

As used herein, the term "specific binding" refers to the specificity of an antibody such that it preferentially binds to a target antigen, such as a polypeptide antigen, or a heartworm (*Dirofilaria immitis*) antigen. Recognition by an antibody of a particular target in the presence of other potential interfering substances is one characteristic of such binding. Preferably, antibodies or antibody fragments that are specific for or bind specifically to a target antigen bind to the target antigen with higher affinity than binding to other non-target substances. Also preferably, antibodies or antibody fragments that are specific for or bind specifically to a target antigen avoid binding to a significant percentage of non-target substances, e.g., non-target substances present in a testing sample. In some embodiments, antibodies or antibody fragments of the present disclosure avoid binding greater than about 90% of non-target substances, although higher percentages are clearly contemplated and preferred. For example, antibodies or antibody fragments of the present disclosure avoid binding about 91%, about 92%, about 93%, about 94%, about 95%, about 96%, about 97%, about 98%, about 99%, and about 99% or more of non-target substances. In other embodiments, antibodies or antibody fragments of the present disclosure avoid binding greater than about 10%, 20%, 30%, 40%, 50%, 60%, or 70%, or greater than about 75%, or greater than about 80%, or greater than about 85% of non-target substances.

As used herein, the term "specific binding" also refers to the specificity of a polypeptide such that it preferentially binds to a target antibody, such as a target antibody in a testing sample, e.g., antibodies against an *Ehrlichia Canis* gp36 polypeptide, an *Anaplasma phagocytophilum* p44 polypeptide or a *Borrelia burgdorferi* OspA, OspC, OspF, p39, p41 and/or VLsE polypeptide. Recognition by a polypeptide of a particular target antibody in the presence of other antibodies or substances is one characteristic of such binding. Preferably, a polypeptide that is specific for or binds specifically to an antibody binds to the target antibody with higher affinity than binding to other non-target antibodies or substances. Also preferably, a polypeptide that is specific for or binds specifically to a target antibody avoids binding to a significant percentage of non-target antibodies or substances, e.g., non-target antibodies present in a testing sample. In some embodiments, polypeptides of the present disclosure avoid binding greater than about 90% of non-target antibodies or substances, although higher percentages are clearly contemplated and preferred. For example, polypeptides of the present disclosure avoid binding about 91%, about 92%, about 93%, about 94%, about 95%, about 96%, about 97%, about 98%, about 99%, and about 99% or more of non-target antibodies or substances. In other embodiments, polypeptides of the present disclosure avoid binding greater than about 10%, 20%, 30%, 40%, 50%, 60%, or 70%, or greater than about 75%, or greater than about 80%, or greater than about 85% of non-target antibodies or substances.

As used herein, the term "antigen" refers to a target molecule that is specifically bound by an antibody through its antigen recognition site. The antigen may be monovalent or polyvalent, i.e., it may have one or more epitopes recognized by one or more antibodies. Examples of kinds of antigens that can be recognized by antibodies include polypeptides, oligosaccharides, glycoproteins, polynucleotides, lipids, etc.

As used herein, the term "epitope" refers to a peptide sequence of at least about 3 to 5, preferably about 5 to 10 or 15, and not more than about 1,000 amino acids (or any integer there between), which define a sequence that by itself or as part of a larger sequence, binds to an antibody generated in response to such sequence. There is no critical upper limit to the length of the fragment, which may, for example, comprise nearly the full-length of the antigen sequence, or even a fusion protein comprising two or more epitopes from the target antigen. An epitope for use in the subject invention is not limited to a peptide having the exact sequence of the portion of the parent protein from which it is derived, but also encompasses sequences identical to the native sequence, as well as modifications to the native sequence, such as deletions, additions and substitutions (conservative in nature).

As used herein, a "tag" or an "epitope tag" refers to a sequence of amino acids, typically added to the N- and/or C-terminus of a polypeptide. The inclusion of tags fused to a polypeptide can facilitate polypeptide purification and/or detection. Typically a tag or tag polypeptide refers to polypeptide that has enough residues to provide an epitope recognized by an antibody or can serve for detection or purification, yet is short enough such that it does not interfere with activity of chimeric polypeptide to which it is linked. The tag polypeptide typically is sufficiently unique so an antibody that specifically binds thereto does not substantially cross-react with epitopes in the polypeptide to which it is linked. Suitable tag polypeptides generally have at least 5 or 6 amino acid residues and usually between about 8-50 amino acid residues, typically between 9-30 residues. The tags can be linked to one or more chimeric polypeptides in a multimer and permit detection of the multimer or its recovery from a sample or mixture. Such tags are well known and can be readily synthesized and designed. Exemplary tag polypeptides include those used for affinity purification and include His tags, the influenza hemagglutinin (HA) tag polypeptide and its antibody 12CA5; the c-myc tag and the 8F9, 3C7, 6E10, G4, B7 and 9E10 antibodies thereto; and the Herpes Simplex virus glycoprotein D (gD) tag and its antibody. See, e.g., Field et al. (1988) *Mol. Cell. Biol.* 8:2159-2165; Evan et al. (1985) *Mol. Cell. Biol.* 5:3610-3616; Paborsky et al. (1990) *Protein Engineering* 3:547-553.

The terms "polynucleotide," "oligonucleotide," "nucleic acid" and "nucleic acid molecule" are used interchangeably herein to refer to a polymeric form of nucleotides of any length, e.g., at least 8, 9, 10, 20, 30, 40, 50, 100, 200, 300, 400, 500, 1,000 or more nucleotides, and may comprise ribonucleotides, deoxyribonucleotides, analogs thereof, or mixtures thereof. This term refers only to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), including tRNA, rRNA, hRNA, and mRNA, whether spliced or unspliced, any other type of polynucleotide which is an N- or C-glycoside of a purine or pyrimidine base, and other polymers containing normucleotidic backbones, for example, polyamide (e.g., peptide nucleic acids ("PNAs")) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. Thus, these terms include, for example, 3'-deoxy-2',5'-DNA, oligodeoxyribonucleotide N3' to P5' phosphoramidates, 2'-O-alkyl-substituted RNA, hybrids between DNA and RNA or between PNAs and DNA or RNA, and also include known types of modifications, for example, labels, alkylation, "caps," substitution of one or more of the nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, aminoalkylphosphotriesters), those containing pendant moieties, such as, for example, proteins (including enzymes (e.g. nucleases), toxins, antibodies, signal peptides, poly-L-lysine, etc.), those with intercalators (e.g., acridine, psoralen, etc.), those containing chelates (of, e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

It will be appreciated that, as used herein, the terms "nucleoside" and "nucleotide" will include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides can also include modifications on the sugar moiety, e.g., wherein one or more of the hydroxyl groups are replaced with halogen, aliphatic groups, or are functionalized as ethers, amines, or the like. The term "nucleotidic unit" is intended to encompass nucleosides and nucleotides.

"Nucleic acid probe" and "probe" are used interchangeably and refer to a structure comprising a polynucleotide, as defined above, that contains a nucleic acid sequence that can bind to a corresponding target. The polynucleotide regions of probes may be composed of DNA, and/or RNA, and/or synthetic nucleotide analogs.

As used herein, "complementary or matched" means that two nucleic acid sequences have at least 50% sequence identity. Preferably, the two nucleic acid sequences have at least 60%, 70%, 80%, 90%, 95%, 96%, 97%, 98%, 99% or 100% of sequence identity. "Complementary or matched" also means that two nucleic acid sequences can hybridize under low, middle and/or high stringency condition(s).

As used herein, "substantially complementary or substantially matched" means that two nucleic acid sequences have at least 90% sequence identity. Preferably, the two nucleic acid sequences have at least 95%, 96%, 97%, 98%, 99% or 100% of sequence identity. Alternatively, "substantially complementary or substantially matched" means that two nucleic acid sequences can hybridize under high stringency condition(s).

In general, the stability of a hybrid is a function of the ion concentration and temperature. Typically, a hybridization reaction is performed under conditions of lower stringency, followed by washes of varying, but higher, stringency. Moderately stringent hybridization refers to conditions that permit a nucleic acid molecule such as a probe to bind a complementary nucleic acid molecule. The hybridized nucleic acid molecules generally have at least 60% identity, including for example at least any of 70%, 75%, 80%, 85%, 90%, or 95% identity. Moderately stringent conditions are conditions equivalent to hybridization in 50% formamide, 5×Denhardt's solution, 5×SSPE, 0.2% SDS at 42° C., followed by washing in 0.2×SSPE, 0.2% SDS, at 42° C. High stringency conditions can be provided, for example, by hybridization in 50% formamide, 5×Denhardt's solution, 5×SSPE, 0.2% SDS at 42° C., followed by washing in 0.1×SSPE, and 0.1% SDS at 65° C. Low stringency hybridization refers to conditions equivalent to hybridization in 10% formamide, 5×Denhardt's solution, 6×SSPE, 0.2% SDS at 22° C., followed by washing in 1×SSPE, 0.2% SDS, at 37° C. Denhardt's solution contains 1% Ficoll, 1% polyvinylpyrolidone, and 1% bovine serum albumin (BSA). 20×SSPE (sodium chloride, sodium phosphate, ethylene diamide tetraacetic acid (EDTA)) contains 3M sodium chloride, 0.2M sodium phosphate, and 0.025 M EDTA. Other suitable moderate stringency and high stringency hybridization buffers and conditions are well known to those of skill in the art and are described, for example, in Sambrook et al., Molecular Cloning: A Laboratory Manual, 2nd ed., Cold Spring Harbor Press, Plainview, N.Y. (1989); and Ausubel et al., Short Protocols in Molecular Biology, 4th ed., John Wiley & Sons (1999).

Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See Kanehisa (1984) *Nucleic Acids Res.* 12:203-215.

The terms "homologous", "substantially homologous", and "substantial homology" as used herein denote a sequence of amino acids having at least 50%, 60%, 70%, 80% or 90% identity wherein one sequence is compared to a reference sequence of amino acids. The percentage of sequence identity or homology is calculated by comparing one to another when aligned to corresponding portions of the reference sequence.

As used herein, "vector (or plasmid)" refers to discrete elements that are used to introduce heterologous DNA into cells for either expression or replication thereof. Selection and use of such vehicles are well known within the skill of the artisan. An expression vector includes vectors capable of expressing DNA's that are operatively linked with regulatory sequences, such as promoter regions, that are capable of effecting expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eucaryotic cells and/or prokaryotic cells and those that remain episomal or those which integrate into the host cell genome.

As used herein, "a promoter region or promoter element" refers to a segment of DNA or RNA that controls transcription of the DNA or RNA to which it is operatively linked. The promoter region includes specific sequences that are sufficient for RNA polymerase recognition, binding and transcription initiation. This portion of the promoter region is referred to as the promoter. In addition, the promoter region includes sequences that modulate this recognition, binding and transcription initiation activity of RNA polymerase. These sequences may be cis acting or may be responsive to trans acting factors. Promoters, depending upon the nature of the regulation, may be constitutive or regulated. Exemplary promoters contemplated for use in prokaryotes include the bacteriophage T7 and T3 promoters, and the like.

As used herein, "operatively linked or operationally associated" refers to the functional relationship of DNA with regulatory and effector sequences of nucleotides, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA. In order to optimize expression and/or in vitro transcription, it may be necessary to remove, add or alter 5' untranslated portions of the clones to eliminate extra, potential inappropriate alternative translation initiation (i.e., start) codons or other sequences that may interfere with or reduce expression, either at the level of transcription or translation. Alternatively, consensus ribosome binding sites can be inserted immediately 5' of the start codon and may enhance expression. See, e.g., Kozak (1991) *J. Biol. Chem.* 266:19867-19870. The desirability of (or need for) such modification may be empirically determined.

As used herein, "biological sample" refers to any sample obtained from a living or viral source or other source of macromolecules and biomolecules, and includes any cell type or tissue of a subject from which nucleic acid or protein or other macromolecule can be obtained. The biological sample can be a sample obtained directly from a biological source or a sample that is processed. For example, isolated nucleic acids that are amplified constitute a biological sample. Biological samples include, but are not limited to, body fluids, such as blood, plasma, serum, cerebrospinal fluid, synovial fluid, urine and sweat, tissue and organ samples from animals and plants and processed samples derived therefrom. Also included are soil and water samples and other environmental samples, viruses, bacteria, fungi, algae, protozoa and components thereof.

The terms "level" or "levels" are used to refer to the presence and/or amount of protein, and can be determined qualitatively or quantitatively. A "qualitative" change in the protein level refers to the appearance or disappearance of a protein spot that is not detectable or is present in samples obtained from normal controls. A "quantitative" change in the levels of one or more proteins of the profile refers to a measurable increase or decrease in the protein levels when compared to a healthy control.

A "healthy control" or "normal control" is a biological sample taken from an individual who does not suffer from an infectious disorder. A "negative control," is a sample that lacks any of the specific analyte the assay is designed to detect and thus provides a reference baseline for the assay.

It is understood that aspects and embodiments of the invention described herein include "consisting" and/or "consisting essentially of" aspects and embodiments.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Other objects, advantages and features of the present invention will become apparent from the following specification taken in conjunction with the accompanying drawings.

B. Infectious Organisms and Diseases

As discussed above, the present invention is concerned with compositions and methods for detecting infectious organisms including heartworm, *E. Canis, A. phagocytophilum*, and *B. burgdorferi*. The diseases caused by these organisms include, but are not limited to, a heartworm disease, ehrlichiosis, granulocytic anaplasmosis, and Lyme disease. These infectious organisms may cause diseases in mammalian subjects such as dogs, cats, horses, humans, etc.

C. Polypeptides, Antibodies and Antigenic Compositions

In one aspect, provided herein are polypeptides, antibodies and antigenic compositions for detecting infectious organisms including heartworm, *E. Canis, A. phagocytophilum*, and *B. burgdorferi* in a subject. An antigenic composition may comprise a combination of antibodies and antigenic polypeptides that are specific for one or several infectious organisms.

Therefore, provided herein is an *A. phagocytophilum* p44 polypeptide comprising amino acids 222-236 of SEQ ID NO:1, wherein said polypeptide comprises at least one mutation. Additionally, provided herein is an *A. phagocytophilum* p44 polypeptide that exhibits at least 70%, 75%, 80%, 85%, 90%, 95%, or 99% identity to the amino acid sequence of SEQ ID NO:1, wherein said polypeptide is not a wild-type P44 protein, and wherein said polypeptide binds to an antibody that is specific for a wild-type P44 protein. In some embodiments, the polypeptide may further comprise a second polypeptide comprising amino acids 237-247 of SEQ ID NO:1. Also provided herein is an *A. phagocytophilum* p44 polypeptide comprising amino acids 222-237, 222-238, 222-239, 222-240, 222-241, 222-242, 222-243, 222-244, 222-245, 222-246, or 222-247 of SEQ ID NO:1 or an *A. phagocytophilum* p44 polypeptide comprising amino acids 222-237, 222-238, 222-239, 222-240, 222-241, 222-242, 222-243, 222-244, 222-245, 222-246, or 222-247 of SEQ ID NO:1 that comprises at least one mutation. Additionally, provided herein is an *A. phagocytophilum* p44 polypeptide that exhibits at least 70%, 75%, 80%, 85%, 90%, 95%, 99%, or 100% identity to amino acids 222-237, 222-238, 222-239, 222-240, 222-241, 222-242, 222-243, 222-244, 222-245, 222-246, or 222-247 of SEQ ID NO:1, wherein said polypeptide is not a wild-type P44 protein, and wherein said polypeptide binds to an antibody that is specific for a wild-type P44 protein. In some embodiments, the polypeptide may comprise the amino acid sequence selected from the group consisting of SEQ ID NOs:3-6, the amino acids 222-237, 222-238, 222-239, 222-240, 222-241, 222-242, 222-243, 222-244, 222-245, 222-246, or 222-247 of SEQ ID NO:1, or a multimer, a combination, or a chimera of the polypeptides. In some embodiments, the polypeptide may further comprise a tag sequence. In some embodiments, the polypeptide may further comprise an amino acid linker between the polypeptides. In one embodiment, the polypeptide may comprise the amino acid sequence of SEQ ID NO:7, which may further comprise a tag sequence.

In addition, provided herein is an antigenic composition comprising at least two *B. burgdorferi* polypeptides, wherein each of said polypeptides may comprise an amino acid sequence selected from the group consisting of: a) an OspA polypeptide, b) an OspC polypeptide, c) an OspF polypeptide, d) a p39 polypeptide, and e) a fusion peptide of p41 and VLsE, wherein said antigenic composition does not consist of a) and b). In some embodiments, the antigenic composition may comprise at least 3, 4, or all 5 of said *B. burgdorferi* polypeptides. In some embodiments, the OspA polypeptide may be a multimer of a partial or full-length sequence, which may have a molecular weight of about 85 kDa. In some embodiments, the OspA polypeptide may comprise a sequence tag, e.g., a His tag. In some embodiments, the OspA polypeptide may be commercially available, e.g., OspA from Meridian Life Science, Inc. (Catalog #: R8A131), which contains multiple copies of the *B. burgdorferi* OspA sequence and a 6-HIS epitope tag. In some embodiments, the OspC polypeptide may comprise the polypeptide having the amino acid sequence of SEQ ID NO:15 encoded by the polynucleotide which is not a wild-type OspC polynucleotide. In some embodiments, the OspF polypeptide may comprise the polypeptide having the amino acid sequence of SEQ ID NO:18 encoded by the polynucleotide which is not a wild-type OspF polynucleotide. In some embodiments, the p39 polypeptide may comprise the polypeptide having the amino acid sequence of SEQ ID NO:21 encoded by the polynucleotide which is not a wild-type p39 polynucleotide. In some embodiments, the fusion peptide of p41 and VLsE may comprise an amino acid sequence of SEQ ID NO:24. In some embodiments, the polypeptides may form a fusion molecule.

In some embodiments, the at least 3, 4, or all 5 of said *B. burgdorferi* polypeptides form a fusion molecule. The fusion molecule, which may be a fusion protein, may include linkers that separate the individual polypeptides. One or multiple copies of each polypeptide may exist in the fusion molecule, and may exist in any order.

The polypeptide may include the addition of an antibody epitope or other tag, to facilitate identification, targeting, and/or purification of the polypeptide. The use of 6×His and GST (glutathione S transferase) as tags is well known. Inclusion of a cleavage site at or near the fusion junction will facilitate removal of the extraneous polypeptide after purification. Other amino acid sequences that may be included in the polypeptide include functional domains, such as active sites from enzymes such as a hydrolase, glycosylation domains, cellular targeting signals or transmembrane regions. The polypeptide may further include one or more additional tissue-targeting moieties.

Epitope tags are well known to those of skill in the art. Moreover, antibodies specific to a wide variety of epitope tags are commercially available. These include but are not limited to antibodies against the DYKDDDDK epitope, c-myc antibodies (available from Sigma, St. Louis), the HNK-1 carbohydrate epitope, the HA epitope, the HSV epitope, the $His_4$, $His_5$, and $His_6$ epitopes that are recognized by the His epitope specific antibodies (see, e.g., Qiagen), and the like. In addition, vectors for epitope tagging proteins are commercially available. A polypeptide can be tagged with the FLAG® epitope (DYKDDDDK epitope) (N-terminal, C-terminal or internal tagging), the c-myc epitope (C-terminal) or both the FLAG (DYKDDDDK epitope) (N-terminal) and c-myc (C-terminal) epitopes.

In some embodiments, the *A. phagocytophilum* p44 polypeptide, the *B. burgdorferi* polypeptides, or the fusion protein, may contain a tag sequence, either at the N-terminus, or C-terminus, or both. Tag sequences that may be used are set forth in SEQ ID NO:29 and SEQ ID NO:31.

Polypeptides may possess deletions and/or substitutions of amino acids relative to the native sequence. Sequences with amino acid substitutions are contemplated, as are sequences with a deletion, and sequences with a deletion and a substitution. In some embodiments, these polypeptides may further include insertions or added amino acids.

Substitutional or replacement variants typically contain the exchange of one amino acid for another at one or more sites within the protein and may be designed to modulate one or more properties of the polypeptide, particularly to increase its efficacy or specificity. Substitutions of this kind may or may not be conservative substitutions. Conservative substitution is when one amino acid is replaced with one of similar shape and charge. However, if used, conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Changes other than those discussed above are generally considered not to be conservative substitutions. It is specifically contemplated that one or more of the conservative substitutions above may be included as embodiments. In other embodiments, such substitutions are specifically excluded. Furthermore, in additional embodiments, substitutions that are not conservative are employed in variants.

In addition to a deletion or substitution, the polypeptides may possess an insertion of one or more residues.

The variant amino acid sequence may be structurally equivalent to the native counterparts. For example, the variant amino acid sequence forms the appropriate structure and conformation for binding targets, proteins, or peptide segments.

The following is a discussion based upon changing of the amino acids of a polypeptide to create a mutant molecule. For example, certain amino acids may be substituted for other amino acids in a polypeptide without appreciable loss of function, such as ability to interact with an antibody or a target peptide sequence. Since it is the interactive capacity and nature of a polypeptide that defines that polypeptide's functional activity, certain amino acid substitutions can be made in a polypeptide sequence and nevertheless produce a polypeptide with like properties.

In making such changes, the hydropathic index of amino acids may be considered. The importance of the hydropathic amino acid index in conferring interactive function on a protein is generally understood in the art. See Kyte and Doolittle (1982) *J. Mol. Biol.* 157:105-132. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (0.5); histidine (−0.5); cysteine (−1.0); methionine (−1.3); valine (−1.5); leucine (−1.8); isoleucine (−1.8); tyrosine (2.3); phenylalanine (−2.5); tryptophan (−3.4).

It is understood that an amino acid can be substituted for another having a similar hydrophilicity value and still produce a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. However, in some aspects a non-conservative substitution is contemplated. In certain aspects a random substitution is also contemplated. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

In some embodiments, the *A. phagocytophilum* p44 polypeptide may comprise 1 to 10, preferably 3-7, mutations. In some embodiments, the mutations may be selected from the group consisting of a substitution, an insertion and a deletion. Some of the exemplary mutations are: Gly222(Del), His223→Asn, Ser224→Thr, Ser225→Thr, Val227→Ala, Thr228→Ser, Gln229→Asn, Leu233→Val, Leu233→Thr, Phe234→Leu, Ser235→Thr, and Thr236→Ser. In some embodiments, the polypeptide may comprise at least 1, 2, 3, 4, 5, 10 or 12 of the exemplary mutations.

In some embodiments, the second *A. phagocytophilum* p44 polypeptide may comprise at least 1, or 1 to 5, preferably 2 to 3, mutations. Some of the exemplary mutations are: Thr240→Ser, Gln229→Asn, Ile243→Val, Glu245→Asp, Glu245→Asn, Asp246→Lys, and Asp246→Glu. In some embodiments, the polypeptide may comprise at least 1, 2, 3, 4, 5 or 7 of the exemplary mutations.

Further provided herein is a composition for detecting multiple disease antigens and/or antibodies, which composition comprises at least two, preferably three of the following reagents: a) an antibody against a *Dirofilaria immitis* antigen, b) an *E. Canis* gp36 polypeptide, c) an *A. phagocytophilum* p44 polypeptide, and d) an antigenic composition comprising a *B. burgdorferi* polypeptide selected from the group consisting of OspA, OspC, OspF, p39 and a fusion peptide of p41 and VLsE. In some embodiments, the composition may comprise all four of the reagents. In some embodiments, the reagent a) may be a chicken polyclonal antibody. In some embodiments, the chicken polyclonal antibody may be produced by immunizing chickens with a canine heartworm antigen. In some embodiments, the chicken polyclonal antibody may be a type IgY antibody, e.g., IgY antibody isolated from chicken egg yolk or serum. In some embodiments, the reagent b) may comprise a polypeptide having an amino acid sequence of SEQ ID NO:26, which may further comprise a tag sequence. In some embodiments, the reagent c) may comprise an *A. phagocytophilum* p44 polypeptide comprising amino acids 222-236 of SEQ ID NO:1, wherein said polypeptide comprises at least one mutation. In some embodiments, the reagent d) may comprise an antigenic composition comprising at least two *B. burgdorferi* polypeptides, wherein each of said polypeptides comprises an amino acid sequence selected from the group consisting of: a) an OspA polypeptide, b) an OspC polypeptide, c) an OspF polypeptide, d) a p39 polypeptide, and e) a fusion peptide of p41 and VLsE.

D. Polynucleotides, Vectors, Methods of Production

In another aspect, provided herein are polynucleotides, vectors and methods for the production of the polypeptides disclosed above, including the *A. phagocytophilum* P44 polypeptide. Polypeptides, vectors and methods for the production of the *B. burgdorferi* OspC, OspF and p39 polypeptides are also provided.

Therefore, provided herein is a polynucleotide which encodes the *A. phagocytophilum* p44 polypeptide disclosed above, or a complimentary strand thereof. In some embodiments, the polynucleotide may be DNA or RNA. In some embodiments, the polynucleotide may be codon-optimized for expression in a non-human organism. An exemplary codon-optimized polynucleotide that encodes an *A. phagocytophilum* p44 polypeptide comprising amino acids 222-247 of SEQ ID NO:1 comprises the sequence GGTCACTCCAGCG-GCGTTACCCAGAATCCGAAACTGTTCAGTAC-CTTTGTTGATACCGT TAAAATCGCAGAAGA-TAAA (SEQ ID NO:33). In some embodiments, the organism may be a virus, a bacterium, a yeast cell, an insect cell, or a mammalian cell. In one embodiment, the polynucleotide may comprise the nucleotide sequence of SEQ ID NO:8.

Further provided herein is polynucleotide which encodes an *A. phagocytophilum* p44 polypeptide having the amino acid sequence of SEQ ID NO:1, or a complimentary strand thereof, wherein said polynucleotide is not a wild-type P44 polynucleotide. In some embodiments, the polynucleotide may exhibit at least 70%, 75%, 80%, 85%, 90%, 95%, 99%, or 100% identity to the nucleotide sequence of SEQ ID NO:2. In some embodiments, the polynucleotide may hybridize to the nucleotide sequence of SEQ ID NO:2 under moderately or highly stringent conditions. Further provided herein is polynucleotide which encodes an *A. phagocytophilum* p44 polypeptide having the amino acid sequence of 222-237, 222-238, 222-239, 222-240, 222-241, 222-242, 222-243, 222-244, 222-245, 222-246, or 222-247 of SEQ ID NO:1, or a complimentary strand thereof. In some embodiments, said polynucleotide is not a wild-type P44 polynucleotide. In some embodiments, the polynucleotide may exhibit at least 70%, 75%, 80%, 85%, 90%, 95%, 99%, or 100% identity to the nucleotide sequence of SEQ ID NO:33 or SEQ ID NO:36. In some embodiments, the polynucleotide may hybridize to the nucleotide sequence of SEQ ID NO:33 or SEQ ID NO:36, under moderately or highly stringent conditions.

Further provided herein is a polynucleotide which encodes a *B. burgdorferi* OspC polypeptide having the amino acid sequence of SEQ ID NO:15, or a complimentary strand thereof, wherein said polynucleotide is not a wild-type OspC polynucleotide. In some embodiments, the polynucleotide may exhibit at least 70%, 75%, 80%, 90%, 95% or 99% identity to the nucleotide sequence of SEQ ID NO:16. In some embodiments, the polynucleotide may hybridize to the nucleotide sequence of SEQ ID NO:16 under moderately or highly stringent conditions. In some embodiments, the polynucleotide may be codon-optimized for expression in a non-human organism. In some embodiments, the organism may be selected from the group consisting of a virus, a bacterium, a yeast cell, an insect cell and a mammalian cell. In some embodiments, the polynucleotide may be DNA or RNA. In some embodiments, the polynucleotide may comprise the nucleotide sequence of SEQ ID NO:17.

Further provided herein is a polynucleotide which encodes a *B. burgdorferi* OspF polypeptide having the amino acid sequence of SEQ ID NO:18, or a complimentary strand thereof, wherein said polynucleotide is not a wild-type OspF polynucleotide. In some embodiments, the polynucleotide may exhibit at least 70%, 75%, 80%, 90%, 95% or 99% identity to the nucleotide sequence of SEQ ID NO:19. In some embodiments, the polynucleotide may hybridize to the nucleotide sequence of SEQ ID NO:19 under moderately or highly stringent conditions. In some embodiments, the polynucleotide is codon-optimized for expression in a non-human organism. In some embodiments, the organism may be selected from the group consisting of a virus, a bacterium, a yeast cell, an insect cell and a mammalian cell. In some embodiments, the polynucleotide may be DNA or RNA. In some embodiments, the polynucleotide may comprise the nucleotide sequence of SEQ ID NO:20.

Further provided herein is a polynucleotide which encodes a *B. burgdorferi* p39 polypeptide having the amino acid sequence of SEQ ID NO:21, or a complimentary strand thereof, wherein said polynucleotide is not a wild-type p39 polynucleotide. In some embodiments, the polynucleotide may exhibit at least 70%, 75%, 80%, 90%, 95% or 99% identity to the nucleotide sequence of SEQ ID NO:22. In some embodiments, the polynucleotide may hybridize to the nucleotide sequence of SEQ ID NO:22 under moderately or highly stringent conditions. In some embodiments, the polynucleotide may be codon-optimized for expression in a non-human organism. In some embodiments, the organism may be selected from the group consisting of a virus, a bacterium, a yeast cell, an insect cell and a mammalian cell. In some embodiments, the polynucleotide may be DNA or RNA. In some embodiments, the polynucleotide may comprise the nucleotide sequence of SEQ ID NO:23.

Further provided herein is a vector comprising the *A. phagocytophilum* p44 polynucleotide or the *B. burgdorferi* OspC, OspF and p39 polynucleotide disclosed above. In some embodiments, the vector may comprise a promoter sequence. In some embodiments, the vector may comprise a poly-A sequence. In some embodiments, the vector may comprise a translation termination sequence. In some embodiments, the vector may further encode a tag sequence.

Further provided herein is a non-human organism transformed with the vector comprising the *A. phagocytophilum* p44 polynucleotide or the *B. burgdorferi* OspC, OspF and p39 polynucleotide disclosed above. In some embodiments, the organism may be a virus, a bacterium, a yeast cell, an insect cell, or a mammalian cell. In some embodiments, the organism may be used in a method for recombinantly making an *A. phagocytophilum* p44 or *B. burgdorferi* OspC, OspF and p39 polypeptide, which method may comprise culturing the organism, and recovering said polypeptide from said organism. In some embodiments, the method may further comprise isolating the P44, OspC, OspF and p39 polypeptide, optionally by chromatography. Additionally, provided herein is an *A. phagocytophilum* p44 or a *B. burgdorferi* OspC, OspF and p39 polypeptide produced by the method disclosed above. In some embodiments, the polypeptide may comprise a native glycosylation pattern and/or a native phosphorylation pattern.

An expression vector comprising cDNA encoding a polypeptide or a target molecule is introduced into *Escherichia coli*, yeast, an insect cell, an animal cell or the like for expression to obtain the polypeptide. Polypeptides used in the present invention can be produced, for example, by expressing a DNA encoding it in a host cell using a method described in Molecular Cloning, A Laboratory Manual, Second Edition, Cold Spring Harbor Laboratory Press (1989), Current Protocols in Molecular Biology, John Wiley & Sons (1987-1997) or the like. A recombinant vector is produced by inserting a cDNA downstream of a promoter in an appropriate expression vector. The vector is then introduced into a host cell suitable for the expression vector. The host cell can be any cell so long as it can express the gene of interest, and includes bacteria (e.g., *Escherichia coli*), an animal cell and the like. Expression vector can replicate autonomously in the host cell to be used or vectors which can be integrated into a chromosome comprising an appropriate promoter at such a position that the DNA encoding the polypeptide can be transcribed.

Silent modifications can be made to the nucleic acids that do not alter, substitute or delete the respective amino acid in the recombinant protein. Such modification may be necessary to optimize, for example, the codon usage for a specific recombinant host. The nucleotide sequences can be modified to replace codons that are considered rare or have a low frequency of appropriate t-RNA molecules to a more suitable codon appropriate for the expression host. Such codon tables are known to exist and are readily available to one skilled in the art. In addition, silent modification can be made to the nucleic acid that minimizes secondary structure loops at the level of mRNA that may be deleterious to recombinant protein expression.

E. Methods of Detection

In a further aspect, the polypeptides, antibodies and antigenic compositions disclosed above may be used for detecting various infectious organisms including heartworm, *E. Canis, A. phagocytophilum*, and *B. burgdorferi* in a subject. In some embodiments, the method may be used for diagnosis, prognosis, stratification, risk assessment, or treatment monitoring of a disease.

Therefore, provided herein is a method for detecting an antibody that specifically binds to an *A. phagocytophilum* p44 polypeptide in a sample, which method comprises contacting the P44 polypeptide disclosed above with said sample and detecting a polypeptide-antibody complex formed. In some embodiments, the disease may be granulocytic anaplasmosis.

Further provided herein is a method for detecting an antibody that specifically binds to a *B. burgdorferi* antigen in a sample, which method comprises contacting a *B. burgdorferi* polypeptide selected from the group consisting of OspC, OspF and p39 disclosed above with said sample and detecting a polypeptide-antibody complex formed.

Also provided herein is a method for detecting an antibody that specifically binds to a *B. burgdorferi* antigen in a sample, which method comprises contacting an antigenic composition comprising at least two *B. burgdorferi* polypeptides, wherein each of said polypeptides may comprise an amino acid sequence selected from the group consisting of OspA, OspC, OspF, p39 polypeptide and a fusion peptide of p41 and VLsE disclosed above with said sample and detecting a polypeptide-antibody complex formed. A combination of 2, 3, 4, or 5 polypeptides may be used.

In some embodiments, the method may be used to detect Lyme disease. In addition, the method may be used to distinguish between infection by a Lyme disease pathogen and exposure to a Lyme disease vaccine. Several commercially available Lyme disease vaccines, such as NOBIVAC™ Lyme (a vaccine comprises a bacterin that contains two inactivated strains of *Borrelia burgdorferi* comprised of outer surface protein A (OspA) and outer surface protein C (OspC)) (Intervet/Schering-Plough Animal Health, Summit, N.J.), LYMEVAX® (a killed virus vaccine for protection against *Borrelia burgdorferi* or Lyme disease) (Fort Dodge Animal Health, New York, N.Y.), and RECOMBITEK® Lyme (a recombinant OspA vaccine) (Merial Ltd., Duluth, Ga.), provide protection mainly by inducing the production of anti-OspA antibodies. See LaFleur et al. (2009) *Clin. Vacc. Immunol.* 16:253-259; LaFleur et al. (2010) *Clin. Vacc. Immunol.* 17:870-874. Therefore, detection of anti-OspA antibodies but not antibodies to other *B. burgdorferi* polypeptides may indicate that the subject has been vaccinated, while on the other hand, detection of antibodies to other polypeptides in addition to OspA may indicate that the subject has been exposed to a *B. burgdorferi* antigen naturally. Further, the method may be used to distinguish between exposure to a NOBIVAC™ Lyme (a vaccine comprises a bacterin that contains two inactivated strains of *Borrelia burgdorferi* comprised of outer surface protein A (OspA) and outer surface protein C (OspC)) vaccine and exposure to another vaccine, because the NOBIVAC™ Lyme (a vaccine comprises a bacterin that contains two inactivated strains of *Borrelia burgdorferi* comprised of outer surface protein A (OspA) and outer surface protein C (OspC)) vaccine induces both anti-OspA and OspC antibodies. See LaFleur et al. (2009) *Clin. Vacc. Immunol.* 16:253-259. Therefore, detection of both anti-OspA and anti-OspC antibodies but not antibodies to other *B. burgdorferi* polypeptides may indicate that the subject has been vaccinated with a NOBIVAC™ Lyme (a vaccine comprises a bacterin that contains two inactivated strains of *Borrelia burgdorferi* comprised of outer surface protein A (OspA) and outer surface protein C (OspC)) vaccine.

Therefore, the method can be used for classification of Lyme exposure of a mammal, e.g., an animal by calculating levels of antibodies that specifically bind to an OspA, OspC, OspF, p39 polypeptide and/or a fusion peptide of p41 and VLsE using a method for detecting an antibody that specifically binds to a *B. burgdorferi* antigen in a sample disclosed herein; calculating reference values of the levels of the antibodies; and determining the type of *Borrelia burgdorferi* infection of the mammal by comparing the levels of the antibodies to the reference values. The reference values may be calculated using levels of detectable signals of negative controls, and more than one reference values may be calculated for each antibody that specifically binds to a Lyme polypeptide.

The reference values may be established by analyzing results from experimental samples from animals that are infected with or vaccinated against *B. burgdorferi*. Empirical values may be calculated from the analysis of experimental samples, and used for the calculation of reference values for the antibodies. Initially, artificial values may be set for each reference value and adjusted by an algorithm using experimental data. A minimal value for each reference value may also be established from the analysis of experimental samples and in cases where the reference value calculated is less than the minimal value, the minimal value may be used.

In some embodiments, the reference values for the antibody that specifically binds to OspA may be alpLow, alpMid, alpHigh and/or alpHighest, wherein alpMid may be from about 150% to about 250% of alpLow, alpHigh may be from about 300% to about 400% of alpLow, and/or alpHighest may be from about 500% to about 1,000% of alpLow. In some embodiments, the reference values for the antibody that specifically binds to OspC may be ospcLow and/or ospcHigh; wherein ospcHigh may be from about 150% to about 500% of ospcLow. In some embodiments, the reference values for the antibody that specifically binds to OspF may be ospfLow and/or ospfHigh; wherein ospfHigh may be from about 150% to about 300% of ospfLow. In some embodiments, the reference value for the antibody that specifically binds to p39 may be p39Low. In some embodiments, the reference values for the antibody that specifically binds to the fusion peptide of p41 and VLsE may be slpLow, slpMid and/or slpHigh, wherein slpMid may be from about 150% to about 200% of slpLow, and/or slpHigh may be from about 300% to about 500% of slpLow. The level of antibody that specifically binds to the *Anaplasma phagocytophilum* P44 polypeptide may be used for detection of ticks in animals being tested. In some embodiments, the P44 polypeptide may comprise the amino acid sequence of SEQ ID NO:7. In some embodiments, the reference value for the antibody that specifically binds to the amino acid sequence of SEQ ID NO:7 may be sub5Low.

In calculating the reference values for the antibodies to the various Lyme polypeptides, results from negative controls may be used in the calculation. In some embodiments, at least 1, 2, 3, 4, 5, 6, 7, 8, 9, 10 or more negative controls may be included in an assay.

In some embodiments, the mammal may be classified as Lyme exposure (LE) if: a) the level of antibody that specifically binds to OspA is lower than alpHigh, and the level of antibody that specifically binds to OspF is greater than or equal to ospfHigh; b) the level of antibody that specifically binds to OspA is greater than or equal to alpLow and lower than alpMid, the level of antibody that specifically binds to OspF is lower than ospfHigh, the level of antibody that specifically binds to the fusion peptide of p41 and VLsE is greater than or equal to slpLow or the level of antibody that specifically binds to OspC is greater than or equal to ospcLow, and the level of antibody that specifically binds to the amino acid sequence of SEQ ID NO:7 is greater than or equal to sub5Low or the level of antibody that specifically binds to OspF is greater than or equal to ospfLow; c) the level of antibody that specifically binds to OspA is lower than alpLow, the level of antibody that specifically binds to OspC is lower than ospcLow, the level of antibody that specifically binds to OspF is lower than ospfHigh, the level of antibody that specifically binds to the fusion peptide of p41 and VLsE is greater than or equal to slpLow and lower than slpMid, and the level of antibody that specifically binds to the amino acid sequence of SEQ ID NO:7 is greater than or equal to sub5Low or the level of antibody that specifically binds to OspF is greater than or equal to ospfLow; d) the level of antibody that specifically binds to OspA is greater than or equal to alpLow and lower than alpMid, the level of antibody that specifically binds to OspC is greater than or equal to ospcLow, the level of antibody that specifically binds to p39 is greater than or equal to p39Low, the level of antibody that specifically binds to the fusion peptide of p41 and VLsE is greater than or equal to slpLow, the level of antibody that specifically binds to OspF is lower than ospfLow, and the level of antibody that specifically binds to the amino acid sequence of SEQ ID NO:7 is lower than sub5Low; or e) the level of antibody that specifically binds to OspA is lower than alpLow, the level of antibody that specifically binds to OspF is lower than ospfHigh, and the level of antibody that specifically binds to OspC is greater than or equal to ospcLow or the level of antibody that specifically binds to the fusion peptide of p41 and VLsE is greater than or equal to slpMid. In some embodiments, the mammal classified as Lyme exposure may be further classified as Lyme exposure early (LEE) if the level of antibody that specifically binds to OspF is lower than ospfHigh; otherwise Lyme exposure late (LEL).

In some embodiments, the mammal may be classified as Lyme exposure and vaccine (LEV) if: a) the level of antibody that specifically binds to OspA is greater than or equal to alpHigh, and the level of antibody that specifically binds to OspF is greater than or equal to ospfHigh; b) the level of antibody that specifically binds to OspA is greater than or equal to alpMid and lower than alpHighest, the level of antibody that specifically binds to the amino acid sequence of SEQ ID NO:7 is greater than or equal to sub5Low, the level of antibody that specifically binds to OspF is lower than ospfHigh, and the level of antibody that specifically binds to the fusion peptide of p41 and VLsE is greater than or equal to slpLow or the level of antibody that specifically binds to OspC is greater than or equal to ospcLow; c) the level of antibody that specifically binds to OspA is greater than or equal to alpMid and lower than alpHighest, the level of antibody that specifically binds to OspC is greater than or equal to ospcHigh, the level of antibody that specifically binds to the fusion peptide of p41 and VLsE is greater than or equal to slpHigh, the level of antibody that specifically binds to OspF is lower than ospfHigh, and the level of antibody that specifically binds to the amino acid sequence of SEQ ID NO:7 is lower than sub5Low; or d) the level of antibody that specifically binds to OspA is greater than or equal to alpHighest, the level of antibody that specifically binds to OspF is greater than or equal to ospfLow and lower than ospfHigh, the level of antibody that specifically binds to OspC is greater than or equal to ospcLow, the level of antibody that specifically binds to the fusion peptide of p41 and VLsE is greater than or equal to slpLow, and the level of antibody that specifically binds to the amino acid sequence of SEQ ID NO:7 is greater than or equal to sub5Low. In some embodiments, the mammal classified as Lyme exposure and vaccine may be further classified as Lyme exposure and vaccine early (LEEV) if the level of antibody that specifically binds to OspF is lower than ospfHigh; otherwise Lyme exposure and vaccine late (LELV).

In some embodiments, the mammal may be classified as Lyme vaccine (LVR) if: a) the level of antibody that specifically binds to OspA is greater than or equal to alpHighest, and the level of antibody that specifically binds to OspF is lower than ospfLow; b) the level of antibody that specifically binds to OspA is greater than or equal to alpHighest, the level of antibody that specifically binds to OspF is greater than or equal to ospfLow and lower than ospfHigh, the level of antibody that specifically binds to OspC is lower than ospcLow or the level of antibody that specifically binds to the fusion peptide of p41 and VLsE is lower than slpLow but not both, and the level of antibody that specifically binds to the amino acid sequence of SEQ ID NO:7 is lower than sub5Low; c) the level of antibody that specifically binds to OspA is greater than or equal to alpHighest, the level of antibody that specifically binds to OspF is greater than or equal to ospfLow and lower than ospfHigh, the level of antibody that specifically binds to OspC is lower than ospcLow, and the level of antibody that specifically binds to the fusion peptide of p41 and VLsE is lower than slpLow; d) the level of antibody that specifically binds to OspA is greater than or equal to alpMid and lower than alpHighest, the level of antibody that specifically binds to OspF is greater than or equal to ospfLow and lower than ospfHigh, the level of antibody that specifically binds to the amino acid sequence of SEQ ID NO:7 is lower than sub5Low, the level of antibody that specifically binds to the fusion peptide of p41 and VLsE is lower than slpHigh, the level of antibody that specifically binds to OspC is lower than ospcHigh, and the level of antibody that specifically binds to OspC is greater than or equal to ospcLow or the level of antibody that specifically binds to the fusion peptide of p41 and VLsE is greater than or equal to slpLow; e) the level of antibody that specifically binds to OspA is greater than or equal to alpMid and lower than alpHighest, the level of antibody that specifically binds to OspF is lower than ospfLow, the level of antibody that specifically binds to the amino acid sequence of SEQ ID NO:7 is lower than sub5Low, and the level of antibody that specifically binds to the fusion peptide of p41 and VLsE is lower than slpHigh or the level of antibody that specifically binds to OspC is lower than ospcHigh; or f) the level of antibody that specifically binds to OspA is greater than or equal to alpMid and lower than alpHighest, the level of antibody that specifically binds to OspF is lower than ospfHigh, the level of antibody that specifically binds to OspC is lower than ospcLow, the level of antibody that specifically binds to the fusion peptide of p41 and VLsE is lower than slpLow, and the level of antibody that specifically binds to OspF is greater than or equal to ospfLow or the level of antibody that specifically binds to the amino acid sequence of SEQ ID NO:7 is greater than or equal to sub5Low.

In some embodiments, the mammal may be classified as indeterminative (IND) if: a) the level of antibody that specifically binds to OspA is greater than or equal to alpMid and lower than alpHighest, the level of antibody that specifically binds to OspF is greater than or equal to ospfLow and lower than ospfHigh, the level of antibody that specifically binds to the amino acid sequence of SEQ ID NO:7 is lower than sub5Low, and the level of antibody that specifically binds to the fusion peptide of p41 and VLsE is lower than slpHigh or the level of antibody that specifically binds to OspC is lower than ospcHigh but not both; b) the level of antibody that specifically binds to OspA is greater than or equal to alpHighest, the level of antibody that specifically binds to OspF is greater than or equal to ospfLow and lower than ospfHigh, the level of antibody that specifically binds to OspC is lower than ospcLow or the level of antibody that specifically binds to the fusion peptide of p41 and VLsE is lower than slpLow but not both, and the level of antibody that specifically binds to the amino acid sequence of SEQ ID NO:7 is greater than or equal to sub5Low; c) the level of antibody that specifically binds to OspA is greater than or equal to alpHighest, the level of antibody that specifically binds to OspF is greater than or equal to ospfLow and lower than ospfHigh, the level of antibody that specifically binds to OspC is greater than or equal to ospcLow, the level of antibody that specifically binds to the fusion peptide of p41 and VLsE is greater than or equal to slpLow, and the level of antibody that specifically binds to the amino acid sequence of SEQ ID NO:7 is lower than sub5Low; d) the level of antibody that specifically binds to OspA is greater than or equal to alpLow and lower than alpMid, the level of antibody that specifically binds to OspF is Lower than ospfLow, the level of antibody that specifically binds to OspC is greater than or equal to ospcLow, the level of antibody that specifically binds to the fusion peptide of p41 and VLsE is greater than or equal to slpLow, the level of antibody that specifically binds to the amino acid sequence of SEQ ID NO:7 is lower than sub5Low, and the level of antibody that specifically binds to p39 is lower than p39Low; or e) the level of antibody that specifically binds to OspA is greater than or equal to alpLow and lower than alpMid, the level of antibody that specifically binds to OspF is Lower than ospfLow, the level of antibody that specifically binds to OspC is greater than or equal to ospcLow or the level of antibody that specifically binds to the fusion peptide of p41 and VLsE is greater than or equal to slpLow, and the level of antibody that specifically binds to the amino acid sequence of SEQ ID NO:7 is lower than sub5Low. In some embodiments, the mammal classified as indeterminative may be further classified as possible exposure (PE) if the level of antibody that specifically binds to OspA is lower than alpMid; otherwise Lyme vaccine possible exposure (LVPE).

The following is an exemplary protocol for classifying Lyme exposure in a mammal, e.g., an animal by comparing the levels of various antibodies to the reference values:

For all LE Rules: If ospf<ospfHigh it is LEE, else it is LEL.

LE: alp<alphigh, Ospf>=ospfHigh

LE: alpLow<=alp<alpMid, ospf<ospfHigh, (slpResult>=slpLow OR ospc>=ospcLow), (sub5>=sub5Low OR ospf>=ospfLow)

LE: alp<alpLow, ospc<ospcLow, ospf<ospfHigh, slpLow<=slp<slpMid, (sub5>=sub5Low OR ospf>=ospfLow)

LE: alpLow<=alp<alpMid, ospc>=ospcLow, p39>=p39Low, slp>=slpLow, ospf<ospfLow, sub5<sub5Low LE: alp<alpLow, ospf<ospfHigh, (ospc>=ospcLow OR slp>=slpMid)

For all LEV rules: if ospf<ospfHigh it is LEEV, else it is LELV

LEV: alp>=alpHigh, ospf>=ospfHigh

LEV: alpMid<=alp<alpHighest, sub5>=sub5Low, ospf<ospfHigh, (slp>=slpLow OR ospc>=ospcLow)

LEV: alpMid<=alp<alpHighest, ospc>=ospcHigh, slp>=slpHigh, ospf<ospfHigh, sub5Result<sub5Low LEV: alp>=alpHighest, ospfLow<=ospf<ospfHigh, ospc>=ospcLow, slp>=slpLow, sub5>=sub5Low LVR: alp>=alpHighest, ospf<ospfLow LVR: alp>=alpHighest, ospfLow<=ospf<ospfHigh, (ospc<ospcLow XOR slp<slpLow), sub5<sub5Low LVR: alp>=alpHighest, ospfLow<=ospf<ospfHigh, ospc<ospcLow, slp<slpLow LVR: alpMid<=alp<alpHighest, ospfLow<=ospf<ospfHigh, sub5<sub5Low, slp<slpHigh, ospc<ospcHigh, (ospc>=ospcLow OR slp>=slpLow)

LVR: alpMid<=alp<alpHighest, ospf<ospfLow, sub5<sub5Low, (slp<slpHigh OR ospc<ospcHigh)

LVR: alpMid<=alp<alpHighest, ospf<ospfHigh, ospc<ospcLow, slp<slpLow, (ospf>=ospfLow OR sub5>=sub5Low)

For all IND rules: if alp<alpMid it is PE, else it is LVPE

IND: alpMid<=alp<alpHighest, ospfLow<=ospf<ospfHigh, sub5Result<sub5Low, (slp<slpHigh XOR opsc<ospcHigh)

IND: alp>=alpHighest, ospfLow<=ospf<ospfHigh, (ospc<ospcLow XOR slp<slpLow), sub5>=sub5Low IND: alp>=alpHighest, ospfLow<=ospf<ospfHigh, ospc>=ospcLow, slp>=slpLow, sub5<sub5Low IND: alpLow<=alp<alpMid, ospf<ospfLow, ospc>=ospcLow, slp>=slpLow, sub5<sub5Low, p39<p39Low IND: alpLow<=alp<alpMid, ospf<ospfLow, (ospc>=ospcLow XOR slp>=slpLow), sub5<sub5Low Keys:

alp level of antibody that specifically binds to OspA ospc level of antibody that specifically binds to OspC ospf level of antibody that specifically binds to OspF p39 level of antibody that specifically binds to p39 slp level of antibody that specifically binds to the fusion peptide of p41 and VLsE sub5 level of antibody that specifically binds to the multimeric mutant peptide of P44

LEE Lyme exposure early

LEL Lyme exposure late

LVR Lyme vaccine

LELV Lyme exposure late & vaccine

LEEV Lyme exposure early & vaccine

LVRN Lyme vaccine Nobivac™

IND indeterminative

PE possible Lyme exposure

LVPE Lyme vaccine and possible Lyme exposure

XOR one or the other, but not both

Further provided herein is a method for detecting multiple disease antigens and/or antibodies in a sample, which method comprises: a) contacting said sample with a composition for detecting multiple disease antigens and/or antibodies, which composition may comprise at least two, preferably three of the following reagents: an antibody against a *Dirofilaria immitis* antigen, an *E. Canis* gp36 polypeptide, an *A. phagocytophilum* p44 polypeptide, and an antigenic composition comprising a *B. burgdorferi* polypeptide selected from the group consisting of OspA, OspC, OspF, p39 and a fusion peptide of p41 and VLsE; and b) detecting a polypeptide-antibody complex formed. In some embodiments, the composition may comprise all four of the reagents. In some embodiments, the antibody against a *Dirofilaria immitis* antigen may be a chicken polyclonal antibody. In some embodiments, the chicken polyclonal antibody may be produced by immunizing chickens with a canine heartworm antigen. In some embodiments, the chicken polyclonal antibody may be a type IgY antibody. In some embodiments, the *E. Canis* gp36 polypeptide may comprise a polypeptide having an amino acid sequence of SEQ ID NO:26, which may further comprise a tag sequence. In some embodiments, the *A. phagocytophilum* p44 polypeptide may comprise amino acids 222-236 of SEQ ID NO:1, wherein said polypeptide comprises at least one mutation. In some embodiments, the antigenic composition may at least two *B. burgdorferi* polypeptides, wherein each of said polypeptides comprises an amino acid sequence selected from the group consisting of: a) an OspA polypeptide, b) an OspC polypeptide, c) an OspF polypeptide, d) a p39 polypeptide, and e) a fusion peptide of p41 and VLsE.

In some embodiments, the sample may be from a subject selected from the group consisting of dog, cat, human and horse. In some embodiments, the method may be used for diagnosis, prognosis, stratification, risk assessment, or treatment monitoring of a disease. In some embodiments, the sample may be selected from the group consisting of a serum, a plasma and a blood sample. In some embodiments, the sample may be a clinical sample. In some embodiments, the antibody may be a monoclonal or polyclonal antibody or antibody fragment.

The detection of antibodies and/or antigens may be achieved by immunoassays, including any immunoassay known in the art including, but not limited to, radioimmunoassay, enzyme-linked immunosorbent assay (ELISA), "sandwich" assay, precipitin reaction, agglutination assay, fluorescent immunoassay, and chemiluminescence-based immunoassay. In some embodiments, the polypeptide-antibody complex may be assessed by a sandwich or competitive assay format, optionally with a binder or antibody. In some embodiments, the binder or antibody may be attached to a surface and functions as a capture antibody. In some embodiments, the capture binder or antibody may be attached to the surface directly or indirectly. In some embodiments, the binder or antibody may be attached to the surface via a biotin-avidin (or streptavidin) linking pair. In some embodiments, at least one of the binders or antibodies may be labeled. In some embodiments, the polypeptide-antibody complex may be assessed by a format selected from the group consisting of an enzyme-linked immunosorbent assay (ELISA), Western blotting, immunoblotting, immunoprecipitation, radioimmunoassay (RIA), immunostaining, latex agglutination, indirect hemagglutination assay (IHA), complement fixation, indirect immunofluorescent assay (IFA), nephelometry, flow cytometry assay, plasmon resonance assay, chemiluminescence assay, lateral flow immunoassay, u-capture assay, inhibition assay and avidity assay. In some embodiments, the polypeptide-antibody complex may be assessed in a homogeneous or a heterogeneous assay format.

In some embodiments, multiple reagents for detecting infectious organisms may be included in the same assay, such as parallel immunoassay. A parallel immunoassay may include at least 2, 3, 4, 5, 10, 100, 1000 or more reagents, such as antibodies or antigenic polypeptides, in the same assay system.

Numerous technological platforms for performing parallel immunoassays are known. Generally, such methods involve a logical or physical array of either the subject samples, or the protein markers, or both. Common array formats include both liquid and solid phase arrays. For example, assays employing liquid phase arrays, e.g., for hybridization of nucleic acids, binding of antibodies or other receptors to ligand, etc., can be performed in multiwell or microtiter plates. Microtiter plates with 96, 384 or 1536 wells are widely available, and even higher numbers of wells, e.g., 3456 and 9600 can be used. In general, the choice of microtiter plates is determined by the methods and equipment, e.g., robotic handling and loading systems, used for sample preparation and analysis. Exemplary systems include, e.g., the ORCA™ system from Beckman-Coulter, Inc. (Fullerton, Calif.) and the Zymate systems from Zymark Corporation (Hopkinton, Mass.).

Alternatively, a variety of solid phase arrays can favorably be employed for parallel immunoassays in the context of the invention. Exemplary formats include membrane or filter arrays (e.g., nitrocellulose, nylon), pin arrays, and bead arrays (e.g., in a liquid "slurry"). Typically, probes corresponding to nucleic acid or protein reagents that specifically interact with (e.g., hybridize to or bind to) an expression product corresponding to a member of the candidate library, are immobilized, for example by direct or indirect cross-linking, to the solid support. Essentially any solid support capable of withstanding the reagents and conditions necessary for performing the particular expression assay can be utilized. For example, functionalized glass, silicon, silicon dioxide, modified silicon, any of a variety of polymers, such as (poly)tetrafluoroethylene, (poly)vinylidenedifluoride, polystyrene, polycarbonate, or combinations thereof can all serve as the substrate for a solid phase array.

The polypeptides/antibodies may be immobilized to a solid phase support for the detection of antibody binding. As used herein, "solid phase support" is not limited to a specific type of support. Rather a large number of supports are available and are known to one of ordinary skill in the art. Solid phase supports include silica gels, resins, derivatized plastic films, glass beads, cotton, plastic beads and alumina gels. A suitable solid phase support may be selected on the basis of desired end use and suitability for various synthetic protocols. For example, for peptide synthesis, solid phase support may refer to resins such as polystyrene (e.g., PAM-resin obtained from Bachem Inc., Peninsula Laboratories, etc.), POLYHIPE® resin (obtained from Aminotech, Canada), polyamide resin (obtained from Peninsula Laboratories), polystyrene resin grafted with polyethylene glycol (TENTAGEL®, Rapp Polymere, Tubingen, Germany) or polydimethylacrylamide resin (obtained from Milligen/Biosearch, California). In a preferred embodiment for peptide synthesis, solid phase support refers to polydimethylacrylamide resin In one embodiment, the array may be a "chip" composed, e.g., of one of the above-specified materials. Polynucleotide probes, e.g., RNA or DNA, such as cDNA, synthetic oligonucleotides, and the like, or binding proteins such as antibodies or antigen-binding fragments or derivatives thereof may be affixed to the chip in a logically ordered manner, i.e., in an array. Detailed discussions of methods for linking nucleic acids and proteins to a chip substrate, are found in, e.g., U.S. Pat. No. 5,143,854, U.S. Pat. No. 5,837,832, U.S. Pat. No. 6,087,112, U.S. Pat. No. 5,215,882, U.S. Pat. No. 5,707,807, U.S. Pat. No. 5,807,522, U.S. Pat. No. 5,958,342, U.S. Pat. No. 5,994,076, U.S. Pat. No. 6,004,755, U.S. Pat. No. 6,048,695, U.S. Pat. No. 6,060,240, U.S. Pat. No. 6,090,556, and U.S. Pat. No. 6,040,138, each of which is hereby incorporated in its entirety.

Microarray signals may be detected by scanning the microarray with a variety of laser or CCD-based scanners, and extracting features with numerous software packages, for example, Imagene (Biodiscovery), Feature Extraction Software (Agilent), Scanalyze (Eisen, M. 1999. SCANALYZE User Manual; Stanford Univ., Stanford, Calif. Ver 2.32.), GenePix (Axon Instruments).

High-throughput protein systems include commercially available systems from Ciphergen Biosystems, Inc. (Fremont, Calif.) such as PROTEIN CHIP® arrays and the Schleicher and Schuell protein microspot array (FastQuant Human Chemokine, S&S Bioscences Inc., Keene, N.H., US). In one embodiment, the high-throughput protein assay system may be the Bio-CD system using the SDI™ (Spinning Disc Interferometry) technology by Quadraspec, Inc. (West Lafayette, Ind.). Detailed discussions of the Bio-CD system are found in, e.g., U.S. Pat. No. 6,685,885, U.S. Pat. No. 7,405,831, U.S. Pat. No. 7,552,282, U.S. Pat. No. 7,659,968, U.S. Pat. No. 7,663,092, U.S. Pat. No. 7,787,126, U.S. Pat. No. 7,910,356, U.S. Pat. Pub. No. 2004/0166593, U.S. Pat. Pub. No. 2006/0256676, U.S. Pat. Pub. No. 2007/0023643, U.S. Pat. Pub. No. 2007/0212257, U.S. Pat. Pub. No. 2007/0259366, U.S. Pat. Pub. No. 2008/0175755, U.S. Pat. Pub. No. 2009/0002716, U.S. Pat. Pub. No. 2009/0263913, U.S. Pat. Pub. No. 2010/0145627, and Canadian Pat. Pub. No. 2681722, each of which is hereby incorporated in its entirety.

The parallel immunoassay results obtained as described above can then be used for diagnosis of the specific disorder. The individual proteins/antibodies can be detected or quantified by any of a number of means well known to those of skill in the art. In one aspect, a qualitative change in one or more proteins/antibodies is determined. Qualitative changes include the appearance of a proteins/antibodies spot that is not detectable in samples obtained from normal controls or the disappearance of a proteins/antibodies spot which is detectable in normal controls but not in the sample taken from an affected subject.

In another aspect, a quantitative change in one or more proteins/antibodies may be measured. The concentration of protein/antibody levels may be expressed in absolute terms, for example, optical density as read by image analysis. Alternatively, the concentrations can be expressed as a fraction, relative to normal levels of the same protein/antibody.

F. Computer Readable Medium

In another aspect, provided herein is a computer readable medium containing executable instructions that when executed perform a method of classifying *Borrelia burgdorferi* infection of a mammal, e.g., an animal, the method comprising: calculating levels of antibodies that specifically bind to an OspA, OspC, OspF, p39 polypeptide and/or a fusion peptide of p41 and VLsE using a method for detecting an antibody that specifically binds to a *B. burgdorferi* antigen in a sample, which method may comprise contacting the antigenic composition comprising at least two *B. burgdorferi* polypeptides, wherein each of said polypeptides may comprise an amino acid sequence selected from the group consisting of OspA, OspC, OspF, p39 polypeptide and a fusion peptide of p41 and VLsE disclosed above with said sample and detecting a polypeptide-antibody complex formed; calculating reference values of the levels of the antibodies; and determining the type of *Borrelia burgdorferi* infection of the mammal by comparing the levels of the antibodies to the reference values.

Further provided herein is a system for classifying *Borrelia burgdorferi* infection of a mammal, e.g., an animal comprising the computer readable medium disclosed herein and an antigenic composition comprising at least two *B. burgdorferi* polypeptides, wherein each of said polypeptides may comprise an amino acid sequence selected from the group consisting of: a) an OspA polypeptide, b) an OspC polypeptide, c) an OspF polypeptide, d) a p39 polypeptide, and e) a fusion peptide of p41 and VLsE.

G. Kits

In an additional aspect, provided herein are kits for detecting the various infectious organisms, which kit comprises, in a container, the polypeptides or antigenic compositions. For instance, a polypeptide of the present invention can be included in a kit. A kit can be included in a sealed container. Non-limiting examples of containers include a microtiter plate, a bottle, a metal tube, a laminate tube, a plastic tube, a dispenser, a pressurized container, a barrier container, a package, a compartment, or other types of containers such as injection or blow-molded plastic containers into which the dispersions or compositions or desired bottles, dispensers, or packages are retained. Other examples of containers include glass or plastic vials or bottles. The kit and/or container can include indicia on its surface. The indicia, for example, can be a word, a phrase, an abbreviation, a picture, or a symbol.

The containers can dispense or contain a pre-determined amount of a composition of the present invention. The composition can be dispensed as a liquid, a fluid, or a semi-solid. A kit can also include instructions for using the kit and/or compositions. Instructions can include an explanation of how to use and maintain the compositions.

H. Examples

The following examples are offered to illustrate but not to limit the invention.

Clinical samples of dogs were tested for infection by *Borrelia burgdorferi, A. phagocytophilum* (AP), and *E. canis* (EC) using conventional assays such as immunofluorescence assay (IFA) or Western blot analysis, SNAP™ tests (IDEXX Laboratories, Fremont, Calif.) and a new multiplex assay (ACCUPLEX™, VCA Antech Inc., Los Angeles, Calif.). IFA for Lyme disease was conducted using an ELISA assay (Zeus Scientific Inc., Raritan, N.J.).

ACCUPLEX™ is a multiplex assay for detecting various infectious organisms including heartworm, E. *Canis, A. phagocytophilum*, and *B. burgdorferi* in a subject using the polypeptides, antibodies and antigenic compositions disclosed herein. Chicken polyclonal antibodies made by immunizing chickens with a canine heartworm antigen were used for heartworm detection. A gp36 polypeptide (SEQ ID NO:26) produced using the pET46 Ek/LIC vector (Novagen) with an inserted coding sequence of SEQ ID NO:27 was used for E. *Canis* detection. The *A. phagocytophilum* antigen was a multimeric polypeptide (SEQ ID NO:7) produced using the pET46 Ek/LIC vector with an inserted coding sequence of SEQ ID NO:8. For *B. burgdorferi* detection, an antigenic composition comprising the OspA, OspC, OspF, p39 polypeptides and a fusion peptide of p41 and VLsE was used. The OspA polypeptide is commercially available from Meridian Life Science, Inc. (Catalog #: R8A131), which contains multiple copies of the *B. burgdorferi* OspA sequence and a 6-HIS epitope tag. The OspA polypeptide has a total molecular weight of 85 kDa, and reacts with human *B. burgdorferi* positive serum. The OspC polypeptide having the amino acid sequence of SEQ ID NO:15 was produced using the pET46 Ek/LIC vector with an inserted coding sequence of SEQ ID NO:17. The OspF polypeptide having the amino acid sequence of SEQ ID NO:18 was produced using the pET46 Ek/LIC vector with an inserted coding sequence of SEQ ID NO:20. The p39 polypeptide having the amino acid sequence of SEQ ID NO:21 was produced using the pEV-L8: His8-TEV-LIC vector with an inserted coding sequence of SEQ ID NO:23. The fusion peptide of p41 and VLsE has the amino acid sequence of SEQ ID NO:24 was produced using the pET46 Ek/LIC vector with an inserted coding sequence of SEQ ID NO:25. The polypeptides produced contain tag sequences encoded by the vectors: MAHHHHHHVDDDDK (SEQ ID NO:29) for the pET46 Ek/LIC vector; MHHHHHHHH-GVDLGTENLYFQSNA (SEQ ID NO:31) for the pEV-L8: His8-TEV-LIC vector.

Experiments were performed by infecting and/or vaccinating dogs, followed by testing with ACCUPLEX™, SNAP™ (a test for *Borrelia burgdorferi* infection, *A. phagocytophilum* infection and *E. canis* infection from IDEXX Laboratories) and other assays. Results from various testing methods are shown in the tables below.

For classification of *B. burgdorferi* infections, a value x was calculated using the following formula, wherein multiple negative controls, e.g., six negative controls, were included for each assay:

$$x=3*\text{STDEV(Negative Controls)}+\text{MEDIAN(Negative Controls)}.$$

A static value y is used for adjustment when calculating each reference value. A specific y value, which may equal 0, is assigned to each reference value for each antigen based upon data from an experimental study conducted for each test. The following formulas were used to calculate the reference values:

$$\text{alpLow}=0.5x+\underline{250};[\text{min}1500]$$

$$\text{alpMid}=x+\underline{500};[\text{min}2750]$$

$$\text{alpHigh}=x+\underline{2500};[\text{min}4500]$$

$$\text{alpHighest}=x+\underline{11500};[\text{min}13000]$$

$$\text{ospfLow}=0.5x+\underline{250};[\text{min}1500]$$

$$\text{ospfHigh}=x+\underline{500};[\text{min}3000]$$

$$p39\text{Low}=x;[\text{min}3750]$$

$$\text{slpLow}=x;[\text{min}2350]$$

$$\text{slpMid}=x+\underline{2500};[\text{min}4500]$$

$$\text{slpHigh}=x+\underline{5500};[\text{min}7000]$$

$$\text{ospcLow}=x;[\text{min}4500]$$

$$\text{ospcHigh}=x+\underline{15000};[\text{min}18000]$$

$$\text{sub5Low}=x+\underline{2000};[\text{min}4500]$$

wherein the underlined values are the y values, and the minimal value for each reference value is included in brackets. In cases where the reference value calculated is less than the minimal value, the minimal value may be used. For example, if x is calculated to be 2000, then the calculated alpLow=1250; alpMid=2500; alpHigh=4500 and alpHighest=13500. Because the calculated alpLow (1250) and alpMid (2500) are less than the minimal values for each reference value (1500 and 2750), the minimal values of 1500 and 2750 will be used for alpLow and alpMid, respectively. For alpHigh, the calculated alpHigh is 4500, which is identical to the minimal value; the alpHigh is set at 4500. And because the calculated alpHighest (13500) is greater than the minimal value (13000), the calculated value of 13500 will be used for alpHighest. Therefore, samples with an OspA value of less than alpLow (1500 in this example) will be OspA negative; samples with an OspA value between alpLow (1500 in this example) and alpMid (2750 in this example) will be OspA low; samples with an OspA value between alpMid (2750 in this example) and alpHigh (4500 in this example) will be OspA mid; samples with an OspA value between alpHigh (4500 in this example) and alpHighest (13500 in this example) will be OspA high; and samples with an OspA value greater than alpHighest (13500 in this example) will be OspA highest, etc. The unit for all the values is fluorescent counts from the Dual Channel Bio-CD detection system by Quadraspec, Inc., using both fluorescence and SDI™ (Spinning Disc Interferometry).

Abbreviations Used in the Tables

ACCUPLEX™ Interpretation Code:
Lyme
LEE: Lyme exposure early
LEL: Lyme exposure late
LVR: Lyme vaccine
LELV: Lyme exposure late & vaccine
LEEV: Lyme exposure early & vaccine
LVRN: Lyme vaccine Nobivac™
AP
P44: >5000=*A. phagocytophilum* infection
EC
P36: >7000=*E. canis* infection
SNAP™ Interpretation Code:
BB: *Borrelia burgdorferi* infection
AP: *A. phagocytophilum* infection
EC: *E. canis* infection
Keys for IgG Titers in IFA Tests:
Lyme
<1:64=NEG
BL=Borderline
1:64 to '1:128=POS(1)
1:256=POS(2)
1:512=POS(3)
≥1:1024=POS(4)
AP
>1:40=Positive
EC
>1:80=Positive.

Example 1

Clinical Samples Compared with ACCUPLEX™ Test and SNAP™ Test for Lyme Infection

Clinical samples from dogs tested positive for Lyme antigen using Western blot analysis were assayed using the ACCUPLEX™ test and SNAP™ test. The results are summarized in Table 1. The results show that the ACCUPLEX™ test is capable of distinguishing between exposure to Lyme due to natural exposure and vaccination, and between early and late exposure to Lyme.

TABLE 1

ACCUPLEX ™ and SNAP ™ lyme summary data

| Sample ID | Accuplex (Lyme) | SNAP |
|---|---|---|
| NYAB23845910 | LEEV | BB, AP |
| NYAB14276093 | LEL | BB |
| MEEA21838961 | LEL | BB |
| NYAB19867241 | LEL | BB |
| NYAB20898769 | LEL | BB |
| NYAB14561186 | LEL | BB |
| NYAB15599034 | LEL | BB |
| NYAB18814396 | LEL | BB |
| NYAB19579568 | LEL | BB |
| NYAB17172299 | LEL | BB, AP |
| MEEA21882351 | LEL | BB, AP, EC |

TABLE 1-continued

| ACCUPLEX ™ and SNAP ™ lyme summary data | | |
|---|---|---|
| Sample ID | Accuplex (Lyme) | SNAP |
| MEEA21708724 | LEL | BB, EC |
| NYAB21157842 | LEL | NEG |
| NYAB23251781 | LEL | NEG |
| NYAB15588219 | LELV | AP |
| MEEA22162220 | LELV | BB |
| NYAB16810718 | LELV | BB |
| NYAB22071411 | LELV | BB |
| NYAB22314072 | LELV | BB |
| NYAB20322601 | LELV | BB |
| NYAB20490384 | LELV | BB |
| NYAB14363054 | LELV | BB |
| NYAB16843479 | LELV | BB |
| NYAB21157501 | LELV | BB |
| NYAB22314063 | LELV | BB |
| NYAB22891506 | LELV | BB |
| NYAB15679421 | LELV | BB |
| NYAB15679411 | LELV | BB, AP |
| NYAB24065421 | LELV | BB, AP |
| NYAB15241127 | LELV | BB, AP |
| MEAA05083795 | LELV | NEG |
| NYAB21825963 | LELV | NEG |
| NYAB16275952 | LVR | AP |
| NYAB16959643 | LVR | AP |
| NYAB21718838 | LVR | AP |
| NYAB18826870 | LVR | BB |
| NYAB21064627 | LVR | BB |
| ATAA15994531 | LVR | NEG |
| MECT05674538 | LVR | NEG |
| NYAB14384911 | LVR | NEG |
| NYAB15679402 | LVR | NEG |
| NYAB15679430 | LVR | NEG |
| NYAB16201547 | LVR | NEG |
| NYAB16207228 | LVR | NEG |
| NYAB16787932 | LVR | NEG |
| NYAB16907342 | LVR | NEG |
| NYAB16915461 | LVR | NEG |
| NYAB17043602 | LVR | NEG |
| NYAB17142558 | LVR | NEG |
| NYAB17195177 | LVR | NEG |
| NYAB17580130 | LVR | NEG |
| NYAB17916981 | LVR | NEG |
| NYAB17957563 | LVR | NEG |
| NYAB18468045 | LVR | NEG |
| NYAB18810664 | LVR | NEG |
| NYAB19554971 | LVR | NEG |
| NYAB19795590 | LVR | NEG |
| NYAB19801884 | LVR | NEG |
| NYAB19808929 | LVR | NEG |
| NYAB19872213 | LVR | NEG |
| NYAB20197262 | LVR | NEG |
| NYAB20481287 | LVR | NEG |
| NYAB20518645 | LVR | NEG |
| NYAB20531039 | LVR | NEG |
| NYAB21157861 | LVR | NEG |
| NYAB21265394 | LVR | NEG |
| NYAB21318676 | LVR | NEG |
| NYAB21836214 | LVR | NEG |
| NYAB21842795 | LVR | NEG |
| NYAB22183293 | LVR | NEG |
| NYAB22319471 | LVR | NEG |
| NYAB22640604 | LVR | NEG |
| NYAB22918280 | LVR | NEG |
| NYAB23484335 | LVR | NEG |
| NYAB23737609 | LVR | NEG |
| NYAB23885325 | LVR | NEG |
| NYAB24535653 | LVR | NEG |
| MEAA04952891 | LVR | NEG |
| NYAB16270160 | LVR | NEG |
| NYAB21176721 | LVR | NEG |
| MEEA22176225 | LVRN | NEG |
| NYAB25531917 | NEG | BB |
| MECT05553846 | NEG | EC |
| NYAB14413540 | NEG | NEG |
| NYAB14446934 | NEG | NEG |
| NYAB21327021 | NEG | NEG |

TABLE 1-continued

| ACCUPLEX ™ and SNAP ™ lyme summary data | | |
|---|---|---|
| Sample ID | Accuplex (Lyme) | SNAP |
| NYAB21327165 | NEG | NEG |
| NYAB23709257 | NEG | NEG |
| NYAB23709266 | NEG | NEG |
| NYAB23848401 | NEG | NEG |
| NYAB24107657 | NEG | NEG |
| NYAB21157851 | NEG | NEG |
| NYAB21836107 | NEG | NEG |
| NYAB25531981 | NEG | NEG |
| NYAB16364730 | NEG | NEG |
| NYAB14097305 | NEG | NEG |

Example 2

Clinical Samples Compared ACCUPLEX™ to Both SNAP™ Test and IFA Test for *A. phagocytophilum* Infection Table 2 shows test data from clinical samples using ACCUPLEX™ Lyme and AP tests, IFA AP test and SNAP™ test.

TABLE 2

| *A. phagocytophilum* clinical samples | | | | |
|---|---|---|---|---|
| Sample ID | Accuplex (Lyme) | Accuplex (AP) | IFA (AP) | SNAP |
| NYAB17977735 | LELV | NEG | 1:20 | BB |
| NYAB22437706 | LVR | NEG | 1:20 | AP |
| NYAB09319261 | NEG | NEG | 1:40 | AP |
| NYAB20021616 | NEG | NEG | 1:40 | AP |
| NYAB22487181 | LVR | NEG | 1:40 | AP |
| NYAB22114410 | NEG | NEG | 1:40 | BB |
| NYAB21882324 | LELV | AP+ | 1:40 | BB, AP |
| NYAB22581700 | NEG | NEG | 1:40 | BB, AP |
| NYAB22554051 | NEG | AP+ | 1:40 | AP |
| NYAB22659858 | LVR | AP+ | 1:40 | AP |
| NYAB22554257 | LVR | AP+ | 1:40 | AP |
| NYAB13118278 | LEL | NEG | 1:80 | NEG |
| NYAB16474633 | LVR | NEG | 1:80 | AP |
| NYAB17679411 | LELV | NEG | 1:80 | NEG |
| NYAB17127041 | LVR | AP+ | 1:80 | AP |
| NYAB17689435 | LVR | AP+ | 1:80 | AP |
| NYAB18410706 | NEG | NEG | 1:80 | AP |
| NYAB18129247 | LVR | NEG | 1:80 | NEG |
| NYAB18010894 | LVR | AP+ | 1:80 | AP |
| NYAB20096724 | LEL | NEG | 1:80 | AP |
| NYAB20028608 | LVR | AP+ | 1:80 | AP |
| NYAB22515929 | LVR | AP+ | 1:80 | AP |
| NYAB25122738 | LELV | AP+ | 1:80 | BB, AP |
| NYAB07869968 | LVR | AP+ | 1:160 | AP |
| NYAB09447725 | LVR | AP+ | 1:160 | AP |
| NYAB09764240 | LVR | AP+ | 1:160 | NEG |
| NYAB11348288 | LEL | AP+ | 1:160 | AP |
| NYAB11174349 | LELV | NEG | 1:160 | BB |
| NYAB13127114 | LEL | AP+ | 1:160 | BB |
| NYAB13115113 | NEG | NEG | 1:160 | AP |
| NYAB17178416 | LVR | AP+ | 1:160 | AP |
| NYAB17184128 | LELV | AP+ | 1:160 | AP |
| NYAB17177240 | LVR | AP+ | 1:160 | AP |
| NYAB17237132 | LEL | AP+ | 1:160 | BB, AP |
| NYAB18371091 | LVR | AP+ | 1:160 | AP |
| NYAB20075653 | LEL | AP+ | 1:160 | BB, AP |
| NYAB20554801 | LVR | AP+ | 1:160 | AP |
| NYAB20530748 | LVR | AP+ | 1:160 | AP |
| NYAB20518181 | LVR | AP+ | 1:160 | AP |
| NYAB24623291 | LVR | AP+ | 1:160 | AP |
| NYAB25746939 | LVR | AP+ | 1:160 | AP |
| NYAB25904448 | LELV | AP+ | 1:160 | BB |
| NYAB25742180 | LELV | AP+ | 1:160 | AP |
| NYAB07880286 | LEL | AP+ | 1:320 | BB |
| NYAB07819741 | LVR | AP+ | 1:320 | AP |

TABLE 2-continued

| *A. phagocytophilum* clinical samples | | | | |
|---|---|---|---|---|
| Sample ID | Accuplex (Lyme) | Accuplex (AP) | IFA (AP) | SNAP |
| MEEA19685758 | LVR | AP+ | 1:320 | AP |
| NYAB09647388 | LVR | AP+ | 1:320 | AP |
| NYAB20392632 | LEL | AP+ | 1:320 | BB, AP |
| NYAB10563191 | LEL | AP+ | 1:320 | BB, AP |
| NYAB10568671 | LELV | AP+ | 1:320 | BB, AP |
| NYAB10973547 | LEL | AP+ | 1:320 | AP |
| NYAB10812260 | LVR | AP+ | 1:320 | AP |
| NYAB11650818 | LVR | NEG | 1:320 | AP |
| NYAB13154096 | LEL | NEG | 1:320 | BB, AP |
| NYAB14286920 | LVR | AP+ | 1:320 | AP |
| NYAB14345029 | NEG | AP+ | 1:320 | AP |
| NYAB16511101 | LEL | AP+ | 1:320 | BB, AP |
| NWST00016815 | NEG | AP+ | 1:320 | AP |
| NYAB17185466 | LV-PE | AP+ | 1:320 | AP |
| NYAB18795334 | LELV | AP+ | 1:320 | BB, AP |
| NYAB19462995 | LVR | AP+ | 1:320 | AP |
| NYAB20028519 | LELV | AP+ | 1:320 | AP |
| NYAB20882581 | LVR | AP+ | 1:320 | AP |
| NYAB22222140 | LEL | AP+ | 1:320 | BB |
| NYAB22138510 | LVR | AP+ | 1:320 | AP |
| NYAB23304615 | LVR | AP+ | 1:320 | AP |
| NYAB23685306 | LEL | AP+ | 1:320 | BB, AP |
| NYAB25598451 | LEEV | AP+ | 1:320 | AP |
| NYAB07794796 | LEL | AP+ | 1:640 | AP |
| NYAB09491429 | LV-PE | AP+ | 1:640 | BB, AP |
| NYAB09473387 | LELV | AP+ | 1:640 | BB, AP |
| NYAB09723434 | NEG | AP+ | 1:640 | AP |
| NYAB10481111 | LEL | AP+ | 1:640 | BB |
| NYAB10482511 | LELV | AP+ | 1:640 | BB |
| NYAB11131566 | LVR | AP+ | 1:640 | AP |
| NYAB10828949 | LEL | AP+ | 1:640 | NEG |
| NYAB11082274 | LVR | AP+ | 1:640 | AP |
| NYAB10818423 | LVR | AP+ | 1:640 | AP |
| NYAB11741206 | LEEV | AP+ | 1:640 | AP |
| NYAB13156887 | LVR | NEG | 1:640 | NEG |
| NYAB13370312 | NEG | AP+ | 1:640 | AP |
| NYAB13692380 | LVR | AP+ | 1:640 | AP |
| NYAB16474796 | LVR | AP+ | 1:640 | BB |
| NYAB14378496 | LEL | AP+ | 1:640 | AP |
| NYAB16514416 | LVR | AP+ | 1:640 | AP |
| NYAB16900388 | LELV | AP+ | 1:640 | AP |
| NYAB16538042 | LEL | AP+ | 1:640 | BB, AP |
| NYAB17632933 | LVR | AP+ | 1:640 | AP |
| NYAB17610954 | LEE | AP+ | 1:640 | AP |
| NYAB18175571 | LELV | AP+ | 1:640 | AP |
| NYAB18486606 | LELV | AP+ | 1:640 | BB, AP |
| NYAB19498110 | LEL | AP+ | 1:640 | BB, AP |
| NYAB20533571 | NEG | AP+ | 1:640 | AP |
| NYAB20122904 | LELV | AP+ | 1:640 | NEG |
| NYAB21919264 | LVR | AP+ | 1:640 | AP |
| NYAB22173671 | LVR | AP+ | 1:640 | AP |
| MDAA00263128 | LVR | AP+ | 1:640 | AP |
| NYAB24006304 | LVR | AP+ | 1:640 | AP |
| NYAB06481311 | LVR | AP+ | 1:1280 | AP |
| NYAB09647056 | LELV | AP+ | 1:1280 | BB, AP |
| NYAB09448160 | LVR | AP+ | 1:1280 | AP |
| NYAB11001641 | LVR | AP+ | 1:1280 | AP |
| NYAB12253616 | LELV | AP+ | 1:1280 | BB, AP |
| NYAB14248464 | LELV | AP+ | 1:1280 | AP |
| NYAB18825308 | LVR | AP+ | 1:1280 | NEG |
| NYAB20794361 | LEE | AP+ | 1:1280 | BB, AP |
| NYAB06661374 | LELV | AP+ | 1:2560 | AP |
| NYAB08823373 | LVR | AP+ | 1:2560 | AP |
| NYAB09216817 | LEL | AP+ | 1:2560 | BB, AP |
| NYAB09160613 | LELV | AP+ | 1:2560 | BB, AP |
| NYAB16236767 | LEL | AP+ | 1:2560 | BB, AP |
| NYAB06875414 | LVR | AP+ | 1:5120 | AP |
| NYAB06525775 | LELV | AP+ | 1:5120 | BB, AP |
| NYAB09160103 | LEL | AP+ | 1:5120 | BB, AP |
| NYAB08813921 | LVR | AP+ | 1:5120 | AP |
| NYAB08813921 | LVR | AP+ | 1:5120 | AP |
| NYAB21669573 | LEL | NEG | <1:20 | BB |

Example 3

Clinical Samples Compared ACCUPLEX™ to Both SNAP™ Test and IFA Test for *A. phagocytophilum* Infection Table 2 shows test data from clinical samples using ACCUPLEX™ Lyme and AP tests, IFA AP test and SNAP™ test.

TABLE 3

| *E. canis* clinical samples | | | | | |
|---|---|---|---|---|---|
| Sample ID | Accu-plex (Lyme) | Accuplex (AP) | Accu-plex (EC) | IFA (EC) | SNAP |
| NYAB21837338 | NEG | NEG | NEG | 1:40 | AP |
| MEEA21401048 | NEG | NEG | NEG | 1:640 | EC |
| NYAB16543928 | NEG | NEG | NEG | 1:320 | EC |
| NYAB24018744 | LVR | NEG | NEG | 1:160 | EC |
| ATAA15918092 | NEG | NEG | NEG | 1:160 | NEG |
| MEEA21309416 | NEG | NEG | NEG | 1:160 | EC |
| NYAB16288521 | LVR | NEG | NEG | 1:320 | EC |
| MEEA21233944 | NEG | NEG | NEG | 1:320 | NEG |
| MEEA21038583 | NEG | NEG | NEG | 1:640 | EC |
| MEEA19462224 | NEG | NEG | NEG | 1:1280 | EC |
| MEEA21328986 | NEG | NEG | NEG | 1:640 | EC |
| BIAA00147227 | NEG | NEG | NEG | 1:160 | NEG |
| MEEA22728169 | NEG | NEG | NEG | 1:80 | BB |
| ATAA15027065 | NEG | NEG | NEG | 1:80 | EC |
| NYAB10003061 | LVR | NEG | NEG | 1:640 | EC |
| NYAB21422324 | LVR | NEG | NEG | 1:640 | NEG |
| NYAB13105645 | LVR | NEG | NEG | 1:640 | EC |
| NYAB19097630 | LVR | NEG | NEG | 1:320 | NEG |
| MECT05205762 | NEG | NEG | NEG | 1:640 | EC |
| NYAB22285248 | NEG | NEG | NEG | 1:640 | NEG |
| ATAA15054456 | NEG | NEG | NEG | 1:160 | NEG |
| NYAB17772961 | LEL | NEG | NEG | 1:320 | BB, EC |
| NYAB17060078 | LVR | NEG | NEG | 1:320 | EC |
| NYAB11340109 | LVR | NEG | NEG | 1:160 | EC |
| NYAB10530790 | NEG | NEG | NEG | 1:640 | NEG |
| MEEA21168452 | LEL | NEG | NEG | 1:80 | EC |
| NYAB07519450 | NEG | NEG | NEG | 1:640 | EC |
| NYAB06286291 | LVR | NEG | NEG | 1:1280 | NEG |
| NYAB15367479 | LVR | NEG | NEG | 1:160 | EC |
| NYAB20801813 | LVR | NEG | NEG | 1:160 | EC |
| ATAA15783385 | NEG | NEG | NEG | 1:80 | EC |
| NYAB06789540 | NEG | NEG | NEG | 1:5120 | EC |
| MEEA22186114 | NEG | NEG | NEG | 1:160 | EC |
| NYAB12773939 | LVR | AP+ | NEG | 1:320 | EC |
| MECT05446078 | NEG | NEG | NEG | 1:640 | EC |
| TPAA07361701 | NEG | NEG | NEG | 1:320 | CHW |
| NYAB18336860 | NEG | NEG | NEG | 1:2560 | EC |
| NYAB25829700 | LVR | AP+ | NEG | 1:80 | AP, EC |
| ATAA13728811 | LVR | NEG | NEG | 1:80 | NEG |
| NYAB18719637 | NEG | NEG | NEG | 1:320 | EC |
| MEEA21168256 | NEG | AP+ | NEG | 1:80 | NEG |
| MEEA19478959 | NEG | NEG | NEG | 1:160 | NEG |
| NYAB16636179 | LVR | NEG | NEG | 1:160 | EC |
| NYAB12354280 | NEG | NEG | NEG | 1:80 | NEG |
| NYAB06422357 | NEG | NEG | NEG | 1:1280 | NEG |
| NYAB10547204 | LVR | NEG | NEG | 1:320 | NEG |
| MEEA21521912 | NEG | NEG | NEG | 1:160 | EC |
| MEEA21580127 | NEG | NEG | NEG | 1:160 | NEG |
| NYAB09836394 | NEG | NEG | NEG | 1:640 | NEG |
| NYAB17784407 | NEG | NEG | NEG | 1:320 | EC |
| NYAB18563401 | NEG | NEG | NEG | 1:640 | EC |
| MEEA20571437 | LEE | AP+ | NEG | 1:5120 | EC |
| NYAB06864869 | NEG | NEG | NEG | 1:640 | EC |
| NYAB07507898 | NEG | NEG | NEG | 1:80 | NEG |
| MEEA19208828 | NEG | NEG | NEG | 1:640 | EC |
| MECT05190051 | NEG | NEG | NEG | 1:640 | EC |
| NYAB16143121 | LVR | NEG | NEG | 1:320 | EC |
| NYAB24437438 | LEL | AP+ | NEG | 1:80 | BB, AP |
| NYAB21014394 | LELV | NEG | NEG | 1:2560 | BB, EC |
| ROAA02245138 | LVR | NEG | NEG | 1:1280 | EC |
| MEEA21522240 | LVR | NEG | NEG | 1:640 | EC |
| NYAB23825111 | LEL | NEG | NEG | 1:160 | EC |
| NYAB15471726 | NEG | NEG | NEG | 1:640 | EC |
| ATAA14091141 | NEG | NEG | NEG | 1:80 | EC |

TABLE 3-continued

*E. canis* clinical samples

| Sample ID | Accu-plex (Lyme) | Accuplex (AP) | Accu-plex (EC) | IFA (EC) | SNAP |
|---|---|---|---|---|---|
| NYAB07506999 | LVR | NEG | NEG | 1:160 | NEG |
| NYAB10530092 | LVR | NEG | NEG | 1:640 | EC |
| NYAB23232740 | LEE | AP+ | NEG | 1:1280 | EC |
| TPAA06114297 | NEG | AP+ | NEG | 1:80 | NEG |
| NYAB11180892 | NEG | NEG | NEG | 1:160 | EC |
| ATAA14084601 | NEG | NEG | NEG | 1:160 | EC |
| MEEA19456441 | NEG | NEG | NEG | 1:80 | EC |
| NYAB22631919 | NEG | NEG | NEG | 1:5120 | EC |
| ATAA15223245 | NEG | NEG | NEG | 1:80 | EC |
| MEEA19941811 | NEG | NEG | NEG | 1:640 | NEG |
| MEEA21455110 | NEG | NEG | NEG | 1:640 | NEG |
| NYAB08264981 | LVR | NEG | NEG | 1:5120 | EC |
| NYAB11183615 | NEG | NEG | NEG | 1:640 | EC |
| NYAB19496278 | NEG | NEG | NEG | 1:80 | NEG |
| TPAA06051526 | NEG | NEG | NEG | 1:1280 | EC |
| MEEA19220386 | LVR | NEG | NEG | 1:160 | EC |
| NYAB06501853 | LVR | NEG | NEG | 1:2560 | NEG |
| MEEA21132692 | NEG | NEG | NEG | 1:80 | EC |
| NYAB11738078 | NEG | NEG | NEG | 1:320 | EC |
| ATAA15983591 | LVRN | NEG | EC+ | 1:2560 | EC |
| MEDA00852056 | NEG | NEG | EC+ | 1:80 | NEG |
| NYAB08745590 | NEG | NEG | EC+ | 1:80 | NEG |
| NYAB11829744 | LEE | NEG | EC+ | 1:160 | EC |
| MECT05704833 | NEG | NEG | EC+ | 1:80 | NEG |
| NYAB08263133 | LEE | NEG | EC+ | 1:320 | BB |
| NYAB17793578 | NEG | NEG | EC+ | 1:1280 | EC |
| NYAB16432286 | LELV | NEG | EC+ | 1:160 | NEG |
| MEEA20062815 | NEG | NEG | EC+ | 1:320 | EC |
| MEEA19766874 | LEL | NEG | EC+ | 1:160 | NEG |
| NYAB16297065 | LVR | NEG | EC+ | 1:640 | EC |
| MEEA19690408 | NEG | NEG | EC+ | 1:640 | EC |
| NYAB07806565 | NEG | AP+ | EC+ | 1:5120 | AP, EC |
| NYAB06905999 | LEL | NEG | EC+ | 1:80 | BB |
| MECT05335041 | NEG | NEG | EC+ | 1:2560 | EC, CHW |
| NYAB16976564 | LEE | NEG | EC+ | 1:640 | EC |
| NYAB06887872 | NEG | NEG | EC+ | 1:20480 | EC |
| NYAB09924291 | NEG | NEG | EC+ | >1:10240 | EC |
| ATAA15161607 | NEG | NEG | EC+ | 1:10240 | EC |
| ATAA13921464 | NEG | NEG | EC+ | 1:160 | NEG |
| TPAA06013721 | LEE | NEG | EC+ | 1:10240 | AP, EC |
| NYAB08743844 | NEG | NEG | EC+ | 1:5120 | EC |
| NYAB10532678 | NEG | NEG | EC+ | 1:5120 | EC |
| NYAB07758074 | NEG | NEG | EC+ | 1:10240 | EC |
| MEEA20658575 | NEG | NEG | EC+ | 1:10240 | EC |
| MEAA04743532 | NEG | NEG | EC+ | 1:10240 | EC |
| MEEA20303599 | NEG | NEG | EC+ | 1:5120 | EC |

TABLE 3-continued

*E. canis* clinical samples

| Sample ID | Accu-plex (Lyme) | Accuplex (AP) | Accu-plex (EC) | IFA (EC) | SNAP |
|---|---|---|---|---|---|
| ATAA13677641 | LEL | NEG | EC+ | 1:5120 | EC |
| NYAB10539276 | LEE | NEG | EC+ | >1:10240 | EC |
| NYAB16993583 | NEG | NEG | EC+ | 1:5120 | EC |
| NYAB06230607 | LEL | NEG | EC+ | 1:10240 | EC |
| NYAB09999980 | LVR | AP+ | EC+ | >1:10240 | EC |
| NYAB17016338 | LVR | NEG | EC+ | 1:5120 | EC |

Example 4

Test Results of Experimentally Infected Dogs for Lyme

Table 4 shows test results from experimentally infected dogs using the ACCUPLEX™ Lyme test in comparison to SNAP™ (a test for *Borrelia burgdorferi* infection, *A. phagocytophilum* infection and *E. canis* infection from IDEXX Laboratories) test and ELISA assay (Zeus Scientific, Inc.). The dogs were separated into six groups. Groups 1, 3 and 5 were infected with ticks first, followed by vaccination. Groups 2, 4 and 6 were vaccinated first, followed by ticks infection. The vaccines used are NOBIVAC™ Lyme (a vaccine comprises a bacterin that contains two inactivated strains of *Borrelia burgdorferi* comprised of outer surface protein A (OspA) and outer surface protein C (OspC)) (Intervet/Schering-Plough Animal Health, Summit, N.J.), LYMEVAX® (a killed virus vaccine for protection against *Borrelia burgdorferi* or Lyme disease) (Fort Dodge Animal Health, New York, N.Y.), and RECOMBITEK® Lyme (a recombinant OspA vaccine) (Merial Ltd., Duluth, Ga.). Tables 5, 6 and 7 show Lyme Groups 1, 3 & 5 compared with SNAP™ and ELISA tests for mean time to positive (in days from T=0 and before V=0). The average time of detection for all three groups are 26.5 days for ACCUPLEX™, 35.0 days for SNAP™ and 26.8 days for ELISA. The mean time for detection by ACCUPLEX™ of vaccination in Lyme Groups 2, 4 & 6 is: 24.0 (14-36) days for Group 2, 12.7 (6-14) days for Group 4 and 14.0 (14-14) days for Group 6. The average time of detection for all three groups is 16.9 days.

TABLE 4

Results from Lyme experimental study

| Sample ID | Group | Prim | Vaccine | DOS (CSU) | T = 0 | V = 0 | Accuplex (Lyme) | SNAP | ILISA (Lyme) |
|---|---|---|---|---|---|---|---|---|---|
| ALS-8F | 1 | Tick | Nobivac | 18 Oct. 2009 | | | NEG | | Neg |
| ALS-8F | 1 | Tick | Nobivac | 25 Oct. 2009 | | | NEG | NEG | Neg |
| ALS-8F | 1 | Tick | Nobivac | 31 Oct. 2009 | | | NEG | NEG | Neg |
| ALS-8F | 1 | Tick | Nobivac | 08 Nov. 2009 | | | NEG | NEG | Neg |
| ALS-8F | 1 | Tick | Nobivac | 14 Nov. 2009 | | | NEG | NEG | |
| ALS-8F | 1 | Tick | Nobivac | 22 Nov. 2009 | | | NEG | NEG | Neg |
| ALS-8F | 1 | Tick | Nobivac | 27 Nov. 2009 | | | NEG | N/A | N/A |
| ALS-8F | 1 | Tick | Nobivac | 06 Dec. 2009 | | | NEG | NEG | Neg |
| ALS-8F | 1 | Tick | Nobivac | 13 Dec. 2009 | | | NEG | NEG | Neg |
| ALS-8F | 1 | Tick | Nobivac | 03 Jan. 2010 | | | NEG | NEG | Neg |
| ALS-8F | 1 | Tick | Nobivac | 14 Feb. 2010 | | | NEG | N/A | N/A |
| ALS-8F | 1 | Tick | Nobivac | 04 Apr. 2010 | T = 0 | | NEG | NEG | BL |
| ALS-8F | 1 | Tick | Nobivac | 11 Apr. 2010 | 7 | | NEG | NEG | Neg |
| ALS-8F | 1 | Tick | Nobivac | 18 Apr. 2010 | 14 | | NEG | NEG | BL |
| ALS-8F | 1 | Tick | Nobivac | 25 Apr. 2010 | 21 | | LEE | NEG | Pos(2) |
| ALS-8F | 1 | Tick | Nobivac | 02 May 2010 | 28 | | LEE | NEG | Pos(3) |
| ALS-8F | 1 | Tick | Nobivac | 09 May 2010 | 35 | | LEE | NEG | Pos(3) |
| ALS-8F | 1 | Tick | Nobivac | 16 May 2010 | 42 | | LEL | BB, AP | Pos(3) |

TABLE 4-continued

Results from Lyme experimental study

| Sample ID | Group | Prim | Vaccine | DOS (CSU) | T = 0 | V = 0 | Accuplex (Lyme) | SNAP | ILISA (Lyme) |
|---|---|---|---|---|---|---|---|---|---|
| ALS-8F | 1 | Tick | Nobivac | 23 May 2010 | 49 | | LEL | AP | Pos(4) |
| ALS-8F | 1 | Tick | Nobivac | 30 May 2010 | 57 | | LEL | AP | Pos(4) |
| ALS-8F | 1 | Tick | Nobivac | 06 Jun. 2010 | 63 | | LEL | AP | Pos(3) |
| ALS-8F | 1 | Tick | Nobivac | 13 Jun. 2010 | 70 | | LEL | AP | Pos(4) |
| ALS-8F | 1 | Tick | Nobivac | 20 Jun. 2010 | 77 | | LEL | AP | Pos(3) |
| ALS-8F | 1 | Tick | Nobivac | 27 Jun. 2010 | 84 | V = 0 | LEL | BB, AP | Pos(3) |
| ALS-8F | 1 | Tick | Nobivac | 04 Jul. 2010 | 92 | 7 | LEL | BB, AP | Pos(4) |
| ALS-8F | 1 | Tick | Nobivac | 11 Jul. 2010 | 98 | 14 | LEL | BB, AP | Pos(4) |
| ALS-8F | 1 | Tick | Nobivac | 18 Jul. 2010 | 105 | 21 | LELV | BB, AP | Pos(4) |
| ALS-8F | 1 | Tick | Nobivac | 01 Aug. 2010 | 119 | 35 | LELV | BB, AP | Pos(4) |
| ALS-8F | 1 | Tick | Nobivac | 08 Aug. 2010 | 126 | 42 | LELV | BB | Pos(4) |
| ALS-8F | 1 | Tick | Nobivac | 15 Aug. 2010 | 133 | 49 | LELV | BB, AP | Pos(4) |
| ALS-8F | 1 | Tick | Nobivac | 22 Aug. 2010 | 140 | 56 | LELV | BB, AP | Pos(4) |
| ALS-8F | 1 | Tick | Nobivac | 29 Aug. 2010 | 147 | 63 | LELV | BB, AP | Pos(4) |
| ALS-8F | 1 | Tick | Nobivac | 05 Sep. 2010 | 154 | 70 | LELV | N/A | N/A |
| EGS-8F | 1 | Tick | Nobivac | 18 Oct. 2009 | | | NEG | N/A | N/A |
| EGS-8F | 1 | Tick | Nobivac | 25 Oct. 2009 | | | NEG | NEG | Neg |
| EGS-8F | 1 | Tick | Nobivac | 31 Oct. 2009 | | | NEG | NEG | Neg |
| EGS-8F | 1 | Tick | Nobivac | 08 Nov. 2009 | | | NEG | NEG | Neg |
| EGS-8F | 1 | Tick | Nobivac | 14 Nov. 2009 | | | NEG | NEG | |
| EGS-8F | 1 | Tick | Nobivac | 22 Nov. 2009 | | | NEG | NEG | Neg |
| EGS-8F | 1 | Tick | Nobivac | 27 Nov. 2009 | | | NEG | N/A | N/A |
| EGS-8F | 1 | Tick | Nobivac | 06 Dec. 2009 | | | NEG | NEG | Neg |
| EGS-8F | 1 | Tick | Nobivac | 13 Dec. 2009 | | | NEG | NEG | Neg |
| EGS-8F | 1 | Tick | Nobivac | 03 Jan. 2010 | | | NEG | NEG | Neg |
| EGS-8F | 1 | Tick | Nobivac | 14 Feb. 2010 | | | NEG | N/A | N/A |
| EGS-8F | 1 | Tick | Nobivac | 04 Apr. 2010 | T = 0 | | NEG | NEG | BL |
| EGS-8F | 1 | Tick | Nobivac | 11 Apr. 2010 | 7 | | NEG | NEG | Neg |
| EGS-8F | 1 | Tick | Nobivac | 18 Apr. 2010 | 14 | | NEG | NEG | BL |
| EGS-8F | 1 | Tick | Nobivac | 25 Apr. 2010 | 21 | | NEG | NEG | Neg |
| EGS-8F | 1 | Tick | Nobivac | 02 May 2010 | 28 | | NEG | BB, AP | BL |
| EGS-8F | 1 | Tick | Nobivac | 09 May 2010 | 35 | | NEG | AP | Pos(2) |
| EGS-8F | 1 | Tick | Nobivac | 16 May 2010 | 42 | | NEG | BB, AP | Pos(2) |
| EGS-8F | 1 | Tick | Nobivac | 23 May 2010 | 49 | | LEL | BB, AP | Pos(3) |
| EGS-8F | 1 | Tick | Nobivac | 30 May 2010 | 57 | | LEL | BB, AP | Pos(3) |
| EGS-8F | 1 | Tick | Nobivac | 06 Jun. 2010 | 63 | | LEL | BB, AP | Pos(3) |
| EGS-8F | 1 | Tick | Nobivac | 13 Jun. 2010 | 70 | | LEL | BB, AP | Pos(4) |
| EGS-8F | 1 | Tick | Nobivac | 20 Jun. 2010 | 77 | | LEL | BB, AP | Pos(3) |
| EGS-8F | 1 | Tick | Nobivac | 27 Jun. 2010 | 84 | V = 0 | LEL | BB, AP | Pos(3) |
| EGS-8F | 1 | Tick | Nobivac | 04 Jul. 2010 | 92 | 7 | LEL | BB, AP | Pos(2) |
| EGS-8F | 1 | Tick | Nobivac | 11 Jul. 2010 | 98 | 14 | LELV | BB, AP | Pos(4) |
| EGS-8F | 1 | Tick | Nobivac | 18 Jul. 2010 | 105 | 21 | LELV | BB, AP | Pos(4) |
| EGS-8F | 1 | Tick | Nobivac | 01 Aug. 2010 | 119 | 35 | LELV | BB, AP | Pos(4) |
| EGS-8F | 1 | Tick | Nobivac | 08 Aug. 2010 | 126 | 42 | LELV | AP | Pos(4) |
| EGS-8F | 1 | Tick | Nobivac | 15 Aug. 2010 | 133 | 49 | LELV | AP | Pos(4) |
| EGS-8F | 1 | Tick | Nobivac | 22 Aug. 2010 | 140 | 56 | LELV | BB, AP | Pos(4) |
| EGS-8F | 1 | Tick | Nobivac | 29 Aug. 2010 | 147 | 63 | LELV | BB, AP | Pos(4) |
| EGS-8F | 1 | Tick | Nobivac | 05 Sep. 2010 | 154 | 70 | LELV | N/A | N/A |
| KKV-8M | 1 | Tick | Nobivac | 18 Oct. 2009 | | | NEG | | Neg |
| KKV-8M | 1 | Tick | Nobivac | 25 Oct. 2009 | | | NEG | NEG | Neg |
| KKV-8M | 1 | Tick | Nobivac | 31 Oct. 2009 | | | NEG | NEG | BL |
| KKV-8M | 1 | Tick | Nobivac | 08 Nov. 2009 | | | NEG | NEG | Neg |
| KKV-8M | 1 | Tick | Nobivac | 14 Nov. 2009 | | | NEG | NEG | |
| KKV-8M | 1 | Tick | Nobivac | 22 Nov. 2009 | | | NEG | NEG | Neg |
| KKV-8M | 1 | Tick | Nobivac | 27 Nov. 2009 | | | NEG | N/A | N/A |
| KKV-8M | 1 | Tick | Nobivac | 06 Dec. 2009 | | | NEG | NEG | Neg |
| KKV-8M | 1 | Tick | Nobivac | 13 Dec. 2009 | | | NEG | NEG | Neg |
| KKV-8M | 1 | Tick | Nobivac | 03 Jan. 2010 | | | NEG | NEG | Neg |
| KKV-8M | 1 | Tick | Nobivac | 14 Feb. 2010 | | | NEG | N/A | N/A |
| KKV-8M | 1 | Tick | Nobivac | 04 Apr. 2010 | T = 0 | | NEG | NEG | BL |
| KKV-8M | 1 | Tick | Nobivac | 18 Apr. 2010 | 14 | | NEG | NEG | BL |
| KKV-8M | 1 | Tick | Nobivac | 25 Apr. 2010 | 21 | | LEE | NEG | Pos(3) |
| KKV-8M | 1 | Tick | Nobivac | 02 May 2010 | 28 | | LEE | BB | Pos(3) |
| KKV-8M | 1 | Tick | Nobivac | 09 May 2010 | 35 | | LEE | BB | Pos(3) |
| KKV-8M | 1 | Tick | Nobivac | 16 May 2010 | 42 | | LEE | BB | Pos(3) |
| KKV-8M | 1 | Tick | Nobivac | 23 May 2010 | 49 | | LEL | BB | Pos(4) |
| KKV-8M | 1 | Tick | Nobivac | 30 May 2010 | 57 | | LEL | BB | Pos(4) |
| KKV-8M | 1 | Tick | Nobivac | 06 Jun. 2010 | 63 | | LEL | BB | Pos(3) |
| KKV-8M | 1 | Tick | Nobivac | 13 Jun. 2010 | 70 | | LEL | BB | Pos(4) |
| KKV-8M | 1 | Tick | Nobivac | 20 Jun. 2010 | 77 | | LEL | BB | Pos(4) |
| KKV-8M | 1 | Tick | Nobivac | 27 Jun. 2010 | 84 | V = 0 | LEL | BB | Pos(4) |
| KKV-8M | 1 | Tick | Nobivac | 04 Jul. 2010 | 92 | 7 | LEL | BB | Pos(4) |
| KKV-8M | 1 | Tick | Nobivac | 11 Jul. 2010 | 98 | 14 | LELV | BB | Pos(4) |
| KKV-8M | 1 | Tick | Nobivac | 18 Jul. 2010 | 105 | 21 | LELV | BB | Pos(4) |
| KKV-8M | 1 | Tick | Nobivac | 01 Aug. 2010 | 119 | 35 | LELV | BB | Pos(4) |

TABLE 4-continued

Results from Lyme experimental study

| Sample ID | Group | Prim | Vaccine | DOS (CSU) | T = 0 | V = 0 | Accuplex (Lyme) | SNAP | ILISA (Lyme) |
|---|---|---|---|---|---|---|---|---|---|
| KKV-8M | 1 | Tick | Nobivac | 08 Aug. 2010 | 126 | 42 | LELV | BB | Pos(4) |
| KKV-8M | 1 | Tick | Nobivac | 15 Aug. 2010 | 133 | 49 | LELV | BB | Pos(4) |
| KKV-8M | 1 | Tick | Nobivac | 22 Aug. 2010 | 140 | 56 | LELV | BB | Pos(4) |
| KKV-8M | 1 | Tick | Nobivac | 29 Aug. 2010 | 147 | 63 | LELV | BB | Pos(4) |
| KKV-8M | 1 | Tick | Nobivac | 05 Sep. 2010 | 154 | 70 | LELV | N/A | N/A |
| SHU-8F | 1 | Tick | Nobivac | 18 Oct. 2009 | | | NEG | N/A | N/A |
| SHU-8F | 1 | Tick | Nobivac | 25 Oct. 2009 | | | NEG | NEG | BL |
| SHU-8F | 1 | Tick | Nobivac | 31 Oct. 2009 | | | NEG | NEG | BL |
| SHU-8F | 1 | Tick | Nobivac | 08 Nov. 2009 | | | NEG | NEG | BL |
| SHU-8F | 1 | Tick | Nobivac | 14 Nov. 2009 | | | NEG | NEG | |
| SHU-8F | 1 | Tick | Nobivac | 22 Nov. 2009 | | | NEG | NEG | BL |
| SHU-8F | 1 | Tick | Nobivac | 27 Nov. 2009 | | | NEG | N/A | N/A |
| SHU-8F | 1 | Tick | Nobivac | 06 Dec. 2009 | | | NEG | NEG | BL |
| SHU-8F | 1 | Tick | Nobivac | 13 Dec. 2009 | | | NEG | NEG | Neg |
| SHU-8F | 1 | Tick | Nobivac | 03 Jan. 2010 | | | NEG | NEG | Neg |
| SHU-8F | 1 | Tick | Nobivac | 14 Feb. 2010 | | | NEG | N/A | N/A |
| SHU-8F | 1 | Tick | Nobivac | 04 Apr. 2010 | T = 0 | | NEG | NEG | Pos(2) |
| SHU-8F | 1 | Tick | Nobivac | 11 Apr. 2010 | 7 | | NEG | NEG | BL |
| SHU-8F | 1 | Tick | Nobivac | 18 Apr. 2010 | 14 | | NEG | NEG | Pos(2) |
| SHU-8F | 1 | Tick | Nobivac | 25 Apr. 2010 | 21 | | LEE | NEG | Pos(3) |
| SHU-8F | 1 | Tick | Nobivac | 02 May 2010 | 28 | | LEE | NEG | Pos(3) |
| SHU-8F | 1 | Tick | Nobivac | 09 May 2010 | 35 | | LEL | NEG | Pos(3) |
| SHU-8F | 1 | Tick | Nobivac | 16 May 2010 | 42 | | LEL | BB, AP | Pos(3) |
| SHU-8F | 1 | Tick | Nobivac | 23 May 2010 | 49 | | LEL | BB, AP | Pos(4) |
| SHU-8F | 1 | Tick | Nobivac | 30 May 2010 | 57 | | LEL | BB, AP | Pos(4) |
| SHU-8F | 1 | Tick | Nobivac | 06 Jun. 2010 | 63 | | LEL | BB, AP | Pos(3) |
| SHU-8F | 1 | Tick | Nobivac | 13 Jun. 2010 | 70 | | LEL | BB, AP | Pos(4) |
| SHU-8F | 1 | Tick | Nobivac | 20 Jun. 2010 | 77 | | LEL | BB, AP | Pos(4) |
| SHU-8F | 1 | Tick | Nobivac | 27 Jun. 2010 | 84 | V = 0 | LELV | BB, AP | Pos(3) |
| SHU-8F | 1 | Tick | Nobivac | 04 Jul. 2010 | 92 | 7 | LELV | BB, AP | Pos(4) |
| SHU-8F | 1 | Tick | Nobivac | 11 Jul. 2010 | 98 | 14 | LEL | BB, AP | Pos(4) |
| SHU-8F | 1 | Tick | Nobivac | 18 Jul. 2010 | 105 | 21 | LELV | BB, AP | Pos(4) |
| SHU-8F | 1 | Tick | Nobivac | 01 Aug. 2010 | 119 | 35 | LELV | BB, AP | Pos(4) |
| SHU-8F | 1 | Tick | Nobivac | 08 Aug. 2010 | 126 | 42 | LELV | BB, AP | Pos(4) |
| SHU-8F | 1 | Tick | Nobivac | 15 Aug. 2010 | 133 | 49 | LELV | BB, AP | Pos(4) |
| SHU-8F | 1 | Tick | Nobivac | 22 Aug. 2010 | 140 | 56 | LELV | BB, AP | Pos(4) |
| SHU-8F | 1 | Tick | Nobivac | 29 Aug. 2010 | 147 | 63 | LELV | BB, AP | Pos(4) |
| SHU-8F | 1 | Tick | Nobivac | 05 Sep. 2010 | 154 | 70 | LELV | N/A | N/A |
| SZV-8M | 1 | Tick | Nobivac | 18 Oct. 2009 | | | NEG | | Neg |
| SZV-8M | 1 | Tick | Nobivac | 25 Oct. 2009 | | | NEG | NEG | Neg |
| SZV-8M | 1 | Tick | Nobivac | 31 Oct. 2009 | | | NEG | NEG | Neg |
| SZV-8M | 1 | Tick | Nobivac | 08 Nov. 2009 | | | NEG | NEG | Neg |
| SZV-8M | 1 | Tick | Nobivac | 14 Nov. 2009 | | | NEG | NEG | |
| SZV-8M | 1 | Tick | Nobivac | 22 Nov. 2009 | | | NEG | NEG | Neg |
| SZV-8M | 1 | Tick | Nobivac | 27 Nov. 2009 | | | NEG | N/A | N/A |
| SZV-8M | 1 | Tick | Nobivac | 06 Dec. 2009 | | | NEG | NEG | Neg |
| SZV-8M | 1 | Tick | Nobivac | 13 Dec. 2009 | | | NEG | NEG | Neg |
| SZV-8M | 1 | Tick | Nobivac | 03 Jan. 2010 | | | NEG | NEG | Neg |
| SZV-8M | 1 | Tick | Nobivac | 14 Feb. 2010 | | | NEG | N/A | N/A |
| SZV-8M | 1 | Tick | Nobivac | 04 Apr. 2010 | T = 0 | | NEG | NEG | BL |
| SZV-8M | 1 | Tick | Nobivac | 11 Apr. 2010 | 7 | | NEG | NEG | Neg |
| SZV-8M | 1 | Tick | Nobivac | 18 Apr. 2010 | 14 | | NEG | NEG | Pos(2) |
| SZV-8M | 1 | Tick | Nobivac | 25 Apr. 2010 | 21 | | LEE | BB | Pos(2) |
| SZV-8M | 1 | Tick | Nobivac | 02 May 2010 | 28 | | LEE | BB | Pos(2) |
| SZV-8M | 1 | Tick | Nobivac | 09 May 2010 | 35 | | LEE | BB | Pos(2) |
| SZV-8M | 1 | Tick | Nobivac | 16 May 2010 | 42 | | LEE | BB | Pos(3) |
| SZV-8M | 1 | Tick | Nobivac | 23 May 2010 | 49 | | LEL | BB | Pos(4) |
| SZV-8M | 1 | Tick | Nobivac | 30 May 2010 | 57 | | LEL | BB | Pos(4) |
| SZV-8M | 1 | Tick | Nobivac | 06 Jun. 2010 | 63 | | LEL | BB | Pos(2) |
| SZV-8M | 1 | Tick | Nobivac | 13 Jun. 2010 | 70 | | LEL | BB | Pos(4) |
| SZV-8M | 1 | Tick | Nobivac | 20 Jun. 2010 | 77 | | LEL | BB | Pos(3) |
| SZV-8M | 1 | Tick | Nobivac | 27 Jun. 2010 | 84 | V = 0 | LEL | BB | Pos(3) |
| SZV-8M | 1 | Tick | Nobivac | 04 Jul. 2010 | 92 | 7 | LEL | BB | Pos(3) |
| SZV-8M | 1 | Tick | Nobivac | 11 Jul. 2010 | 98 | 14 | LEL | BB | Pos(4) |
| SZV-8M | 1 | Tick | Nobivac | 18 Jul. 2010 | 105 | 21 | LELV | BB | Pos(4) |
| SZV-8M | 1 | Tick | Nobivac | 01 Aug. 2010 | 119 | 35 | LELV | BB | Pos(4) |
| SZV-8M | 1 | Tick | Nobivac | 08 Aug. 2010 | 126 | 42 | LELV | BB | Pos(4) |
| SZV-8M | 1 | Tick | Nobivac | 15 Aug. 2010 | 133 | 49 | LELV | BB | Pos(4) |
| SZV-8M | 1 | Tick | Nobivac | 22 Aug. 2010 | 140 | 56 | LELV | BB | Pos(4) |
| SZV-8M | 1 | Tick | Nobivac | 29 Aug. 2010 | 147 | 63 | LELV | BB | Pos(4) |
| SZV-8M | 1 | Tick | Nobivac | 05 Sep. 2010 | 154 | 70 | LELV | N/A | N/A |
| WBV-8M | 1 | Tick | Nobivac | 18 Oct. 2009 | | | NEG | | Neg |
| WBV-8M | 1 | Tick | Nobivac | 25 Oct. 2009 | | | NEG | NEG | Neg |
| WBV-8M | 1 | Tick | Nobivac | 31 Oct. 2009 | | | NEG | NEG | Neg |
| WBV-8M | 1 | Tick | Nobivac | 08 Nov. 2009 | | | NEG | NEG | BL |

TABLE 4-continued

Results from Lyme experimental study

| Sample ID | Group | Prim | Vaccine | DOS (CSU) | T = 0 | V = 0 | Accuplex (Lyme) | SNAP | ILISA (Lyme) |
|---|---|---|---|---|---|---|---|---|---|
| WBV-8M | 1 | Tick | Nobivac | 14 Nov. 2009 | | | NEG | NEG | |
| WBV-8M | 1 | Tick | Nobivac | 22 Nov. 2009 | | | NEG | NEG | Neg |
| WBV-8M | 1 | Tick | Nobivac | 27 Nov. 2009 | | | NEG | N/A | N/A |
| WBV-8M | 1 | Tick | Nobivac | 06 Dec. 2009 | | | NEG | NEG | Neg |
| WBV-8M | 1 | Tick | Nobivac | 13 Dec. 2009 | | | NEG | NEG | Neg |
| WBV-8M | 1 | Tick | Nobivac | 03 Jan. 2010 | | | NEG | NEG | Neg |
| WBV-8M | 1 | Tick | Nobivac | 14 Feb. 2010 | | | NEG | N/A | N/A |
| WBV-8M | 1 | Tick | Nobivac | 04 Apr. 2010 | T = 0 | | NEG | NEG | BL |
| WBV-8M | 1 | Tick | Nobivac | 11 Apr. 2010 | 7 | | NEG | NEG | BL |
| WBV-8M | 1 | Tick | Nobivac | 18 Apr. 2010 | 14 | | NEG | NEG | BL |
| WBV-8M | 1 | Tick | Nobivac | 25 Apr. 2010 | 21 | | LEE | NEG | BL |
| WBV-8M | 1 | Tick | Nobivac | 02 May 2010 | 28 | | LEL | BB | Pos(3) |
| WBV-8M | 1 | Tick | Nobivac | 09 May 2010 | 35 | | LEL | BB | Pos(3) |
| WBV-8M | 1 | Tick | Nobivac | 16 May 2010 | 42 | | LEL | BB | Pos(3) |
| WBV-8M | 1 | Tick | Nobivac | 23 May 2010 | 49 | | LEL | BB | Pos(4) |
| WBV-8M | 1 | Tick | Nobivac | 30 May 2010 | 57 | | LEL | BB | Pos(4) |
| WBV-8M | 1 | Tick | Nobivac | 06 Jun. 2010 | 63 | | LEL | BB | Pos(4) |
| WBV-8M | 1 | Tick | Nobivac | 13 Jun. 2010 | 70 | | LEL | BB | Pos(4) |
| WBV-8M | 1 | Tick | Nobivac | 20 Jun. 2010 | 77 | | LEL | BB | Pos(4) |
| WBV-8M | 1 | Tick | Nobivac | 27 Jun. 2010 | 84 | V = 0 | LEL | BB | Pos(4) |
| WBV-8M | 1 | Tick | Nobivac | 04 Jul. 2010 | 92 | 7 | LEL | BB | Pos(4) |
| WBV-8M | 1 | Tick | Nobivac | 11 Jul. 2010 | 98 | 14 | LEL | BB | Pos(4) |
| WBV-8M | 1 | Tick | Nobivac | 18 Jul. 2010 | 105 | 21 | LEL | BB | Pos(4) |
| WBV-8M | 1 | Tick | Nobivac | 01 Aug. 2010 | 119 | 35 | LELV | BB | Pos(4) |
| WBV-8M | 1 | Tick | Nobivac | 08 Aug. 2010 | 126 | 42 | LELV | BB | Pos(4) |
| WBV-8M | 1 | Tick | Nobivac | 15 Aug. 2010 | 133 | 49 | LELV | BB | Pos(4) |
| WBV-8M | 1 | Tick | Nobivac | 22 Aug. 2010 | 140 | 56 | LELV | BB | Pos(4) |
| WBV-8M | 1 | Tick | Nobivac | 29 Aug. 2010 | 147 | 63 | LELV | BB | Pos(4) |
| WBV-8M | 1 | Tick | Nobivac | 05 Sep. 2010 | 154 | 70 | LELV | N/A | N/A |
| DCS-8F | 2 | Vax | Nobivac | 18 Oct. 2009 | | | NEG | | Neg |
| DCS-8F | 2 | Vax | Nobivac | 25 Oct. 2009 | | | NEG | NEG | Neg |
| DCS-8F | 2 | Vax | Nobivac | 31 Oct. 2009 | | V = 0 | NEG | NEG | BL |
| DCS-8F | 2 | Vax | Nobivac | 08 Nov. 2009 | | 8 | PE | NEG | Pos(2) |
| DCS-8F | 2 | Vax | Nobivac | 14 Nov. 2009 | | 14 | LVRN | NEG | |
| DCS-8F | 2 | Vax | Nobivac | 22 Nov. 2009 | | 22 | LVRN | NEG | Pos(2) |
| DCS-8F | 2 | Vax | Nobivac | 27 Nov. 2009 | | 27 | LVRN | N/A | N/A |
| DCS-8F | 2 | Vax | Nobivac | 06 Dec. 2009 | | 36 | LVRN | NEG | Pos(4) |
| DCS-8F | 2 | Vax | Nobivac | 13 Dec. 2009 | | 43 | LVRN | NEG | Pos(3) |
| DCS-8F | 2 | Vax | Nobivac | 20 Dec. 2009 | | 50 | LVRN | NEG | Pos(2) |
| DCS-8F | 2 | Vax | Nobivac | 27 Dec. 2009 | | 57 | LVRN | NEG | Pos(3) |
| DCS-8F | 2 | Vax | Nobivac | 03 Jan. 2010 | | 64 | LVRN | NEG | Pos(2) |
| DCS-8F | 2 | Vax | Nobivac | 10 Jan. 2010 | | 71 | LVRN | N/A | N/A |
| DCS-8F | 2 | Vax | Nobivac | 17 Jan. 2010 | | 78 | LVRN | N/A | N/A |
| DCS-8F | 2 | Vax | Nobivac | 24 Jan. 2010 | | 85 | LVRN | N/A | N/A |
| DCS-8F | 2 | Vax | Nobivac | 31 Jan. 2010 | | 92 | LVRN | N/A | N/A |
| DCS-8F | 2 | Vax | Nobivac | 07 Feb. 2010 | | 99 | LVRN | N/A | N/A |
| DCS-8F | 2 | Vax | Nobivac | 14 Feb. 2010 | | 106 | LVRN | N/A | N/A |
| DCS-8F | 2 | Vax | Nobivac | 21 Feb. 2010 | | 113 | LVR | N/A | N/A |
| DCS-8F | 2 | Vax | Nobivac | 28 Feb. 2010 | | 120 | NEG | N/A | N/A |
| DCS-8F | 2 | Vax | Nobivac | 07 Mar. 2010 | | 127 | NEG | N/A | N/A |
| DCS-8F | 2 | Vax | Nobivac | 14 Mar. 2010 | | 134 | LVR | N/A | N/A |
| DCS-8F | 2 | Vax | Nobivac | 21 Mar. 2010 | | 141 | LVR | N/A | N/A |
| DCS-8F | 2 | Vax | Nobivac | 28 Mar. 2010 | | 148 | NEG | N/A | N/A |
| DCS-8F | 2 | Vax | Nobivac | 04 Apr. 2010 | T = 0 | 155 | LVR | NEG | Pos(3) |
| DCS-8F | 2 | Vax | Nobivac | 11 Apr. 2010 | 7 | 162 | LVR | NEG | Pos(2) |
| DCS-8F | 2 | Vax | Nobivac | 18 Apr. 2010 | 14 | 169 | LVR | NEG | Pos(2) |
| DCS-8F | 2 | Vax | Nobivac | 25 Apr. 2010 | 21 | 176 | NEG | NEG | Pos(3) |
| DCS-8F | 2 | Vax | Nobivac | 02 May 2010 | 28 | 183 | LVR | NEG | Pos(2) |
| DCS-8F | 2 | Vax | Nobivac | 09 May 2010 | 35 | 190 | NEG | NEG | Pos(2) |
| DCS-8F | 2 | Vax | Nobivac | 16 May 2010 | 42 | 197 | NEG | NEG | BL |
| DCS-8F | 2 | Vax | Nobivac | 23 May 2010 | 49 | 204 | LVR | NEG | Pos(2) |
| DCS-8F | 2 | Vax | Nobivac | 30 May 2010 | 57 | 211 | LVR | NEG | Pos(2) |
| DCS-8F | 2 | Vax | Nobivac | 06 Jun. 2010 | 63 | 218 | LVR | NEG | BL |
| DCS-8F | 2 | Vax | Nobivac | 13 Jun. 2010 | 70 | 225 | NEG | NEG | Pos(2) |
| DCS-8F | 2 | Vax | Nobivac | 20 Jun. 2010 | 77 | 232 | NEG | NEG | Pos(2) |
| DCS-8F | 2 | Vax | Nobivac | 27 Jun. 2010 | 84 | 239 | NEG | NEG | BL |
| DCS-8F | 2 | Vax | Nobivac | 04 Jul. 2010 | 92 | 246 | NEG | NEG | Pos(2) |
| DCS-8F | 2 | Vax | Nobivac | 11 Jul. 2010 | 98 | 253 | NEG | NEG | Pos(2) |
| DCS-8F | 2 | Vax | Nobivac | 18 Jul. 2010 | 105 | 260 | NEG | NEG | Pos(2) |
| DCS-8F | 2 | Vax | Nobivac | 25 Jul. 2010 | 112 | 267 | NEG | N/A | N/A |
| DCS-8F | 2 | Vax | Nobivac | 01 Aug. 2010 | 119 | 274 | NEG | NEG | BL |
| DCS-8F | 2 | Vax | Nobivac | 08 Aug. 2010 | 126 | 281 | NEG | NEG | Pos(2) |
| EUS-8F | 2 | Vax | Nobivac | 18 Oct. 2009 | | | NEG | | Neg |
| EUS-8F | 2 | Vax | Nobivac | 25 Oct. 2009 | | | NEG | NEG | Neg |
| EUS-8F | 2 | Vax | Nobivac | 31 Oct. 2009 | | V = 0 | NEG | N/A | N/A |

TABLE 4-continued

Results from Lyme experimental study

| Sample ID | Group | Prim | Vaccine | DOS (CSU) | T = 0 | V = 0 | Accuplex (Lyme) | SNAP | ILISA (Lyme) |
|---|---|---|---|---|---|---|---|---|---|
| EUS-8F | 2 | Vax | Nobivac | 08 Nov. 2009 | | 8 | PE | NEG | Pos(3) |
| EUS-8F | 2 | Vax | Nobivac | 14 Nov. 2009 | | 14 | PE | NEG | |
| EUS-8F | 2 | Vax | Nobivac | 22 Nov. 2009 | | 22 | PE | NEG | BL |
| EUS-8F | 2 | Vax | Nobivac | 27 Nov. 2009 | | 27 | PE | N/A | N/A |
| EUS-8F | 2 | Vax | Nobivac | 06 Dec. 2009 | | 36 | LVRN | NEG | Pos(3) |
| EUS-8F | 2 | Vax | Nobivac | 13 Dec. 2009 | | 43 | LVRN | NEG | Pos(2) |
| EUS-8F | 2 | Vax | Nobivac | 20 Dec. 2009 | | 50 | LVRN | NEG | Pos(2) |
| EUS-8F | 2 | Vax | Nobivac | 27 Dec. 2009 | | 57 | LVRN | N/A | N/A |
| EUS-8F | 2 | Vax | Nobivac | 03 Jan. 2010 | | 64 | LVR | NEG | Pos(2) |
| EUS-8F | 2 | Vax | Nobivac | 10 Jan. 2010 | | 71 | LVR | N/A | N/A |
| EUS-8F | 2 | Vax | Nobivac | 17 Jan. 2010 | | 78 | LVR | N/A | N/A |
| EUS-8F | 2 | Vax | Nobivac | 24 Jan. 2010 | | 85 | LVR | N/A | N/A |
| EUS-8F | 2 | Vax | Nobivac | 31 Jan. 2010 | | 92 | LVR | N/A | N/A |
| EUS-8F | 2 | Vax | Nobivac | 07 Feb. 2010 | | 99 | LVR | N/A | N/A |
| EUS-8F | 2 | Vax | Nobivac | 14 Feb. 2010 | | 106 | LVR | N/A | N/A |
| EUS-8F | 2 | Vax | Nobivac | 21 Feb. 2010 | | 113 | LVR | N/A | N/A |
| EUS-8F | 2 | Vax | Nobivac | 28 Feb. 2010 | | 120 | LVR | N/A | N/A |
| EUS-8F | 2 | Vax | Nobivac | 07 Mar. 2010 | | 127 | LVR | N/A | N/A |
| EUS-8F | 2 | Vax | Nobivac | 14 Mar. 2010 | | 134 | LVR | N/A | N/A |
| EUS-8F | 2 | Vax | Nobivac | 21 Mar. 2010 | | 141 | LVR | N/A | N/A |
| EUS-8F | 2 | Vax | Nobivac | 28 Mar. 2010 | | 148 | LVR | N/A | N/A |
| EUS-8F | 2 | Vax | Nobivac | 04 Apr. 2010 | T = 0 | 155 | LVR | NEG | Pos(3) |
| EUS-8F | 2 | Vax | Nobivac | 11 Apr. 2010 | 7 | 162 | LVR | NEG | Pos(3) |
| EUS-8F | 2 | Vax | Nobivac | 18 Apr. 2010 | 14 | 169 | LVR | NEG | Pos(4) |
| EUS-8F | 2 | Vax | Nobivac | 25 Apr. 2010 | 21 | 176 | LEEV | BB, AP | Pos(4) |
| EUS-8F | 2 | Vax | Nobivac | 02 May 2010 | 28 | 183 | LELV | BB, AP | Pos(4) |
| EUS-8F | 2 | Vax | Nobivac | 09 May 2010 | 35 | 190 | LELV | BB, AP | Pos(4) |
| EUS-8F | 2 | Vax | Nobivac | 16 May 2010 | 42 | 197 | LELV | BB, AP | Pos(3) |
| EUS-8F | 2 | Vax | Nobivac | 23 May 2010 | 49 | 204 | LELV | BB, AP | Pos(4) |
| EUS-8F | 2 | Vax | Nobivac | 30 May 2010 | 57 | 211 | LELV | BB, AP | Pos(4) |
| EUS-8F | 2 | Vax | Nobivac | 06 Jun. 2010 | 63 | 218 | LELV | BB, AP | Pos(4) |
| EUS-8F | 2 | Vax | Nobivac | 13 Jun. 2010 | 70 | 225 | LELV | BB, AP | Pos(4) |
| EUS-8F | 2 | Vax | Nobivac | 20 Jun. 2010 | 77 | 232 | LELV | BB, AP | Pos(4) |
| EUS-8F | 2 | Vax | Nobivac | 27 Jun. 2010 | 84 | 239 | LELV | BB, AP | Pos(4) |
| EUS-8F | 2 | Vax | Nobivac | 04 Jul. 2010 | 92 | 246 | LEL | BB, AP | Pos(4) |
| EUS-8F | 2 | Vax | Nobivac | 11 Jul. 2010 | 98 | 253 | LELV | BB, AP | Pos(4) |
| EUS-8F | 2 | Vax | Nobivac | 18 Jul. 2010 | 105 | 260 | LEL | BB, AP | Pos(4) |
| EUS-8F | 2 | Vax | Nobivac | 25 Jul. 2010 | 112 | 267 | LELV | N/A | N/A |
| EUS-8F | 2 | Vax | Nobivac | 01 Aug. 2010 | 119 | 274 | LEL | BB, AP | Pos(4) |
| EUS-8F | 2 | Vax | Nobivac | 08 Aug. 2010 | 126 | 281 | LEL | BB, AP | Pos(4) |
| KYV-8M | 2 | Vax | Nobivac | 18 Oct. 2009 | | | NEG | | Neg |
| KYV-8M | 2 | Vax | Nobivac | 25 Oct. 2009 | | | NEG | N/A | N/A |
| KYV-8M | 2 | Vax | Nobivac | 31 Oct. 2009 | | V = 0 | NEG | NEG | Neg |
| KYV-8M | 2 | Vax | Nobivac | 08 Nov. 2009 | | 8 | PE | NEG | Pos(2) |
| KYV-8M | 2 | Vax | Nobivac | 14 Nov. 2009 | | 14 | LVRN | NEG | |
| KYV-8M | 2 | Vax | Nobivac | 22 Nov. 2009 | | 22 | LVRN | NEG | Pos(2) |
| KYV-8M | 2 | Vax | Nobivac | 27 Nov. 2009 | | 27 | LVRN | N/A | N/A |
| KYV-8M | 2 | Vax | Nobivac | 06 Dec. 2009 | | 36 | LVRN | NEG | Pos(3) |
| KYV-8M | 2 | Vax | Nobivac | 13 Dec. 2009 | | 43 | LVRN | NEG | Pos(3) |
| KYV-8M | 2 | Vax | Nobivac | 20 Dec. 2009 | | 50 | LVRN | NEG | BL |
| KYV-8M | 2 | Vax | Nobivac | 27 Dec. 2009 | | 57 | LVRN | N/A | N/A |
| KYV-8M | 2 | Vax | Nobivac | 03 Jan. 2010 | | 64 | LVRN | NEG | Pos(2) |
| KYV-8M | 2 | Vax | Nobivac | 10 Jan. 2010 | | 71 | LVRN | N/A | N/A |
| KYV-8M | 2 | Vax | Nobivac | 17 Jan. 2010 | | 78 | LVRN | N/A | N/A |
| KYV-8M | 2 | Vax | Nobivac | 24 Jan. 2010 | | 85 | LVRN | N/A | N/A |
| KYV-8M | 2 | Vax | Nobivac | 31 Jan. 2010 | | 92 | NEG | N/A | N/A |
| KYV-8M | 2 | Vax | Nobivac | 07 Feb. 2010 | | 99 | NEG | N/A | N/A |
| KYV-8M | 2 | Vax | Nobivac | 14 Feb. 2010 | | 106 | NEG | N/A | N/A |
| KYV-8M | 2 | Vax | Nobivac | 21 Feb. 2010 | | 113 | NEG | N/A | N/A |
| KYV-8M | 2 | Vax | Nobivac | 28 Feb. 2010 | | 120 | NEG | N/A | N/A |
| KYV-8M | 2 | Vax | Nobivac | 07 Mar. 2010 | | 127 | NEG | N/A | N/A |
| KYV-8M | 2 | Vax | Nobivac | 14 Mar. 2010 | | 134 | NEG | N/A | N/A |
| KYV-8M | 2 | Vax | Nobivac | 21 Mar. 2010 | | 141 | NEG | N/A | N/A |
| KYV-8M | 2 | Vax | Nobivac | 28 Mar. 2010 | | 148 | NEG | N/A | N/A |
| KYV-8M | 2 | Vax | Nobivac | 04 Apr. 2010 | T = 0 | 155 | NEG | NEG | Pos(2) |
| KYV-8M | 2 | Vax | Nobivac | 11 Apr. 2010 | 7 | 162 | NEG | NEG | BL |
| KYV-8M | 2 | Vax | Nobivac | 18 Apr. 2010 | 14 | 169 | NEG | NEG | Pos(2) |
| KYV-8M | 2 | Vax | Nobivac | 25 Apr. 2010 | 21 | 176 | LEE | NEG | Pos(3) |
| KYV-8M | 2 | Vax | Nobivac | 02 May 2010 | 28 | 183 | LEE | BB, AP | Pos(4) |
| KYV-8M | 2 | Vax | Nobivac | 09 May 2010 | 35 | 190 | LEE | BB, AP | Pos(3) |
| KYV-8M | 2 | Vax | Nobivac | 16 May 2010 | 42 | 197 | LEL | BB, AP | Pos(3) |
| KYV-8M | 2 | Vax | Nobivac | 23 May 2010 | 49 | 204 | LEL | AP | Pos(4) |
| KYV-8M | 2 | Vax | Nobivac | 30 May 2010 | 57 | 211 | LEL | BB, AP | Pos(4) |
| KYV-8M | 2 | Vax | Nobivac | 06 Jun. 2010 | 63 | 218 | LEL | BB, AP | Pos(4) |
| KYV-8M | 2 | Vax | Nobivac | 13 Jun. 2010 | 70 | 225 | LEL | BB, AP | Pos(4) |

TABLE 4-continued

Results from Lyme experimental study

| Sample ID | Group | Prim | Vaccine | DOS (CSU) | T = 0 | V = 0 | Accuplex (Lyme) | SNAP | ILISA (Lyme) |
|---|---|---|---|---|---|---|---|---|---|
| KYV-8M | 2 | Vax | Nobivac | 20 Jun. 2010 | 77 | 232 | LEL | BB, AP | Pos(4) |
| KYV-8M | 2 | Vax | Nobivac | 27 Jun. 2010 | 84 | 239 | LEL | BB, AP | Pos(4) |
| KYV-8M | 2 | Vax | Nobivac | 04 Jul. 2010 | 92 | 246 | LEL | BB, AP | Pos(4) |
| KYV-8M | 2 | Vax | Nobivac | 11 Jul. 2010 | 98 | 253 | LEL | AP | Pos(4) |
| KYV-8M | 2 | Vax | Nobivac | 18 Jul. 2010 | 105 | 260 | LEL | AP | Pos(4) |
| KYV-8M | 2 | Vax | Nobivac | 25 Jul. 2010 | 112 | 267 | LEL | N/A | N/A |
| KYV-8M | 2 | Vax | Nobivac | 01 Aug. 2010 | 119 | 274 | LEL | AP | Pos(4) |
| KYV-8M | 2 | Vax | Nobivac | 08 Aug. 2010 | 126 | 281 | LEL | BB, AP | Pos(3) |
| TGV-8M | 2 | Vax | Nobivac | 18 Oct. 2009 | | | NEG | | Neg |
| TGV-8M | 2 | Vax | Nobivac | 25 Oct. 2009 | | | NEG | NEG | Neg |
| TGV-8M | 2 | Vax | Nobivac | 31 Oct. 2009 | | V = 0 | NEG | NEG | Neg |
| TGV-8M | 2 | Vax | Nobivac | 08 Nov. 2009 | | 8 | PE | NEG | Pos(2) |
| TGV-8M | 2 | Vax | Nobivac | 14 Nov. 2009 | | 14 | PE | N/A | N/A |
| TGV-8M | 2 | Vax | Nobivac | 22 Nov. 2009 | | 22 | LVRN | N/A | N/A |
| TGV-8M | 2 | Vax | Nobivac | 27 Nov. 2009 | | 27 | LVR | N/A | N/A |
| TGV-8M | 2 | Vax | Nobivac | 06 Dec. 2009 | | 36 | LVRN | NEG | Pos(3) |
| TGV-8M | 2 | Vax | Nobivac | 13 Dec. 2009 | | 43 | LVRN | NEG | Pos(3) |
| TGV-8M | 2 | Vax | Nobivac | 20 Dec. 2009 | | 50 | LVRN | NEG | Pos(2) |
| TGV-8M | 2 | Vax | Nobivac | 27 Dec. 2009 | | 57 | LVRN | N/A | N/A |
| TGV-8M | 2 | Vax | Nobivac | 03 Jan. 2010 | | 64 | LVRN | NEG | Pos(2) |
| TGV-8M | 2 | Vax | Nobivac | 10 Jan. 2010 | | 71 | LVRN | N/A | N/A |
| TGV-8M | 2 | Vax | Nobivac | 17 Jan. 2010 | | 78 | LVRN | N/A | N/A |
| TGV-8M | 2 | Vax | Nobivac | 24 Jan. 2010 | | 85 | PE | N/A | N/A |
| TGV-8M | 2 | Vax | Nobivac | 31 Jan. 2010 | | 92 | NEG | N/A | N/A |
| TGV-8M | 2 | Vax | Nobivac | 07 Feb. 2010 | | 99 | NEG | N/A | N/A |
| TGV-8M | 2 | Vax | Nobivac | 14 Feb. 2010 | | 106 | NEG | N/A | N/A |
| TGV-8M | 2 | Vax | Nobivac | 21 Feb. 2010 | | 113 | NEG | N/A | N/A |
| TGV-8M | 2 | Vax | Nobivac | 28 Feb. 2010 | | 120 | NEG | N/A | N/A |
| TGV-8M | 2 | Vax | Nobivac | 07 Mar. 2010 | | 127 | NEG | N/A | N/A |
| TGV-8M | 2 | Vax | Nobivac | 14 Mar. 2010 | | 134 | NEG | N/A | N/A |
| TGV-8M | 2 | Vax | Nobivac | 21 Mar. 2010 | | 141 | NEG | N/A | N/A |
| TGV-8M | 2 | Vax | Nobivac | 28 Mar. 2010 | | 148 | LVR | N/A | N/A |
| TGV-8M | 2 | Vax | Nobivac | 04 Apr. 2010 | T = 0 | 155 | NEG | NEG | Pos(3) |
| TGV-8M | 2 | Vax | Nobivac | 11 Apr. 2010 | 7 | 162 | NEG | NEG | BL |
| TGV-8M | 2 | Vax | Nobivac | 18 Apr. 2010 | 14 | 169 | NEG | NEG | Pos(2) |
| TGV-8M | 2 | Vax | Nobivac | 25 Apr. 2010 | 21 | 176 | LEE | NEG | Pos(3) |
| TGV-8M | 2 | Vax | Nobivac | 02 May 2010 | 28 | 183 | LEE | NEG | Pos(4) |
| TGV-8M | 2 | Vax | Nobivac | 09 May 2010 | 35 | 190 | LEE | AP | Pos(3) |
| TGV-8M | 2 | Vax | Nobivac | 16 May 2010 | 42 | 197 | LEE | BB, AP | Pos(3) |
| TGV-8M | 2 | Vax | Nobivac | 23 May 2010 | 49 | 204 | LEL | BB, AP | Pos(4) |
| TGV-8M | 2 | Vax | Nobivac | 30 May 2010 | 57 | 211 | LEL | BB, AP | Pos(4) |
| TGV-8M | 2 | Vax | Nobivac | 06 Jun. 2010 | 63 | 218 | LEL | BB, AP | Pos(3) |
| TGV-8M | 2 | Vax | Nobivac | 13 Jun. 2010 | 70 | 225 | LEL | BB, AP | Pos(4) |
| TGV-8M | 2 | Vax | Nobivac | 20 Jun. 2010 | 77 | 232 | LEL | BB, AP | Pos(4) |
| TGV-8M | 2 | Vax | Nobivac | 27 Jun. 2010 | 84 | 239 | LEL | BB, AP | Pos(3) |
| TGV-8M | 2 | Vax | Nobivac | 04 Jul. 2010 | 92 | 246 | LEL | BB, AP | Pos(4) |
| TGV-8M | 2 | Vax | Nobivac | 11 Jul. 2010 | 98 | 253 | LEL | BB, AP | Pos(4) |
| TGV-8M | 2 | Vax | Nobivac | 18 Jul. 2010 | 105 | 260 | LELV | BB, AP | Pos(4) |
| TGV-8M | 2 | Vax | Nobivac | 25 Jul. 2010 | 112 | 267 | LEL | N/A | N/A |
| TGV-8M | 2 | Vax | Nobivac | 01 Aug. 2010 | 119 | 274 | LEL | BB, AP | Pos(4) |
| TGV-8M | 2 | Vax | Nobivac | 08 Aug. 2010 | 126 | 281 | LEL | BB, AP | Pos(4) |
| THU-8F | 2 | Vax | Nobivac | 18 Oct. 2009 | | | NEG | | Neg |
| THU-8F | 2 | Vax | Nobivac | 25 Oct. 2009 | | | NEG | NEG | Neg |
| THU-8F | 2 | Vax | Nobivac | 31 Oct. 2009 | | V = 0 | NEG | NEG | Neg |
| THU-8F | 2 | Vax | Nobivac | 08 Nov. 2009 | | 8 | PE | NEG | Pos(2) |
| THU-8F | 2 | Vax | Nobivac | 14 Nov. 2009 | | 14 | PE | NEG | |
| THU-8F | 2 | Vax | Nobivac | 22 Nov. 2009 | | 22 | PE | NEG | Pos(2) |
| THU-8F | 2 | Vax | Nobivac | 27 Nov. 2009 | | 27 | PE | N/A | N/A |
| THU-8F | 2 | Vax | Nobivac | 06 Dec. 2009 | | 36 | LVRN | NEG | Pos(3) |
| THU-8F | 2 | Vax | Nobivac | 13 Dec. 2009 | | 43 | LV-PE | NEG | Pos(3) |
| THU-8F | 2 | Vax | Nobivac | 20 Dec. 2009 | | 50 | LVRN | NEG | Pos(2) |
| THU-8F | 2 | Vax | Nobivac | 27 Dec. 2009 | | 57 | LVRN | NEG | Pos(2) |
| THU-8F | 2 | Vax | Nobivac | 03 Jan. 2010 | | 64 | LVR | NEG | Pos(2) |
| THU-8F | 2 | Vax | Nobivac | 10 Jan. 2010 | | 71 | LVR | N/A | N/A |
| THU-8F | 2 | Vax | Nobivac | 17 Jan. 2010 | | 78 | LVR | N/A | N/A |
| THU-8F | 2 | Vax | Nobivac | 24 Jan. 2010 | | 85 | LVR | N/A | N/A |
| THU-8F | 2 | Vax | Nobivac | 31 Jan. 2010 | | 92 | LVR | N/A | N/A |
| THU-8F | 2 | Vax | Nobivac | 07 Feb. 2010 | | 99 | LVR | N/A | N/A |
| THU-8F | 2 | Vax | Nobivac | 14 Feb. 2010 | | 106 | LVR | N/A | N/A |
| THU-8F | 2 | Vax | Nobivac | 21 Feb. 2010 | | 113 | LVR | N/A | N/A |
| THU-8F | 2 | Vax | Nobivac | 28 Feb. 2010 | | 120 | LVR | N/A | N/A |
| THU-8F | 2 | Vax | Nobivac | 07 Mar. 2010 | | 127 | LVR | N/A | N/A |
| THU-8F | 2 | Vax | Nobivac | 14 Mar. 2010 | | 134 | LVR | N/A | N/A |
| THU-8F | 2 | Vax | Nobivac | 21 Mar. 2010 | | 141 | LVR | N/A | N/A |
| THU-8F | 2 | Vax | Nobivac | 28 Mar. 2010 | | 148 | LVR | N/A | N/A |

TABLE 4-continued

Results from Lyme experimental study

| Sample ID | Group | Prim | Vaccine | DOS (CSU) | T = 0 | V = 0 | Accuplex (Lyme) | SNAP | ILISA (Lyme) |
|---|---|---|---|---|---|---|---|---|---|
| THU-8F | 2 | Vax | Nobivac | 04 Apr. 2010 | T = 0 | 155 | LVR | NEG | Pos(3) |
| THU-8F | 2 | Vax | Nobivac | 11 Apr. 2010 | 7 | 162 | LVR | NEG | Pos(2) |
| THU-8F | 2 | Vax | Nobivac | 18 Apr. 2010 | 14 | 169 | LVR | NEG | Pos(3) |
| THU-8F | 2 | Vax | Nobivac | 25 Apr. 2010 | 21 | 176 | LVRN | NEG | Pos(4) |
| THU-8F | 2 | Vax | Nobivac | 02 May 2010 | 28 | 183 | LVRN | NEG | Pos(4) |
| THU-8F | 2 | Vax | Nobivac | 09 May 2010 | 35 | 190 | LELV | BB | Pos(3) |
| THU-8F | 2 | Vax | Nobivac | 16 May 2010 | 42 | 197 | LELV | BB | Pos(3) |
| THU-8F | 2 | Vax | Nobivac | 23 May 2010 | 49 | 204 | LELV | BB | Pos(4) |
| THU-8F | 2 | Vax | Nobivac | 30 May 2010 | 57 | 211 | LELV | BB | Pos(4) |
| THU-8F | 2 | Vax | Nobivac | 06 Jun. 2010 | 63 | 218 | LELV | BB | Pos(4) |
| THU-8F | 2 | Vax | Nobivac | 13 Jun. 2010 | 70 | 225 | LEL | BB | Pos(4) |
| THU-8F | 2 | Vax | Nobivac | 20 Jun. 2010 | 77 | 232 | LEL | BB | Pos(4) |
| THU-8F | 2 | Vax | Nobivac | 27 Jun. 2010 | 84 | 239 | LELV | BB | Pos(3) |
| THU-8F | 2 | Vax | Nobivac | 04 Jul. 2010 | 92 | 246 | LELV | BB | Pos(4) |
| THU-8F | 2 | Vax | Nobivac | 11 Jul. 2010 | 98 | 253 | LEL | BB | Pos(4) |
| THU-8F | 2 | Vax | Nobivac | 18 Jul. 2010 | 105 | 260 | LELV | BB | Pos(4) |
| THU-8F | 2 | Vax | Nobivac | 25 Jul. 2010 | 112 | 267 | LELV | N/A | N/A |
| THU-8F | 2 | Vax | Nobivac | 01 Aug. 2010 | 119 | 274 | LELV | BB | Pos(4) |
| THU-8F | 2 | Vax | Nobivac | 08 Aug. 2010 | 126 | 281 | LELV | BB | Pos(4) |
| WIT-8M | 2 | Vax | Nobivac | 25 Oct. 2009 | | | NEG | NEG | Neg |
| WIT-8M | 2 | Vax | Nobivac | 31 Oct. 2009 | | V = 0 | NEG | NEG | Neg |
| WIT-8M | 2 | Vax | Nobivac | 08 Nov. 2009 | | 8 | PE | NEG | Pos(3) |
| WIT-8M | 2 | Vax | Nobivac | 14 Nov. 2009 | | 14 | NEG | NEG | |
| WIT-8M | 2 | Vax | Nobivac | 22 Nov. 2009 | | 22 | LVRN | NEG | Pos(3) |
| WIT-8M | 2 | Vax | Nobivac | 27 Nov. 2009 | | 27 | LVRN | N/A | N/A |
| WIT-8M | 2 | Vax | Nobivac | 06 Dec. 2009 | | 36 | LVRN | NEG | Pos(3) |
| WIT-8M | 2 | Vax | Nobivac | 13 Dec. 2009 | | 43 | LVRN | NEG | Pos(3) |
| WIT-8M | 2 | Vax | Nobivac | 20 Dec. 2009 | | 50 | LVRN | NEG | Pos(2) |
| WIT-8M | 2 | Vax | Nobivac | 27 Dec. 2009 | | 57 | LVRN | NEG | Pos(3) |
| WIT-8M | 2 | Vax | Nobivac | 03 Jan. 2010 | | 64 | LVRN | NEG | Pos(3) |
| WIT-8M | 2 | Vax | Nobivac | 10 Jan. 2010 | | 71 | LVRN | N/A | N/A |
| WIT-8M | 2 | Vax | Nobivac | 17 Jan. 2010 | | 78 | LVRN | N/A | N/A |
| WIT-8M | 2 | Vax | Nobivac | 24 Jan. 2010 | | 85 | LVRN | N/A | N/A |
| WIT-8M | 2 | Vax | Nobivac | 31 Jan. 2010 | | 92 | LVRN | N/A | N/A |
| WIT-8M | 2 | Vax | Nobivac | 07 Feb. 2010 | | 99 | LVRN | N/A | N/A |
| WIT-8M | 2 | Vax | Nobivac | 14 Feb. 2010 | | 106 | LVRN | N/A | N/A |
| WIT-8M | 2 | Vax | Nobivac | 21 Feb. 2010 | | 113 | LVRN | N/A | N/A |
| WIT-8M | 2 | Vax | Nobivac | 28 Feb. 2010 | | 120 | LVRN | N/A | N/A |
| WIT-8M | 2 | Vax | Nobivac | 07 Mar. 2010 | | 127 | LVRN | N/A | N/A |
| WIT-8M | 2 | Vax | Nobivac | 14 Mar. 2010 | | 134 | LVRN | N/A | N/A |
| WIT-8M | 2 | Vax | Nobivac | 21 Mar. 2010 | | 141 | LVRN | N/A | N/A |
| WIT-8M | 2 | Vax | Nobivac | 28 Mar. 2010 | | 148 | LVRN | N/A | N/A |
| WIT-8M | 2 | Vax | Nobivac | 04 Apr. 2010 | T = 0 | 155 | LVRN | NEG | Pos(3) |
| WIT-8M | 2 | Vax | Nobivac | 11 Apr. 2010 | 7 | 162 | LVRN | NEG | Pos(2) |
| WIT-8M | 2 | Vax | Nobivac | 18 Apr. 2010 | 14 | 169 | LVRN | NEG | Pos(3) |
| WIT-8M | 2 | Vax | Nobivac | 25 Apr. 2010 | 21 | 176 | LEEV | BB, AP | Pos(4) |
| WIT-8M | 2 | Vax | Nobivac | 02 May 2010 | 28 | 183 | LEEV | BB, AP | Pos(4) |
| WIT-8M | 2 | Vax | Nobivac | 09 May 2010 | 35 | 190 | LEEV | BB, AP | Pos(4) |
| WIT-8M | 2 | Vax | Nobivac | 16 May 2010 | 42 | 197 | LELV | BB, AP | Pos(4) |
| WIT-8M | 2 | Vax | Nobivac | 23 May 2010 | 49 | 204 | LELV | BB, AP | Pos(4) |
| WIT-8M | 2 | Vax | Nobivac | 30 May 2010 | 57 | 211 | LELV | BB, AP | Pos(4) |
| WIT-8M | 2 | Vax | Nobivac | 06 Jun. 2010 | 63 | 218 | LELV | BB, AP | Pos(4) |
| WIT-8M | 2 | Vax | Nobivac | 13 Jun. 2010 | 70 | 225 | LELV | BB, AP | Pos(4) |
| WIT-8M | 2 | Vax | Nobivac | 20 Jun. 2010 | 77 | 232 | LELV | BB, AP | Pos(4) |
| WIT-8M | 2 | Vax | Nobivac | 27 Jun. 2010 | 84 | 239 | LELV | BB, AP | Pos(4) |
| WIT-8M | 2 | Vax | Nobivac | 04 Jul. 2010 | 92 | 246 | LELV | BB, AP | Pos(4) |
| WIT-8M | 2 | Vax | Nobivac | 11 Jul. 2010 | 98 | 253 | LELV | BB, AP | Pos(4) |
| WIT-8M | 2 | Vax | Nobivac | 18 Jul. 2010 | 105 | 260 | LELV | BB, AP | Pos(4) |
| WIT-8M | 2 | Vax | Nobivac | 25 Jul. 2010 | 112 | 267 | LELV | N/A | N/A |
| WIT-8M | 2 | Vax | Nobivac | 01 Aug. 2010 | 119 | 274 | LELV | BB | Pos(4) |
| WIT-8M | 2 | Vax | Nobivac | 08 Aug. 2010 | 126 | 281 | LELV | BB, AP | Pos(4) |
| DDS-8F | 3 | Tick | LymeVax | 18 Oct. 2009 | | | NEG | N/A | N/A |
| DDS-8F | 3 | Tick | LymeVax | 25 Oct. 2009 | | | NEG | NEG | Neg |
| DDS-8F | 3 | Tick | LymeVax | 08 Nov. 2009 | | | NEG | NEG | Neg |
| DDS-8F | 3 | Tick | LymeVax | 14 Nov. 2009 | | | NEG | NEG | |
| DDS-8F | 3 | Tick | LymeVax | 22 Nov. 2009 | | | NEG | NEG | Neg |
| DDS-8F | 3 | Tick | LymeVax | 27 Nov. 2009 | | | NEG | N/A | N/A |
| DDS-8F | 3 | Tick | LymeVax | 06 Dec. 2009 | | | NEG | NEG | Neg |
| DDS-8F | 3 | Tick | LymeVax | 13 Dec. 2009 | | | NEG | NEG | Neg |
| DDS-8F | 3 | Tick | LymeVax | 03 Jan. 2010 | | | NEG | NEG | Neg |
| DDS-8F | 3 | Tick | LymeVax | 14 Feb. 2010 | | | NEG | N/A | N/A |
| DDS-8F | 3 | Tick | LymeVax | 11 Apr. 2010 | T = 0 | | NEG | NEG | Pos(4) |
| DDS-8F | 3 | Tick | LymeVax | 18 Apr. 2010 | 7 | | NEG | NEG | Neg |
| DDS-8F | 3 | Tick | LymeVax | 25 Apr. 2010 | 14 | | NEG | NEG | Neg |
| DDS-8F | 3 | Tick | LymeVax | 02 May 2010 | 21 | | LEE | NEG | Pos(3) |

TABLE 4-continued

Results from Lyme experimental study

| Sample ID | Group | Prim | Vaccine | DOS (CSU) | T = 0 | V = 0 | Accuplex (Lyme) | SNAP | ILISA (Lyme) |
|---|---|---|---|---|---|---|---|---|---|
| DDS-8F | 3 | Tick | LymeVax | 09 May 2010 | 28 | | LEE | BB | Pos(3) |
| DDS-8F | 3 | Tick | LymeVax | 16 May 2010 | 35 | | LEE | BB | Pos(3) |
| DDS-8F | 3 | Tick | LymeVax | 23 May 2010 | 42 | | LEL | BB | Pos(4) |
| DDS-8F | 3 | Tick | LymeVax | 30 May 2010 | 49 | | LEL | BB | Pos(4) |
| DDS-8F | 3 | Tick | LymeVax | 06 Jun. 2010 | 56 | | LEL | BB | Pos(3) |
| DDS-8F | 3 | Tick | LymeVax | 13 Jun. 2010 | 63 | | LEL | BB | Pos(4) |
| DDS-8F | 3 | Tick | LymeVax | 20 Jun. 2010 | 70 | | LEL | BB | Pos(4) |
| DDS-8F | 3 | Tick | LymeVax | 27 Jun. 2010 | 77 | | LEL | BB | Pos(4) |
| DDS-8F | 3 | Tick | LymeVax | 04 Jul. 2010 | 84 | V = 0 | LEL | BB | Pos(4) |
| DDS-8F | 3 | Tick | LymeVax | 11 Jul. 2010 | 91 | 7 | LEL | BB | Pos(4) |
| DDS-8F | 3 | Tick | LymeVax | 18 Jul. 2010 | 98 | 14 | LELV | BB | Pos(4) |
| DDS-8F | 3 | Tick | LymeVax | 01 Aug. 2010 | 112 | 28 | LELV | BB | Pos(4) |
| DDS-8F | 3 | Tick | LymeVax | 08 Aug. 2010 | 119 | 35 | LELV | BB | Pos(4) |
| DDS-8F | 3 | Tick | LymeVax | 15 Aug. 2010 | 126 | 42 | LELV | BB | Pos(4) |
| DDS-8F | 3 | Tick | LymeVax | 22 Aug. 2010 | 133 | 49 | LELV | BB | Pos(4) |
| DDS-8F | 3 | Tick | LymeVax | 29 Aug. 2010 | 140 | 56 | LELV | BB | Pos(4) |
| DDS-8F | 3 | Tick | LymeVax | 05 Sep. 2010 | 147 | 63 | LELV | N/A | N/A |
| EZS-8F | 3 | Tick | LymeVax | 18 Oct. 2009 | | | NEG | N/A | N/A |
| EZS-8F | 3 | Tick | LymeVax | 25 Oct. 2009 | | | NEG | NEG | Neg |
| EZS-8F | 3 | Tick | LymeVax | 08 Nov. 2009 | | | NEG | NEG | Neg |
| EZS-8F | 3 | Tick | LymeVax | 14 Nov. 2009 | | | NEG | NEG | |
| EZS-8F | 3 | Tick | LymeVax | 22 Nov. 2009 | | | NEG | NEG | Neg |
| EZS-8F | 3 | Tick | LymeVax | 27 Nov. 2009 | | | NEG | N/A | N/A |
| EZS-8F | 3 | Tick | LymeVax | 06 Dec. 2009 | | | NEG | NEG | Pos(3) |
| EZS-8F | 3 | Tick | LymeVax | 13 Dec. 2009 | | | NEG | NEG | Neg |
| EZS-8F | 3 | Tick | LymeVax | 03 Jan. 2010 | | | NEG | NEG | Neg |
| EZS-8F | 3 | Tick | LymeVax | 14 Feb. 2010 | | | NEG | N/A | N/A |
| EZS-8F | 3 | Tick | LymeVax | 11 Apr. 2010 | T = 0 | | NEG | NEG | Neg |
| EZS-8F | 3 | Tick | LymeVax | 18 Apr. 2010 | 7 | | NEG | NEG | Neg |
| EZS-8F | 3 | Tick | LymeVax | 25 Apr. 2010 | 14 | | NEG | NEG | Neg |
| EZS-8F | 3 | Tick | LymeVax | 02 May 2010 | 21 | | LEE | NEG | Pos(2) |
| EZS-8F | 3 | Tick | LymeVax | 09 May 2010 | 28 | | LEE | NEG | Pos(2) |
| EZS-8F | 3 | Tick | LymeVax | 16 May 2010 | 35 | | LEL | BB, AP | Pos(3) |
| EZS-8F | 3 | Tick | LymeVax | 23 May 2010 | 42 | | LEL | BB, AP | Pos(4) |
| EZS-8F | 3 | Tick | LymeVax | 30 May 2010 | 49 | | LEL | BB, AP | Pos(4) |
| EZS-8F | 3 | Tick | LymeVax | 06 Jun. 2010 | 56 | | LEL | BB, AP | Pos(3) |
| EZS-8F | 3 | Tick | LymeVax | 13 Jun. 2010 | 63 | | LEL | BB, AP | Pos(4) |
| EZS-8F | 3 | Tick | LymeVax | 20 Jun. 2010 | 70 | | LEL | BB, AP | Pos(4) |
| EZS-8F | 3 | Tick | LymeVax | 27 Jun. 2010 | 77 | | LEL | BB, AP | Pos(3) |
| EZS-8F | 3 | Tick | LymeVax | 04 Jul. 2010 | 84 | V = 0 | LEL | BB, AP | Pos(4) |
| EZS-8F | 3 | Tick | LymeVax | 11 Jul. 2010 | 91 | 7 | LEL | BB, AP | Pos(4) |
| EZS-8F | 3 | Tick | LymeVax | 18 Jul. 2010 | 98 | 14 | LEL | BB, AP | Pos(4) |
| EZS-8F | 3 | Tick | LymeVax | 01 Aug. 2010 | 112 | 28 | LELV | BB, AP | Pos(4) |
| EZS-8F | 3 | Tick | LymeVax | 08 Aug. 2010 | 119 | 35 | LELV | BB, AP | Pos(4) |
| EZS-8F | 3 | Tick | LymeVax | 15 Aug. 2010 | 126 | 42 | LELV | AP | Pos(4) |
| EZS-8F | 3 | Tick | LymeVax | 22 Aug. 2010 | 133 | 49 | LELV | BB, AP | Pos(4) |
| EZS-8F | 3 | Tick | LymeVax | 29 Aug. 2010 | 140 | 56 | LELV | BB, AP | Pos(4) |
| EZS-8F | 3 | Tick | LymeVax | 05 Sep. 2010 | 147 | 63 | LELV | N/A | N/A |
| OUV-8M | 3 | Tick | LymeVax | 18 Oct. 2009 | | | NEG | N/A | N/A |
| OUV-8M | 3 | Tick | LymeVax | 25 Oct. 2009 | | | NEG | NEG | Neg |
| OUV-8M | 3 | Tick | LymeVax | 08 Nov. 2009 | | | NEG | NEG | Neg |
| OUV-8M | 3 | Tick | LymeVax | 14 Nov. 2009 | | | NEG | N/A | N/A |
| OUV-8M | 3 | Tick | LymeVax | 22 Nov. 2009 | | | NEG | NEG | Neg |
| OUV-8M | 3 | Tick | LymeVax | 27 Nov. 2009 | | | NEG | N/A | N/A |
| OUV-8M | 3 | Tick | LymeVax | 06 Dec. 2009 | | | NEG | | Neg |
| OUV-8M | 3 | Tick | LymeVax | 13 Dec. 2009 | | | NEG | NEG | Neg |
| OUV-8M | 3 | Tick | LymeVax | 03 Jan. 2010 | | | NEG | NEG | Neg |
| OUV-8M | 3 | Tick | LymeVax | 14 Feb. 2010 | | | NEG | N/A | N/A |
| OUV-8M | 3 | Tick | LymeVax | 11 Apr. 2010 | T = 0 | | NEG | NEG | Neg |
| OUV-8M | 3 | Tick | LymeVax | 18 Apr. 2010 | 7 | | NEG | NEG | Neg |
| OUV-8M | 3 | Tick | LymeVax | 25 Apr. 2010 | 14 | | NEG | NEG | Neg |
| OUV-8M | 3 | Tick | LymeVax | 02 May 2010 | 21 | | NEG | NEG | Neg |
| OUV-8M | 3 | Tick | LymeVax | 09 May 2010 | 28 | | NEG | NEG | Neg |
| OUV-8M | 3 | Tick | LymeVax | 16 May 2010 | 35 | | NEG | NEG | Neg |
| OUV-8M | 3 | Tick | LymeVax | 23 May 2010 | 42 | | NEG | NEG | Neg |
| OUV-8M | 3 | Tick | LymeVax | 30 May 2010 | 49 | | NEG | NEG | Neg |
| OUV-8M | 3 | Tick | LymeVax | 06 Jun. 2010 | 56 | | NEG | NEG | Neg |
| OUV-8M | 3 | Tick | LymeVax | 13 Jun. 2010 | 63 | | NEG | NEG | Neg |
| OUV-8M | 3 | Tick | LymeVax | 20 Jun. 2010 | 70 | | NEG | NEG | Neg |
| OUV-8M | 3 | Tick | LymeVax | 27 Jun. 2010 | 77 | | NEG | NEG | Neg |
| OUV-8M | 3 | Tick | LymeVax | 04 Jul. 2010 | 84 | V = 0 | NEG | NEG | Neg |
| OUV-8M | 3 | Tick | LymeVax | 11 Jul. 2010 | 91 | 7 | NEG | NEG | BL |
| OUV-8M | 3 | Tick | LymeVax | 18 Jul. 2010 | 98 | 14 | LVR | NEG | Pos(3) |
| OUV-8M | 3 | Tick | LymeVax | 01 Aug. 2010 | 112 | 28 | LVR | NEG | Pos(3) |
| OUV-8M | 3 | Tick | LymeVax | 08 Aug. 2010 | 119 | 35 | LVR | NEG | Pos(4) |

TABLE 4-continued

Results from Lyme experimental study

| Sample ID | Group | Prim | Vaccine | DOS (CSU) | T = 0 | V = 0 | Accuplex (Lyme) | SNAP | ILISA (Lyme) |
|---|---|---|---|---|---|---|---|---|---|
| OUV-8M | 3 | Tick | LymeVax | 15 Aug. 2010 | 126 | 42 | LV-PE | NEG | Pos(4) |
| OUV-8M | 3 | Tick | LymeVax | 22 Aug. 2010 | 133 | 49 | LV-PE | BB | Pos(4) |
| OUV-8M | 3 | Tick | LymeVax | 29 Aug. 2010 | 140 | 56 | LVR | NEG | Pos(4) |
| OUV-8M | 3 | Tick | LymeVax | 05 Sep. 2010 | 147 | 63 | LVR | N/A | N/A |
| UTV-8M | 3 | Tick | LymeVax | 18 Oct. 2009 | | | NEG | N/A | N/A |
| UTV-8M | 3 | Tick | LymeVax | 25 Oct. 2009 | | | NEG | NEG | Neg |
| UTV-8M | 3 | Tick | LymeVax | 08 Nov. 2009 | | | NEG | NEG | Neg |
| UTV-8M | 3 | Tick | LymeVax | 14 Nov. 2009 | | | NEG | NEG | |
| UTV-8M | 3 | Tick | LymeVax | 22 Nov. 2009 | | | NEG | NEG | Neg |
| UTV-8M | 3 | Tick | LymeVax | 27 Nov. 2009 | | | NEG | N/A | N/A |
| UTV-8M | 3 | Tick | LymeVax | 06 Dec. 2009 | | | NEG | NEG | Neg |
| UTV-8M | 3 | Tick | LymeVax | 13 Dec. 2009 | | | NEG | NEG | Neg |
| UTV-8M | 3 | Tick | LymeVax | 03 Jan. 2010 | | | NEG | NEG | Neg |
| UTV-8M | 3 | Tick | LymeVax | 14 Feb. 2010 | | | NEG | N/A | N/A |
| UTV-8M | 3 | Tick | LymeVax | 11 Apr. 2010 | T = 0 | | NEG | NEG | Neg |
| UTV-8M | 3 | Tick | LymeVax | 18 Apr. 2010 | 7 | | NEG | NEG | BL |
| UTV-8M | 3 | Tick | LymeVax | 25 Apr. 2010 | 14 | | NEG | NEG | BL |
| UTV-8M | 3 | Tick | LymeVax | 02 May 2010 | 21 | | LEE | NEG | Pos(3) |
| UTV-8M | 3 | Tick | LymeVax | 09 May 2010 | 28 | | LEE | NEG | Pos(3) |
| UTV-8M | 3 | Tick | LymeVax | 16 May 2010 | 35 | | LEE | BB | Pos(3) |
| UTV-8M | 3 | Tick | LymeVax | 23 May 2010 | 42 | | LEE | BB | Pos(4) |
| UTV-8M | 3 | Tick | LymeVax | 30 May 2010 | 49 | | LEE | BB | Pos(4) |
| UTV-8M | 3 | Tick | LymeVax | 06 Jun. 2010 | 56 | | LEE | BB | Pos(3) |
| UTV-8M | 3 | Tick | LymeVax | 13 Jun. 2010 | 63 | | LEE | BB | Pos(4) |
| UTV-8M | 3 | Tick | LymeVax | 20 Jun. 2010 | 70 | | LEL | BB | Pos(4) |
| UTV-8M | 3 | Tick | LymeVax | 27 Jun. 2010 | 77 | | LEL | BB | Pos(3) |
| UTV-8M | 3 | Tick | LymeVax | 04 Jul. 2010 | 84 | V = 0 | LEL | BB | Pos(4) |
| UTV-8M | 3 | Tick | LymeVax | 11 Jul. 2010 | 91 | 7 | LEL | BB | Pos(4) |
| UTV-8M | 3 | Tick | LymeVax | 18 Jul. 2010 | 98 | 14 | LELV | BB | Pos(4) |
| UTV-8M | 3 | Tick | LymeVax | 01 Aug. 2010 | 112 | 28 | LELV | BB | Pos(4) |
| UTV-8M | 3 | Tick | LymeVax | 08 Aug. 2010 | 119 | 35 | LELV | BB | Pos(4) |
| UTV-8M | 3 | Tick | LymeVax | 15 Aug. 2010 | 126 | 42 | LELV | BB | Pos(4) |
| UTV-8M | 3 | Tick | LymeVax | 22 Aug. 2010 | 133 | 49 | LELV | BB | Pos(4) |
| UTV-8M | 3 | Tick | LymeVax | 29 Aug. 2010 | 140 | 56 | LELV | BB | Pos(4) |
| UTV-8M | 3 | Tick | LymeVax | 05 Sep. 2010 | 147 | 63 | LELV | N/A | N/A |
| VVS-8F | 3 | Tick | LymeVax | 18 Oct. 2009 | | | NEG | N/A | N/A |
| VVS-8F | 3 | Tick | LymeVax | 25 Oct. 2009 | | | NEG | NEG | Neg |
| VVS-8F | 3 | Tick | LymeVax | 08 Nov. 2009 | | | NEG | NEG | Neg |
| VVS-8F | 3 | Tick | LymeVax | 14 Nov. 2009 | | | NEG | NEG | |
| VVS-8F | 3 | Tick | LymeVax | 22 Nov. 2009 | | | NEG | NEG | Neg |
| VVS-8F | 3 | Tick | LymeVax | 27 Nov. 2009 | | | NEG | N/A | N/A |
| VVS-8F | 3 | Tick | LymeVax | 06 Dec. 2009 | | | NEG | NEG | Neg |
| VVS-8F | 3 | Tick | LymeVax | 13 Dec. 2009 | | | NEG | NEG | Neg |
| VVS-8F | 3 | Tick | LymeVax | 03 Jan. 2010 | | | NEG | NEG | Neg |
| VVS-8F | 3 | Tick | LymeVax | 14 Feb. 2010 | | | NEG | N/A | N/A |
| VVS-8F | 3 | Tick | LymeVax | 11 Apr. 2010 | T = 0 | | NEG | NEG | BL |
| VVS-8F | 3 | Tick | LymeVax | 18 Apr. 2010 | 7 | | NEG | NEG | Neg |
| VVS-8F | 3 | Tick | LymeVax | 25 Apr. 2010 | 14 | | LEE | NEG | BL |
| VVS-8F | 3 | Tick | LymeVax | 02 May 2010 | 21 | | LEE | NEG | Pos(2) |
| VVS-8F | 3 | Tick | LymeVax | 09 May 2010 | 28 | | LEE | NEG | Pos(2) |
| VVS-8F | 3 | Tick | LymeVax | 16 May 2010 | 35 | | LEL | BB | Pos(3) |
| VVS-8F | 3 | Tick | LymeVax | 23 May 2010 | 42 | | LEL | BB | Pos(4) |
| VVS-8F | 3 | Tick | LymeVax | 30 May 2010 | 49 | | LEL | BB | Pos(4) |
| VVS-8F | 3 | Tick | LymeVax | 06 Jun. 2010 | 56 | | LEL | BB | Pos(3) |
| VVS-8F | 3 | Tick | LymeVax | 13 Jun. 2010 | 63 | | LEL | BB | Pos(4) |
| VVS-8F | 3 | Tick | LymeVax | 20 Jun. 2010 | 70 | | LEL | BB | Pos(4) |
| VVS-8F | 3 | Tick | LymeVax | 27 Jun. 2010 | 77 | | LEL | BB | Pos(3) |
| VVS-8F | 3 | Tick | LymeVax | 04 Jul. 2010 | 84 | V = 0 | LEL | BB | Pos(4) |
| VVS-8F | 3 | Tick | LymeVax | 11 Jul. 2010 | 91 | 7 | LEL | BB | Pos(4) |
| VVS-8F | 3 | Tick | LymeVax | 18 Jul. 2010 | 98 | 14 | LELV | BB | Pos(4) |
| VVS-8F | 3 | Tick | LymeVax | 01 Aug. 2010 | 112 | 28 | LELV | BB | Pos(4) |
| VVS-8F | 3 | Tick | LymeVax | 08 Aug. 2010 | 119 | 35 | LELV | BB | Pos(4) |
| VVS-8F | 3 | Tick | LymeVax | 15 Aug. 2010 | 126 | 42 | LELV | BB | Pos(4) |
| VVS-8F | 3 | Tick | LymeVax | 22 Aug. 2010 | 133 | 49 | LELV | BB | Pos(4) |
| VVS-8F | 3 | Tick | LymeVax | 29 Aug. 2010 | 140 | 56 | LELV | BB | Pos(4) |
| VVS-8F | 3 | Tick | LymeVax | 05 Sep. 2010 | 147 | 63 | LELV | N/A | N/A |
| WOV-8M | 3 | Tick | LymeVax | 18 Oct. 2009 | | | NEG | | Neg |
| WOV-8M | 3 | Tick | LymeVax | 25 Oct. 2009 | | | NEG | NEG | Neg |
| WOV-8M | 3 | Tick | LymeVax | 08 Nov. 2009 | | | NEG | NEG | Neg |
| WOV-8M | 3 | Tick | LymeVax | 14 Nov. 2009 | | | NEG | N/A | N/A |
| WOV-8M | 3 | Tick | LymeVax | 22 Nov. 2009 | | | NEG | NEG | Neg |
| WOV-8M | 3 | Tick | LymeVax | 27 Nov. 2009 | | | NEG | N/A | N/A |
| WOV-8M | 3 | Tick | LymeVax | 06 Dec. 2009 | | | NEG | N/A | N/A |
| WOV-8M | 3 | Tick | LymeVax | 13 Dec. 2009 | | | NEG | NEG | Neg |
| WOV-8M | 3 | Tick | LymeVax | 03 Jan. 2010 | | | NEG | NEG | Neg |

TABLE 4-continued

| Results from Lyme experimental study | | | | | | | | | |
|---|---|---|---|---|---|---|---|---|---|
| Sample ID | Group | Prim | Vaccine | DOS (CSU) | T = 0 | V = 0 | Accuplex (Lyme) | SNAP | ILISA (Lyme) |
| WOV-8M | 3 | Tick | LymeVax | 14 Feb. 2010 | | | NEG | N/A | N/A |
| WOV-8M | 3 | Tick | LymeVax | 11 Apr. 2010 | T = 0 | | NEG | NEG | Neg |
| WOV-8M | 3 | Tick | LymeVax | 18 Apr. 2010 | 7 | | NEG | NEG | Neg |
| WOV-8M | 3 | Tick | LymeVax | 25 Apr. 2010 | 14 | | NEG | NEG | Neg |
| WOV-8M | 3 | Tick | LymeVax | 02 May 2010 | 21 | | NEG | NEG | Neg |
| WOV-8M | 3 | Tick | LymeVax | 09 May 2010 | 28 | | LEE | NEG | BL |
| WOV-8M | 3 | Tick | LymeVax | 16 May 2010 | 35 | | LEE | NEG | BL |
| WOV-8M | 3 | Tick | LymeVax | 23 May 2010 | 42 | | LEE | BB, AP | Pos(2) |
| WOV-8M | 3 | Tick | LymeVax | 30 May 2010 | 49 | | LEE | BB, AP | Pos(3) |
| WOV-8M | 3 | Tick | LymeVax | 06 Jun. 2010 | 56 | | LEE | BB, AP | Pos(3) |
| WOV-8M | 3 | Tick | LymeVax | 13 Jun. 2010 | 63 | | LEE | BB, AP | Pos(4) |
| WOV-8M | 3 | Tick | LymeVax | 20 Jun. 2010 | 70 | | LEL | BB, AP | Pos(3) |
| WOV-8M | 3 | Tick | LymeVax | 27 Jun. 2010 | 77 | | LEL | BB, AP | Pos(3) |
| WOV-8M | 3 | Tick | LymeVax | 04 Jul. 2010 | 84 | V = 0 | LEL | BB, AP | Pos(3) |
| WOV-8M | 3 | Tick | LymeVax | 11 Jul. 2010 | 91 | 7 | LEL | BB, AP | Pos(3) |
| WOV-8M | 3 | Tick | LymeVax | 18 Jul. 2010 | 98 | 14 | LELV | BB, AP | Pos(4) |
| WOV-8M | 3 | Tick | LymeVax | 01 Aug. 2010 | 112 | 28 | LELV | BB, AP | Pos(4) |
| WOV-8M | 3 | Tick | LymeVax | 08 Aug. 2010 | 119 | 35 | LELV | BB, AP | Pos(4) |
| WOV-8M | 3 | Tick | LymeVax | 15 Aug. 2010 | 126 | 42 | LELV | BB, AP | Pos(4) |
| WOV-8M | 3 | Tick | LymeVax | 22 Aug. 2010 | 133 | 49 | LELV | BB, AP | Pos(4) |
| WOV-8M | 3 | Tick | LymeVax | 29 Aug. 2010 | 140 | 56 | LELV | BB, AP | Pos(4) |
| WOV-8M | 3 | Tick | LymeVax | 05 Sep. 2010 | 147 | 63 | LELV | N/A | N/A |
| DES-8F | 4 | Vax | LymeVax | 18 Oct. 2009 | | | NEG | N/A | N/A |
| DES-8F | 4 | Vax | LymeVax | 25 Oct. 2009 | | | NEG | NEG | Neg |
| DES-8F | 4 | Vax | LymeVax | 08 Nov. 2009 | | V = 0 | NEG | NEG | Neg |
| DES-8F | 4 | Vax | LymeVax | 14 Nov. 2009 | | 6 | NEG | NEG | |
| DES-8F | 4 | Vax | LymeVax | 22 Nov. 2009 | | 14 | LVR | NEG | Pos(2) |
| DES-8F | 4 | Vax | LymeVax | 27 Nov. 2009 | | 19 | LVR | N/A | N/A |
| DES-8F | 4 | Vax | LymeVax | 06 Dec. 2009 | | 28 | LVR | NEG | Pos(3) |
| DES-8F | 4 | Vax | LymeVax | 13 Dec. 2009 | | 35 | LVR | NEG | Pos(3) |
| DES-8F | 4 | Vax | LymeVax | 20 Dec. 2009 | | 42 | LVR | NEG | Pos(3) |
| DES-8F | 4 | Vax | LymeVax | 27 Dec. 2009 | | 49 | LVR | NEG | Pos(3) |
| DES-8F | 4 | Vax | LymeVax | 03 Jan. 2010 | | 56 | LVR | NEG | Pos(3) |
| DES-8F | 4 | Vax | LymeVax | 10 Jan. 2010 | | 63 | LVR | N/A | N/A |
| DES-8F | 4 | Vax | LymeVax | 17 Jan. 2010 | | 70 | LVR | N/A | N/A |
| DES-8F | 4 | Vax | LymeVax | 24 Jan. 2010 | | 77 | LVR | N/A | N/A |
| DES-8F | 4 | Vax | LymeVax | 31 Jan. 2010 | | 84 | LVR | N/A | N/A |
| DES-8F | 4 | Vax | LymeVax | 07 Feb. 2010 | | 91 | LVR | N/A | N/A |
| DES-8F | 4 | Vax | LymeVax | 14 Feb. 2010 | | 98 | LVR | N/A | N/A |
| DES-8F | 4 | Vax | LymeVax | 21 Feb. 2010 | | 105 | LVR | N/A | N/A |
| DES-8F | 4 | Vax | LymeVax | 28 Feb. 2010 | | 112 | LVR | N/A | N/A |
| DES-8F | 4 | Vax | LymeVax | 07 Mar. 2010 | | 119 | LVR | N/A | N/A |
| DES-8F | 4 | Vax | LymeVax | 14 Mar. 2010 | | 126 | LVR | N/A | N/A |
| DES-8F | 4 | Vax | LymeVax | 21 Mar. 2010 | | 133 | LVR | N/A | N/A |
| DES-8F | 4 | Vax | LymeVax | 28 Mar. 2010 | | 140 | LVR | N/A | N/A |
| DES-8F | 4 | Vax | LymeVax | 11 Apr. 2010 | T = 0 | 154 | LVR | NEG | Pos(3) |
| DES-8F | 4 | Vax | LymeVax | 18 Apr. 2010 | 7 | 161 | LVR | NEG | Pos(3) |
| DES-8F | 4 | Vax | LymeVax | 25 Apr. 2010 | 14 | 168 | LVR | NEG | Pos(3) |
| DES-8F | 4 | Vax | LymeVax | 02 May 2010 | 21 | 175 | LVR | AP | Pos(3) |
| DES-8F | 4 | Vax | LymeVax | 09 May 2010 | 28 | 182 | LVR | AP | Pos(3) |
| DES-8F | 4 | Vax | LymeVax | 16 May 2010 | 35 | 189 | LVR | AP | Pos(2) |
| DES-8F | 4 | Vax | LymeVax | 23 May 2010 | 42 | 196 | LVR | AP | Pos(3) |
| DES-8F | 4 | Vax | LymeVax | 30 May 2010 | 49 | 203 | LVR | AP | Pos(3) |
| DES-8F | 4 | Vax | LymeVax | 06 Jun. 2010 | 56 | 210 | LVR | AP | BL |
| DES-8F | 4 | Vax | LymeVax | 13 Jun. 2010 | 63 | 217 | LVR | AP | Pos(3) |
| DES-8F | 4 | Vax | LymeVax | 20 Jun. 2010 | 70 | 224 | LVR | AP | Pos(3) |
| DES-8F | 4 | Vax | LymeVax | 27 Jun. 2010 | 77 | 231 | LVR | BB, AP | Pos(2) |
| DES-8F | 4 | Vax | LymeVax | 04 Jul. 2010 | 84 | 238 | LVR | AP | Pos(3) |
| DES-8F | 4 | Vax | LymeVax | 11 Jul. 2010 | 91 | 245 | LVR | AP | Pos(2) |
| DES-8F | 4 | Vax | LymeVax | 18 Jul. 2010 | 98 | 252 | LVR | AP | Pos(3) |
| DES-8F | 4 | Vax | LymeVax | 25 Jul. 2010 | 105 | 259 | LVR | N/A | N/A |
| DES-8F | 4 | Vax | LymeVax | 01 Aug. 2010 | 112 | 266 | NEG | AP | Pos(2) |
| DES-8F | 4 | Vax | LymeVax | 08 Aug. 2010 | 119 | 273 | NEG | AP | Pos(2) |
| HLS-8F | 4 | Vax | LymeVax | 18 Oct. 2009 | | | NEG | N/A | N/A |
| HLS-8F | 4 | Vax | LymeVax | 25 Oct. 2009 | | | NEG | NEG | Neg |
| HLS-8F | 4 | Vax | LymeVax | 08 Nov. 2009 | | V = 0 | NEG | NEG | BL |
| HLS-8F | 4 | Vax | LymeVax | 14 Nov. 2009 | | 6 | LVR | NEG | |
| HLS-8F | 4 | Vax | LymeVax | 22 Nov. 2009 | | 14 | LVR | NEG | Pos(3) |
| HLS-8F | 4 | Vax | LymeVax | 27 Nov. 2009 | | 19 | LVR | N/A | N/A |
| HLS-8F | 4 | Vax | LymeVax | 06 Dec. 2009 | | 28 | LVR | NEG | Pos(3) |
| HLS-8F | 4 | Vax | LymeVax | 13 Dec. 2009 | | 35 | LVR | NEG | Pos(3) |
| HLS-8F | 4 | Vax | LymeVax | 20 Dec. 2009 | | 42 | LVR | NEG | Pos(3) |
| HLS-8F | 4 | Vax | LymeVax | 27 Dec. 2009 | | 49 | LVR | N/A | N/A |
| HLS-8F | 4 | Vax | LymeVax | 03 Jan. 2010 | | 56 | LVR | NEG | Pos(3) |
| HLS-8F | 4 | Vax | LymeVax | 10 Jan. 2010 | | 63 | LVR | N/A | N/A |

TABLE 4-continued

Results from Lyme experimental study

| Sample ID | Group | Prim | Vaccine | DOS (CSU) | T = 0 | V = 0 | Accuplex (Lyme) | SNAP | ILISA (Lyme) |
|---|---|---|---|---|---|---|---|---|---|
| HLS-8F | 4 | Vax | LymeVax | 17 Jan. 2010 | | 70 | LVR | N/A | N/A |
| HLS-8F | 4 | Vax | LymeVax | 24 Jan. 2010 | | 77 | LVR | N/A | N/A |
| HLS-8F | 4 | Vax | LymeVax | 31 Jan. 2010 | | 84 | LVR | N/A | N/A |
| HLS-8F | 4 | Vax | LymeVax | 07 Feb. 2010 | | 91 | LVR | N/A | N/A |
| HLS-8F | 4 | Vax | LymeVax | 14 Feb. 2010 | | 98 | LVR | N/A | N/A |
| HLS-8F | 4 | Vax | LymeVax | 21 Feb. 2010 | | 105 | LVR | N/A | N/A |
| HLS-8F | 4 | Vax | LymeVax | 28 Feb. 2010 | | 112 | LVR | N/A | N/A |
| HLS-8F | 4 | Vax | LymeVax | 07 Mar. 2010 | | 119 | LVR | N/A | N/A |
| HLS-8F | 4 | Vax | LymeVax | 14 Mar. 2010 | | 126 | LVR | N/A | N/A |
| HLS-8F | 4 | Vax | LymeVax | 21 Mar. 2010 | | 133 | LVR | N/A | N/A |
| HLS-8F | 4 | Vax | LymeVax | 28 Mar. 2010 | | 140 | LVR | N/A | N/A |
| HLS-8F | 4 | Vax | LymeVax | 11 Apr. 2010 | T = 0 | 154 | LVR | NEG | Pos(3) |
| HLS-8F | 4 | Vax | LymeVax | 18 Apr. 2010 | 7 | 161 | LVR | NEG | Pos(4) |
| HLS-8F | 4 | Vax | LymeVax | 25 Apr. 2010 | 14 | 168 | LVR | NEG | Pos(3) |
| HLS-8F | 4 | Vax | LymeVax | 02 May 2010 | 21 | 175 | LVR | NEG | Pos(3) |
| HLS-8F | 4 | Vax | LymeVax | 09 May 2010 | 28 | 182 | LVR | AP | Pos(3) |
| HLS-8F | 4 | Vax | LymeVax | 16 May 2010 | 35 | 189 | LVR | AP | Pos(2) |
| HLS-8F | 4 | Vax | LymeVax | 23 May 2010 | 42 | 196 | LVR | AP | Pos(3) |
| HLS-8F | 4 | Vax | LymeVax | 30 May 2010 | 49 | 203 | LVR | AP | Pos(3) |
| HLS-8F | 4 | Vax | LymeVax | 06 Jun. 2010 | 56 | 210 | LVR | AP | BL |
| HLS-8F | 4 | Vax | LymeVax | 13 Jun. 2010 | 63 | 217 | LVR | AP | M-A |
| HLS-8F | 4 | Vax | LymeVax | 20 Jun. 2010 | 70 | 224 | LVR | AP | Pos(3) |
| HLS-8F | 4 | Vax | LymeVax | 27 Jun. 2010 | 77 | 231 | LVR | BB, AP | Pos(2) |
| HLS-8F | 4 | Vax | LymeVax | 04 Jul. 2010 | 84 | 238 | LVR | AP | Pos(3) |
| HLS-8F | 4 | Vax | LymeVax | 11 Jul. 2010 | 91 | 245 | LVR | AP | Pos(2) |
| HLS-8F | 4 | Vax | LymeVax | 18 Jul. 2010 | 98 | 252 | LVR | AP | Pos(3) |
| HLS-8F | 4 | Vax | LymeVax | 25 Jul. 2010 | 105 | 259 | LVR | N/A | N/A |
| HLS-8F | 4 | Vax | LymeVax | 01 Aug. 2010 | 112 | 266 | LVR | AP | Pos(2) |
| HLS-8F | 4 | Vax | LymeVax | 08 Aug. 2010 | 119 | 273 | LVR | AP | Pos(2) |
| PZV-8F | 4 | Vax | LymeVax | 18 Oct. 2009 | | | NEG | | Neg |
| PZV-8F | 4 | Vax | LymeVax | 25 Oct. 2009 | | | NEG | N/A | N/A |
| PZV-8F | 4 | Vax | LymeVax | 08 Nov. 2009 | | V = 0 | NEG | NEG | Neg |
| PZV-8F | 4 | Vax | LymeVax | 14 Nov. 2009 | | 6 | NEG | NEG | |
| PZV-8F | 4 | Vax | LymeVax | 22 Nov. 2009 | | 14 | LVR | NEG | Pos(3) |
| PZV-8F | 4 | Vax | LymeVax | 27 Nov. 2009 | | 19 | LVR | N/A | N/A |
| PZV-8F | 4 | Vax | LymeVax | 06 Dec. 2009 | | 28 | LVR | NEG | Pos(3) |
| PZV-8F | 4 | Vax | LymeVax | 13 Dec. 2009 | | 35 | LVR | NEG | Pos(3) |
| PZV-8F | 4 | Vax | LymeVax | 20 Dec. 2009 | | 42 | LVR | NEG | Pos(3) |
| PZV-8F | 4 | Vax | LymeVax | 27 Dec. 2009 | | 49 | LVR | NEG | Pos(3) |
| PZV-8F | 4 | Vax | LymeVax | 03 Jan. 2010 | | 56 | LVR | NEG | Pos(3) |
| PZV-8F | 4 | Vax | LymeVax | 10 Jan. 2010 | | 63 | LVR | N/A | N/A |
| PZV-8F | 4 | Vax | LymeVax | 17 Jan. 2010 | | 70 | LVR | N/A | N/A |
| PZV-8F | 4 | Vax | LymeVax | 24 Jan. 2010 | | 77 | LVR | N/A | N/A |
| PZV-8F | 4 | Vax | LymeVax | 31 Jan. 2010 | | 84 | LVR | N/A | N/A |
| PZV-8F | 4 | Vax | LymeVax | 07 Feb. 2010 | | 91 | LVR | N/A | N/A |
| PZV-8F | 4 | Vax | LymeVax | 14 Feb. 2010 | | 98 | LVR | N/A | N/A |
| PZV-8F | 4 | Vax | LymeVax | 21 Feb. 2010 | | 105 | LVR | N/A | N/A |
| PZV-8F | 4 | Vax | LymeVax | 28 Feb. 2010 | | 112 | LVR | N/A | N/A |
| PZV-8F | 4 | Vax | LymeVax | 07 Mar. 2010 | | 119 | LVR | N/A | N/A |
| PZV-8F | 4 | Vax | LymeVax | 14 Mar. 2010 | | 126 | LVR | N/A | N/A |
| PZV-8F | 4 | Vax | LymeVax | 21 Mar. 2010 | | 133 | LVR | N/A | N/A |
| PZV-8F | 4 | Vax | LymeVax | 28 Mar. 2010 | | 140 | LVR | N/A | N/A |
| PZV-8F | 4 | Vax | LymeVax | 11 Apr. 2010 | T = 0 | 154 | LVR | NEG | Pos(4) |
| PZV-8F | 4 | Vax | LymeVax | 18 Apr. 2010 | 7 | 161 | LVR | NEG | Pos(4) |
| PZV-8F | 4 | Vax | LymeVax | 25 Apr. 2010 | 14 | 168 | LVR | NEG | Pos(4) |
| PZV-8F | 4 | Vax | LymeVax | 02 May 2010 | 21 | 175 | LVR | NEG | Pos(4) |
| PZV-8F | 4 | Vax | LymeVax | 09 May 2010 | 28 | 182 | LVR | NEG | Pos(4) |
| PZV-8F | 4 | Vax | LymeVax | 16 May 2010 | 35 | 189 | LVR | NEG | Pos(3) |
| PZV-8F | 4 | Vax | LymeVax | 23 May 2010 | 42 | 196 | LVR | NEG | Pos(4) |
| PZV-8F | 4 | Vax | LymeVax | 30 May 2010 | 49 | 203 | LVR | NEG | Pos(4) |
| PZV-8F | 4 | Vax | LymeVax | 06 Jun. 2010 | 56 | 210 | LVR | NEG | Pos(3) |
| PZV-8F | 4 | Vax | LymeVax | 13 Jun. 2010 | 63 | 217 | LVR | NEG | Pos(4) |
| PZV-8F | 4 | Vax | LymeVax | 20 Jun. 2010 | 70 | 224 | LVR | NEG | Pos(4) |
| PZV-8F | 4 | Vax | LymeVax | 27 Jun. 2010 | 77 | 231 | LVR | NEG | Pos(4) |
| PZV-8F | 4 | Vax | LymeVax | 04 Jul. 2010 | 84 | 238 | LVR | NEG | Pos(4) |
| PZV-8F | 4 | Vax | LymeVax | 11 Jul. 2010 | 91 | 245 | LVR | NEG | Pos(4) |
| PZV-8F | 4 | Vax | LymeVax | 18 Jul. 2010 | 98 | 252 | LVR | NEG | Pos(4) |
| PZV-8F | 4 | Vax | LymeVax | 25 Jul. 2010 | 105 | 259 | LVR | N/A | N/A |
| PZV-8F | 4 | Vax | LymeVax | 01 Aug. 2010 | 112 | 266 | LVR | NEG | Pos(4) |
| PZV-8F | 4 | Vax | LymeVax | 08 Aug. 2010 | 119 | 273 | LVR | NEG | Pos(3) |
| UVV-8M | 4 | Vax | LymeVax | 18 Oct. 2009 | | | NEG | N/A | N/A |
| UVV-8M | 4 | Vax | LymeVax | 25 Oct. 2009 | | | NEG | NEG | Neg |
| UVV-8M | 4 | Vax | LymeVax | 08 Nov. 2009 | | V = 0 | NEG | NEG | Neg |
| UVV-8M | 4 | Vax | LymeVax | 14 Nov. 2009 | | 6 | NEG | NEG | |
| UVV-8M | 4 | Vax | LymeVax | 22 Nov. 2009 | | 14 | LVR | NEG | Pos(3) |

TABLE 4-continued

Results from Lyme experimental study

| Sample ID | Group | Prim | Vaccine | DOS (CSU) | T = 0 | V = 0 | Accuplex (Lyme) | SNAP | ILISA (Lyme) |
|---|---|---|---|---|---|---|---|---|---|
| UVV-8M | 4 | Vax | LymeVax | 27 Nov. 2009 | | 19 | LVR | N/A | N/A |
| UVV-8M | 4 | Vax | LymeVax | 06 Dec. 2009 | | 28 | LVR | NEG | Pos(3) |
| UVV-8M | 4 | Vax | LymeVax | 13 Dec. 2009 | | 35 | LVR | NEG | Pos(3) |
| UVV-8M | 4 | Vax | LymeVax | 20 Dec. 2009 | | 42 | LVR | NEG | Pos(3) |
| UVV-8M | 4 | Vax | LymeVax | 27 Dec. 2009 | | 49 | LV-PE | N/A | N/A |
| UVV-8M | 4 | Vax | LymeVax | 03 Jan. 2010 | | 56 | LVR | NEG | Pos(3) |
| UVV-8M | 4 | Vax | LymeVax | 10 Jan. 2010 | | 63 | LVR | N/A | N/A |
| UVV-8M | 4 | Vax | LymeVax | 17 Jan. 2010 | | 70 | LVR | N/A | N/A |
| UVV-8M | 4 | Vax | LymeVax | 24 Jan. 2010 | | 77 | LVR | N/A | N/A |
| UVV-8M | 4 | Vax | LymeVax | 31 Jan. 2010 | | 84 | LVR | N/A | N/A |
| UVV-8M | 4 | Vax | LymeVax | 07 Feb. 2010 | | 91 | LVR | N/A | N/A |
| UVV-8M | 4 | Vax | LymeVax | 14 Feb. 2010 | | 98 | LVR | N/A | N/A |
| UVV-8M | 4 | Vax | LymeVax | 21 Feb. 2010 | | 105 | LVR | N/A | N/A |
| UVV-8M | 4 | Vax | LymeVax | 28 Feb. 2010 | | 112 | LVR | N/A | N/A |
| UVV-8M | 4 | Vax | LymeVax | 07 Mar. 2010 | | 119 | LVR | N/A | N/A |
| UVV-8M | 4 | Vax | LymeVax | 14 Mar. 2010 | | 126 | LVR | N/A | N/A |
| UVV-8M | 4 | Vax | LymeVax | 21 Mar. 2010 | | 133 | LVR | N/A | N/A |
| UVV-8M | 4 | Vax | LymeVax | 28 Mar. 2010 | | 140 | LVR | N/A | N/A |
| UVV-8M | 4 | Vax | LymeVax | 11 Apr. 2010 | T = 0 | 154 | LVR | NEG | Pos(4) |
| UVV-8M | 4 | Vax | LymeVax | 18 Apr. 2010 | 7 | 161 | LVR | NEG | Pos(4) |
| UVV-8M | 4 | Vax | LymeVax | 25 Apr. 2010 | 14 | 168 | LVR | NEG | Pos(3) |
| UVV-8M | 4 | Vax | LymeVax | 02 May 2010 | 21 | 175 | LVR | NEG | Pos(4) |
| UVV-8M | 4 | Vax | LymeVax | 09 May 2010 | 28 | 182 | LVR | AP | Pos(4) |
| UVV-8M | 4 | Vax | LymeVax | 16 May 2010 | 35 | 189 | LVR | AP | Pos(3) |
| UVV-8M | 4 | Vax | LymeVax | 23 May 2010 | 42 | 196 | LVR | AP | Pos(4) |
| UVV-8M | 4 | Vax | LymeVax | 30 May 2010 | 49 | 203 | LVR | AP | Pos(3) |
| UVV-8M | 4 | Vax | LymeVax | 06 Jun. 2010 | 56 | 210 | LVR | AP | Pos(3) |
| UVV-8M | 4 | Vax | LymeVax | 13 Jun. 2010 | 63 | 217 | LVR | AP | Pos(4) |
| UVV-8M | 4 | Vax | LymeVax | 20 Jun. 2010 | 70 | 224 | LVR | AP | Pos(4) |
| UVV-8M | 4 | Vax | LymeVax | 27 Jun. 2010 | 77 | 231 | LVR | BB, AP | Pos(3) |
| UVV-8M | 4 | Vax | LymeVax | 04 Jul. 2010 | 84 | 238 | LVR | AP | Pos(4) |
| UVV-8M | 4 | Vax | LymeVax | 11 Jul. 2010 | 91 | 245 | LVR | AP | Pos(4) |
| UVV-8M | 4 | Vax | LymeVax | 18 Jul. 2010 | 98 | 252 | LVR | AP | Pos(4) |
| UVV-8M | 4 | Vax | LymeVax | 25 Jul. 2010 | 105 | 259 | LVR | N/A | N/A |
| UVV-8M | 4 | Vax | LymeVax | 01 Aug. 2010 | 112 | 266 | LVR | AP | Pos(3) |
| UVV-8M | 4 | Vax | LymeVax | 08 Aug. 2010 | 119 | 273 | LVR | AP | Pos(3) |
| WEU-8F | 4 | Vax | LymeVax | 18 Oct. 2009 | | | NEG | N/A | N/A |
| WEU-8F | 4 | Vax | LymeVax | 25 Oct. 2009 | | | NEG | NEG | Neg |
| WEU-8F | 4 | Vax | LymeVax | 08 Nov. 2009 | | V = 0 | NEG | NEG | Neg |
| WEU-8F | 4 | Vax | LymeVax | 14 Nov. 2009 | | 6 | NEG | NEG | |
| WEU-8F | 4 | Vax | LymeVax | 22 Nov. 2009 | | 14 | LVR | NEG | Pos(3) |
| WEU-8F | 4 | Vax | LymeVax | 27 Nov. 2009 | | 19 | LVR | N/A | N/A |
| WEU-8F | 4 | Vax | LymeVax | 06 Dec. 2009 | | 28 | LVR | | Pos(3) |
| WEU-8F | 4 | Vax | LymeVax | 13 Dec. 2009 | | 35 | LVR | NEG | Pos(3) |
| WEU-8F | 4 | Vax | LymeVax | 20 Dec. 2009 | | 42 | LVR | NEG | Pos(3) |
| WEU-8F | 4 | Vax | LymeVax | 27 Dec. 2009 | | 49 | LVR | N/A | N/A |
| WEU-8F | 4 | Vax | LymeVax | 03 Jan. 2010 | | 56 | LVR | NEG | Pos(3) |
| WEU-8F | 4 | Vax | LymeVax | 10 Jan. 2010 | | 63 | LVR | N/A | N/A |
| WEU-8F | 4 | Vax | LymeVax | 17 Jan. 2010 | | 70 | LVR | N/A | N/A |
| WEU-8F | 4 | Vax | LymeVax | 24 Jan. 2010 | | 77 | LVR | N/A | N/A |
| WEU-8F | 4 | Vax | LymeVax | 31 Jan. 2010 | | 84 | LVR | N/A | N/A |
| WEU-8F | 4 | Vax | LymeVax | 07 Feb. 2010 | | 91 | LVR | N/A | N/A |
| WEU-8F | 4 | Vax | LymeVax | 14 Feb. 2010 | | 98 | LVR | N/A | N/A |
| WEU-8F | 4 | Vax | LymeVax | 21 Feb. 2010 | | 105 | LVR | N/A | N/A |
| WEU-8F | 4 | Vax | LymeVax | 28 Feb. 2010 | | 112 | LVR | N/A | N/A |
| WEU-8F | 4 | Vax | LymeVax | 07 Mar. 2010 | | 119 | LVR | N/A | N/A |
| WEU-8F | 4 | Vax | LymeVax | 14 Mar. 2010 | | 126 | LVR | N/A | N/A |
| WEU-8F | 4 | Vax | LymeVax | 21 Mar. 2010 | | 133 | LVR | N/A | N/A |
| WEU-8F | 4 | Vax | LymeVax | 28 Mar. 2010 | | 140 | LVR | N/A | N/A |
| WEU-8F | 4 | Vax | LymeVax | 11 Apr. 2010 | T = 0 | 154 | LVR | NEG | Pos(3) |
| WEU-8F | 4 | Vax | LymeVax | 18 Apr. 2010 | 7 | 161 | LVR | NEG | Pos(4) |
| WEU-8F | 4 | Vax | LymeVax | 25 Apr. 2010 | 14 | 168 | LVR | NEG | Pos(3) |
| WEU-8F | 4 | Vax | LymeVax | 02 May 2010 | 21 | 175 | LVR | NEG | Pos(4) |
| WEU-8F | 4 | Vax | LymeVax | 09 May 2010 | 28 | 182 | LVR | NEG | Pos(3) |
| WEU-8F | 4 | Vax | LymeVax | 16 May 2010 | 35 | 189 | LVR | NEG | Pos(3) |
| WEU-8F | 4 | Vax | LymeVax | 23 May 2010 | 42 | 196 | LVR | NEG | Pos(4) |
| WEU-8F | 4 | Vax | LymeVax | 30 May 2010 | 49 | 203 | LVR | NEG | Pos(4) |
| WEU-8F | 4 | Vax | LymeVax | 06 Jun. 2010 | 56 | 210 | LVR | NEG | Pos(3) |
| WEU-8F | 4 | Vax | LymeVax | 13 Jun. 2010 | 63 | 217 | LVR | NEG | Pos(4) |
| WEU-8F | 4 | Vax | LymeVax | 20 Jun. 2010 | 70 | 224 | LVR | NEG | Pos(4) |
| WEU-8F | 4 | Vax | LymeVax | 27 Jun. 2010 | 77 | 231 | LVR | NEG | Pos(3) |
| WEU-8F | 4 | Vax | LymeVax | 04 Jul. 2010 | 84 | 238 | LVR | NEG | Pos(4) |
| WEU-8F | 4 | Vax | LymeVax | 11 Jul. 2010 | 91 | 245 | LVR | NEG | Pos(4) |
| WEU-8F | 4 | Vax | LymeVax | 18 Jul. 2010 | 98 | 252 | LVR | NEG | Pos(4) |
| WEU-8F | 4 | Vax | LymeVax | 25 Jul. 2010 | 105 | 259 | LVR | N/A | N/A |

TABLE 4-continued

Results from Lyme experimental study

| Sample ID | Group | Prim | Vaccine | DOS (CSU) | T = 0 | V = 0 | Accuplex (Lyme) | SNAP | ILISA (Lyme) |
|---|---|---|---|---|---|---|---|---|---|
| WEU-8F | 4 | Vax | LymeVax | 01 Aug. 2010 | 112 | 266 | LVR | NEG | Pos(3) |
| WEU-8F | 4 | Vax | LymeVax | 08 Aug. 2010 | 119 | 273 | LVR | NEG | Pos(3) |
| WUV-8M | 4 | Vax | LymeVax | 18 Oct. 2009 | | | NEG | | Neg |
| WUV-8M | 4 | Vax | LymeVax | 25 Oct. 2009 | | | NEG | NEG | Neg |
| WUV-8M | 4 | Vax | LymeVax | 08 Nov. 2009 | | V = 0 | NEG | NEG | Neg |
| WUV-8M | 4 | Vax | LymeVax | 14 Nov. 2009 | | 6 | NEG | NEG | |
| WUV-8M | 4 | Vax | LymeVax | 22 Nov. 2009 | | 14 | LVR | NEG | Pos(3) |
| WUV-8M | 4 | Vax | LymeVax | 27 Nov. 2009 | | 19 | LVR | N/A | N/A |
| WUV-8M | 4 | Vax | LymeVax | 06 Dec. 2009 | | 28 | LVR | NEG | Pos(3) |
| WUV-8M | 4 | Vax | LymeVax | 13 Dec. 2009 | | 35 | LVR | NEG | Pos(3) |
| WUV-8M | 4 | Vax | LymeVax | 20 Dec. 2009 | | 42 | LVR | NEG | Pos(3) |
| WUV-8M | 4 | Vax | LymeVax | 27 Dec. 2009 | | 49 | LVR | NEG | Pos(3) |
| WUV-8M | 4 | Vax | LymeVax | 03 Jan. 2010 | | 56 | LVR | NEG | Pos(3) |
| WUV-8M | 4 | Vax | LymeVax | 10 Jan. 2010 | | 63 | LVR | N/A | N/A |
| WUV-8M | 4 | Vax | LymeVax | 17 Jan. 2010 | | 70 | LVR | N/A | N/A |
| WUV-8M | 4 | Vax | LymeVax | 24 Jan. 2010 | | 77 | LVR | N/A | N/A |
| WUV-8M | 4 | Vax | LymeVax | 31 Jan. 2010 | | 84 | LVR | N/A | N/A |
| WUV-8M | 4 | Vax | LymeVax | 07 Feb. 2010 | | 91 | LVR | N/A | N/A |
| WUV-8M | 4 | Vax | LymeVax | 14 Feb. 2010 | | 98 | LVR | N/A | N/A |
| WUV-8M | 4 | Vax | LymeVax | 21 Feb. 2010 | | 105 | LVR | N/A | N/A |
| WUV-8M | 4 | Vax | LymeVax | 28 Feb. 2010 | | 112 | LVR | N/A | N/A |
| WUV-8M | 4 | Vax | LymeVax | 07 Mar. 2010 | | 119 | LVR | N/A | N/A |
| WUV-8M | 4 | Vax | LymeVax | 14 Mar. 2010 | | 126 | LVR | N/A | N/A |
| WUV-8M | 4 | Vax | LymeVax | 21 Mar. 2010 | | 133 | LVR | N/A | N/A |
| WUV-8M | 4 | Vax | LymeVax | 28 Mar. 2010 | | 140 | LVR | N/A | N/A |
| WUV-8M | 4 | Vax | LymeVax | 11 Apr. 2010 | T = 0 | 154 | LVR | NEG | Pos(2) |
| WUV-8M | 4 | Vax | LymeVax | 18 Apr. 2010 | 7 | 161 | LVR | NEG | Pos(3) |
| WUV-8M | 4 | Vax | LymeVax | 25 Apr. 2010 | 14 | 168 | LVR | NEG | Pos(2) |
| WUV-8M | 4 | Vax | LymeVax | 02 May 2010 | 21 | 175 | LVR | NEG | Pos(3) |
| WUV-8M | 4 | Vax | LymeVax | 09 May 2010 | 28 | 182 | LVR | AP | Pos(2) |
| WUV-8M | 4 | Vax | LymeVax | 16 May 2010 | 35 | 189 | LVR | AP | Pos(2) |
| WUV-8M | 4 | Vax | LymeVax | 23 May 2010 | 42 | 196 | LVR | AP | Pos(2) |
| WUV-8M | 4 | Vax | LymeVax | 30 May 2010 | 49 | 203 | LVR | AP | Pos(2) |
| WUV-8M | 4 | Vax | LymeVax | 06 Jun. 2010 | 56 | 210 | LVR | AP | BL |
| WUV-8M | 4 | Vax | LymeVax | 13 Jun. 2010 | 63 | 217 | LVR | AP | Pos(3) |
| WUV-8M | 4 | Vax | LymeVax | 20 Jun. 2010 | 70 | 224 | LVR | AP | Pos(2) |
| WUV-8M | 4 | Vax | LymeVax | 27 Jun. 2010 | 77 | 231 | LVR | BB, AP | Pos(2) |
| WUV-8M | 4 | Vax | LymeVax | 04 Jul. 2010 | 84 | 238 | LVR | AP | Pos(2) |
| WUV-8M | 4 | Vax | LymeVax | 11 Jul. 2010 | 91 | 245 | LVR | AP | Pos(2) |
| WUV-8M | 4 | Vax | LymeVax | 18 Jul. 2010 | 98 | 252 | LVR | AP | Pos(3) |
| WUV-8M | 4 | Vax | LymeVax | 25 Jul. 2010 | 105 | 259 | LVR | N/A | N/A |
| WUV-8M | 4 | Vax | LymeVax | 01 Aug. 2010 | 112 | 266 | NEG | AP | BL |
| WUV-8M | 4 | Vax | LymeVax | 08 Aug. 2010 | 119 | 273 | NEG | AP | Pos(2) |
| DFS-8F | 5 | Tick | Recombitek | 18 Oct. 2009 | | | NEG | | Neg |
| DFS-8F | 5 | Tick | Recombitek | 25 Oct. 2009 | | | NEG | NEG | BL |
| DFS-8F | 5 | Tick | Recombitek | 08 Nov. 2009 | | | NEG | NEG | BL |
| DFS-8F | 5 | Tick | Recombitek | 14 Nov. 2009 | | | NEG | NEG | |
| DFS-8F | 5 | Tick | Recombitek | 22 Nov. 2009 | | | NEG | NEG | Neg |
| DFS-8F | 5 | Tick | Recombitek | 27 Nov. 2009 | | | NEG | N/A | N/A |
| DFS-8F | 5 | Tick | Recombitek | 06 Dec. 2009 | | | NEG | NEG | Neg |
| DFS-8F | 5 | Tick | Recombitek | 13 Dec. 2009 | | | NEG | NEG | Neg |
| DFS-8F | 5 | Tick | Recombitek | 03 Jan. 2010 | | | NEG | NEG | Neg |
| DFS-8F | 5 | Tick | Recombitek | 14 Feb. 2010 | | | NEG | N/A | N/A |
| DFS-8F | 5 | Tick | Recombitek | 18 Apr. 2010 | T = 0 | | NEG | NEG | Neg |
| DFS-8F | 5 | Tick | Recombitek | 25 Apr. 2010 | 7 | | NEG | NEG | BL |
| DFS-8F | 5 | Tick | Recombitek | 02 May 2010 | 14 | | NEG | NEG | BL |
| DFS-8F | 5 | Tick | Recombitek | 09 May 2010 | 21 | | LEE | AP | Pos(2) |
| DFS-8F | 5 | Tick | Recombitek | 16 May 2010 | 28 | | LEE | AP | Pos(2) |
| DFS-8F | 5 | Tick | Recombitek | 23 May 2010 | 35 | | LEE | AP | Pos(3) |
| DFS-8F | 5 | Tick | Recombitek | 30 May 2010 | 42 | | LEE | BB, AP | Pos(3) |
| DFS-8F | 5 | Tick | Recombitek | 06 Jun. 2010 | 49 | | LEE | BB, AP | Pos(3) |
| DFS-8F | 5 | Tick | Recombitek | 13 Jun. 2010 | 56 | | LEE | BB, AP | Pos(4) |
| DFS-8F | 5 | Tick | Recombitek | 20 Jun. 2010 | 63 | | LEL | BB, AP | Pos(3) |
| DFS-8F | 5 | Tick | Recombitek | 27 Jun. 2010 | 70 | | LEL | BB, AP | Pos(3) |
| DFS-8F | 5 | Tick | Recombitek | 04 Jul. 2010 | 77 | | LEL | BB, AP | Pos(3) |
| DFS-8F | 5 | Tick | Recombitek | 11 Jul. 2010 | 84 | V = 0 | LEL | BB, AP | Pos(4) |
| DFS-8F | 5 | Tick | Recombitek | 18 Jul. 2010 | 91 | 7 | LEL | BB, AP | Pos(4) |
| DFS-8F | 5 | Tick | Recombitek | 01 Aug. 2010 | 105 | 21 | LELV | BB, AP | Pos(3) |
| DFS-8F | 5 | Tick | Recombitek | 08 Aug. 2010 | 112 | 28 | LELV | BB, AP | Pos(3) |
| DFS-8F | 5 | Tick | Recombitek | 15 Aug. 2010 | 119 | 35 | LELV | BB, AP | Pos(4) |
| DFS-8F | 5 | Tick | Recombitek | 22 Aug. 2010 | 126 | 42 | LELV | BB, AP | Pos(4) |
| DFS-8F | 5 | Tick | Recombitek | 29 Aug. 2010 | 133 | 49 | LELV | BB, AP | Pos(4) |
| DFS-8F | 5 | Tick | Recombitek | 05 Sep. 2010 | 140 | 56 | LELV | N/A | N/A |
| LXU-8F | 5 | Tick | Recombitek | 18 Oct. 2009 | | | NEG | N/A | N/A |
| LXU-8F | 5 | Tick | Recombitek | 25 Oct. 2009 | | | NEG | NEG | BL |

TABLE 4-continued

Results from Lyme experimental study

| Sample ID | Group | Prim | Vaccine | DOS (CSU) | T = 0 | V = 0 | Accuplex (Lyme) | SNAP | ILISA (Lyme) |
|---|---|---|---|---|---|---|---|---|---|
| LXU-8F | 5 | Tick | Recombitek | 08 Nov. 2009 | | | NEG | NEG | BL |
| LXU-8F | 5 | Tick | Recombitek | 14 Nov. 2009 | | | NEG | NEG | |
| LXU-8F | 5 | Tick | Recombitek | 22 Nov. 2009 | | | NEG | NEG | Neg |
| LXU-8F | 5 | Tick | Recombitek | 27 Nov. 2009 | | | NEG | N/A | N/A |
| LXU-8F | 5 | Tick | Recombitek | 06 Dec. 2009 | | | NEG | NEG | Neg |
| LXU-8F | 5 | Tick | Recombitek | 13 Dec. 2009 | | | NEG | NEG | Neg |
| LXU-8F | 5 | Tick | Recombitek | 03 Jan. 2010 | | | NEG | NEG | Neg |
| LXU-8F | 5 | Tick | Recombitek | 14 Feb. 2010 | | | NEG | N/A | N/A |
| LXU-8F | 5 | Tick | Recombitek | 18 Apr. 2010 | T = 0 | | NEG | NEG | BL |
| LXU-8F | 5 | Tick | Recombitek | 25 Apr. 2010 | 7 | | NEG | NEG | BL |
| LXU-8F | 5 | Tick | Recombitek | 02 May 2010 | 14 | | NEG | NEG | BL |
| LXU-8F | 5 | Tick | Recombitek | 09 May 2010 | 21 | | NEG | NEG | BL |
| LXU-8F | 5 | Tick | Recombitek | 16 May 2010 | 28 | | NEG | AP | BL |
| LXU-8F | 5 | Tick | Recombitek | 23 May 2010 | 35 | | NEG | AP | BL |
| LXU-8F | 5 | Tick | Recombitek | 30 May 2010 | 42 | | NEG | AP | BL |
| LXU-8F | 5 | Tick | Recombitek | 06 Jun. 2010 | 49 | | NEG | AP | Neg |
| LXU-8F | 5 | Tick | Recombitek | 13 Jun. 2010 | 56 | | NEG | AP | BL |
| LXU-8F | 5 | Tick | Recombitek | 20 Jun. 2010 | 63 | | NEG | AP | Neg |
| LXU-8F | 5 | Tick | Recombitek | 27 Jun. 2010 | 70 | | NEG | BB, AP | Neg |
| LXU-8F | 5 | Tick | Recombitek | 04 Jul. 2010 | 77 | | NEG | AP | BL |
| LXU-8F | 5 | Tick | Recombitek | 11 Jul. 2010 | 84 | V = 0 | NEG | AP | BL |
| LXU-8F | 5 | Tick | Recombitek | 18 Jul. 2010 | 91 | 7 | NEG | AP | BL |
| LXU-8F | 5 | Tick | Recombitek | 01 Aug. 2010 | 105 | 21 | LVR | AP | Pos(3) |
| LXU-8F | 5 | Tick | Recombitek | 08 Aug. 2010 | 112 | 28 | LVR | AP | Pos(3) |
| LXU-8F | 5 | Tick | Recombitek | 15 Aug. 2010 | 119 | 35 | LVR | AP | Pos(4) |
| LXU-8F | 5 | Tick | Recombitek | 22 Aug. 2010 | 126 | 42 | LVR | AP | Pos(4) |
| LXU-8F | 5 | Tick | Recombitek | 29 Aug. 2010 | 133 | 49 | LVR | AP | Pos(4) |
| LXU-8F | 5 | Tick | Recombitek | 05 Sep. 2010 | 140 | 56 | LVR | N/A | N/A |
| QZV-8M | 5 | Tick | Recombitek | 18 Oct. 2009 | | | NEG | N/A | N/A |
| QZV-8M | 5 | Tick | Recombitek | 25 Oct. 2009 | | | NEG | NEG | Neg |
| QZV-8M | 5 | Tick | Recombitek | 08 Nov. 2009 | | | NEG | NEG | Neg |
| QZV-8M | 5 | Tick | Recombitek | 14 Nov. 2009 | | | NEG | NEG | |
| QZV-8M | 5 | Tick | Recombitek | 22 Nov. 2009 | | | NEG | NEG | Neg |
| QZV-8M | 5 | Tick | Recombitek | 27 Nov. 2009 | | | NEG | N/A | N/A |
| QZV-8M | 5 | Tick | Recombitek | 06 Dec. 2009 | | | NEG | NEG | Neg |
| QZV-8M | 5 | Tick | Recombitek | 13 Dec. 2009 | | | NEG | NEG | Neg |
| QZV-8M | 5 | Tick | Recombitek | 03 Jan. 2010 | | | NEG | NEG | Pos(2) |
| QZV-8M | 5 | Tick | Recombitek | 14 Feb. 2010 | | | NEG | N/A | N/A |
| QZV-8M | 5 | Tick | Recombitek | 18 Apr. 2010 | T = 0 | | NEG | NEG | Neg |
| QZV-8M | 5 | Tick | Recombitek | 25 Apr. 2010 | 7 | | NEG | NEG | Neg |
| QZV-8M | 5 | Tick | Recombitek | 02 May 2010 | 14 | | NEG | NEG | Neg |
| QZV-8M | 5 | Tick | Recombitek | 09 May 2010 | 21 | | NEG | NEG | Neg |
| QZV-8M | 5 | Tick | Recombitek | 16 May 2010 | 28 | | NEG | NEG | Neg |
| QZV-8M | 5 | Tick | Recombitek | 23 May 2010 | 35 | | NEG | NEG | Neg |
| QZV-8M | 5 | Tick | Recombitek | 30 May 2010 | 42 | | NEG | NEG | Neg |
| QZV-8M | 5 | Tick | Recombitek | 06 Jun. 2010 | 49 | | NEG | NEG | Neg |
| QZV-8M | 5 | Tick | Recombitek | 13 Jun. 2010 | 56 | | NEG | NEG | Neg |
| QZV-8M | 5 | Tick | Recombitek | 20 Jun. 2010 | 63 | | NEG | NEG | Neg |
| QZV-8M | 5 | Tick | Recombitek | 27 Jun. 2010 | 70 | | NEG | NEG | Neg |
| QZV-8M | 5 | Tick | Recombitek | 04 Jul. 2010 | 77 | | NEG | NEG | Neg |
| QZV-8M | 5 | Tick | Recombitek | 11 Jul. 2010 | 84 | V = 0 | NEG | NEG | Neg |
| QZV-8M | 5 | Tick | Recombitek | 18 Jul. 2010 | 91 | 7 | NEG | NEG | BL |
| QZV-8M | 5 | Tick | Recombitek | 01 Aug. 2010 | 105 | 21 | LVR | NEG | Pos(4) |
| QZV-8M | 5 | Tick | Recombitek | 08 Aug. 2010 | 112 | 28 | LVR | NEG | Pos(3) |
| QZV-8M | 5 | Tick | Recombitek | 15 Aug. 2010 | 119 | 35 | LVR | NEG | Pos(4) |
| QZV-8M | 5 | Tick | Recombitek | 22 Aug. 2010 | 126 | 42 | LVR | NEG | Pos(4) |
| QZV-8M | 5 | Tick | Recombitek | 29 Aug. 2010 | 133 | 49 | LVR | NEG | Pos(4) |
| QZV-8M | 5 | Tick | Recombitek | 05 Sep. 2010 | 140 | 56 | LVR | N/A | N/A |
| UZV-8M | 5 | Tick | Recombitek | 18 Oct. 2009 | | | NEG | N/A | N/A |
| UZV-8M | 5 | Tick | Recombitek | 25 Oct. 2009 | | | NEG | NEG | Neg |
| UZV-8M | 5 | Tick | Recombitek | 08 Nov. 2009 | | | NEG | NEG | Neg |
| UZV-8M | 5 | Tick | Recombitek | 14 Nov. 2009 | | | NEG | NEG | |
| UZV-8M | 5 | Tick | Recombitek | 22 Nov. 2009 | | | NEG | NEG | Neg |
| UZV-8M | 5 | Tick | Recombitek | 27 Nov. 2009 | | | NEG | N/A | N/A |
| UZV-8M | 5 | Tick | Recombitek | 06 Dec. 2009 | | | NEG | NEG | Neg |
| UZV-8M | 5 | Tick | Recombitek | 13 Dec. 2009 | | | NEG | NEG | Neg |
| UZV-8M | 5 | Tick | Recombitek | 03 Jan. 2010 | | | NEG | NEG | Neg |
| UZV-8M | 5 | Tick | Recombitek | 14 Feb. 2010 | | | NEG | N/A | N/A |
| UZV-8M | 5 | Tick | Recombitek | 18 Apr. 2010 | T = 0 | | NEG | NEG | BL |
| UZV-8M | 5 | Tick | Recombitek | 25 Apr. 2010 | 7 | | NEG | NEG | BL |
| UZV-8M | 5 | Tick | Recombitek | 02 May 2010 | 14 | | NEG | NEG | Neg |
| UZV-8M | 5 | Tick | Recombitek | 09 May 2010 | 21 | | LEE | NEG | Pos(3) |
| UZV-8M | 5 | Tick | Recombitek | 16 May 2010 | 28 | | LEE | BB, AP | Pos(3) |
| UZV-8M | 5 | Tick | Recombitek | 23 May 2010 | 35 | | LEL | AP | Pos(4) |
| UZV-8M | 5 | Tick | Recombitek | 30 May 2010 | 42 | | LEL | AP | Pos(4) |

TABLE 4-continued

Results from Lyme experimental study

| Sample ID | Group | Prim | Vaccine | DOS (CSU) | T = 0 | V = 0 | Accuplex (Lyme) | SNAP | ILISA (Lyme) |
|---|---|---|---|---|---|---|---|---|---|
| UZV-8M | 5 | Tick | Recombitek | 06 Jun. 2010 | 49 | | LEL | BB, AP | Pos(3) |
| UZV-8M | 5 | Tick | Recombitek | 13 Jun. 2010 | 56 | | LEL | AP | Pos(4) |
| UZV-8M | 5 | Tick | Recombitek | 20 Jun. 2010 | 63 | | LEL | BB, AP | Pos(4) |
| UZV-8M | 5 | Tick | Recombitek | 27 Jun. 2010 | 70 | | LEL | BB, AP | Pos(3) |
| UZV-8M | 5 | Tick | Recombitek | 04 Jul. 2010 | 77 | | LEL | BB, AP | Pos(4) |
| UZV-8M | 5 | Tick | Recombitek | 11 Jul. 2010 | 84 | V = 0 | LEL | BB, AP | Pos(4) |
| UZV-8M | 5 | Tick | Recombitek | 18 Jul. 2010 | 91 | 7 | LEL | BB, AP | Pos(4) |
| UZV-8M | 5 | Tick | Recombitek | 01 Aug. 2010 | 105 | 21 | LELV | BB, AP | Pos(4) |
| UZV-8M | 5 | Tick | Recombitek | 08 Aug. 2010 | 112 | 28 | LELV | BB, AP | Pos(4) |
| UZV-8M | 5 | Tick | Recombitek | 15 Aug. 2010 | 119 | 35 | LELV | BB, AP | Pos(4) |
| UZV-8M | 5 | Tick | Recombitek | 22 Aug. 2010 | 126 | 42 | LELV | BB, AP | Pos(4) |
| UZV-8M | 5 | Tick | Recombitek | 29 Aug. 2010 | 133 | 49 | LELV | BB, AP | Pos(4) |
| UZV-8M | 5 | Tick | Recombitek | 05 Sep. 2010 | 140 | 56 | LELV | N/A | N/A |
| XGS-8F | 5 | Tick | Recombitek | 18 Oct. 2009 | | | NEG | N/A | N/A |
| XGS-8F | 5 | Tick | Recombitek | 25 Oct. 2009 | | | NEG | NEG | Neg |
| XGS-8F | 5 | Tick | Recombitek | 08 Nov. 2009 | | | NEG | NEG | Neg |
| XGS-8F | 5 | Tick | Recombitek | 14 Nov. 2009 | | | NEG | NEG | |
| XGS-8F | 5 | Tick | Recombitek | 22 Nov. 2009 | | | NEG | NEG | Neg |
| XGS-8F | 5 | Tick | Recombitek | 27 Nov. 2009 | | | NEG | N/A | N/A |
| XGS-8F | 5 | Tick | Recombitek | 06 Dec. 2009 | | | NEG | NEG | Neg |
| XGS-8F | 5 | Tick | Recombitek | 13 Dec. 2009 | | | NEG | NEG | Neg |
| XGS-8F | 5 | Tick | Recombitek | 03 Jan. 2010 | | | NEG | NEG | Neg |
| XGS-8F | 5 | Tick | Recombitek | 14 Feb. 2010 | | | NEG | N/A | N/A |
| XGS-8F | 5 | Tick | Recombitek | 18 Apr. 2010 | T = 0 | | NEG | NEG | Neg |
| XGS-8F | 5 | Tick | Recombitek | 25 Apr. 2010 | 7 | | NEG | NEG | Neg |
| XGS-8F | 5 | Tick | Recombitek | 02 May 2010 | 14 | | NEG | NEG | Neg |
| XGS-8F | 5 | Tick | Recombitek | 09 May 2010 | 21 | | NEG | NEG | Neg |
| XGS-8F | 5 | Tick | Recombitek | 16 May 2010 | 28 | | NEG | AP | Neg |
| XGS-8F | 5 | Tick | Recombitek | 23 May 2010 | 35 | | NEG | AP | Neg |
| XGS-8F | 5 | Tick | Recombitek | 30 May 2010 | 42 | | NEG | AP | Neg |
| XGS-8F | 5 | Tick | Recombitek | 06 Jun. 2010 | 49 | | NEG | AP | BL |
| XGS-8F | 5 | Tick | Recombitek | 13 Jun. 2010 | 56 | | NEG | BB, AP | Pos(2) |
| XGS-8F | 5 | Tick | Recombitek | 20 Jun. 2010 | 63 | | NEG | BB, AP | Pos(2) |
| XGS-8F | 5 | Tick | Recombitek | 27 Jun. 2010 | 70 | | LEE | BB, AP | Pos(2) |
| XGS-8F | 5 | Tick | Recombitek | 04 Jul. 2010 | 77 | | LEE | BB, AP | Pos(2) |
| XGS-8F | 5 | Tick | Recombitek | 11 Jul. 2010 | 84 | V = 0 | LEL | BB, AP | Pos(3) |
| XGS-8F | 5 | Tick | Recombitek | 18 Jul. 2010 | 91 | 7 | LEL | BB, AP | Pos(3) |
| XGS-8F | 5 | Tick | Recombitek | 01 Aug. 2010 | 105 | 21 | LELV | BB, AP | Pos(4) |
| XGS-8F | 5 | Tick | Recombitek | 08 Aug. 2010 | 112 | 28 | LELV | BB | Pos(4) |
| XGS-8F | 5 | Tick | Recombitek | 15 Aug. 2010 | 119 | 35 | LELV | BB, AP | Pos(4) |
| XGS-8F | 5 | Tick | Recombitek | 22 Aug. 2010 | 126 | 42 | LELV | BB | Pos(4) |
| XGS-8F | 5 | Tick | Recombitek | 29 Aug. 2010 | 133 | 49 | LVR | BB, AP | Pos(4) |
| XGS-8F | 5 | Tick | Recombitek | 05 Sep. 2010 | 140 | 56 | LVR | N/A | N/A |
| XQV-8M | 5 | Tick | Recombitek | 18 Oct. 2009 | | | NEG | | Neg |
| XQV-8M | 5 | Tick | Recombitek | 25 Oct. 2009 | | | NEG | NEG | Neg |
| XQV-8M | 5 | Tick | Recombitek | 08 Nov. 2009 | | | NEG | NEG | BL |
| XQV-8M | 5 | Tick | Recombitek | 14 Nov. 2009 | | | NEG | NEG | |
| XQV-8M | 5 | Tick | Recombitek | 22 Nov. 2009 | | | NEG | NEG | Neg |
| XQV-8M | 5 | Tick | Recombitek | 27 Nov. 2009 | | | NEG | N/A | N/A |
| XQV-8M | 5 | Tick | Recombitek | 06 Dec. 2009 | | | NEG | NEG | Neg |
| XQV-8M | 5 | Tick | Recombitek | 13 Dec. 2009 | | | NEG | NEG | Neg |
| XQV-8M | 5 | Tick | Recombitek | 03 Jan. 2010 | | | NEG | NEG | Neg |
| XQV-8M | 5 | Tick | Recombitek | 14 Feb. 2010 | | | NEG | N/A | N/A |
| XQV-8M | 5 | Tick | Recombitek | 18 Apr. 2010 | T = 0 | | NEG | NEG | Neg |
| XQV-8M | 5 | Tick | Recombitek | 25 Apr. 2010 | 7 | | NEG | NEG | Neg |
| XQV-8M | 5 | Tick | Recombitek | 02 May 2010 | 14 | | NEG | NEG | Neg |
| XQV-8M | 5 | Tick | Recombitek | 09 May 2010 | 21 | | NEG | NEG | Neg |
| XQV-8M | 5 | Tick | Recombitek | 16 May 2010 | 28 | | NEG | NEG | Neg |
| XQV-8M | 5 | Tick | Recombitek | 23 May 2010 | 35 | | NEG | NEG | BL |
| XQV-8M | 5 | Tick | Recombitek | 30 May 2010 | 42 | | NEG | AP | Neg |
| XQV-8M | 5 | Tick | Recombitek | 06 Jun. 2010 | 49 | | NEG | AP | Neg |
| XQV-8M | 5 | Tick | Recombitek | 13 Jun. 2010 | 56 | | NEG | AP | Neg |
| XQV-8M | 5 | Tick | Recombitek | 20 Jun. 2010 | 63 | | NEG | AP | Neg |
| XQV-8M | 5 | Tick | Recombitek | 27 Jun. 2010 | 70 | | NEG | NEG | Neg |
| XQV-8M | 5 | Tick | Recombitek | 04 Jul. 2010 | 77 | | NEG | NEG | Neg |
| XQV-8M | 5 | Tick | Recombitek | 11 Jul. 2010 | 84 | V = 0 | NEG | NEG | Neg |
| XQV-8M | 5 | Tick | Recombitek | 18 Jul. 2010 | 91 | 7 | NEG | NEG | BL |
| XQV-8M | 5 | Tick | Recombitek | 01 Aug. 2010 | 105 | 21 | LVR | NEG | Pos(4) |
| XQV-8M | 5 | Tick | Recombitek | 08 Aug. 2010 | 112 | 28 | LVR | NEG | Pos(4) |
| XQV-8M | 5 | Tick | Recombitek | 15 Aug. 2010 | 119 | 35 | LVR | NEG | Pos(4) |
| XQV-8M | 5 | Tick | Recombitek | 22 Aug. 2010 | 126 | 42 | LVR | NEG | Pos(4) |
| XQV-8M | 5 | Tick | Recombitek | 29 Aug. 2010 | 133 | 49 | LVR | NEG | Pos(4) |
| XQV-8M | 5 | Tick | Recombitek | 05 Sep. 2010 | 140 | 56 | LVR | N/A | N/A |
| EBS-8F | 6 | Vax | Recombitek | 18 Oct. 2009 | | | NEG | N/A | N/A |
| EBS-8F | 6 | Vax | Recombitek | 25 Oct. 2009 | | | NEG | NEG | Neg |

TABLE 4-continued

Results from Lyme experimental study

| Sample ID | Group | Prim | Vaccine | DOS (CSU) | T = 0 | V = 0 | Accuplex (Lyme) | SNAP | ILISA (Lyme) |
|---|---|---|---|---|---|---|---|---|---|
| EBS-8F | 6 | Vax | Recombitek | 08 Nov. 2009 | | V = 0 | NEG | NEG | Neg |
| EBS-8F | 6 | Vax | Recombitek | 14 Nov. 2009 | | 6 | NEG | | |
| EBS-8F | 6 | Vax | Recombitek | 22 Nov. 2009 | | 14 | LVR | NEG | BL |
| EBS-8F | 6 | Vax | Recombitek | 27 Nov. 2009 | | 19 | LVR | N/A | N/A |
| EBS-8F | 6 | Vax | Recombitek | 06 Dec. 2009 | | 28 | LVR | NEG | Pos(2) |
| EBS-8F | 6 | Vax | Recombitek | 13 Dec. 2009 | | 35 | LVR | NEG | Pos(3) |
| EBS-8F | 6 | Vax | Recombitek | 20 Dec. 2009 | | 42 | LVR | NEG | Pos(2) |
| EBS-8F | 6 | Vax | Recombitek | 27 Dec. 2009 | | 49 | LVR | N/A | N/A |
| EBS-8F | 6 | Vax | Recombitek | 03 Jan. 2010 | | 56 | LVR | NEG | Pos(3) |
| EBS-8F | 6 | Vax | Recombitek | 10 Jan. 2010 | | 63 | LVR | N/A | N/A |
| EBS-8F | 6 | Vax | Recombitek | 17 Jan. 2010 | | 70 | LVR | N/A | N/A |
| EBS-8F | 6 | Vax | Recombitek | 24 Jan. 2010 | | 77 | LVR | N/A | N/A |
| EBS-8F | 6 | Vax | Recombitek | 31 Jan. 2010 | | 84 | LVR | N/A | N/A |
| EBS-8F | 6 | Vax | Recombitek | 07 Feb. 2010 | | 91 | LVR | N/A | N/A |
| EBS-8F | 6 | Vax | Recombitek | 14 Feb. 2010 | | 98 | LVR | N/A | N/A |
| EBS-8F | 6 | Vax | Recombitek | 21 Feb. 2010 | | 105 | LVR | N/A | N/A |
| EBS-8F | 6 | Vax | Recombitek | 28 Feb. 2010 | | 112 | LVR | N/A | N/A |
| EBS-8F | 6 | Vax | Recombitek | 07 Mar. 2010 | | 119 | LVR | N/A | N/A |
| EBS-8F | 6 | Vax | Recombitek | 14 Mar. 2010 | | 126 | LVR | N/A | N/A |
| EBS-8F | 6 | Vax | Recombitek | 21 Mar. 2010 | | 133 | LVR | N/A | N/A |
| EBS-8F | 6 | Vax | Recombitek | 28 Mar. 2010 | | 140 | LVR | N/A | N/A |
| EBS-8F | 6 | Vax | Recombitek | 18 Apr. 2010 | T = 0 | 161 | LVR | NEG | Pos(4) |
| EBS-8F | 6 | Vax | Recombitek | 25 Apr. 2010 | 7 | 168 | LVR | NEG | Pos(4) |
| EBS-8F | 6 | Vax | Recombitek | 02 May 2010 | 14 | 175 | LVR | NEG | Pos(4) |
| EBS-8F | 6 | Vax | Recombitek | 09 May 2010 | 21 | 182 | LVR | NEG | Pos(3) |
| EBS-8F | 6 | Vax | Recombitek | 16 May 2010 | 28 | 189 | LVR | AP | Pos(3) |
| EBS-8F | 6 | Vax | Recombitek | 23 May 2010 | 35 | 196 | LVR | AP | Pos(4) |
| EBS-8F | 6 | Vax | Recombitek | 30 May 2010 | 42 | 203 | LVR | AP | Pos(4) |
| EBS-8F | 6 | Vax | Recombitek | 06 Jun. 2010 | 49 | 210 | LVR | AP | Pos(3) |
| EBS-8F | 6 | Vax | Recombitek | 13 Jun. 2010 | 56 | 217 | LVR | AP | Pos(4) |
| EBS-8F | 6 | Vax | Recombitek | 20 Jun. 2010 | 63 | 224 | LVR | AP | Pos(3) |
| EBS-8F | 6 | Vax | Recombitek | 27 Jun. 2010 | 70 | 231 | LVR | BB, AP | Pos(3) |
| EBS-8F | 6 | Vax | Recombitek | 04 Jul. 2010 | 77 | 238 | LVR | AP | Pos(3) |
| EBS-8F | 6 | Vax | Recombitek | 11 Jul. 2010 | 84 | 245 | LVR | AP | Pos(3) |
| EBS-8F | 6 | Vax | Recombitek | 18 Jul. 2010 | 91 | 252 | LVR | AP | Pos(4) |
| EBS-8F | 6 | Vax | Recombitek | 25 Jul. 2010 | 98 | 259 | LVR | N/A | N/A |
| EBS-8F | 6 | Vax | Recombitek | 01 Aug. 2010 | 105 | 266 | LVR | AP | Pos(3) |
| EBS-8F | 6 | Vax | Recombitek | 08 Aug. 2010 | 112 | 273 | LVR | AP | Pos(3) |
| REU-8F | 6 | Vax | Recombitek | 18 Oct. 2009 | | | NEG | N/A | N/A |
| REU-8F | 6 | Vax | Recombitek | 25 Oct. 2009 | | | NEG | NEG | Neg |
| REU-8F | 6 | Vax | Recombitek | 08 Nov. 2009 | | V = 0 | NEG | NEG | Neg |
| REU-8F | 6 | Vax | Recombitek | 14 Nov. 2009 | | 6 | NEG | NEG | |
| REU-8F | 6 | Vax | Recombitek | 22 Nov. 2009 | | 14 | LVR | NEG | BL |
| REU-8F | 6 | Vax | Recombitek | 27 Nov. 2009 | | 19 | LVR | N/A | N/A |
| REU-8F | 6 | Vax | Recombitek | 06 Dec. 2009 | | 28 | LVR | NEG | Pos(3) |
| REU-8F | 6 | Vax | Recombitek | 13 Dec. 2009 | | 35 | LVR | NEG | Pos(3) |
| REU-8F | 6 | Vax | Recombitek | 20 Dec. 2009 | | 42 | LVR | NEG | Pos(3) |
| REU-8F | 6 | Vax | Recombitek | 27 Dec. 2009 | | 49 | LVR | N/A | N/A |
| REU-8F | 6 | Vax | Recombitek | 03 Jan. 2010 | | 56 | LVR | NEG | Pos(3) |
| REU-8F | 6 | Vax | Recombitek | 10 Jan. 2010 | | 63 | LVR | N/A | N/A |
| REU-8F | 6 | Vax | Recombitek | 17 Jan. 2010 | | 70 | LVR | N/A | N/A |
| REU-8F | 6 | Vax | Recombitek | 24 Jan. 2010 | | 77 | LVR | N/A | N/A |
| REU-8F | 6 | Vax | Recombitek | 31 Jan. 2010 | | 84 | LVR | N/A | N/A |
| REU-8F | 6 | Vax | Recombitek | 07 Feb. 2010 | | 91 | LVR | N/A | N/A |
| REU-8F | 6 | Vax | Recombitek | 14 Feb. 2010 | | 98 | LVR | N/A | N/A |
| REU-8F | 6 | Vax | Recombitek | 21 Feb. 2010 | | 105 | LVR | N/A | N/A |
| REU-8F | 6 | Vax | Recombitek | 28 Feb. 2010 | | 112 | LVR | N/A | N/A |
| REU-8F | 6 | Vax | Recombitek | 07 Mar. 2010 | | 119 | LVR | N/A | N/A |
| REU-8F | 6 | Vax | Recombitek | 14 Mar. 2010 | | 126 | LVR | N/A | N/A |
| REU-8F | 6 | Vax | Recombitek | 21 Mar. 2010 | | 133 | LVR | N/A | N/A |
| REU-8F | 6 | Vax | Recombitek | 28 Mar. 2010 | | 140 | LVR | N/A | N/A |
| REU-8F | 6 | Vax | Recombitek | 18 Apr. 2010 | T = 0 | 161 | LVR | NEG | Pos(3) |
| REU-8F | 6 | Vax | Recombitek | 25 Apr. 2010 | 7 | 168 | LVR | NEG | Pos(3) |
| REU-8F | 6 | Vax | Recombitek | 02 May 2010 | 14 | 175 | LVR | AP | Pos(3) |
| REU-8F | 6 | Vax | Recombitek | 09 May 2010 | 21 | 182 | LVR | AP | Pos(3) |
| REU-8F | 6 | Vax | Recombitek | 16 May 2010 | 28 | 189 | LVR | AP | Pos(2) |
| REU-8F | 6 | Vax | Recombitek | 23 May 2010 | 35 | 196 | LVR | AP | Pos(3) |
| REU-8F | 6 | Vax | Recombitek | 30 May 2010 | 42 | 203 | LVR | AP | Pos(3) |
| REU-8F | 6 | Vax | Recombitek | 06 Jun. 2010 | 49 | 210 | LVR | AP | Pos(2) |
| REU-8F | 6 | Vax | Recombitek | 13 Jun. 2010 | 56 | 217 | LVR | AP | Pos(3) |
| REU-8F | 6 | Vax | Recombitek | 20 Jun. 2010 | 63 | 224 | LVR | AP | Pos(3) |
| REU-8F | 6 | Vax | Recombitek | 27 Jun. 2010 | 70 | 231 | LVR | BB, AP | Pos(3) |
| REU-8F | 6 | Vax | Recombitek | 04 Jul. 2010 | 77 | 238 | LVR | AP | Pos(3) |
| REU-8F | 6 | Vax | Recombitek | 11 Jul. 2010 | 84 | 245 | LVR | AP | Pos(3) |
| REU-8F | 6 | Vax | Recombitek | 18 Jul. 2010 | 91 | 252 | LVR | AP | Pos(3) |

TABLE 4-continued

| Results from Lyme experimental study | | | | | | | | | |
|---|---|---|---|---|---|---|---|---|---|
| Sample ID | Group | Prim | Vaccine | DOS (CSU) | T = 0 | V = 0 | Accuplex (Lyme) | SNAP | ILISA (Lyme) |
| REU-8F | 6 | Vax | Recombitek | 25 Jul. 2010 | 98 | 259 | LVR | N/A | N/A |
| REU-8F | 6 | Vax | Recombitek | 01 Aug. 2010 | 105 | 266 | LVR | AP | Pos(3) |
| REU-8F | 6 | Vax | Recombitek | 08 Aug. 2010 | 112 | 273 | LVR | AP | Pos(3) |
| RXV-8M | 6 | Vax | Recombitek | 18 Oct. 2009 | | | NEG | N/A | N/A |
| RXV-8M | 6 | Vax | Recombitek | 25 Oct. 2009 | | | NEG | NEG | Neg |
| RXV-8M | 6 | Vax | Recombitek | 08 Nov. 2009 | | V = 0 | NEG | NEG | Neg |
| RXV-8M | 6 | Vax | Recombitek | 14 Nov. 2009 | | 6 | NEG | NEG | |
| RXV-8M | 6 | Vax | Recombitek | 22 Nov. 2009 | | 14 | LVR | NEG | Pos(3) |
| RXV-8M | 6 | Vax | Recombitek | 27 Nov. 2009 | | 19 | LVR | N/A | N/A |
| RXV-8M | 6 | Vax | Recombitek | 06 Dec. 2009 | | 28 | LVR | NEG | Pos(3) |
| RXV-8M | 6 | Vax | Recombitek | 13 Dec. 2009 | | 35 | LVR | NEG | Pos(3) |
| RXV-8M | 6 | Vax | Recombitek | 20 Dec. 2009 | | 42 | LVR | NEG | Pos(3) |
| RXV-8M | 6 | Vax | Recombitek | 27 Dec. 2009 | | 49 | LVR | NEG | Pos(3) |
| RXV-8M | 6 | Vax | Recombitek | 03 Jan. 2010 | | 56 | LVR | NEG | Pos(3) |
| RXV-8M | 6 | Vax | Recombitek | 10 Jan. 2010 | | 63 | LVR | N/A | N/A |
| RXV-8M | 6 | Vax | Recombitek | 17 Jan. 2010 | | 70 | LVR | N/A | N/A |
| RXV-8M | 6 | Vax | Recombitek | 24 Jan. 2010 | | 77 | LVR | N/A | N/A |
| RXV-8M | 6 | Vax | Recombitek | 31 Jan. 2010 | | 84 | LVR | N/A | N/A |
| RXV-8M | 6 | Vax | Recombitek | 07 Feb. 2010 | | 91 | LVR | N/A | N/A |
| RXV-8M | 6 | Vax | Recombitek | 14 Feb. 2010 | | 98 | LVR | N/A | N/A |
| RXV-8M | 6 | Vax | Recombitek | 21 Feb. 2010 | | 105 | LVR | N/A | N/A |
| RXV-8M | 6 | Vax | Recombitek | 28 Feb. 2010 | | 112 | LVR | N/A | N/A |
| RXV-8M | 6 | Vax | Recombitek | 07 Mar. 2010 | | 119 | LVR | N/A | N/A |
| RXV-8M | 6 | Vax | Recombitek | 14 Mar. 2010 | | 126 | LVR | N/A | N/A |
| RXV-8M | 6 | Vax | Recombitek | 21 Mar. 2010 | | 133 | LVR | N/A | N/A |
| RXV-8M | 6 | Vax | Recombitek | 28 Mar. 2010 | | 140 | LVR | N/A | N/A |
| RXV-8M | 6 | Vax | Recombitek | 18 Apr. 2010 | T = 0 | 161 | LVR | NEG | Pos(4) |
| RXV-8M | 6 | Vax | Recombitek | 25 Apr. 2010 | 7 | 168 | LVR | NEG | Pos(4) |
| RXV-8M | 6 | Vax | Recombitek | 02 May 2010 | 14 | 175 | LVR | NEG | Pos(4) |
| RXV-8M | 6 | Vax | Recombitek | 09 May 2010 | 21 | 182 | LVR | NEG | Pos(4) |
| RXV-8M | 6 | Vax | Recombitek | 16 May 2010 | 28 | 189 | LVR | NEG | Pos(3) |
| RXV-8M | 6 | Vax | Recombitek | 23 May 2010 | 35 | 196 | LVR | NEG | Pos(4) |
| RXV-8M | 6 | Vax | Recombitek | 30 May 2010 | 42 | 203 | LVR | NEG | Pos(4) |
| RXV-8M | 6 | Vax | Recombitek | 06 Jun. 2010 | 49 | 210 | LVR | NEG | Pos(3) |
| RXV-8M | 6 | Vax | Recombitek | 13 Jun. 2010 | 56 | 217 | LVR | NEG | Pos(4) |
| RXV-8M | 6 | Vax | Recombitek | 20 Jun. 2010 | 63 | 224 | LVR | NEG | Pos(4) |
| RXV-8M | 6 | Vax | Recombitek | 27 Jun. 2010 | 70 | 231 | LVR | NEG | Pos(4) |
| RXV-8M | 6 | Vax | Recombitek | 04 Jul. 2010 | 77 | 238 | LVR | NEG | Pos(4) |
| RXV-8M | 6 | Vax | Recombitek | 11 Jul. 2010 | 84 | 245 | LVR | NEG | Pos(4) |
| RXV-8M | 6 | Vax | Recombitek | 18 Jul. 2010 | 91 | 252 | LVR | NEG | Pos(4) |
| RXV-8M | 6 | Vax | Recombitek | 25 Jul. 2010 | 98 | 259 | LVR | N/A | N/A |
| RXV-8M | 6 | Vax | Recombitek | 01 Aug. 2010 | 105 | 266 | LVR | NEG | Pos(4) |
| RXV-8M | 6 | Vax | Recombitek | 08 Aug. 2010 | 112 | 273 | LVR | NEG | Pos(3) |
| VRV-8M | 6 | Vax | Recombitek | 18 Oct. 2009 | | | NEG | N/A | N/A |
| VRV-8M | 6 | Vax | Recombitek | 25 Oct. 2009 | | | NEG | N/A | N/A |
| VRV-8M | 6 | Vax | Recombitek | 14 Nov. 2009 | | 6 | NEG | NEG | |
| VRV-8M | 6 | Vax | Recombitek | 22 Nov. 2009 | | 14 | LVR | NEG | Pos(3) |
| VRV-8M | 6 | Vax | Recombitek | 27 Nov. 2009 | | 19 | LVR | N/A | N/A |
| VRV-8M | 6 | Vax | Recombitek | 06 Dec. 2009 | | 28 | LVR | NEG | Pos(3) |
| VRV-8M | 6 | Vax | Recombitek | 13 Dec. 2009 | | 35 | LVR | | |
| VRV-8M | 6 | Vax | Recombitek | 20 Dec. 2009 | | 42 | LVR | NEG | Pos(3) |
| VRV-8M | 6 | Vax | Recombitek | 27 Dec. 2009 | | 49 | LVR | N/A | N/A |
| VRV-8M | 6 | Vax | Recombitek | 03 Jan. 2010 | | 56 | LVR | NEG | Pos(3) |
| VRV-8M | 6 | Vax | Recombitek | 10 Jan. 2010 | | 63 | LVR | N/A | N/A |
| VRV-8M | 6 | Vax | Recombitek | 17 Jan. 2010 | | 70 | LVR | N/A | N/A |
| VRV-8M | 6 | Vax | Recombitek | 24 Jan. 2010 | | 77 | LVR | N/A | N/A |
| VRV-8M | 6 | Vax | Recombitek | 31 Jan. 2010 | | 84 | LVR | N/A | N/A |
| VRV-8M | 6 | Vax | Recombitek | 07 Feb. 2010 | | 91 | LVR | N/A | N/A |
| VRV-8M | 6 | Vax | Recombitek | 14 Feb. 2010 | | 98 | LVR | N/A | N/A |
| VRV-8M | 6 | Vax | Recombitek | 21 Feb. 2010 | | 105 | LVR | N/A | N/A |
| VRV-8M | 6 | Vax | Recombitek | 28 Feb. 2010 | | 112 | LVR | N/A | N/A |
| VRV-8M | 6 | Vax | Recombitek | 07 Mar. 2010 | | 119 | LVR | N/A | N/A |
| VRV-8M | 6 | Vax | Recombitek | 14 Mar. 2010 | | 126 | LVR | N/A | N/A |
| VRV-8M | 6 | Vax | Recombitek | 21 Mar. 2010 | | 133 | LVR | N/A | N/A |
| VRV-8M | 6 | Vax | Recombitek | 28 Mar. 2010 | | 140 | LVR | N/A | N/A |
| VRV-8M | 6 | Vax | Recombitek | 18 Apr. 2010 | T = 0 | 161 | LVR | | Pos(3) |
| VRV-8M | 6 | Vax | Recombitek | 25 Apr. 2010 | 7 | 168 | LVR | NEG | Pos(3) |
| VRV-8M | 6 | Vax | Recombitek | 02 May 2010 | 14 | 175 | LVR | NEG | Pos(4) |
| VRV-8M | 6 | Vax | Recombitek | 09 May 2010 | 21 | 182 | LVR | NEG | Pos(3) |
| VRV-8M | 6 | Vax | Recombitek | 16 May 2010 | 28 | 189 | LELV | NEG | Pos(3) |
| VRV-8M | 6 | Vax | Recombitek | 23 May 2010 | 35 | 196 | LELV | BB, AP | Pos(4) |
| VRV-8M | 6 | Vax | Recombitek | 30 May 2010 | 42 | 203 | LELV | BB, AP | Pos(4) |
| VRV-8M | 6 | Vax | Recombitek | 06 Jun. 2010 | 49 | 210 | LELV | BB, AP | Pos(3) |
| VRV-8M | 6 | Vax | Recombitek | 13 Jun. 2010 | 56 | 217 | LELV | BB, AP | Pos(4) |
| VRV-8M | 6 | Vax | Recombitek | 20 Jun. 2010 | 63 | 224 | LELV | BB, AP | Pos(4) |

TABLE 4-continued

Results from Lyme experimental study

| Sample ID | Group | Prim | Vaccine | DOS (CSU) | T = 0 | V = 0 | Accuplex (Lyme) | SNAP | ILISA (Lyme) |
|---|---|---|---|---|---|---|---|---|---|
| VRV-8M | 6 | Vax | Recombitek | 27 Jun. 2010 | 70 | 231 | LELV | BB, AP | Pos(3) |
| VRV-8M | 6 | Vax | Recombitek | 04 Jul. 2010 | 77 | 238 | LELV | BB, AP | Pos(4) |
| VRV-8M | 6 | Vax | Recombitek | 11 Jul. 2010 | 84 | 245 | LELV | BB, AP | Pos(4) |
| VRV-8M | 6 | Vax | Recombitek | 18 Jul. 2010 | 91 | 252 | LELV | BB, AP | Pos(4) |
| VRV-8M | 6 | Vax | Recombitek | 25 Jul. 2010 | 98 | 259 | LELV | N/A | N/A |
| VRV-8M | 6 | Vax | Recombitek | 01 Aug. 2010 | 105 | 266 | LELV | BB, AP | Pos(4) |
| VRV-8M | 6 | Vax | Recombitek | 08 Aug. 2010 | 112 | 273 | LELV | BB, AP | Pos(3) |
| XRV-8M | 6 | Vax | Recombitek | 18 Oct. 2009 | | | NEG | | Neg |
| XRV-8M | 6 | Vax | Recombitek | 25 Oct. 2009 | | | NEG | NEG | BL |
| XRV-8M | 6 | Vax | Recombitek | 08 Nov. 2009 | | V = 0 | NEG | NEG | BL |
| XRV-8M | 6 | Vax | Recombitek | 14 Nov. 2009 | | 6 | NEG | NEG | |
| XRV-8M | 6 | Vax | Recombitek | 22 Nov. 2009 | | 14 | LVR | NEG | Pos(2) |
| XRV-8M | 6 | Vax | Recombitek | 27 Nov. 2009 | | 19 | LVR | N/A | N/A |
| XRV-8M | 6 | Vax | Recombitek | 06 Dec. 2009 | | 28 | LVR | NEG | Pos(3) |
| XRV-8M | 6 | Vax | Recombitek | 13 Dec. 2009 | | 35 | LVR | NEG | Pos(3) |
| XRV-8M | 6 | Vax | Recombitek | 20 Dec. 2009 | | 42 | LVR | NEG | Pos(3) |
| XRV-8M | 6 | Vax | Recombitek | 27 Dec. 2009 | | 49 | LVR | NEG | Pos(3) |
| XRV-8M | 6 | Vax | Recombitek | 03 Jan. 2010 | | 56 | LVR | NEG | Pos(3) |
| XRV-8M | 6 | Vax | Recombitek | 10 Jan. 2010 | | 63 | LVR | N/A | N/A |
| XRV-8M | 6 | Vax | Recombitek | 17 Jan. 2010 | | 70 | LVR | N/A | N/A |
| XRV-8M | 6 | Vax | Recombitek | 24 Jan. 2010 | | 77 | LVR | N/A | N/A |
| XRV-8M | 6 | Vax | Recombitek | 31 Jan. 2010 | | 84 | LVR | N/A | N/A |
| XRV-8M | 6 | Vax | Recombitek | 07 Feb. 2010 | | 91 | LVR | N/A | N/A |
| XRV-8M | 6 | Vax | Recombitek | 14 Feb. 2010 | | 98 | LVR | N/A | N/A |
| XRV-8M | 6 | Vax | Recombitek | 21 Feb. 2010 | | 105 | LVR | N/A | N/A |
| XRV-8M | 6 | Vax | Recombitek | 28 Feb. 2010 | | 112 | LVR | N/A | N/A |
| XRV-8M | 6 | Vax | Recombitek | 07 Mar. 2010 | | 119 | LVR | N/A | N/A |
| XRV-8M | 6 | Vax | Recombitek | 14 Mar. 2010 | | 126 | LVR | N/A | N/A |
| XRV-8M | 6 | Vax | Recombitek | 21 Mar. 2010 | | 133 | LVR | N/A | N/A |
| XRV-8M | 6 | Vax | Recombitek | 28 Mar. 2010 | | 140 | LVR | N/A | N/A |
| XRV-8M | 6 | Vax | Recombitek | 18 Apr. 2010 | T = 0 | 161 | LVR | NEG | Pos(3) |
| XRV-8M | 6 | Vax | Recombitek | 25 Apr. 2010 | 7 | 168 | LVR | NEG | Pos(3) |
| XRV-8M | 6 | Vax | Recombitek | 02 May 2010 | 14 | 175 | LVR | NEG | Pos(4) |
| XRV-8M | 6 | Vax | Recombitek | 09 May 2010 | 21 | 182 | LVR | NEG | Pos(3) |
| XRV-8M | 6 | Vax | Recombitek | 16 May 2010 | 28 | 189 | LVR | NEG | Pos(3) |
| XRV-8M | 6 | Vax | Recombitek | 23 May 2010 | 35 | 196 | LVR | NEG | Pos(4) |
| XRV-8M | 6 | Vax | Recombitek | 30 May 2010 | 42 | 203 | LVR | NEG | Pos(3) |
| XRV-8M | 6 | Vax | Recombitek | 06 Jun. 2010 | 49 | 210 | LVR | NEG | Pos(2) |
| XRV-8M | 6 | Vax | Recombitek | 13 Jun. 2010 | 56 | 217 | LVR | NEG | Pos(4) |
| XRV-8M | 6 | Vax | Recombitek | 20 Jun. 2010 | 63 | 224 | LVR | NEG | Pos(4) |
| XRV-8M | 6 | Vax | Recombitek | 27 Jun. 2010 | 70 | 231 | LVR | NEG | Pos(3) |
| XRV-8M | 6 | Vax | Recombitek | 04 Jul. 2010 | 77 | 238 | LVR | NEG | Pos(3) |
| XRV-8M | 6 | Vax | Recombitek | 11 Jul. 2010 | 84 | 245 | LVR | NEG | Pos(3) |
| XRV-8M | 6 | Vax | Recombitek | 18 Jul. 2010 | 91 | 252 | LVR | NEG | Pos(4) |
| XRV-8M | 6 | Vax | Recombitek | 25 Jul. 2010 | 98 | 259 | LVR | N/A | N/A |
| XRV-8M | 6 | Vax | Recombitek | 01 Aug. 2010 | 105 | 266 | LVR | NEG | Pos(3) |
| XRV-8M | 6 | Vax | Recombitek | 08 Aug. 2010 | 112 | 273 | LVR | NEG | Pos(3) |
| YRS-8F | 6 | Vax | Recombitek | 18 Oct. 2009 | | | NEG | N/A | N/A |
| YRS-8F | 6 | Vax | Recombitek | 25 Oct. 2009 | | | NEG | NEG | Neg |
| YRS-8F | 6 | Vax | Recombitek | 08 Nov. 2009 | | V = 0 | NEG | NEG | Neg |
| YRS-8F | 6 | Vax | Recombitek | 14 Nov. 2009 | | 6 | NEG | NEG | |
| YRS-8F | 6 | Vax | Recombitek | 22 Nov. 2009 | | 14 | LVR | NEG | Pos(2) |
| YRS-8F | 6 | Vax | Recombitek | 27 Nov. 2009 | | 19 | LVR | N/A | N/A |
| YRS-8F | 6 | Vax | Recombitek | 06 Dec. 2009 | | 28 | LVR | NEG | Pos(2) |
| YRS-8F | 6 | Vax | Recombitek | 13 Dec. 2009 | | 35 | LVR | NEG | Pos(3) |
| YRS-8F | 6 | Vax | Recombitek | 20 Dec. 2009 | | 42 | LVR | NEG | Pos(3) |
| YRS-8F | 6 | Vax | Recombitek | 27 Dec. 2009 | | 49 | LVR | NEG | Pos(3) |
| YRS-8F | 6 | Vax | Recombitek | 03 Jan. 2010 | | 56 | LVR | NEG | Pos(3) |
| YRS-8F | 6 | Vax | Recombitek | 10 Jan. 2010 | | 63 | LVR | N/A | N/A |
| YRS-8F | 6 | Vax | Recombitek | 17 Jan. 2010 | | 70 | LVR | N/A | N/A |
| YRS-8F | 6 | Vax | Recombitek | 24 Jan. 2010 | | 77 | LVR | N/A | N/A |
| YRS-8F | 6 | Vax | Recombitek | 31 Jan. 2010 | | 84 | LVR | N/A | N/A |
| YRS-8F | 6 | Vax | Recombitek | 07 Feb. 2010 | | 91 | LVR | N/A | N/A |
| YRS-8F | 6 | Vax | Recombitek | 14 Feb. 2010 | | 98 | LVR | N/A | N/A |
| YRS-8F | 6 | Vax | Recombitek | 21 Feb. 2010 | | 105 | LVR | N/A | N/A |
| YRS-8F | 6 | Vax | Recombitek | 28 Feb. 2010 | | 112 | LVR | N/A | N/A |
| YRS-8F | 6 | Vax | Recombitek | 07 Mar. 2010 | | 119 | LVR | N/A | N/A |
| YRS-8F | 6 | Vax | Recombitek | 14 Mar. 2010 | | 126 | LVR | N/A | N/A |
| YRS-8F | 6 | Vax | Recombitek | 21 Mar. 2010 | | 133 | LVR | N/A | N/A |
| YRS-8F | 6 | Vax | Recombitek | 28 Mar. 2010 | | 140 | LVR | N/A | N/A |
| YRS-8F | 6 | Vax | Recombitek | 18 Apr. 2010 | T = 0 | 161 | LVR | NEG | Pos(4) |
| YRS-8F | 6 | Vax | Recombitek | 25 Apr. 2010 | 7 | 168 | LVR | NEG | Pos(4) |
| YRS-8F | 6 | Vax | Recombitek | 02 May 2010 | 14 | 175 | LVR | NEG | Pos(4) |
| YRS-8F | 6 | Vax | Recombitek | 09 May 2010 | 21 | 182 | LVR | NEG | Pos(4) |
| YRS-8F | 6 | Vax | Recombitek | 16 May 2010 | 28 | 189 | LVR | AP | Pos(4) |

TABLE 4-continued

Results from Lyme experimental study

| Sample ID | Group | Prim | Vaccine | DOS (CSU) | T = 0 | V = 0 | Accuplex (Lyme) | SNAP | ILISA (Lyme) |
|---|---|---|---|---|---|---|---|---|---|
| YRS-8F | 6 | Vax | Recombitek | 23 May 2010 | 35 | 196 | LVR | AP | Pos(4) |
| YRS-8F | 6 | Vax | Recombitek | 30 May 2010 | 42 | 203 | LVR | AP | Pos(4) |
| YRS-8F | 6 | Vax | Recombitek | 06 Jun. 2010 | 49 | 210 | LVR | AP | Pos(4) |
| YRS-8F | 6 | Vax | Recombitek | 13 Jun. 2010 | 56 | 217 | LVR | NEG | Pos(4) |
| YRS-8F | 6 | Vax | Recombitek | 20 Jun. 2010 | 63 | 224 | LVR | AP | Pos(4) |
| YRS-8F | 6 | Vax | Recombitek | 27 Jun. 2010 | 70 | 231 | LVR | BB, AP | Pos(3) |
| YRS-8F | 6 | Vax | Recombitek | 04 Jul. 2010 | 77 | 238 | LVR | AP | Pos(4) |
| YRS-8F | 6 | Vax | Recombitek | 11 Jul. 2010 | 84 | 245 | LVR | AP | Pos(4) |
| YRS-8F | 6 | Vax | Recombitek | 18 Jul. 2010 | 91 | 252 | LVR | AP | Pos(4) |
| YRS-8F | 6 | Vax | Recombitek | 25 Jul. 2010 | 98 | 259 | LVR | N/A | N/A |
| YRS-8F | 6 | Vax | Recombitek | 01 Aug. 2010 | 105 | 266 | LVR | AP | Pos(4) |
| YRS-8F | 6 | Vax | Recombitek | 08 Aug. 2010 | 112 | 273 | LVR | AP | Pos(4) |

TABLE 5

Lyme Group 1 compared for mean time to positive

| Sample ID | Accuplex | SNAP | IFA |
|---|---|---|---|
| ALS-8F | 21 | 42 | 21 |
| EGS-8F | 49 | 28 | 35 |
| KKV-8M | 21 | 28 | 21 |
| SHU-8F | 21 | 42 | 0 |
| SZV-8M | 21 | 21 | 14 |
| WBV-8M | 21 | 28 | 28 |
| Mean | 25.7 | 31.5 | 23.8 |
| Range | 21-49 | 21-42 | 21-35 |

TABLE 6

Lyme Group 3 compared for mean time to positive

| Sample ID | Accuplex | SNAP | IFA |
|---|---|---|---|
| DDS-8F | 21 | 28 | 0 |
| EZS-8F | 21 | 35 | 21 |
| OUV-8M | N/A | N/A | N/A |
| UTV-8M | 21 | 35 | 21 |
| VVS-8F | 14 | 35 | 21 |
| WOV-8M | 28 | 42 | 42 |
| Mean | 21.0 | 35.0 | 26.3 |
| Range | 14-28 | 28-42 | 21-42 |

TABLE 7

Lyme Group 5 compared for mean time to positive

| Sample ID | Accuplex | SNAP | IFA |
|---|---|---|---|
| DFS-8F | 21 | 42 | 21 |
| LXU-8F | N/A | N/A | N/A |
| QZV-8M | N/A | N/A | N/A |
| UZV-8M | 21 | 28 | 21 |
| XGS-8F | 70 | 56 | 56 |
| XQV-8M | N/A | N/A | N/A |
| Mean | 37.3 | 42.0 | 32.7 |
| Range | 21-70 | 28-56 | 21-56 |

Example 5

Test of Experimentally Infected Dogs for *A. phagocytophilum* Infection

Table 8 shows test results from experimentally infected dogs using the ACCUPLEX™ AP test in comparison to the SNAP™ and IFA tests. *A. phagocytophilum* (OK Sate University isolate) was administered to all dogs on 22 Feb. 2010 (i=0). All dogs were administered 100 mg of doxycycline for 28 days staring on 7 Jun. 2010. Table 9 shows the comparison of days for detection among ACCUPLEX™, SNAP™, PCR and IFA tests.

TABLE 8

*A. phagocytophilum* test results from experimentally infected dogs

| Sample ID | DOR (Antech) | DOS (CSU) | Day of Sampling (CSU) | Accuplex (AP) | SNAP | PCR (AP) | IFA (AP) |
|---|---|---|---|---|---|---|---|
| BCX8 | 23 Feb. 2010 | 22 Feb. 2010 | *i* = 0 | 1640 | NEG | NEG | <1:20 |
| | 26 Feb. 2010 | 25 Feb. 2010 | 3 | 2969 | NEG | NEG | <1:20 |
| | 02 Mar. 2010 | 01 Mar. 2010 | 7 | 1263 | NEG | NEG | <1:20 |
| | 05 Mar. 2010 | 04 Mar. 2010 | 10 | 2034 | NEG | POS | <1:20 |
| | 09 Mar. 2010 | 08 Mar. 2010 | 14 | 1229 | NEG | N/A | <1:20 |
| | 12 Mar. 2010 | 11 Mar. 2010 | 17 | 2340 | NEG | POS | ‘1:80 |
| | 16 Mar. 2010 | 15 Mar. 2010 | 21 | 2857 | NEG | POS | ‘1:160 |
| | 23 Mar. 2010 | 22 Mar. 2010 | 28 | 32984 | AP | NEG | ‘1:2560 |
| | 31 Mar. 2010 | 29 Mar. 2010 | 35 | 28998 | AP | POS | ‘1:1280 |
| | 06 Apr. 2010 | 05 Apr. 2010 | 42 | 28787 | AP | POS | ‘1:320 |
| | 13 Apr. 2010 | 12 Apr. 2010 | 49 | 21919 | AP | POS | ‘1:320 |
| | 20 Apr. 2010 | 19 Apr. 2010 | 56 | 19524 | AP | POS | ‘1:1280 |
| | 27 Apr. 2010 | 26 Apr. 2010 | 63 | 22244 | AP | NEG | ‘1:5120 |
| | 04 May 2010 | 03 May 2010 | 70 | 21707 | AP | POS | ‘1:640 |
| | 11 May 2010 | 10 May 2010 | 77 | 21253 | AP | POS | ‘1:320 |
| | 18 May 2010 | 17 May 2010 | 84 | 13074 | AP | POS | ‘1:320 |
| | 25 May 2010 | 24 May 2010 | 91 | 15581 | AP | POS | ‘1:2560 |

TABLE 8-continued

*A. phagocytophilum* test results from experimentally infected dogs

| Sample ID | DOR (Antech) | DOS (CSU) | Day of Sampling (CSU) | Accuplex (AP) | SNAP | PCR (AP) | IFA (AP) |
|---|---|---|---|---|---|---|---|
| | 02 Jun. 2010 | 31 May 2010 | 98 | 19010 | AP | NEG | ‘1:2560 |
| | 08 Jun. 2010 | 07 Jun. 2010 | 105 | 17788 | AP | NEG | ‘1:2560 |
| | 15 Jun. 2010 | 14 Jun. 2010 | 112 | 19041 | AP | NEG | ‘1:2560 |
| | 22 Jun. 2010 | 21 Jun. 2010 | 119 | 17707 | AP | NEG | ‘1:1280 |
| | 29 Jun. 2010 | 28 Jun. 2010 | 126 | 8313 | AP | NEG | ‘1:640 |
| | 07 Jul. 2010 | 05 Jul. 2010 | 133 | 5910 | AP | NEG | ‘1:160 |
| | 13 Jul. 2010 | 12 Jul. 2010 | 140 | 8832 | AP | NEG | ‘1:640 |
| | 20 Jul. 2010 | 19 Jul. 2010 | 147 | 6158 | AP | NEG | ‘1:640 |
| | 27 Jul. 2010 | 26 Jul. 2010 | 154 | 11618 | AP | NEG | ‘1:640 |
| | 03 Aug. 2010 | 02 Aug. 2010 | 161 | 7791 | AP | NEG | 1:320 |
| | N/A | 18 Aug. 2010 | 168 | 7623 | N/A | N/A | N/A |
| DAX8 | 23 Feb. 2010 | 22 Feb. 2010 | *i* = 0 | 369 | NEG | NEG | <1:20 |
| | 26 Feb. 2010 | 25 Feb. 2010 | 3 | 432 | NEG | NEG | <1:20 |
| | 02 Mar. 2010 | 01 Mar. 2010 | 7 | 328 | NEG | NEG | <1:20 |
| | 05 Mar. 2010 | 04 Mar. 2010 | 10 | 467 | NEG | POS | <1:20 |
| | 09 Mar. 2010 | 08 Mar. 2010 | 14 | 1144 | NEG | N/A | <1:20 |
| | 12 Mar. 2010 | 11 Mar. 2010 | 17 | 375 | AP | POS | ‘1:40 |
| | 16 Mar. 2010 | 15 Mar. 2010 | 21 | 1395 | AP | POS | ‘1:80 |
| | 23 Mar. 2010 | 22 Mar. 2010 | 28 | 19858 | AP | POS | ‘1:320 |
| | 31 Mar. 2010 | 29 Mar. 2010 | 35 | 13481 | AP | POS | ‘1:640 |
| | 06 Apr. 2010 | 05 Apr. 2010 | 42 | 16629 | AP | POS | ‘1:320 |
| | 13 Apr. 2010 | 12 Apr. 2010 | 49 | 17505 | AP | POS | ‘1:640 |
| | 20 Apr. 2010 | 19 Apr. 2010 | 56 | 17795 | AP | POS | ‘1:640 |
| | 27 Apr. 2010 | 26 Apr. 2010 | 63 | 13393 | AP | POS | ‘1:320 |
| | 27 Apr. 2010 | 26 Apr. 2010 | 63 | 15070 | AP | POS | ‘1:320 |
| | 04 May 2010 | 03 May 2010 | 70 | 18751 | AP | NEG | ‘1:640 |
| | 11 May 2010 | 10 May 2010 | 77 | 16807 | AP | POS | ‘1:320 |
| | 18 May 2010 | 17 May 2010 | 84 | 16829 | AP | POS | ‘1:320 |
| | 25 May 2010 | 24 May 2010 | 91 | 18417 | AP | POS | ‘1:2560 |
| | 02 Jun. 2010 | 31 May 2010 | 98 | 20341 | AP | POS | ‘1:1280 |
| | 08 Jun. 2010 | 07 Jun. 2010 | 105 | 9007 | AP | NEG | ‘1:640 |
| | 15 Jun. 2010 | 14 Jun. 2010 | 112 | 7324 | AP | NEG | ‘1:640 |
| | 22 Jun. 2010 | 21 Jun. 2010 | 119 | 6590 | AP | NEG | ‘1:640 |
| | 29 Jun. 2010 | 28 Jun. 2010 | 126 | 10588 | AP | NEG | ‘1:640 |
| | 07 Jul. 2010 | 05 Jul. 2010 | 133 | 5786 | AP | NEG | ‘1:320 |
| | 13 Jul. 2010 | 12 Jul. 2010 | 140 | 9108 | AP | NEG | ‘1:160 |
| | 20 Jul. 2010 | 19 Jul. 2010 | 147 | 8073 | AP | NEG | ‘1:160 |
| | 27 Jul. 2010 | 26 Jul. 2010 | 154 | 6737 | AP | NEG | ‘1:320 |
| | 03 Aug. 2010 | 02 Aug. 2010 | 161 | 5439 | AP | NEG | 1:320 |
| | N/A | 18 Aug. 2010 | 168 | 4089 | N/A | N/A | N/A |
| DOX8 | 23 Feb. 2010 | 22 Feb. 2010 | *i* = 0 | 1010 | NEG | NEG | <1:20 |
| | 26 Feb. 2010 | 25 Feb. 2010 | 3 | 1026 | NEG | NEG | <1:20 |
| | 02 Mar. 2010 | 01 Mar. 2010 | 7 | 1187 | NEG | NEG | <1:20 |
| | 05 Mar. 2010 | 04 Mar. 2010 | 10 | 1412 | NEG | POS | <1:20 |
| | 09 Mar. 2010 | 08 Mar. 2010 | 14 | 1106 | NEG | N/A | <1:20 |
| | 12 Mar. 2010 | 11 Mar. 2010 | 17 | 1248 | NEG | NEG | <1:20 |
| | 16 Mar. 2010 | 15 Mar. 2010 | 21 | 2082 | NEG | NEG | <1:20 |
| | 23 Mar. 2010 | 22 Mar. 2010 | 28 | 6994 | NEG | POS | ‘1:640 |
| | 31 Mar. 2010 | 29 Mar. 2010 | 35 | 17526 | AP | NEG | ‘1:1280 |
| | 06 Apr. 2010 | 05 Apr. 2010 | 42 | 16462 | AP | NEG | ‘1:640 |
| | 13 Apr. 2010 | 12 Apr. 2010 | 49 | 17356 | AP | NEG | ‘1:2560 |
| | 20 Apr. 2010 | 19 Apr. 2010 | 56 | 14720 | AP | POS | ‘1:1280 |
| | 04 May 2010 | 03 May 2010 | 70 | 13124 | AP | NEG | ‘1:10240 |
| | 11 May 2010 | 10 May 2010 | 77 | 16870 | AP | NEG | ‘1:640 |
| | 18 May 2010 | 17 May 2010 | 84 | 19938 | AP | NEG | ‘1:640 |
| | 25 May 2010 | 24 May 2010 | 91 | 19470 | AP | NEG | ‘1:320 |
| | 02 Jun. 2010 | 31 May 2010 | 98 | 18761 | AP | NEG | ‘1:1280 |
| | 08 Jun. 2010 | 07 Jun. 2010 | 105 | 12409 | AP | NEG | ‘1:640 |
| | 15 Jun. 2010 | 14 Jun. 2010 | 112 | 9406 | AP | NEG | ‘1:640 |
| | 22 Jun. 2010 | 21 Jun. 2010 | 119 | 8408 | AP | NEG | ‘1:640 |
| | 29 Jun. 2010 | 28 Jun. 2010 | 126 | 5553 | AP | NEG | ‘1:160 |
| | 07 Jul. 2010 | 05 Jul. 2010 | 133 | 5836 | AP | NEG | ‘1:160 |
| | 13 Jul. 2010 | 12 Jul. 2010 | 140 | 8244 | AP | NEG | ‘1:320 |
| | 20 Jul. 2010 | 19 Jul. 2010 | 147 | 9093 | AP | NEG | ‘1:320 |
| | 27 Jul. 2010 | 26 Jul. 2010 | 154 | 7609 | AP | NEG | ‘1:640 |
| | 03 Aug. 2010 | 02 Aug. 2010 | 161 | 8105 | AP | NEG | 1:320 |
| | N/A | 18 Aug. 2010 | 168 | 9476 | N/A | N/A | N/A |
| EOX8 | 23 Feb. 2010 | 22 Feb. 2010 | *i* = 0 | 769 | NEG | NEG | <1:20 |
| | 26 Feb. 2010 | 25 Feb. 2010 | 3 | 679 | NEG | NEG | <1:20 |
| | 02 Mar. 2010 | 01 Mar. 2010 | 7 | 615 | NEG | NEG | <1:20 |
| | 05 Mar. 2010 | 04 Mar. 2010 | 10 | 680 | NEG | NEG | <1:20 |
| | 09 Mar. 2010 | 08 Mar. 2010 | 14 | 1028 | NEG | N/A | <1:20 |
| | 12 Mar. 2010 | 11 Mar. 2010 | 17 | 881 | AP | NEG | <1:20 |
| | 16 Mar. 2010 | 15 Mar. 2010 | 21 | 4075 | AP | POS | <1:20 |

TABLE 8-continued

*A. phagocytophilum* test results from experimentally infected dogs

| Sample ID | DOR (Antech) | DOS (CSU) | Day of Sampling (CSU) | Accuplex (AP) | SNAP | PCR (AP) | IFA (AP) |
|---|---|---|---|---|---|---|---|
| | 23 Mar. 2010 | 22 Mar. 2010 | 28 | 33925 | AP | NEG | ‘1:160 |
| | 31 Mar. 2010 | 29 Mar. 2010 | 35 | 33180 | AP | NEG | ‘1:640 |
| | 06 Apr. 2010 | 05 Apr. 2010 | 42 | 29336 | AP | NEG | ‘1:160 |
| | 13 Apr. 2010 | 12 Apr. 2010 | 49 | 24874 | AP | NEG | ‘1:640 |
| | 20 Apr. 2010 | 19 Apr. 2010 | 56 | 23144 | AP | NEG | ‘1:640 |
| | 27 Apr. 2010 | 26 Apr. 2010 | 63 | 22632 | AP | NEG | ‘1:160 |
| | 04 May 2010 | 03 May 2010 | 70 | 20047 | AP | NEG | ‘1:320 |
| | 11 May 2010 | 10 May 2010 | 77 | 16528 | AP | NEG | ‘1:160 |
| | 18 May 2010 | 17 May 2010 | 84 | 17389 | AP | NEG | ‘1:160 |
| | 25 May 2010 | 24 May 2010 | 91 | 16648 | AP | NEG | ‘1:160 |
| | 02 Jun. 2010 | 31 May 2010 | 98 | 16632 | AP | NEG | ‘1:160 |
| | 08 Jun. 2010 | 07 Jun. 2010 | 105 | 11712 | AP | NEG | ‘1:160 |
| | 15 Jun. 2010 | 14 Jun. 2010 | 112 | 14238 | AP | NEG | ‘1:80 |
| | 22 Jun. 2010 | 21 Jun. 2010 | 119 | 16731 | AP | NEG | ‘1:80 |
| | 29 Jun. 2010 | 28 Jun. 2010 | 126 | 13590 | AP | NEG | ‘1:160 |
| | 07 Jul. 2010 | 05 Jul. 2010 | 133 | 12342 | AP | NEG | ‘1:20 |
| | 13 Jul. 2010 | 12 Jul. 2010 | 140 | 12862 | AP | NEG | ‘1:160 |
| | 20 Jul. 2010 | 19 Jul. 2010 | 147 | 12831 | AP | NEG | ‘1:160 |
| | 27 Jul. 2010 | 26 Jul. 2010 | 154 | 11344 | AP | NEG | ‘1:160 |
| | 03 Aug. 2010 | 02 Aug. 2010 | 161 | 11031 | AP | NEG | 1:80 |
| | N/A | 18 Aug. 2010 | 168 | 10900 | N/A | N/A | N/A |
| JSW8 | 23 Feb. 2010 | 22 Feb. 2010 | *i* = 0 | 2823 | NEG | NEG | <1:20 |
| | 26 Feb. 2010 | 25 Feb. 2010 | 3 | 1882 | NEG | POS | <1:20 |
| | 02 Mar. 2010 | 01 Mar. 2010 | 7 | 1533 | NEG | POS | <1:20 |
| | 05 Mar. 2010 | 04 Mar. 2010 | 10 | 2629 | NEG | POS | <1:40 |
| | 09 Mar. 2010 | 08 Mar. 2010 | 14 | 5724 | NEG | N/A | 1:320 |
| | 12 Mar. 2010 | 11 Mar. 2010 | 17 | 12076 | AP | POS | ‘1:320 |
| | 16 Mar. 2010 | 15 Mar. 2010 | 21 | 20558 | AP | POS | ‘1:160 |
| | 23 Mar. 2010 | 22 Mar. 2010 | 28 | 29531 | AP | POS | ‘1:640 |
| | 31 Mar. 2010 | 29 Mar. 2010 | 35 | 20922 | AP | POS | ‘1:1280 |
| | 06 Apr. 2010 | 05 Apr. 2010 | 42 | 23876 | AP | NEG | ‘1:640 |
| | 13 Apr. 2010 | 12 Apr. 2010 | 49 | 21910 | AP | POS | ‘1:1280 |
| | 20 Apr. 2010 | 19 Apr. 2010 | 56 | 20635 | AP | POS | ‘1:640 |
| | 27 Apr. 2010 | 26 Apr. 2010 | 63 | 23345 | AP | POS | ‘1:320 |
| | 04 May 2010 | 03 May 2010 | 70 | 32000 | AP | NEG | ‘1:10240 |
| | 11 May 2010 | 10 May 2010 | 77 | 19207 | AP | POS | ‘1:320 |
| | 18 May 2010 | 17 May 2010 | 84 | 14193 | AP | POS | ‘1:1280 |
| | 25 May 2010 | 24 May 2010 | 91 | 13850 | AP | POS | ‘1:640 |
| | 02 Jun. 2010 | 31 May 2010 | 98 | 11582 | AP | NEG | ‘1:640 |
| | 08 Jun. 2010 | 07 Jun. 2010 | 105 | 10636 | AP | POS | ‘1:1280 |
| | 15 Jun. 2010 | 14 Jun. 2010 | 112 | 11212 | AP | NEG | ‘1:2560 |
| | 22 Jun. 2010 | 21 Jun. 2010 | 119 | 10251 | AP | NEG | ‘1:640 |
| | 29 Jun. 2010 | 28 Jun. 2010 | 126 | 5821 | AP | NEG | ‘1:640 |
| | 07 Jul. 2010 | 05 Jul. 2010 | 133 | 5689 | AP | NEG | ‘1:320 |
| | 13 Jul. 2010 | 12 Jul. 2010 | 140 | 7043 | AP | NEG | ‘1:640 |
| | 20 Jul. 2010 | 19 Jul. 2010 | 147 | 6859 | AP | NEG | ‘1:640 |
| | 27 Jul. 2010 | 26 Jul. 2010 | 154 | 5945 | AP | NEG | ‘1:320 |
| | 03 Aug. 2010 | 02 Aug. 2010 | 161 | 6462 | AP | NEG | 1:320 |
| JXX8 | 23 Feb. 2010 | 22 Feb. 2010 | *i* = 0 | 709 | NEG | NEG | <1:20 |
| | 26 Feb. 2010 | 25 Feb. 2010 | 3 | 703 | NEG | NEG | <1:20 |
| | 02 Mar. 2010 | 01 Mar. 2010 | 7 | 820 | NEG | NEG | <1:20 |
| | 05 Mar. 2010 | 04 Mar. 2010 | 10 | 1052 | NEG | POS | <1:20 |
| | 09 Mar. 2010 | 08 Mar. 2010 | 14 | 5120 | NEG | N/A | <1:20 |
| | 12 Mar. 2010 | 11 Mar. 2010 | 17 | 20488 | NEG | POS | ‘1:160 |
| | 16 Mar. 2010 | 15 Mar. 2010 | 21 | 20205 | NEG | POS | ‘1:160 |
| | 23 Mar. 2010 | 22 Mar. 2010 | 28 | 25119 | AP | POS | ‘1:320 |
| | 31 Mar. 2010 | 29 Mar. 2010 | 35 | 23879 | AP | POS | ‘1:640 |
| | 06 Apr. 2010 | 05 Apr. 2010 | 42 | 17842 | AP | POS | ‘1:160 |
| | 13 Apr. 2010 | 12 Apr. 2010 | 49 | 17213 | AP | POS | ‘1:2560 |
| | 20 Apr. 2010 | 19 Apr. 2010 | 56 | 18407 | AP | NEG | ‘1:320 |
| | 27 Apr. 2010 | 26 Apr. 2010 | 63 | 23775 | AP | POS | ‘1:640 |
| | 04 May 2010 | 03 May 2010 | 70 | 25162 | AP | POS | ‘1:10240 |
| | 11 May 2010 | 10 May 2010 | 77 | 24139 | AP | NEG | ‘1:640 |
| | 18 May 2010 | 17 May 2010 | 84 | 21620 | AP | NEG | ‘1:1280 |
| | 25 May 2010 | 24 May 2010 | 91 | 19156 | AP | NEG | ‘1:640 |
| | 02 Jun. 2010 | 31 May 2010 | 98 | 16575 | AP | POS | ‘1:640 |
| | 08 Jun. 2010 | 07 Jun. 2010 | 105 | 13215 | AP | POS | ‘1:1280 |
| | 15 Jun. 2010 | 14 Jun. 2010 | 112 | 15281 | AP | NEG | ‘1:1280 |
| | 22 Jun. 2010 | 21 Jun. 2010 | 119 | 17794 | AP | NEG | ‘1:640 |
| | 29 Jun. 2010 | 28 Jun. 2010 | 126 | 17202 | AP | NEG | ‘1:640 |

TABLE 8-continued

| A. phagocytophilum test results from experimentally infected dogs | | | | | | | |
|---|---|---|---|---|---|---|---|
| Sample ID | DOR (Antech) | DOS (CSU) | Day of Sampling (CSU) | Accuplex (AP) | SNAP | PCR (AP) | IFA (AP) |
| | 07 Jul. 2010 | 05 Jul. 2010 | 133 | 9624 | AP | NEG | ‘1:160 |
| | 13 Jul. 2010 | 12 Jul. 2010 | 140 | 9077 | AP | NEG | ‘1:320 |
| | 20 Jul. 2010 | 19 Jul. 2010 | 147 | 12147 | AP | NEG | ‘1:640 |
| | 27 Jul. 2010 | 26 Jul. 2010 | 154 | 12445 | AP | NEG | ‘1:640 |
| | 03 Aug. 2010 | 02 Aug. 2010 | 161 | 16884 | AP | NEG | 1:320 |
| | N/A | 18 Aug. 2010 | 168 | 12946 | N/A | N/A | N/A |
| LSW8 | 23 Feb. 2010 | 22 Feb. 2010 | *i* = 0 | 569 | NEG | NEG | <1:20 |
| | 26 Feb. 2010 | 25 Feb. 2010 | 3 | 379 | NEG | POS | <1:20 |
| | 02 Mar. 2010 | 01 Mar. 2010 | 7 | 431 | NEG | POS | <1:20 |
| | 05 Mar. 2010 | 04 Mar. 2010 | 10 | 440 | NEG | POS | <1:40 |
| | 09 Mar. 2010 | 08 Mar. 2010 | 14 | 486 | NEG | N/A | <1:20 |
| | 12 Mar. 2010 | 11 Mar. 2010 | 17 | 1015 | NEG | POS | ‘1:160 |
| | 16 Mar. 2010 | 15 Mar. 2010 | 21 | 3770 | NEG | NEG | ‘1:160 |
| | 23 Mar. 2010 | 22 Mar. 2010 | 28 | 8544 | NEG | NEG | ‘1:640 |
| | 31 Mar. 2010 | 29 Mar. 2010 | 35 | 11628 | AP | NEG | ‘1:640 |
| | 06 Apr. 2010 | 05 Apr. 2010 | 42 | 11217 | AP | NEG | ‘1:320 |
| | 13 Apr. 2010 | 12 Apr. 2010 | 49 | 10865 | AP | NEG | ‘1:320 |
| | 20 Apr. 2010 | 19 Apr. 2010 | 56 | 9510 | AP | NEG | ‘1:160 |
| | 27 Apr. 2010 | 26 Apr. 2010 | 63 | 9246 | AP | POS | ‘1:320 |
| | 04 May 2010 | 03 May 2010 | 70 | 12596 | AP | POS | ‘1:5120 |
| | 11 May 2010 | 10 May 2010 | 77 | 11373 | AP | NEG | ‘1:320 |
| | 18 May 2010 | 17 May 2010 | 84 | 11152 | AP | NEG | ‘1:320 |
| | 25 May 2010 | 24 May 2010 | 91 | 12237 | AP | NEG | ‘1:640 |
| | 02 Jun. 2010 | 31 May 2010 | 98 | 18052 | AP | NEG | ‘1:640 |
| | 08 Jun. 2010 | 07 Jun. 2010 | 105 | 15482 | AP | NEG | ‘1:1280 |
| | 15 Jun. 2010 | 14 Jun. 2010 | 112 | 15936 | AP | NEG | ‘1:1280 |
| | 22 Jun. 2010 | 21 Jun. 2010 | 119 | 15764 | AP | NEG | ‘1:320 |
| | 29 Jun. 2010 | 28 Jun. 2010 | 126 | 20683 | AP | NEG | ‘1:320 |
| | 07 Jul. 2010 | 05 Jul. 2010 | 133 | 17797 | AP | NEG | ‘1:640 |
| | 13 Jul. 2010 | 12 Jul. 2010 | 140 | 15125 | AP | NEG | ‘1:320 |
| | 20 Jul. 2010 | 19 Jul. 2010 | 147 | 11935 | AP | NEG | ‘1:640 |
| | 27 Jul. 2010 | 26 Jul. 2010 | 154 | 16614 | AP | NEG | ‘1:320 |
| | 03 Aug. 2010 | 02 Aug. 2010 | 161 | 16313 | AP | NEG | 1:320 |
| | N/A | 18 Aug. 2010 | 168 | 15635 | N/A | N/A | N/A |
| ZPX8 | 23 Feb. 2010 | 22 Feb. 2010 | *i* = 0 | 4270 | NEG | NEG | <1:20 |
| | 26 Feb. 2010 | 25 Feb. 2010 | 3 | 2801 | NEG | NEG | <1:20 |
| | 02 Mar. 2010 | 01 Mar. 2010 | 7 | 1716 | NEG | NEG | <1:20 |
| | 05 Mar. 2010 | 4 Mar. 2010 | 10 | 2558 | NEG | NEG | <1:20 |
| | 09 Mar. 2010 | 08 Mar. 2010 | 14 | 2509 | NEG | N/A | <1:20 |
| | 12 Mar. 2010 | 11 Mar. 2010 | 17 | 2772 | NEG | NEG | <1:20 |
| | 16 Mar. 2010 | 15 Mar. 2010 | 21 | 1713 | NEG | NEG | <1:20 |
| | 23 Mar. 2010 | 22 Mar. 2010 | 28 | 2678 | NEG | NEG | <1:20 |
| | 31 Mar. 2010 | 29 Mar. 2010 | 35 | 2849 | NEG | NEG | <1:20 |
| | 06 Apr. 2010 | 05 Apr. 2010 | 42 | 1802 | NEG | NEG | <1:20 |
| | 13 Apr. 2010 | 12 Apr. 2010 | 49 | 2261 | NEG | NEG | <1:20 |
| | 20 Apr. 2010 | 19 Apr. 2010 | 56 | 2187 | NEG | NEG | <1:20 |
| | 27 Apr. 2010 | 26 Apr. 2010 | 63 | 1483 | NEG | NEG | <1:20 |
| | 04 May 2010 | 03 May 2010 | 70 | 1446 | NEG | NEG | <1:40 |
| | 11 May 2010 | 10 May 2010 | 77 | 1196 | NEG | NEG | <1:20 |
| | 18 May 2010 | 17 May 2010 | 84 | 1015 | NEG | NEG | <1:20 |
| | 25 May 2010 | 24 May 2010 | 91 | 1507 | NEG | NEG | <1:20 |
| | 02 Jun. 2010 | 31 May 2010 | 98 | 1127 | NEG | NEG | <1:20 |
| | N/A | 18 Aug. 2010 | 168 | 3219 | N/A | N/A | N/A |

TABLE 9

| Comparison of time of detection between different *A. phagocytophilum* tests | | | | |
|---|---|---|---|---|
| Sample ID | Accuplex | SNAP | PCR | IFA |
| BCX8 | 28 | 28 | 10 | 17 |
| DAX8 | 28 | 17 | 10 | 17 |
| DOX8 | 28 | 35 | 10 | 28 |
| EOX8 | 28 | 17 | 21 | 28 |
| JSW8 | 14 | 17 | 3 | 14 |
| JXX8 | 14 | 28 | 10 | 17 |
| LSW8 | 28 | 35 | 3 | 17 |

TABLE 9-continued

| Comparison of time of detection between different *A. phagocytophilum* tests | | | | |
|---|---|---|---|---|
| Sample ID | Accuplex | SNAP | PCR | IFA |
| ZPX8 | N/A | N/A | N/A | N/A |
| Averages | 24.00 | 25.29 | 9.57 | 19.71 |
| Max | 28 | 35 | 21 | 28 |
| Min | 14 | 17 | 3 | 14 |
| Range | 14-28 | 17-35 | 3-21 | 14-28 |

Example 6

Test of Experimentally Infected Dogs for *E. canis* Infection

Table 10 shows test results from experimentally infected dogs using the new ACCUPLEX™ *E. canis* test in comparison to the SNAP™, PCR and IFA tests. *E. canis* (OK Sate University isolate "EBONY") was administered to all dogs on 11 Jan. 2010. All Dogs were administered 100 mg (PO/BID) of doxycycline for 28 days staring on 8 Mar. 2010. Table 11 shows the comparison of days for detection among different tests.

TABLE 10

Results from *E. canis* experimental study

| Sample ID | DOR (Antech) | DOS (CSU) | Day of Sampling (CSU) | Accuplex (EC) | IFA (EC) | PCR (EC) | SNAP |
|---|---|---|---|---|---|---|---|
| ADW8 | 12 Jan. 2010 | 11 Jan. 2010 | *i* = 0 | 429 | <1:80 | NEG | NEG |
| | 15 Jan. 2010 | 14 Jan. 2010 | 3 | 197 | <1:20 | NEG | NEG |
| | 20 Jan. 2010 | 18 Jan. 2010 | 7 | 411 | <1:20 | NEG | NEG |
| | 22 Jan. 2010 | 21 Jan. 2010 | 10 | 321 | <1:80 | NEG | NEG |
| | 26 Jan. 2010 | 25 Jan. 2010 | 14 | 1156 | <1:80 | POS | NEG |
| | 29 Jan. 2010 | 28 Jan. 2010 | 17 | 9214 | <1:80 | POS | NEG |
| | 02 Feb. 2010 | 01 Feb. 2010 | 21 | 34152 | <1:20 | POS | NEG |
| | 09 Feb. 2010 | 08 Feb. 2010 | 28 | 28840 | ‘1:10240 | POS | EC |
| | 16 Feb. 2010 | 15 Feb. 2010 | 35 | 28951 | ‘1:1280 | POS | EC |
| | 23 Feb. 2010 | 22 Feb. 2010 | 42 | 23797 | ‘1:10240 | POS | EC |
| | 02 Mar. 2010 | 01 Mar. 2010 | 49 | 11253 | ‘1:2560 | POS | EC |
| | 09 Mar. 2010 | 08 Mar. 2010 | 56 | 20742 | ‘1:10240 | N/A | EC |
| | 16 Mar. 2010 | 15 Mar. 2010 | 63 | 17760 | ‘1:80 | NEG | EC |
| | 23 Mar. 2010 | 22 Mar. 2010 | 70 | 17020 | ‘1:320 | NEG | EC |
| | 31 Mar. 2010 | 29 Mar. 2010 | 77 | 10006 | ‘1:2560 | NEG | EC |
| | 06 Apr. 2010 | 05 Apr. 2010 | 84 | 13251 | ‘1:640 | NEG | EC |
| | 21 Apr. 2010 | 19 Apr. 2010 | 98 | 6544 | ‘1:320 | NEG | EC |
| BTX8 | 12 Jan. 2010 | 11 Jan. 2010 | *i* = 0 | 598 | <1:80 | NEG | NEG |
| | 15 Jan. 2010 | 14 Jan. 2010 | 3 | 443 | <1:20 | NEG | NEG |
| | 20 Jan. 2010 | 18 Jan. 2010 | 7 | 1429 | <1:20 | NEG | NEG |
| | 22 Jan. 2010 | 21 Jan. 2010 | 10 | 914 | <1:80 | NEG | NEG |
| | 26 Jan. 2010 | 25 Jan. 2010 | 14 | 2181 | <1:80 | POS | NEG |
| | 29 Jan. 2010 | 28 Jan. 2010 | 17 | 24893 | ‘1:160 | POS | NEG |
| | 02 Feb. 2010 | 01 Feb. 2010 | 21 | 33019 | <1:20 | POS | NEG |
| | 09 Feb. 2010 | 08 Feb. 2010 | 28 | 34660 | ‘1:10240 | POS | NEG |
| | 16 Feb. 2010 | 15 Feb. 2010 | 35 | 34594 | ‘1:5120 | POS | EC |
| | 23 Feb. 2010 | 22 Feb. 2010 | 42 | 32876 | ‘1:10240 | POS | EC |
| | 02 Mar. 2010 | 01 Mar. 2010 | 49 | 34355 | ‘1:10240 | POS | EC |
| | 09 Mar. 2010 | 08 Mar. 2010 | 56 | 34480 | ‘1:10240 | N/A | EC |
| | 16 Mar. 2010 | 15 Mar. 2010 | 63 | 33717 | ‘1:160 | NEG | EC |
| | 23 Mar. 2010 | 22 Mar. 2010 | 70 | 34704 | ‘1:640 | NEG | EC |
| | 31 Mar. 2010 | 29 Mar. 2010 | 77 | 34591 | ‘1:5120 | NEG | EC |
| | 06 Apr. 2010 | 05 Apr. 2010 | 84 | 35110 | ‘1:2560 | NEG | EC |
| | 21 Apr. 2010 | 19 Apr. 2010 | 98 | 34425 | ‘1:640 | NEG | EC |
| BZX8 | 12 Jan. 2010 | 11 Jan. 2010 | *i* = 0 | 1208 | <1:80 | NEG | NEG |
| | 15 Jan. 2010 | 14 Jan. 2010 | 3 | 1002 | <1:20 | NEG | NEG |
| | 20 Jan. 2010 | 18 Jan. 2010 | 7 | 539 | <1:20 | NEG | NEG |
| | 22 Jan. 2010 | 21 Jan. 2010 | 10 | 761 | <1:80 | NEG | NEG |
| | 26 Jan. 2010 | 25 Jan. 2010 | 14 | 7011 | <1:80 | POS | NEG |
| | 29 Jan. 2010 | 28 Jan. 2010 | 17 | 34549 | ‘1:320 | POS | NEG |
| | 02 Feb. 2010 | 01 Feb. 2010 | 21 | 35145 | <1:20 | POS | NEG |
| | 09 Feb. 2010 | 08 Feb. 2010 | 28 | 35291 | ‘1:10240 | POS | EC |
| | 16 Feb. 2010 | 15 Feb. 2010 | 35 | 34672 | ‘1:2560 | POS | EC |
| | 23 Feb. 2010 | 22 Feb. 2010 | 42 | 35004 | ‘1:20480 | POS | EC |
| | 02 Mar. 2010 | 01 Mar. 2010 | 49 | 30262 | ‘1:10240 | POS | EC |
| | 09 Mar. 2010 | 08 Mar. 2010 | 56 | 35218 | ‘1:10240 | N/A | EC |
| | 16 Mar. 2010 | 15 Mar. 2010 | 63 | 32598 | ‘1:5120 | NEG | EC |
| | 23 Mar. 2010 | 22 Mar. 2010 | 70 | 29931 | ‘1:640 | NEG | EC |
| | 31 Mar. 2010 | 29 Mar. 2010 | 77 | 23457 | ‘1:5120 | NEG | EC |
| | 06 Apr. 2010 | 05 Apr. 2010 | 84 | 22186 | ‘1:1280 | NEG | EC |
| | 21 Apr. 2010 | 19 Apr. 2010 | 98 | 22936 | ‘1:160 | NEG | EC |
| CSX8 | 12 Jan. 2010 | 11 Jan. 2010 | *i* = 0 | 1155 | <1:80 | NEG | NEG |
| | 15 Jan. 2010 | 14 Jan. 2010 | 3 | 805 | <1:20 | NEG | NEG |
| | 20 Jan. 2010 | 18 Jan. 2010 | 7 | 746 | <1:20 | NEG | NEG |
| | 22 Jan. 2010 | 21 Jan. 2010 | 10 | 564 | <1:80 | NEG | NEG |
| | 26 Jan. 2010 | 25 Jan. 2010 | 14 | 1197 | <1:80 | NEG | NEG |
| | 29 Jan. 2010 | 28 Jan. 2010 | 17 | 13835 | <1:80 | POS | NEG |
| | 02 Feb. 2010 | 01 Feb. 2010 | 21 | 35106 | ‘1:640 | POS | EC |
| | 09 Feb. 2010 | 08 Feb. 2010 | 28 | 34316 | ‘1:2560 | POS | NEG |
| | 16 Feb. 2010 | 15 Feb. 2010 | 35 | 34346 | ‘1:1280 | POS | EC |
| | 23 Feb. 2010 | 22 Feb. 2010 | 42 | 34447 | ‘1:20480 | POS | EC |
| | 02 Mar. 2010 | 01 Mar. 2010 | 49 | 28743 | ‘1:5120 | POS | EC |
| | 09 Mar. 2010 | 08 Mar. 2010 | 56 | 34907 | ‘1:10240 | N/A | EC |
| | 16 Mar. 2010 | 15 Mar. 2010 | 63 | 31107 | ‘1:2560 | NEG | EC |
| | 23 Mar. 2010 | 22 Mar. 2010 | 70 | 34607 | ‘1:1280 | NEG | EC |

TABLE 10-continued

Results from *E. canis* experimental study

| Sample ID | DOR (Antech) | DOS (CSU) | Day of Sampling (CSU) | Accuplex (EC) | IFA (EC) | PCR (EC) | SNAP |
|---|---|---|---|---|---|---|---|
| | 31 Mar. 2010 | 29 Mar. 2010 | 77 | 20368 | N/A | N/A | EC |
| | 06 Apr. 2010 | 05 Apr. 2010 | 84 | 32386 | ‘1:640 | NEG | EC |
| | 21 Apr. 2010 | 19 Apr. 2010 | 98 | 24398 | ‘1:320 | NEG | EC |
| DSX8 | 12 Jan. 2010 | 11 Jan. 2010 | *i* = 0 | 804 | <1:80 | NEG | NEG |
| | 15 Jan. 2010 | 14 Jan. 2010 | 3 | 581 | <1:20 | NEG | NEG |
| | 20 Jan. 2010 | 18 Jan. 2010 | 7 | 415 | <1:20 | NEG | NEG |
| | 22 Jan. 2010 | 21 Jan. 2010 | 10 | 346 | <1:80 | NEG | NEG |
| | 26 Jan. 2010 | 25 Jan. 2010 | 14 | 5784 | <1:80 | POS | NEG |
| | 29 Jan. 2010 | 28 Jan. 2010 | 17 | 35252 | ‘1:160 | POS | EC |
| | 02 Feb. 2010 | 01 Feb. 2010 | 21 | 34845 | ‘1:1280 | POS | NEG |
| | 09 Feb. 2010 | 08 Feb. 2010 | 28 | 35098 | ‘1:20480 | POS | NEG |
| | 16 Feb. 2010 | 15 Feb. 2010 | 35 | 35133 | ‘1:2560 | POS | EC |
| | 23 Feb. 2010 | 22 Feb. 2010 | 42 | 35076 | ‘1:10240 | POS | EC |
| | 02 Mar. 2010 | 01 Mar. 2010 | 49 | 34962 | ‘1:10240 | POS | EC |
| | 09 Mar. 2010 | 08 Mar. 2010 | 56 | 35105 | ‘1:10240 | N/A | EC |
| | 16 Mar. 2010 | 15 Mar. 2010 | 63 | 34815 | ‘1:5120 | NEG | EC |
| | 23 Mar. 2010 | 22 Mar. 2010 | 70 | 35153 | ‘1:1280 | NEG | EC |
| | 31 Mar. 2010 | 29 Mar. 2010 | 77 | 34565 | ‘1:10240 | NEG | EC |
| | 06 Apr. 2010 | 05 Apr. 2010 | 84 | 35152 | ‘1:640 | NEG | EC |
| | 21 Apr. 2010 | 19 Apr. 2010 | 98 | 34192 | ‘1:320 | NEG | EC |
| EEW8 | 12 Jan. 2010 | 11 Jan. 2010 | *i* = 0 | 599 | <1:80 | NEG | NEG |
| | 15 Jan. 2010 | 14 Jan. 2010 | 3 | 256 | <1:20 | NEG | NEG |
| | 20 Jan. 2010 | 18 Jan. 2010 | 7 | 389 | <1:20 | NEG | NEG |
| | 22 Jan. 2010 | 21 Jan. 2010 | 10 | 625 | <1:80 | NEG | NEG |
| | 26 Jan. 2010 | 25 Jan. 2010 | 14 | 1613 | <1:80 | POS | NEG |
| | 29 Jan. 2010 | 28 Jan. 2010 | 17 | 31118 | <1:80 | POS | NEG |
| | 02 Feb. 2010 | 01 Feb. 2010 | 21 | 30680 | ‘1:1280 | POS | NEG |
| | 09 Feb. 2010 | 08 Feb. 2010 | 28 | 35077 | ‘1:10240 | POS | NEG |
| | 16 Feb. 2010 | 15 Feb. 2010 | 35 | 35089 | ‘1:2560 | POS | EC |
| | 23 Feb. 2010 | 22 Feb. 2010 | 42 | 34959 | ‘1:20480 | POS | EC |
| | 02 Mar. 2010 | 01 Mar. 2010 | 49 | 34672 | ‘1:5120 | POS | EC |
| | 09 Mar. 2010 | 08 Mar. 2010 | 56 | 34973 | ‘1:10240 | N/A | EC |
| | 16 Mar. 2010 | 15 Mar. 2010 | 63 | 33510 | ‘1:5120 | NEG | EC |
| | 23 Mar. 2010 | 22 Mar. 2010 | 70 | 35166 | ‘1:1280 | NEG | EC |
| | 31 Mar. 2010 | 29 Mar. 2010 | 77 | 30469 | ‘1:5120 | NEG | EC |
| | 06 Apr. 2010 | 05 Apr. 2010 | 84 | 33812 | ‘1:640 | NEG | EC |
| | 21 Apr. 2010 | 19 Apr. 2010 | 98 | 26468 | ‘1:640 | NEG | EC |
| IJX8 | 12 Jan. 2010 | 11 Jan. 2010 | *i* = 0 | 32102 | ‘1:320 | POS | EC |
| | 15 Jan. 2010 | 14 Jan. 2010 | 3 | 31156 | ‘1:80 | NEG | EC |
| | 20 Jan. 2010 | 18 Jan. 2010 | 7 | 31037 | ‘1:160 | POS | EC |
| | 22 Jan. 2010 | 21 Jan. 2010 | 10 | 29207 | ‘1:160 | POS | EC |
| | 26 Jan. 2010 | 25 Jan. 2010 | 14 | 26535 | ‘1:160 | POS | EC |
| | 29 Jan. 2010 | 28 Jan. 2010 | 17 | 17434 | ‘1:160 | POS | EC |
| | 02 Feb. 2010 | 01 Feb. 2010 | 21 | 4093 | ‘1:640 | POS | EC |
| | 09 Feb. 2010 | 08 Feb. 2010 | 28 | 20442 | ‘1:1280 | POS | EC |
| | 16 Feb. 2010 | 15 Feb. 2010 | 35 | 21619 | ‘1:1280 | POS | EC |
| | 23 Feb. 2010 | 22 Feb. 2010 | 42 | 22308 | ‘1:5120 | NEG | EC |
| | 02 Mar. 2010 | 01 Mar. 2010 | 49 | 17389 | ‘1:2560 | NEG | EC |
| | 09 Mar. 2010 | 08 Mar. 2010 | 56 | 24161 | ‘1:640 | N/A | EC |
| | 16 Mar. 2010 | 15 Mar. 2010 | 63 | 17122 | ‘1:640 | NEG | EC |
| | 23 Mar. 2010 | 22 Mar. 2010 | 70 | 19757 | ‘1:160 | NEG | EC |
| | 31 Mar. 2010 | 29 Mar. 2010 | 77 | 19853 | ‘1:1280 | NEG | EC |
| | 06 Apr. 2010 | 05 Apr. 2010 | 84 | 23343 | ‘1:320 | NEG | EC |
| | 21 Apr. 2010 | 19 Apr. 2010 | 98 | 16498 | ‘1:160 | NEG | EC |
| ZGX8 | 12 Jan. 2010 | 11 Jan. 2010 | *i* = 0 | 549 | <1:80 | NEG | NEG |
| | 15 Jan. 2010 | 14 Jan. 2010 | 3 | 362 | <1:20 | NEG | NEG |
| | 20 Jan. 2010 | 18 Jan. 2010 | 7 | 310 | <1:20 | NEG | NEG |
| | 22 Jan. 2010 | 21 Jan. 2010 | 10 | 465 | <1:80 | NEG | NEG |
| | 26 Jan. 2010 | 25 Jan. 2010 | 14 | 994 | <1:80 | POS | NEG |
| | 29 Jan. 2010 | 28 Jan. 2010 | 17 | 28233 | ‘1:160 | POS | NEG |
| | 02 Feb. 2010 | 01 Feb. 2010 | 21 | 33182 | ‘1:1280 | POS | NEG |
| | 09 Feb. 2010 | 08 Feb. 2010 | 28 | 31715 | ‘1:20480 | POS | NEG |
| | 16 Feb. 2010 | 15 Feb. 2010 | 35 | 31692 | ‘1:10240 | POS | NEG |
| | 23 Feb. 2010 | 02 Feb. 2010 | 42 | 33667 | ‘1:10240 | NEG | EC |
| | 02 Mar. 2010 | 01 Mar. 2010 | 49 | 33274 | ‘1:10240 | NEG | EC |
| | 09 Mar. 2010 | 08 Mar. 2010 | 56 | 33837 | ‘1:640 | N/A | EC |
| | 16 Mar. 2010 | 15 Mar. 2010 | 63 | 27576 | ‘1:1280 | NEG | EC |
| | 23 Mar. 2010 | 22 Mar. 2010 | 70 | 34335 | ‘1:320 | NEG | EC |
| | 31 Mar. 2010 | 29 Mar. 2010 | 77 | 33054 | ‘1:1280 | NEG | EC |
| | 06 Apr. 2010 | 05 Apr. 2010 | 84 | 33374 | ‘1:320 | NEG | EC |
| | 21 Apr. 2010 | 19 Apr. 2010 | 98 | 27605 | ‘1:320 | NEG | EC |
| ZIW8 | 12 Jan. 2010 | 11 Jan. 2010 | *i* = 0 | 1654 | <1:80 | NEG | NEG |
| | 15 Jan. 2010 | 14 Jan. 2010 | 3 | 560 | <1:20 | NEG | NEG |
| | 20 Jan. 2010 | 18 Jan. 2010 | 7 | 828 | <1:20 | NEG | NEG |

TABLE 10-continued

| Results from *E. canis* experimental study | | | | | | | |
|---|---|---|---|---|---|---|---|
| Sample ID | DOR (Antech) | DOS (CSU) | Day of Sampling (CSU) | Accuplex (EC) | IFA (EC) | PCR (EC) | SNAP |
| | 22 Jan. 2010 | 21 Jan. 2010 | 10 | 533 | <1:80 | NEG | NEG |
| | 26 Jan. 2010 | 25 Jan. 2010 | 14 | 606 | <1:80 | NEG | NEG |
| | 29 Jan. 2010 | 28 Jan. 2010 | 17 | 4475 | <1:80 | NEG | NEG |
| | 02 Feb. 2010 | 01 Feb. 2010 | 21 | 34217 | '1:80 | POS | NEG |
| | 09 Feb. 2010 | 08 Feb. 2010 | 28 | 34218 | '1:5120 | POS | EC |
| | 16 Feb. 2010 | 15 Feb. 2010 | 35 | 34073 | '1:2560 | POS | EC |
| | 23 Feb. 2010 | 22 Feb. 2010 | 42 | 34102 | '1:40960 | POS | EC |
| | 02 Mar. 2010 | 01 Mar. 2010 | 49 | 31502 | '1:10240 | POS | EC |
| | 09 Mar. 2010 | 08 Mar. 2010 | 56 | 32904 | '1:5120 | N/A | EC |
| | 16 Mar. 2010 | 15 Mar. 2010 | 63 | 34854 | '1:10240 | NEG | EC |
| | 23 Mar. 2010 | 22 Mar. 2010 | 70 | 34847 | '1:1280 | NEG | EC |
| | 31 Mar. 2010 | 29 Mar. 2010 | 77 | 34915 | N/A | N/A | EC |
| | 06 Apr. 2010 | 05 Apr. 2010 | 84 | 33870 | '1:640 | NEG | EC |
| | 21 Apr. 2010 | 19 Apr. 2010 | 98 | 33318 | '1:160 | NEG | EC |

TABLE 11

| Comparison of time for detection among different *E. canis* tests | | | | |
|---|---|---|---|---|
| Sample ID | GP36 | IFA | PCR | SNAP |
| ADW8 | 17 | 28 | 14 | 28 |
| BTX8 | 17 | 17 | 14 | 35 |
| BZX8 | 14 | 17 | 14 | 28 |
| CSX8 | 17 | 21 | 17 | 21 |
| DSX8 | 17 | 17 | 14 | 17 |
| EEW8 | 17 | 21 | 14 | 35 |
| LJX8 | N/A | N/A | N/A | N/A |
| ZGX8 | 17 | 17 | 14 | 42 |
| ZIW8 | 21 | 21 | 21 | 28 |
| Averages | 17.125 | 19.875 | 15.25 | 29.25 |
| Max | 21 | 28 | 21 | 42 |
| Min | 14 | 17 | 14 | 17 |
| Range | 14-21 | 17-28 | 14-21 | 17-42 |

Example 7

Detection of Antibodies Against *Anaplasma phagocytophilum* in Experimentally Infected Dogs Using an Automated Fluorescence Based System Objective:

To evaluate a new automated system for detection of *Anaplasma phagocytophilum* antibodies in serum of dogs after parenteral inoculation or exposure to wild-caught *Ixodes scapularis.*

Sample Population:

26 laboratory reared, mixed sex beagles.

Procedures.

Serum and blood was collected temporally from beagles inoculated with culture derived *A. phagocytophilum* intravenously (5 dogs) or subcutaneously (3 dogs) and 18 dogs that were exposed to wild-caught, adult *Ixodes scapularis*. An automated fluorescence system based on a silicon wafer was optimized to detect *A. phagocytophilum* antibodies to a novel mutant peptide and applied to the canine sera. *Anaplasma phagocytophilum* antibodies were also detected by indirect fluorescent antibody assay and a commercially available kit. *Anaplasma phagocytophilum* DNA was amplified from blood by polymerase chain reaction (PCR) assay.

Results:

All seven parenterally inoculated dogs that remained in the study and 10 of 18 dogs exposed to *I. scapularis* were infected by *A. phagocytophilum*. The time to first positive result for these 10 dogs varied by assay but was only statistically significant amongst groups on week 3 when more samples were PCR positive compared to the antibody assays.

Conclusions:

Results of the three *A. phagocytophilum* antibody tests were similar which validates the use of the fluorescence-based system. Performance of *A. phagocytophilum* PCR assays is indicated in dogs with suspected acute anaplasmosis if serum antibody assays are negative.

Introduction

*Anaplasma phagocytophilum* is a rickettsial organism that is vectored by *Ixodes* spp. (Dumler et al., *Int J Syst Evol Microbiol* 51:2145 (2001)). The organism is associated with granulocytic anaplasmosis in a variety of species including humans, horses, dogs, and cats (Chen et al., *J Clin Microbiol* 32:589 (1994); Foley et al., *Vet Rec* 160:159 (2007); Lappin et al., *J Am Vet Med Assoc* (2004) 225:893-896). Distinct strains exist which are associated with host tropisms (Rejmanek et al., *J Med. Microbiol.* (2012) 61:204-212). Some infected dogs develop clinical illness that is most commonly manifested as fever, polyarthritis, or thrombocytopenia. Detection of antibodies against *A. phagocytophilum* in serum and amplification of *A. phagocytophilum* DNA from blood by polymerase chain reaction (PCR) are used most frequently to aid in the diagnosis of canine anaplasmosis (Kirtz et al., *J Small Anim Pract* 46:300 (2005); Ravnik et al., *Vet Microbiol.* (2011) 149:172-176; Beall et al., *Vector Borne Zoonotic Dis.* (2008) 8:455-464).

Serum antibodies against *A. phagocytophilum* in dog serum can be detected in several types of assays. Many diagnostic laboratories use indirect fluorescent antibody assays (IFA) to detect antibodies against cell culture grown *A. phagocytophilum* morulae (Prototek Reference Laboratory, Chandler, Ariz.). Western blot immunoassay is used by some laboratories and can be used to determine the immunodominant antigens recognized by individual sera if whole organism preparations are utilized or can be used to determine antibody responses to individual antigens (Chandrashekar et al., *Am J Vet Res.* (2010) 71:1443-1450; Ge et al., *J. Bacteriol.* (2007) 189:7819-7828). Based on previous studies, the P44 peptide of *A. phagocytophilum* is immunodominant and is a common target used to assess for serum antibody responses (Chandrashekar et al., *Am J Vet Res.* (2010) 71:1443-1450; Ge et al., *J. Bacteriol.* (2007) 189:7819-7828). One ELISA based protocol for detection of antibodies against *A. phagocytophilum* is available commercially in the United States (Beall et al., *Vector Borne Zoonotic Dis*. (2008) 8:455-464; SNAP 4DX, IDEXX Laboratories, Portland, Me.).

Recently, new automated multiplex systems have been developed that are capable of testing for antigens and antibodies against multiple antigens using small volumes of serum (Zhao et al., *Appl Opt*. (2007) 46:6196-6209). These assays can be very beneficial in service laboratories because the automated system can lessen interassay variability and large numbers of samples can be assayed concurrently. In addition, for some organisms like *Borrelia burgdorferi*, detection of antibodies against multiple antigens can be used to differentiate vaccinated dogs from those that are naturally infection and acute infections, from chronic infections (Moroff et al., *J Vet Diag Invest* (In review, 2012)).

The objectives of this study were to validate an automated system (-ACCUPLEX™ 4 BioCD) for detection of serum antibodies against a peptide of *A. phagocytophilum* and to compare the results of the new assay to those of IFA and a commercially available point of care assay as well as to the results of a polymerase chain reaction (PCR) assay that amplifies the DNA of *A. phagocytophilum* from blood.

Materials and Methods

Animals.

This study was approved by the Institutional Animal Care and Use Committee at Colorado State University (*Ixodes* exposure) or an independent research laboratory (IV inoculation). The mixed sex beagles (n=26) used in this study were from a laboratory animal facility and ranged in age from 12 to 13 months at the beginning of the experiments. Prior to shipment to the respective research facilities, all dogs were shown to be negative for antibodies against *A. phagocytophilum, B. burgdorferi*, and *Ehrlichia canis* as well as for *Dirofilaria immitis* antigen by use of a commercially available kit (SNAP 4DX, IDEXX Laboratories, Portland, Me.). On arrival, the males were neutered using the facility standard operating procedures. The dogs were housed in groups of two or three dogs and fed ad libitum. Daily animal care was provided by research facility staff members.

Parenteral Inoculation with Cell Cultured *A. phagocytophilum.*

A field isolate of *A. phagocytophilum* was grown on HL-60 cells and delivered to Colorado State University by a same day air service stored at ambient temperature (Dr. Susan Little, Oklahoma State University, Stillwater, Okla.). Eight beagles were pre-medicated with 2.2 mg/kg of diphenhydramine administered SQ. The inoculum was divided into eight 2 ml aliquots and administered slowly IV to five dogs. All five dogs had evidence of adverse reactions characterized by panting (five dogs), pale mucous membranes (four dogs), weakness (three dogs), and vomiting and defecation (two dogs) and so the remaining three dogs were inoculated SQ with the inoculum divided into three sites. The adverse events were self-limited in four of the IV dogs over approximately 30 minutes but persisted in one female that was removed from the study. Side-effects were not noted in the dogs inoculated SQ. Samples were collected on Days 0, 3, 7, 10, 14, 17, 21, 24, 28, 35, 42, 49, 56, 63, 70, 77, 84, 91, 98, 105, 112, 119, 126, 133, 140, 147, 154, and 161. Doxycycline was administered at 10 mg/kg, once daily for 28 days starting on Day 105 after inoculation. These dogs were infected to provide sera and blood for assay development as well as to provide temporal information about test results after experimental inoculation.

*Anaplasma phagocytophilum* Infection by Tick Exposure.

Adult *Ixodes scapularis* wild-caught in Rhode Island in March 2010 were purchased for use in a parallel study on *Borrelia burgdorferi* infection (Moroff et al., *J Vet Diag Invest* (In review, 2012); Dr. Thomas Mather, University of Rhode Island). The prevalence rate of *A. phagocytophilum* DNA in a representative aliquot of adult ticks from the capture area was approximately 15%. The ticks were maintained at room temperature in humidified chambers until used in the experiments. When placed on 18 of the dogs, 13 female and 12 male ticks were allowed to attach under a tick chamber made of adhesive bandage materials. After 7 days, the ticks were removed with forceps, counted, and stored at −80° C. for future assays. At that time, a tick control product was placed topically (Frontline, Merial LTD, Athens, Ga.). Samples were collected from these 18 dogs weekly for 18 weeks.

Samples.

Blood (6 ml) was collected by jugular venipuncture. After collection, 1.5 ml was placed into EDTA and maintained at 4° C. until assayed. After the remaining blood was allowed to clot, the sample was centrifuged at 1,500×g for 10 minutes and the sera stored in multiple aliquots at −80° C. until assayed.

Assays.

The EDTA blood (cold packs) and sera were shipped by overnight express to a commercial laboratory for performance of a proprietary PCR assay (FASTPANEL™) that amplifies the of DNA of *A. phagocytophilum, A. platys, Ehrlichia canis, E. chaffeensis*, and *E. ewingii* using the standard operating procedures of the laboratory (Antech Laboratories, Lake Success, N.Y.).

Sera were ultimately assayed for *A. phagocytophilum* antibodies by IFA us using slides purchased from a commercial laboratory (Prototek Reference Laboratory, Chandler, Ariz.), a commercially available kit following the manufacturer's guidelines (SNAP 4DX, IDEXX Laboratories, Portland, Me.), and the in automated system using a novel mutant peptide derived from *A. phagocytophilum* as the antigen source as described in the section that follows. An *A. phagocytophilum* IFA titer of >1:40 was considered positive.

ACCUPLEX™ BioCD System.

This automated system was based on a silicon wafer with a thermal oxide layer (Yamato convection oven DVS-4000, Santa Clara, Calif.). The wafer was treated with both a 3-aminopropyldimethylethoxysilane (APMES) vapor deposition as well as a 1,6-diisocyanatohexane (Di-Iso) liquid deposition. A fluorescent hydrophobic mask was screen printed on the surface to create a 288 well pattern. Using a contact protein printer, 11 different markers were used to print 64 spots in a specific spot pattern in every well. Eight spots were dedicated to each peptide or protein antigen used to capture target antibodies. The assay as currently designed detected infections of *Dirofilaria immitis, Borrelia burgdorferi, E. canis*, and *A. phagocytophilum*. After printing of the peptides and antibody, the disc surface was blocked with ethanolamine vapor for 15 minutes at 30° C. to lessen potential for nonspecific binding and was coated in trehalose (2% by volume diluted in deionized water; Sigma—Fluka Analytical, St. Louis, Mo.) for added stability. The finished Accuplex4 disc could hold up to 274 patient samples along with 8 positive controls and 6 negative controls for each of the assays.

Each disc was loaded onto a sample processor which was used for liquid handling and dispensing using a keyed chuck to ensure proper disc loading (SIAS MODEL, Xantus manufactured by Sias, Hombrechtikon Switzerland). The disc was washed with a phosphate buffered saline solution (pH of 7.4) with Tween-20 (PBS-T) for 20 seconds at 400 RPM and then rinsed with deionized water for 20 seconds at the same speed before being centrifuged at 3000 RPM for 15 seconds to dry. Patient serum was loaded into each reaction well (5 μl) and incubated for 30 minutes at 80% humidity. The disc was again washed with PBS-T and deionized water for 20 seconds and centrifuged as described to dry. The fluorescent conjugate was dispensed into each well (6 μl) and incubated for 10 minutes (Protein-A/Alexafluor532, Invitrogen Carlsbad, Calif.). The disc was then washed for the final time with PBS-T and deionized water for 20 seconds and centrifuged as described to dry.

The dual channel reader included both a fluorescent and interferometric detector and also contained the same keyed chuck as the sample processor to ensure proper disc orientation (BioCD reader, Dual Channel Reader, Antech Diagnostics, West Lafayette, Ind.). Once the disc was loaded, it was centrifuged at 4,800 RPM and a 20 mW, 532 nm laser attached to the optical stage was "stepped" across the disc in the x-orientation. As the stage swept across the disc, 2401 data points were recorded through both detectors and sent to the computer workstation.

The interferometric data was used for disc image transformation and well mapping. These data points produced not only the disc image, but an individual image for each well. Using image processing, a spot pattern template was then applied to the fluorescent image where fluorescent counts were taken for each protein spot in all 288 wells. The median value of fluorescent counts was assigned to each individual immunologic reaction. The fluorescent counts for the six negative control wells were used to calculate the cutoffs for each assay. The median was taken from the six negative control wells and added to three standard deviations of the negative control well values along with a constant (Y). The constant was created using increases in fluorescent counts over time post-infection in the IV inoculated dogs. The cutoff format for each immunologic reaction was Median (Negative Controls)+3 STDEV (Negative Controls)+Y. This allowed the cutoffs to adjust for minor variation in discs. These cutoffs were then applied to each reaction, measured in fluorescent counts for an individual patient sample. A suspect sample was considered positive for antibodies against *Anaplasma phagocytophilum* when the result was greater than the specified threshold.

ACCUPLEX™ 4 BioCD *A. phagocytophilum* Antibody Assay Optimization Experiments.

The positive and negative control sera used in assay titrations were obtained from the dogs inoculated IV in the study described here. The positive and negative samples were defined by results of PCR for *A. phagocytophilum* to confirm infection and by IFA for serologic responses. The *A. phagocytophilum* peptide was a proprietary mutant synthetic peptide derived from *A. phagocytophilum* P44 that was produced by the commercial laboratory (Antech Laboratories, Lake Success, N.Y.). The optimal concentration was determined by assessing optimal signal:noise, with varying printed mutant peptide concentrations, and buffer compositions. The cut-off point for a positive test result was determined by assay of serum from dogs with known infection status based specifically on differential responses compared to IFA results on serum collected pre-infection (negative IFA) and post-infection (positive IFA).

The intra-assay variation of the assay was calculated by determining the mean and standard deviation for the fluorescent counts for 20 positive control sample wells and calculating the coefficient of variation on one disc. This experiment was performed with the same positive control samples on separate discs on three different days. The inter-assay variation was determined by comparing the coefficient of variations among the three discs.

Statistical Evaluation.

Dogs that became PCR positive for *A. phagocytophilum* DNA on at least 2 sample dates or that had antibodies against *A. phagocytophilum* as detected by IFA on at least 2 sample dates were considered to have developed infection by the organism. Results in all 4 assays were recorded as positive or negative. The proportions of dogs that were positive in each assay on each date were analyzed using a generalized linear model with test, week, and the test by week interaction included as fixed effects in the model. Where a significant test effect was detected within a week, all pair-wise comparisons were made. The time to first positive test result was compared among the assays by ANOVA including test as the only fixed effect. Significance was defined as $P<0.05$.

Results

ACCUPLEX™ 4 BioCD *A. phagocytophilum* Antibody Assay Optimization Experiments.

In the optimized assay, the intra-assay variation of 20 positive control wells per disc evaluated on separate discs was 15.9%, 15.5%, and 16.3%, respectively. The inter-assay variation of these results among the three discs was 1.5%.

Parenteral Inoculation with Cell Cultured *A. phagocytophilum.*

All seven dogs inoculated parenterally with cell culture grown *A. phagocytophilum* met the definition of *A. phagocytophilum* infection. Clinical signs of disease consistent with anaplasmosis were not recognized in any dog over the duration of the study.

*Anaplasma phagocytophilum* DNA was first amplified from blood by PCR assay on Day 3 (two dogs) after inoculation (FIG. 9). Antibodies against *A. phagocytophilum* were first detected on Day 14 in two dogs in the ACCUPLEX™ 4 BioCD assay only. Once serum antibodies were first detected in each of the three serological assays, all dogs were positive for the duration of the study, including during and after doxycycline administration. The time to first positive result was significantly faster for PCR when compared to each of the 3 serological assays ($p=0.0023$). However, blood from Day 14 was not available for PCR assay. There were no significant differences in proportions of dogs positive in the three serum antibody tests over the course of the experiment. *Anaplasma phagocytophilum* DNA was amplified from the blood of the dogs intermittently, ranging from Day 3 to Day 105. While two dogs were still positive by PCR assay at the start of the doxycycline treatment protocol, on day 105, none of the samples collected during or after treatment were positive. There were no apparent differences in the serum antibody responses or PCR assay test results between the dogs inoculated IV or SQ.

*Anaplasma phagocytophilum* Infection by Tick Exposure.

Of the 18 dogs exposed to wild-caught *Ixodes* spp., 10 dogs met the definition of *A. phagocytophilum* infection. Clinical signs of disease consistent with anaplasmosis were not recognized in any dog over the duration of the study.

Figure 10:
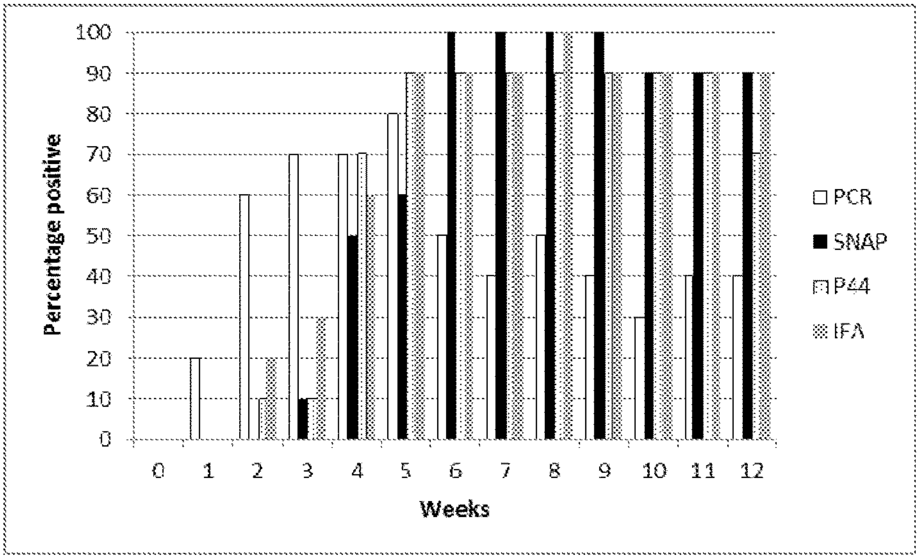
FIG. 10 shows Percentages of *Anaplasma phagocytophilum* positive assay results in three serological assays and a PCR assay the first 12 weeks after exposure to *Ixodes scapularis* ticks. P44=-ACCUPLEX™ BioCD system P44 antibody assay; SNAP=SNAP 4DX, IDEXX Laboratories, Portland, Me.; IFA=Indirect fluorescent antibody assay. =A statistically significant greater proportion of dogs were PCR assay positive than SNAP 4DX positive or P44 positive.

*Anaplasma phagocytophilum* DNA was first amplified from blood by PCR assay on week 1 (two dogs) after exposure to *I. scapularis* (FIG. 10). Antibodies against *A. phagocytophilum* were first detected week 2 by IFA (2 dogs) or peptide ACCUPLEX™ 4 BioCD (one dog) after exposure to *I. scapularis*. PCR assay results were positive prior to detection of antibodies in any of the three assays for 9 dogs (Table 12). A statistically significant proportion of dogs were more likely to have PCR assay positive results than any of the 3 serological test results only on week 3 after exposure to *I. scapularis* (FIG. 10). One dog never developed antibodies detectable by the mutant peptide, however this dog was positive for *A. phagocytophilum* antibodies by IFA on one date (week 8) and by commercial kit on three dates (weeks 6, 7, and 8). This dog was PCR positive on three dates (weeks 3, 4 and 5). While there were no significant differences among the results of the three serum antibody tests over the course of the experiment, antibodies were detected by ACCUPLEX™ 4 BioCD earlier than by the commercial kit for 5 dogs (Table 12). From weeks 13 through 18, *A. phagocytophilum* DNA was amplified consistently from 3 dogs and *A. phagocytophilum* antibodies were detected consistently in 9 dogs by the commercial kit or IFA. Antibodies were detected by the mutant peptide in 5 to 8 dogs after week 12.

TABLE 12

Time to the first positive test result in three *Anaplasma phagocytophilum* serological assays and a PCR assay in dogs exposed to wild-caught *I. scapularis* ticks.

| Dog | PCR | ACCUPLEX ™ | SNAP ™ | IFA |
|---|---|---|---|---|
| 1 | 28 | 35 | 42 | 35 |
| 2 | 7 | 28 | 28 | 21 |
| 3 | 14 | 28 | 42 | 35 |
| 4 | 14 | 28 | 35 | 21 |
| 5 | 35 | 28 | 42 | 35 |
| 6 | 7 | 14 | 21 | 14 |
| 7 | 7 | 35 | 28 | 28 |
| 8 | 14 | 28 | 28 | 28 |
| 9 | 21 | 28 | 28 | 28 |
| 10 | 21 | All negative | 42 | 56 |

P44 = ACCUPLEX ™ BioCD system P44 antibody assay
SNAP = SNAP ™ 4DX, IDEXX Laboratories, Portland, ME
IFA = Indirect fluorescent antibody assay Least squares mean for PCR (2.5 weeks), IFA (3.7 weeks), SNAP™ (4.8 weeks), and P44 antibody assay (5.4 weeks) were not significantly different (p=0.0624).

Based on the titration experiments, the ACCUPLEX™ 4 BioCD *A. phagocytophilum* antibody assay described here was accurate and reproducible for the detection of *A. phagocytophilum* antibodies in canine sera. As the majority of the assay was automated and rigorous controls were included, thus potential for laboratory error was minimal. While the assay required sera to be transported to a central laboratory, antibodies against *A. phagocytophilum* were robust and were minimally affected by temperature change as documented by use of the same positive and negative control samples repeatedly without changes in results.

In this study, results from three serological assays and a PCR assay were reported for dogs inoculated parenterally with *A. phagocytophilum* as well as for those infected by exposure to wild-caught *I. scapularis*. Samples from dogs inoculated parenterally were primarily used to generate sera for assay titrations. The samples from dogs exposed to *I. scapularis* more closely paralleled results expected from *A. phagocytophilum* infection in client-owned dogs. While approximately 15% of the *I. scapularis* in this region of Rhode Island are PCR positive for *A. phagocytophilum* DNA, only 10 of 18 dogs in this experiment developed *A. phagocytophilum* infection as defined. The ticks were allowed to feed for up to 7 days and the majority of female ticks attached. These results suggest that some adult beagles can limit infection with *A. phagocytophilum*. This was most evident in one of the 10 dogs (Table 12; dog 10) that was PCR positive and antibody positive on a few dates after tick attachment but then became PCR negative and serum antibody negative in all tests on all samples collected after week 9.

DNA of *A. phagocytophilum* could be amplified from blood prior to seroconversion in any of the three serological assays. The results from the dogs described here support the recommendation to perform PCR assays on blood of dogs with suspected *A. phagocytophilum* infection, particularly if the disease syndrome is acute and serum antibody assay results are negative.

Time to first positive serological test result was in part related to the positive cut-off point selected for each individual assay. The three serological assays performed in the study described here incorporated three different methodologies and had individual positive cut-off points. The cut-off point in the ACCUPLEX™ 4 BioCD *A. phagocytophilum* was selected to minimize the possibility for false positive reactions being reported based on the inherent interassay variation that occurs with all assays. When the three assays were applied to the sera from the dogs exposed to *I. scapularis* ticks (Table 12), time to first positive varied between the IFA (Range=Day 14 to Day 56), peptide assay (Range=Day 14-35; one dog never seroconverted), and commercial kit (Range=Day 21-42). While day to first positive result was the same for some dogs in some assays, the commercial kit had the latest first positive test result for five dogs. This differed from a previous report which showed the commercial kit to detect antibodies as soon as 8 days after infection with the NY18 strain (Chandrashekar et al., *Am J Vet Res*. (2010) 71:1443-1450). The differences in results between the previous study and the one described here may relate to the strains of *A. phagocytophilum* used or the inoculation dose.

In this study, antibody titers as measured by IFA and the commercially available kit were positive in nine of 10 dogs infected by exposure to *I. scapularis* ticks up to 12 weeks. In contrast, results of the peptide assay began to fall below the positive cut-off point after week 11 in some of the 9 dogs. These results suggest that the peptide assay results are most strongly correlated to recent infection.

Few data are available evaluating long-term infection of dogs after experimental infections with *A. phagocytophilum*. In this study, infected dogs were evaluated by PCR assay for 18 weeks (*I. scapularis* exposure; 10 dogs) or 15 weeks (parenteral inoculation; 7 dogs) prior to doxycycline administration. Several dogs in both groups maintained long term infections based on PCR assay results however, had no apparent clinical signs of illness. These results may reflect the suspected variation in *A. phagocytophilum* pathogenicity (Foley J et al., *Vet Rec* 160:159 (2007)). The predominant strain or strains in the area of Rhode Island where these ticks were collected may be relatively non-pathogenic. However, further evaluation of the role played by *A. phagocytophilum* in chronic illness in dogs should be performed. After parenterally inoculated dogs were administered doxycycline, PCR positive test results were never positive again. However, PCR was only performed on blood and the dogs were not splenectomized or otherwise immune suppressed and so whether infection was cleared by treatment is unknown.

H. Exemplary Embodiments

The present invention is further illustrated by the following exemplary embodiments:

1. An *Anaplasma* phagocytophilum p44 polypeptide comprising amino acids 222-236 of SEQ ID NO:1 (P44-2 disclosed in U.S. Pat. No. 6,436,399 B1), wherein said polypeptide comprises at least one mutation, an *A. phagocytophilum* p44 polypeptide comprising amino acids 222-237, 222-238, 222-239, 222-240, 222-241, 222-242, 222-243, 222-244, 222-245, 222-246, or 222-247 of SEQ ID NO:1 or an *A. phagocytophilum* p44 polypeptide comprising amino acids 222-237, 222-238, 222-239, 222-240, 222-241, 222-242, 222-243, 222-244, 222-245, 222-246, or 222-247 of SEQ ID NO:1 that comprises at least one mutation.

2. The polypeptide of embodiment 1, wherein the polypeptide comprises 1 to 10 mutations.

3. The polypeptide of embodiment 2, wherein the polypeptide comprises 3 to 7 mutations.

4. The polypeptide of embodiment 1, wherein the mutation is selected from the group consisting of a substitution, an insertion and a deletion.

5. The polypeptide of embodiment 4, wherein the peptide comprises at least 1, 2, 3, 4, 5, 10 or 12 mutations selected from the group consisting of Gly222(Del), His223→Asn, Ser224→Thr, Ser225→Thr, Val227→Ala, Thr228→Ser, Gln229→Asn, Leu233→Val, Leu233→Thr, Phe234→Leu, Ser235→Thr, and Thr236→Ser.

6. The polypeptide of embodiment 1, wherein the polypeptide further comprises a second polypeptide comprising amino acids 237-247 of SEQ ID NO:1.

7. The polypeptide of embodiment 6, wherein the second polypeptide comprises at least one mutation.

8. The polypeptide of embodiment 7, wherein the second polypeptide comprises 1 to 5 mutations.

9. The polypeptide of embodiment 8, wherein the second polypeptide comprises 2 or 3 mutations.

10. The polypeptide of embodiment 7, wherein the mutation is selected from the group consisting of a substitution, an insertion and a deletion.

11. The polypeptide of embodiment 10, wherein the peptide comprises at least 1, 2, 3, 4, 5 or 7 mutations selected from the group consisting of Thr240→Ser, Gln229→Asn, Ile243→Val, Glu245→Asp, Glu245→Asn, Asp246→Lys, and Asp246→Glu.

12. The polypeptide of embodiment 1, wherein the polypeptide comprises the amino acid sequence selected from the group consisting of SEQ ID Nos:3-6 (SP44-1 to 4).

13. A polypeptide comprising a multimer, a combination, or a chimera of the polypeptides of embodiment 12.

14. The polypeptide of embodiment 13, wherein the polypeptide further comprises a tag sequence.

15. The polypeptide of embodiment 13, wherein the polypeptide further comprises an amino acid linker between the polypeptides of embodiment 12.

16. The polypeptide of embodiment 15, wherein the polypeptide comprises the amino acid sequence of SEQ ID NO:7 (SP44-134).

17. The polypeptide of embodiment 16, further comprising a tag sequence.

18. An *Anaplasma phagocytophilum* p44 polypeptide that exhibits at least 75% identity to the amino acid sequence of SEQ ID NO:1, or the amino acids 222-247 of SEQ ID NO:1, wherein said polypeptide is not a wild-type P44 protein, and wherein said polypeptide binds to an antibody that is specific for a wild-type P44 protein.

19. The polypeptide of embodiment 18, wherein the polypeptide exhibits at least 80% identity to the amino acid sequence of SEQ ID NO:1, or the amino acids 222-247 of SEQ ID NO:1.

20. The polypeptide of embodiment 19, wherein the polypeptide exhibits at least 90% identity to the amino acid sequence of SEQ ID NO:1, or the amino acids 222-247 of SEQ ID NO:1.

21. The polypeptide of embodiment 20, wherein the polypeptide exhibits at least 95% identity to the amino acid sequence of SEQ ID NO:1, or the amino acids 222-247 of SEQ ID NO:1.

22. The polypeptide of embodiment 21, wherein the polypeptide exhibits at least 99% identity to the amino acid sequence of SEQ ID NO:1, or the amino acids 222-247 of SEQ ID NO:1.

23. A polynucleotide which encodes an *Anaplasma phagocytophilum* p44 polypeptide comprising the amino acid sequence of SEQ ID NO:1, or a complimentary strand thereof, wherein said polynucleotide is not a wild-type P44 polynucleotide, or a polynucleotide which encodes an *A. phagocytophilum* p44 polypeptide having the amino acid sequence of 222-237, 222-238, 222-239, 222-240, 222-241, 222-242, 222-243, 222-244, 222-245, 222-246, or 222-247 of SEQ ID NO:1, or a complimentary strand thereof, and in some embodiments, said polynucleotide is not a wild-type P44 polynucleotide.

24. The polynucleotide of embodiment 23, wherein the polynucleotide exhibits at least 75% identity to the nucleotide sequence of SEQ ID NO:2 (P44-2 disclosed in U.S. Pat. No. 6,436,399 B1), SEQ ID NO:33 or SEQ ID NO:36.

25. The polynucleotide of embodiment 24, wherein the polynucleotide exhibits at least 80% identity to the nucleotide sequence of SEQ ID NO:2, SEQ ID NO:33 or SEQ ID NO:36.

26. The polynucleotide of embodiment 25, wherein the polynucleotide exhibits at least 90% identity to the nucleotide sequence of SEQ ID NO:2, SEQ ID NO:33 or SEQ ID NO:36.

27. The polynucleotide of embodiment 26, wherein the polynucleotide exhibits at least 95% identity to the nucleotide sequence of SEQ ID NO:2, SEQ ID NO:33 or SEQ ID NO:36.

28. The polynucleotide of embodiment 27, wherein the polynucleotide exhibits at least 99% identity to the nucleotide sequence of SEQ ID NO:2, SEQ ID NO:33 or SEQ ID NO:36.

29. The polynucleotide of embodiment 23, wherein the polynucleotide hybridize to the nucleotide sequence of SEQ ID NO:2, SEQ ID NO:33 or SEQ ID NO:36 under moderately stringent conditions.

30. The polynucleotide of embodiment 29, wherein the polynucleotide hybridize to the nucleotide sequence of SEQ ID NO:2, SEQ ID NO:33 or SEQ ID NO:36 under highly stringent conditions.

31. A polynucleotide which encodes the polypeptide of embodiments 1-22, or a complimentary strand thereof.

32. The polynucleotide of embodiment 31, wherein the polynucleotide is codon-optimized for expression in a non-human organism or a cell.

33. The polynucleotide of embodiment 32, wherein the organism is a virus.

34. The polynucleotide of embodiment 32, wherein the organism is a bacterium.

35. The polynucleotide of embodiment 32, wherein the cell is a yeast cell.

36. The polynucleotide of embodiment 32, wherein the cell is an insect cell.

37. The polynucleotide of embodiment 32, wherein the cell is a mammalian cell.

38. The polynucleotide of embodiment 31, wherein the polynucleotide is DNA or RNA.

39. The polynucleotide of embodiment 31, wherein the polynucleotide comprises the nucleotide sequence of SEQ ID NO:8 (SP44-134).

40. A vector comprising the polynucleotide of embodiment 31.

41. The vector of embodiment 40, wherein the polynucleotide comprises a promoter sequence.

42. The vector of embodiment 40, wherein the polynucleotide further encodes a tag sequence.

43. The vector of embodiment 40, wherein the polynucleotide comprises a poly-A sequence.

44. The vector of embodiment 40, wherein the polynucleotide comprises a translation termination sequence.

45. A non-human organism or a cell transformed with the vector of embodiment 40.

46. The organism of embodiment 45, wherein the organism is a virus.

47. The organism of embodiment 45, wherein the organism is a bacterium.

48. The organism of embodiment 45, wherein the cell is a yeast cell.

49. The organism of embodiment 45, wherein the cell is an insect cell.

50. The organism of embodiment 45, wherein the cell is a mammalian cell.

51. A method for detecting an antibody that specifically binds an *Anaplasma phagocytophilum* p44 polypeptide in a sample, which method comprises contacting the polypeptide of embodiments 1-22 with said sample and detecting a polypeptide-antibody complex formed.

52. The method of embodiment 51, wherein the sample is from a subject selected from the group consisting of dog, cat, human and horse.

53. The method of embodiment 52, wherein the method is used for diagnosis, prognosis, stratification, risk assessment, or treatment monitoring of a disease.

54. The method of embodiment 53, wherein the disease is granulocytic anaplasmosis.

55. The method of embodiment 51, wherein the sample is selected from the group consisting of a serum, a plasma and a blood sample.

56. The method of embodiment 51, wherein the sample is a clinical sample.

57. The method of embodiment 51, wherein the antibody is a monoclonal or polyclonal antibody or antibody fragment.

58. The method of embodiment 51, wherein the polypeptide-antibody complex is assessed by a sandwich or competitive assay format, optionally with a binder or antibody.

59. The method of embodiment 58, wherein the binder or antibody is attached to a surface and functions as a capture binder or antibody.

60. The method of embodiment 59, wherein the capture binder or antibody is attached to the surface directly or indirectly.

61. The method of embodiment 60, wherein the capture binder or antibody is attached to the surface via a biotin-avidin (or streptavidin) linking pair.

62. The method of embodiment 58, wherein at least one of the binders or antibodies is labeled.

63. The method of embodiment 51, wherein the polypeptide-antibody complex is assessed by a format selected from the group consisting of an enzyme-linked immunosorbent assay (ELISA), immunoblotting, immunoprecipitation, radioimmunoassay (RIA), immunostaining, latex agglutination, indirect hemagglutination assay (IHA), complement fixation, indirect immunofluorescent assay (IFA), nephelometry, flow cytometry assay, lasmon resonance assay, chemiluminescence assay, lateral flow immunoassay, u-capture assay, inhibition assay and avidity assay.

64. The method of embodiment 51, wherein the polypeptide-antibody complex is assessed in a homogeneous or a heterogeneous assay format.

65. A kit for detecting an antibody that specifically binds an *Anaplasma phagocytophilum* p44 polypeptide, which kit comprises, in a container, the polypeptide of embodiments 1-22.

66. A method of recombinantly making an *Anaplasma phagocytophilum* p44 polypeptide, which method comprises culturing the organism of embodiment 45, and recovering said polypeptide from said organism.

67. The method of embodiment 66, further comprising isolating the polypeptide, optionally by chromatography.

68. A polypeptide produced by the method of embodiment 66.

69. The polypeptide of embodiment 68, wherein the polypeptide comprises a native glycosylation pattern.

70. The polypeptide of embodiment 68, wherein the polypeptide comprises a native phosphorylation pattern.

71. A polynucleotide which encodes a *Borrelia burgdorferi* OspC polypeptide comprising the amino acid sequence of SEQ ID NO:15 (OspC), or a complimentary strand thereof, wherein said polynucleotide is not a wild-type OspC polynucleotide.

72. The polynucleotide of embodiment 71, wherein the polynucleotide exhibits at least 70%, 75%, 80%, 90%, 95% or 99% identity to the nucleotide sequence of SEQ ID NO:16.

73. The polynucleotide of embodiment 71, wherein the polynucleotide hybridize to the nucleotide sequence of SEQ ID NO:16 under moderately or highly stringent conditions.

74. The polynucleotide of embodiment 71, wherein the polynucleotide is codon-optimized for expression in a non-human organism or a cell.

75. The polynucleotide of embodiment 74, wherein the organism or cell is selected from the group consisting of a virus, a bacterium, a yeast cell, an insect cell and a mammalian cell.

76. The polynucleotide of embodiment 71, wherein the polynucleotide is DNA or RNA.

77. The polynucleotide of embodiment 71, wherein the polynucleotide comprises the nucleotide sequence of SEQ ID NO:17 (optimized OspC DNA).

78. A vector comprising the polynucleotide of embodiment 71.

79. The vector of embodiment 78, wherein the polynucleotide comprises a promoter sequence.

80. The vector of embodiment 78, wherein the polynucleotide further encodes a tag sequence.

81. The vector of embodiment 78, wherein the polynucleotide comprises a poly-A sequence.

82. The vector of embodiment 78, wherein the polynucleotide comprises a translation termination sequence.

83. A non-human organism or a cell transformed with the vector of embodiment 78.

84. The organism of embodiment 83, wherein the organism or cell is selected from the group consisting of a virus, a bacterium, a yeast cell, an insect cell and a mammalian cell.

85. A method of recombinantly making a *Borrelia burgdorferi* OspC polypeptide, which method comprises culturing the organism of embodiment 83, and recovering said polypeptide from said organism.

86. The method of embodiment 85, further comprising isolating the polypeptide, optionally by chromatography.

87. A *Borrelia burgdorferi* OspC polypeptide produced by the method of embodiment 85.

88. The polypeptide of embodiment 87, wherein the polypeptide comprises a native glycosylation pattern and/or a native phosphorylation pattern.

89. A method for detecting an antibody that specifically binds to a *Borrelia burgdorferi* OspC polypeptide in a sample, which method comprises contacting the polypeptide encoded by the polynucleotide of embodiments 71-77 with said sample and detecting a polypeptide-antibody complex formed.

90. A polynucleotide which encodes a *Borrelia burgdorferi* OspF polypeptide comprising the amino acid sequence of SEQ ID NO:18, or a complimentary strand thereof, wherein said polynucleotide is not a wild-type OspF polynucleotide.

91. The polynucleotide of embodiment 90, wherein the polynucleotide exhibits at least 70%, 75%, 80%, 90%, 95% or 99% identity to the nucleotide sequence of SEQ ID NO:19.

92. The polynucleotide of embodiment 90, wherein the polynucleotide hybridize to the nucleotide sequence of SEQ ID NO:19 under moderately or highly stringent conditions.

93. The polynucleotide of embodiment 90, wherein the polynucleotide is codon-optimized for expression in a non-human organism or a cell.

94. The polynucleotide of embodiment 93, wherein the organism or cell is selected from the group consisting of a virus, a bacterium, a yeast cell, an insect cell and a mammalian cell.

95. The polynucleotide of embodiment 90, wherein the polynucleotide is DNA or RNA.

96. The polynucleotide of embodiment 90, wherein the polynucleotide comprises the nucleotide sequence of SEQ ID NO:20 (optimized OspF DNA).

97. A vector comprising the polynucleotide of embodiment 90.

98. The vector of embodiment 97, wherein the polynucleotide comprises a promoter sequence.

99. The vector of embodiment 97, wherein the polynucleotide further encodes a tag sequence.

100. The vector of embodiment 97, wherein the polynucleotide comprises a poly-A sequence.

101. The vector of embodiment 97, wherein the polynucleotide comprises a translation termination sequence.

102. A non-human organism or a cell transformed with the vector of embodiment 97.

103. The organism of embodiment 102, wherein the organism or cell is selected from the group consisting of a virus, a bacterium, a yeast cell, an insect cell and a mammalian cell.

104. A method of recombinantly making a *Borrelia burgdorferi* OspF polypeptide, which method comprises culturing the organism of embodiment 102, and recovering said polypeptide from said organism.

105. The method of embodiment 104, further comprising isolating the polypeptide, optionally by chromatography.

106. A *Borrelia burgdorferi* OspF polypeptide produced by the method of embodiment 104.

107. The polypeptide of embodiment 106, wherein the polypeptide comprises a native glycosylation pattern and/or a native phosphorylation pattern.

108. A method for detecting an antibody that specifically binds to a *Borrelia burgdorferi* OspF in a sample, which method comprises contacting the polypeptide encoded by the polynucleotide of embodiments 90-96 with said sample and detecting a polypeptide-antibody complex formed.

109. A polynucleotide which encodes a *Borrelia burgdorferi* p39 polypeptide comprising the amino acid sequence of SEQ ID NO:21, or a complimentary strand thereof, wherein said polynucleotide is not a wild-type p39 polynucleotide.

110. The polynucleotide of embodiment 109, wherein the polynucleotide exhibits at least 70%, 75%, 80%, 90%, 95% or 99% identity to the nucleotide sequence of SEQ ID NO:22.

111. The polynucleotide of embodiment 109, wherein the polynucleotide hybridize to the nucleotide sequence of SEQ ID NO:22 under moderately or highly stringent conditions.

112. The polynucleotide of embodiment 109, wherein the polynucleotide is codon-optimized for expression in a non-human organism or a cell.

113. The polynucleotide of embodiment 112, wherein the organism or cell is selected from the group consisting of a virus, a bacterium, a yeast cell, an insect cell and a mammalian cell.

114. The polynucleotide of embodiment 109, wherein the polynucleotide is DNA or RNA.

115. The polynucleotide of embodiment 109, wherein the polynucleotide comprises the nucleotide sequence of SEQ ID NO:23 (optimized p39 DNA).

116. A vector comprising the polynucleotide of embodiment 109.

117. The vector of embodiment 116, wherein the polynucleotide comprises a promoter sequence.

118. The vector of embodiment 116, wherein the polynucleotide further encodes a tag sequence.

119. The vector of embodiment 116, wherein the polynucleotide comprises a poly-A sequence.

120. The vector of embodiment 116, wherein the polynucleotide comprises a translation termination sequence.

121. A non-human organism or a cell transformed with the vector of embodiment 116.

122. The organism of embodiment 121, wherein the organism or cell is selected from the group consisting of a virus, a bacterium, a yeast cell, an insect cell and a mammalian cell.

123. A method of recombinantly making a *Borrelia burgdorferi* p39 polypeptide, which method comprises culturing the organism of embodiment 121, and recovering said polypeptide from said organism.

124. The method of embodiment 123, further comprising isolating the polypeptide, optionally by chromatography.

125. A *Borrelia burgdorferi* p39 polypeptide produced by the method of embodiment 123.

126. The polypeptide of embodiment 125, wherein the polypeptide comprises a native glycosylation pattern and/or a native phosphorylation pattern.

127. A method for detecting an antibody that specifically binds to a *Borrelia burgdorferi* p39 polypeptide in a sample, which method comprises contacting the polypeptide encoded by the polynucleotide of embodiments 109-115 with said sample and detecting a polypeptide-antibody complex formed.

128. An antigenic composition comprising at least two *Borrelia burgdorferi* polypeptides, wherein each of said polypeptides comprises an amino acid sequence selected from the group consisting of:

a) an OspA polypeptide, b) an OspC polypeptide, c) an OspF polypeptide, d) a p39 polypeptide, and e) a fusion peptide of p41 and VlsE, wherein said antigenic composition does not consist of a) and b).

129. The composition of embodiment 128, which comprises at least 3, 4, or all 5 of said *Borrelia burgdorferi* polypeptides.

130. The composition of embodiment 128, wherein the OspC polypeptide comprises an amino acid sequence of SEQ ID NO:15.

131. The composition of embodiment 128, wherein the OspF polypeptide comprises an amino acid sequence of SEQ ID NO:18.

132. The composition of embodiment 128, wherein the p39 polypeptide comprises an amino acid sequence of SEQ ID NO:21.

133. The composition of embodiment 128, wherein the fusion peptide of p41 and VlsE comprises an amino acid sequence of SEQ ID NO:24.

134. The composition of embodiment 133, wherein the fusion peptide of p41 and VlsE further comprises a tag sequence.

135. The composition of embodiment 128, wherein the polypeptides form a fusion molecule.

136. A method for detecting an antibody that specifically binds to a *Borrelia burgdorferi* OspA, OspC, OspF, p39 polypeptide and/or a fusion peptide of p41 and VlsE in a sample, which method comprises a) contacting said sample with the antigenic composition of embodiment 128; and b) detecting a polypeptide-antibody complex formed.

137. The method of embodiment 136, wherein the method is used for diagnosis, prognosis, stratification, risk assessment, or treatment monitoring of a disease.

138. The method of embodiment 137, wherein the disease is Lyme disease.

139. The method of embodiment 138, wherein the method is used to distinguish between infection by a Lyme disease pathogen and exposure to a Lyme disease vaccine.

140. The method of embodiment 138, wherein the method is used to distinguish between exposure to a NOBIVAC™ Lyme vaccine (a vaccine comprises a bacterin that contains two inactivated strains of *Borrelia burgdorferi* comprised of outer surface protein A (OspA) and outer surface protein C (OspC)) and exposure to another vaccine.

141. The method of embodiment 136, wherein the antibody is a monoclonal or polyclonal antibody or antibody fragment.

142. The method of embodiment 136, wherein the polypeptide-antibody complex is assessed by a sandwich or competitive assay format, optionally with a binder or antibody.

143. The method of embodiment 142, wherein the binder or antibody is attached to a surface and functions as a capture binder or antibody.

144. The method of embodiment 143, wherein the binder or capture antibody is attached to the surface directly or indirectly.

145. The method of embodiment 144, wherein the binder or capture antibody is attached to the surface via a biotin-avidin (or streptavidin) linking pair.

146. The method of embodiment 142, wherein at least one of the binders or antibodies is labeled.

147. The method of embodiment 136, wherein the complex is assessed by a format selected from the group consisting of an enzyme-linked immunosorbent assay (ELISA), immunoblotting, immunoprecipitation, radioimmunoassay (RIA), immunostaining, latex agglutination, indirect hemagglutination assay (IHA), complement fixation, indirect immunofluorescent assay (IFA), nephelometry, flow cytometry assay, lasmon resonance assay, chemiluminescence assay, lateral flow immunoassay, u-capture assay, inhibition assay and avidity assay.

148. The method of embodiment 136, wherein the polypeptide-antibody complex is assessed in a homogeneous or a heterogeneous assay format.

149. A kit for detecting an antibody that specifically binds to a *Borrelia burgdorferi* OspA, OspC, OspF, p39 polypeptide and/or a fusion peptide of p41 and VlsE, which kit comprises, in a container, the antigenic composition of embodiment 128.

150. A composition for detecting multiple disease antigens and/or antibodies, which composition comprises at least two, preferably three of the following reagents:

a) an antibody against a heartworm (*Dirofilaria immitis*) antigen, b) an *Ehrlichia Canis* gp36 polypeptide, c) an *Anaplasma phagocytophilum* p44 polypeptide, and d) an antigenic composition comprising a *Borrelia burgdorferi* polypeptide selected from the group consisting of OspA, OspC, OspF, p39 and a fusion peptide of p41 and VlsE.

151. The composition of embodiment 150, which comprises all four of the reagents.

152. The composition of embodiment 150, wherein the reagent a) is a chicken polyclonal antibody.

153. The composition of embodiment 151, wherein the chicken polyclonal antibody is produced by immunizing chickens with a canine heartworm antigen.

154. The composition of embodiment 150, wherein the reagent b) comprises a polypeptide comprising an amino acid sequence of SEQ ID NO:26.

155. The composition of embodiment 154, wherein the polypeptide further comprises a tag sequence.

156. The composition of embodiment 150, wherein the reagent c) comprises the polypeptide of embodiments 1-22.

157. The composition of embodiment 150, wherein the reagent d) comprises the antigenic composition of embodiment 128.

158. A method for detecting multiple disease antigens and/or antibodies in a sample, which method comprises a) contacting said sample with the composition of embodiment 150; and b) detecting a polypeptide-antibody complex formed.

159. The method of embodiment 158, wherein the method is used for diagnosis, prognosis, stratification, risk assessment, or treatment monitoring of a disease.

160. The method of embodiment 159, wherein the disease is selected from the group consisting of a heartworm disease, ehrlichiosis, granulocytic anaplasmosis, and Lyme disease.

161. The method of embodiment 158, wherein the sample is selected from the group consisting of a serum, a plasma and a blood sample.

162. The method of embodiment 158, wherein the sample is a clinical sample.

163. The method of embodiment 158, wherein the polypeptide-antibody complex is assessed by a sandwich or competitive assay format, optionally with a binder or antibody.

164. The method of embodiment 163, wherein the binder or antibody is attached to a surface and functions as a capture binder or antibody.

165. The method of embodiment 164, wherein the capture binder or antibody is attached to the surface directly or indirectly.

166. The method of embodiment 165, wherein the capture binder or antibody is attached to the surface via a biotin-avidin (or streptavidin) linking pair.

167. The method of embodiment 163, wherein at least one of the binders or antibodies is labeled.

168. The method of embodiment 158, wherein the polypeptide-antibody complex is assessed by a format selected from the group consisting of an enzyme-linked immunosorbent assay (ELISA), immunoblotting, immunoprecipitation, radioimmunoassay (RIA), immunostaining, latex agglutination, indirect hemagglutination assay (IHA), complement fixation, indirect immunofluorescent assay (IFA), nephelometry, flow cytometry assay, lasmon resonance assay, chemiluminescence assay, lateral flow immunoassay, u-capture assay, inhibition assay and avidity assay.

169. The method of embodiment 158, wherein the polypeptide-antibody complex is assessed in a homogeneous or a heterogeneous assay format.

170. A kit for detecting multiple infectious organisms, which kit comprises, in a container, the composition of embodiment 150.

171. A computer readable medium containing executable instructions that when executed perform a method of classifying *Borrelia burgdorferi* infection of a mammal, e.g., an animal, the method comprising:

calculating levels of antibodies that specifically bind to an OspA, OspC, OspF, p39 polypeptide and/or a fusion peptide of p41 and VlsE using a method according to any one of embodiments 136-148;

calculating reference values of the levels of the antibodies; and determining the type of *Borrelia burgdorferi* infection of the mammal by comparing the levels of the antibodies to the reference values.

172. The computer readable medium of embodiment 171, further comprising calculating a reference value based on one or more negative controls.

173. The computer readable medium of embodiment 171, wherein one or more reference values are calculated for each antibody.

174. The computer readable medium of embodiment 173, wherein the reference values for the antibody that specifically binds to OspA are alpLow, alpMid, alpHigh and/or alpHighest.

175. The computer readable medium of embodiment 173, wherein the reference values for the antibody that specifically binds to OspC are ospcLow and/or ospcHigh.

176. The computer readable medium of embodiment 173, wherein the reference values for the antibody that specifically binds to OspF are ospfLow and/or ospfHigh.

177. The computer readable medium of embodiment 173, wherein the reference value for the antibody that specifically binds to p39 is p39Low.

178. The computer readable medium of embodiment 173, wherein the reference values for the antibody that specifically binds to the fusion peptide of p41 and VlsE are slpLow, slpMid and/or slpHigh.

179. The computer readable medium of embodiment 173, wherein the method further comprises calculating a level and reference value of an antibody that specifically binds to the *Anaplasma phagocytophilum* P44 polypeptide comprising the amino acid sequence of SEQ ID NO:7, wherein the reference value for the antibody is sub5Low.

180. The computer readable medium of any one of embodiments 174-179, wherein the mammal is classified as Lyme exposure if:

a) the level of antibody that specifically binds to OspA is lower than alpHigh, and the level of antibody that specifically binds to OspF is greater than or equal to ospfHigh;

b) the level of antibody that specifically binds to OspA is greater than or equal to alpLow and lower than alpMid, the level of antibody that specifically binds to OspF is lower than ospfHigh, the level of antibody that specifically binds to the fusion peptide of p41 and VlsE is greater than or equal to slpLow or the level of antibody that specifically binds to OspC is greater than or equal to ospcLow, and the level of antibody that specifically binds to the amino acid sequence of SEQ ID NO:7 is greater than or equal to sub5Low or the level of antibody that specifically binds to OspF is greater than or equal to ospfLow;

c) the level of antibody that specifically binds to OspA is lower than alpLow, the level of antibody that specifically binds to OspC is lower than ospcLow, the level of antibody that specifically binds to OspF is lower than ospfHigh, the level of antibody that specifically binds to the fusion peptide of p41 and VlsE is greater than or equal to slpLow and lower than slpMid, and the level of antibody that specifically binds to the amino acid sequence of SEQ ID NO:7 is greater than or equal to sub5Low or the level of antibody that specifically binds to OspF is greater than or equal to ospfLow;

d) the level of antibody that specifically binds to OspA is greater than or equal to alpLow and lower than alpMid, the level of antibody that specifically binds to OspC is greater than or equal to ospcLow, the level of antibody that specifically binds to p39 is greater than or equal to p39Low, the level of antibody that specifically binds to the fusion peptide of p41 and VlsE is greater than or equal to slpLow, the level of antibody that specifically binds to OspF is lower than ospfLow, and the level of antibody that specifically binds to the amino acid sequence of SEQ ID NO:7 is lower than sub5Low; or e) the level of antibody that specifically binds to OspA is lower than alpLow, the level of antibody that specifically binds to OspF is lower than ospfHigh, and the level of antibody that specifically binds to OspC is greater than or equal to ospcLow or the level of antibody that specifically binds to the fusion peptide of p41 and VlsE is greater than or equal to slpMid.

181. The computer readable medium of embodiment 180, wherein the mammal is classified as Lyme exposure early if the level of antibody that specifically binds to OspF is lower than ospfHigh; otherwise Lyme exposure late.

182. The computer readable medium of any one of embodiments 174-179, wherein the mammal is classified as Lyme exposure and vaccine if:

a) the level of antibody that specifically binds to OspA is greater than or equal to alpHigh, and the level of antibody that specifically binds to OspF is greater than or equal to ospfHigh;

b) the level of antibody that specifically binds to OspA is greater than or equal to alpMid and lower than alpHighest, the level of antibody that specifically binds to the amino acid sequence of SEQ ID NO:7 is greater than or equal to sub5Low, the level of antibody that specifically binds to OspF is lower than ospfHigh, and the level of antibody that specifically binds to the fusion peptide of p41 and VlsE is greater than or equal to slpLow or the level of antibody that specifically binds to OspC is greater than or equal to ospcLow;

c) the level of antibody that specifically binds to OspA is greater than or equal to alpMid and lower than alpHighest, the level of antibody that specifically binds to OspC is greater than or equal to ospcHigh, the level of antibody that specifically binds to the fusion peptide of p41 and VlsE is greater than or equal to slpHigh, the level of antibody that specifically binds to OspF is lower than ospfHigh, and the level of antibody that specifically binds to the amino acid sequence of SEQ ID NO:7 is lower than sub5Low; or d) the level of antibody that specifically binds to OspA is greater than or equal to alpHighest, the level of antibody that specifically binds to OspF is greater than or equal to ospfLow and lower than ospfHigh, the level of antibody that specifically binds to OspC is greater than or equal to ospcLow, the level of antibody that specifically binds to the fusion peptide of p41 and VlsE is greater than or equal to slpLow, and the level of antibody that specifically binds to the amino acid sequence of SEQ ID NO:7 is greater than or equal to sub5Low.

183. The computer readable medium of embodiment 182, wherein the mammal is classified as Lyme exposure and vaccine early if the level of antibody that specifically binds to OspF is lower than ospfHigh; otherwise Lyme exposure and vaccine late.

184. The computer readable medium of any one of embodiments 174-179, wherein the mammal is classified as Lyme vaccine if:

a) the level of antibody that specifically binds to OspA is greater than or equal to alpHighest, and the level of antibody that specifically binds to OspF is lower than ospfLow;

b) the level of antibody that specifically binds to OspA is greater than or equal to alpHighest, the level of antibody that specifically binds to OspF is greater than or equal to ospfLow and lower than ospfHigh, the level of antibody that specifically binds to OspC is lower than ospcLow or the level of antibody that specifically binds to the fusion peptide of p41 and VlsE is lower than slpLow but not both, and the level of antibody that specifically binds to the amino acid sequence of SEQ ID NO:7 is lower than sub5Low;

c) the level of antibody that specifically binds to OspA is greater than or equal to alpHighest, the level of antibody that specifically binds to OspF is greater than or equal to ospfLow and lower than ospfHigh, the level of antibody that specifically binds to OspC is lower than ospcLow, and the level of antibody that specifically binds to the fusion peptide of p41 and VlsE is lower than slpLow;

d) the level of antibody that specifically binds to OspA is greater than or equal to alpMid and lower than alpHighest, the level of antibody that specifically binds to OspF is greater than or equal to ospfLow and lower than ospfHigh, the level of antibody that specifically binds to the amino acid sequence of SEQ ID NO:7 is lower than sub5Low, the level of antibody that specifically binds to the fusion peptide of p41 and VlsE is lower than slpHigh, the level of antibody that specifically binds to OspC is lower than ospcHigh, and the level of antibody that specifically binds to OspC is greater than or equal to ospcLow or the level of antibody that specifically binds to the fusion peptide of p41 and VlsE is greater than or equal to slpLow;

e) the level of antibody that specifically binds to OspA is greater than or equal to alpMid and lower than alpHighest, the level of antibody that specifically binds to OspF is lower than ospfLow, the level of antibody that specifically binds to the amino acid sequence of SEQ ID NO:7 is lower than sub5Low, and the level of antibody that specifically binds to the fusion peptide of p41 and VlsE is lower than slpHigh or the level of antibody that specifically binds to OspC is lower than ospcHigh; or f) the level of antibody that specifically binds to OspA is greater than or equal to alpMid and lower than alpHighest, the level of antibody that specifically binds to OspF is lower than ospfHigh, the level of antibody that specifically binds to OspC is lower than ospcLow, the level of antibody that specifically binds to the fusion peptide of p41 and VlsE is lower than slpLow, and the level of antibody that specifically binds to OspF is greater than or equal to ospfLow or the level of antibody that specifically binds to the amino acid sequence of SEQ ID NO:7 is greater than or equal to sub5Low.

185. The computer readable medium of any one of embodiments 174-179, wherein the mammal is classified as indeterminative if:

a) the level of antibody that specifically binds to OspA is greater than or equal to alpMid and lower than alpHighest, the level of antibody that specifically binds to OspF is greater than or equal to ospfLow and lower than ospfHigh, the level of antibody that specifically binds to the amino acid sequence of SEQ ID NO:7 is lower than sub5Low, and the level of antibody that specifically binds to the fusion peptide of p41 and VlsE is lower than slpHigh or the level of antibody that specifically binds to OspC is lower than ospcHigh but not both;

b) the level of antibody that specifically binds to OspA is greater than or equal to alpHighest, the level of antibody that specifically binds to OspF is greater than or equal to ospfLow and lower than ospfHigh, the level of antibody that specifically binds to OspC is lower than ospcLow or the level of antibody that specifically binds to the fusion peptide of p41 and VlsE is lower than slpLow but not both, and the level of antibody that specifically binds to the amino acid sequence of SEQ ID NO:7 is greater than or equal to sub5Low;

c) the level of antibody that specifically binds to OspA is greater than or equal to alpHighest, the level of antibody that specifically binds to OspF is greater than or equal to ospfLow and lower than ospfHigh, the level of antibody that specifically binds to OspC is greater than or equal to ospcLow, the level of antibody that specifically binds to the fusion peptide of p41 and VlsE is greater than or equal to slpLow, and the level of antibody that specifically binds to the amino acid sequence of SEQ ID NO:7 is lower than sub5Low;

d) the level of antibody that specifically binds to OspA is greater than or equal to alpLow and lower than alpMid, the level of antibody that specifically binds to OspF is Lower than ospfLow, the level of antibody that specifically binds to OspC is greater than or equal to ospcLow, the level of antibody that specifically binds to the fusion peptide of p41 and VlsE is greater than or equal to slpLow, the level of antibody that specifically binds to the amino acid sequence of SEQ ID NO:7 is lower than sub5Low, and the level of antibody that specifically binds to p39 is lower than p39Low; or e) the level of antibody that specifically binds to OspA is greater than or equal to alpLow and lower than alpMid, the level of antibody that specifically binds to OspF is Lower than ospfLow, the level of antibody that specifically binds to OspC is greater than or equal to ospcLow or the level of antibody that specifically binds to the fusion peptide of p41 and VlsE is greater than or equal to slpLow but not both, and the level of antibody that specifically binds to the amino acid sequence of SEQ ID NO:7 is lower than sub5Low.

186. The computer readable medium of embodiment 185, wherein the mammal is classified as possible exposure if the level of antibody that specifically binds to OspA is lower than alpMid; otherwise lyme vaccine possible exposure.

187. A method of classifying *Borrelia burgdorferi* infection of a mammal, e.g., an animal, the method comprising:

calculating levels of antibodies that specifically bind to an OspA, OspC, OspF, p39 polypeptide and/or a fusion peptide of p41 and VlsE using a method according to any one of embodiments 136-148;

calculating reference values of the levels of the antibodies; and determining the type of *Borrelia burgdorferi* infection of the mammal by comparing the levels of the antibodies to the reference values.

188. The method of embodiment 187, further comprising calculating a reference value based on negative controls.

189. The method of embodiment 187, wherein one or more reference values are calculated for each antibody.

190. The method of embodiment 189, wherein the reference values for the antibody that specifically binds to OspA are alpLow, alpMid, alpHigh and/or alpHighest.

191. The method of embodiment 189, wherein the reference values for the antibody that specifically binds to OspC are ospcLow and/or ospcHigh.

192. The method of embodiment 189, wherein the reference values for the antibody that specifically binds to OspF are ospfLow and/or ospfHigh.

193. The method of embodiment 189, wherein the reference value for the antibody that specifically binds to p39 is p39Low.

194. The method of embodiment 189, wherein the reference values for the antibody that specifically binds to the fusion peptide of p41 and VlsE are slpLow, slpMid and/or slpHigh.

195. The method of embodiment 189, which further comprises calculating a level and reference value of an antibody that specifically binds to the *Anaplasma* phagocytophilum P44 polypeptide comprising the amino acid sequence of SEQ ID NO:7, wherein the reference value for the antibody is sub5Low.

196. The method of any one of embodiments 190-195, wherein the mammal is classified as Lyme exposure if:

a) the level of antibody that specifically binds to OspA is lower than alpHigh, and the level of antibody that specifically binds to OspF is greater than or equal to ospfHigh;

b) the level of antibody that specifically binds to OspA is greater than or equal to alpLow and lower than alpMid, the level of antibody that specifically binds to OspF is lower than ospfHigh, the level of antibody that specifically binds to the fusion peptide of p41 and VlsE is greater than or equal to slpLow or the level of antibody that specifically binds to OspC is greater than or equal to ospcLow, and the level of antibody that specifically binds to the amino acid sequence of SEQ ID NO:7 is greater than or equal to sub5Low or the level of antibody that specifically binds to OspF is greater than or equal to ospfLow;

c) the level of antibody that specifically binds to OspA is lower than alpLow, the level of antibody that specifically binds to OspC is lower than ospcLow, the level of antibody that specifically binds to OspF is lower than ospfHigh, the level of antibody that specifically binds to the fusion peptide of p41 and VlsE is greater than or equal to slpLow and lower than slpMid, and the level of antibody that specifically binds to the amino acid sequence of SEQ ID NO:7 is greater than or equal to sub5Low or the level of antibody that specifically binds to OspF is greater than or equal to ospfLow;

d) the level of antibody that specifically binds to OspA is greater than or equal to alpLow and lower than alpMid, the level of antibody that specifically binds to OspC is greater than or equal to ospcLow, the level of antibody that specifically binds to p39 is greater than or equal to p39Low, the level of antibody that specifically binds to the fusion peptide of p41 and VlsE is greater than or equal to slpLow, the level of antibody that specifically binds to OspF is lower than ospfLow, and the level of antibody that specifically binds to the amino acid sequence of SEQ ID NO:7 is lower than sub5Low; or e) the level of antibody that specifically binds to OspA is lower than alpLow, the level of antibody that specifically binds to OspF is lower than ospfHigh, and the level of antibody that specifically binds to OspC is greater than or equal to ospcLow or the level of antibody that specifically binds to the fusion peptide of p41 and VlsE is greater than or equal to slpMid.

197. The method of embodiment 196, wherein the mammal is classified as Lyme exposure early if the level of antibody that specifically binds to OspF is lower than ospfHigh; otherwise Lyme exposure late.

198. The method of any one of embodiments 190-195, wherein the mammal is classified as Lyme exposure and vaccine if:

a) the level of antibody that specifically binds to OspA is greater than or equal to alpHigh, and the level of antibody that specifically binds to OspF is greater than or equal to ospfHigh;

b) the level of antibody that specifically binds to OspA is greater than or equal to alpMid and lower than alpHighest, the level of antibody that specifically binds to the amino acid sequence of SEQ ID NO:7 is greater than or equal to sub5Low, the level of antibody that specifically binds to OspF is lower than ospfHigh, and the level of antibody that specifically binds to the fusion peptide of p41 and VlsE is greater than or equal to slpLow or the level of antibody that specifically binds to OspC is greater than or equal to ospcLow;

c) the level of antibody that specifically binds to OspA is greater than or equal to alpMid and lower than alpHighest, the level of antibody that specifically binds to OspC is greater than or equal to ospcHigh, the level of antibody that specifically binds to the fusion peptide of p41 and VlsE is greater than or equal to slpHigh, the level of antibody that specifically binds to OspF is lower than ospfHigh, and the level of antibody that specifically binds to the amino acid sequence of SEQ ID NO:7 is lower than sub5Low; or d) the level of antibody that specifically binds to OspA is greater than or equal to alpHighest, the level of antibody that specifically binds to OspF is greater than or equal to ospfLow and lower than ospfHigh, the level of antibody that specifically binds to OspC is greater than or equal to ospcLow, the level of antibody that specifically binds to the fusion peptide of p41 and VlsE is greater than or equal to slpLow, and the level of antibody that specifically binds to the amino acid sequence of SEQ ID NO:7 is greater than or equal to sub5Low.

199. The method of embodiment 198, wherein the mammal is classified as Lyme exposure and vaccine early if the level of antibody that specifically binds to OspF is lower than ospfHigh; otherwise Lyme exposure and vaccine late.

200. The method of any one of embodiments 190-195, wherein the mammal is classified as Lyme vaccine if:

a) the level of antibody that specifically binds to OspA is greater than or equal to alpHighest, and the level of antibody that specifically binds to OspF is lower than ospfLow;

b) the level of antibody that specifically binds to OspA is greater than or equal to alpHighest, the level of antibody that specifically binds to OspF is greater than or equal to ospfLow and lower than ospfHigh, the level of antibody that specifically binds to OspC is lower than ospcLow or the level of antibody that specifically binds to the fusion peptide of p41 and VlsE is lower than slpLow but not both, and the level of antibody that specifically binds to the amino acid sequence of SEQ ID NO:7 is lower than sub5Low;

c) the level of antibody that specifically binds to OspA is greater than or equal to alpHighest, the level of antibody that specifically binds to OspF is greater than or equal to ospfLow and lower than ospfHigh, the level of antibody that specifically binds to OspC is lower than ospcLow, and the level of antibody that specifically binds to the fusion peptide of p41 and VlsE is lower than slpLow;

d) the level of antibody that specifically binds to OspA is greater than or equal to alpMid and lower than alpHighest, the level of antibody that specifically binds to OspF is greater than or equal to ospfLow and lower than ospfHigh, the level of antibody that specifically binds to the amino acid sequence of SEQ ID NO:7 is lower than sub5Low, the level of antibody that specifically binds to the fusion peptide of p41 and VlsE is lower than slpHigh, the level of antibody that specifically binds to OspC is lower than ospcHigh, and the level of antibody that specifically binds to OspC is greater than or equal to ospcLow or the level of antibody that specifically binds to the fusion peptide of p41 and VlsE is greater than or equal to slpLow;

e) the level of antibody that specifically binds to OspA is greater than or equal to alpMid and lower than alpHighest, the level of antibody that specifically binds to OspF is lower than ospfLow, the level of antibody that specifically binds to the amino acid sequence of SEQ ID NO:7 is lower than sub5Low, and the level of antibody that specifically binds to the fusion peptide of p41 and VlsE is lower than slpHigh or the level of antibody that specifically binds to OspC is lower than ospcHigh; or f) the level of antibody that specifically binds to OspA is greater than or equal to alpMid and lower than alpHighest, the level of antibody that specifically binds to OspF is lower than ospfHigh, the level of antibody that specifically binds to OspC is lower than ospcLow, the level of antibody that specifically binds to the fusion peptide of p41 and VlsE is lower than slpLow, and the level of antibody that specifically binds to OspF is greater than or equal to ospfLow or the level of antibody that specifically binds to the amino acid sequence of SEQ ID NO:7 is greater than or equal to sub5Low.

201. The method of any one of embodiments 190-195, wherein the mammal is classified as indeterminative if:

a) the level of antibody that specifically binds to OspA is greater than or equal to alpMid and lower than alpHighest, the level of antibody that specifically binds to OspF is greater than or equal to ospfLow and lower than ospfHigh, the level of antibody that specifically binds to the amino acid sequence of SEQ ID NO:7 is lower than sub5Low, and the level of antibody that specifically binds to the fusion peptide of p41 and VlsE is lower than slpHigh or the level of antibody that specifically binds to OspC is lower than ospcHigh but not both;

b) the level of antibody that specifically binds to OspA is greater than or equal to alpHighest, the level of antibody that specifically binds to OspF is greater than or equal to ospfLow and lower than ospfHigh, the level of antibody that specifically binds to OspC is lower than ospcLow or the level of antibody that specifically binds to the fusion peptide of p41 and VlsE is lower than slpLow but not both, and the level of antibody that specifically binds to the amino acid sequence of SEQ ID NO:7 is greater than or equal to sub5Low;

c) the level of antibody that specifically binds to OspA is greater than or equal to alpHighest, the level of antibody that specifically binds to OspF is greater than or equal to ospfLow and lower than ospfHigh, the level of antibody that specifically binds to OspC is greater than or equal to ospcLow, the level of antibody that specifically binds to the fusion peptide of p41 and VlsE is greater than or equal to slpLow, and the level of antibody that specifically binds to the amino acid sequence of SEQ ID NO:7 is lower than sub5Low;

d) the level of antibody that specifically binds to OspA is greater than or equal to alpLow and lower than alpMid, the level of antibody that specifically binds to OspF is Lower than ospfLow, the level of antibody that specifically binds to OspC is greater than or equal to ospcLow, the level of antibody that specifically binds to the fusion peptide of p41 and VlsE is greater than or equal to slpLow, the level of antibody that specifically binds to the amino acid sequence of SEQ ID NO:7 is lower than sub5Low, and the level of antibody that specifically binds to p39 is lower than p39Low; or e) the level of antibody that specifically binds to OspA is greater than or equal to alpLow and lower than alpMid, the level of antibody that specifically binds to OspF is Lower than ospfLow, the level of antibody that specifically binds to OspC is greater than or equal to ospcLow or the level of antibody that specifically binds to the fusion peptide of p41 and VlsE is greater than or equal to slpLow but not both, and the level of antibody that specifically binds to the amino acid sequence of SEQ ID NO:7 is lower than sub5Low.

202. The method of embodiment 201, wherein the mammal is classified as possible exposure if the level of antibody that specifically binds to OspA is lower than alpMid; otherwise Lyme vaccine possible exposure.

203. A system for classifying *Borrelia burgdorferi* infection of a mammal, e.g., an animal comprising the computer readable medium of embodiment 171 and the antigenic composition of embodiment 128.

Further provided are exemplary *Anaplasma phagocytophilum* (*A. phagocytophilum*) tests that are intended to detect *A. phagocytophilum* infection in canines. Specifically, an exemplary *A. phagocytophilum* test uses a P20C peptide having the sequence (GHSSGVTQNPKLFSTFVDTVKIAEDK) (SEQ ID NO:34), or a multimer of P20C peptide (a chimeric P20C polypeptide), to detect antibodies to *A. phagocytophilum* from a sample, e.g., a canine blood sample.

A chimeric P20C polypeptide can comprise any suitable number of P20C peptide, e.g., 2, 3, 4, 5, 6, 7, 8, 9, 10, 15, 20, 30, 40, 50, 60, 70, 80, 90, 100 or more of P20C peptide. A chimeric P20C polypeptide can comprise any suitable tag and/or linker sequence(s). In some embodiments, the tag can be a tag from pEV-L8: His8-TEV-LIC vector (from Purdue University, IN) with the amino acid sequence MHHHHHHHHGVDLGTENLYFQSNA (SEQ ID NO: 31). In other embodiments, the tag can be a tag from pET46 Ek/LIC vector (Novagen) with the amino acid sequence MAHHHHHHVDDDDK (SEQ ID NO: 29). The tag can be located at any suitable location(s) within the chimeric P20C polypeptide. For example, the tag can be located at the N-terminus, C-terminus and/or in the middle of the chimeric P20C polypeptide. In some embodiments, an exemplary P20C polypeptide comprises the following amino acid sequence (SEQ ID NO:35):

GGHSSGVTQNPKLFSTFVDTVKIAEDKGGGHSSGVTQNPKLFSTFVDTV
KIAEDKGGGHSSGVTQNPKLFSTFVDTVKIAEDKGGGHSSGVTQNPKLF
STFVDTVKIAEDKGGPGHSSGVTQNPKLFSTFVDTVKIAEDKGGGHSSG
VTQNPKLFSTFVDTVKIAEDKGGHSSGVTQNPKLFSTFVDTVKIAEDKG
PGGHSSGVTQNPKLFSTFVDTVKIAEDKGGGHSSGVTQNPKLFSTFVDT
VKIAEDK.

The chimeric P20C polypeptide can be made by any suitable methods. For example, the chimeric P20C polypeptide can be made recombinantly, e.g., can be made recombinantly in *E. coli*, using the following DNA sequence (SEQ ID NO:36):

GGTGGTCACTCCAGCGGCGTTACCCAGAATCCGAAACTGTTCAGTACC
TTTGTTGATACCGTTAAAATCGCAGAAGATAAAGGCGGCGGCCATAGC
TCTGGTGTTACCCAGAACCCGAAACTGTTTAGCACCTTCGTGGATACG
GTTAAAATTGCAGAAGACAAAGGCGGTGGCCACAGTTCCGGCGTCACG
CAAAATCCGAAACTGTTTTCTACCTTCGTCGATACGGTGAAAATCGCT
GAAGACAAAGGTGGCGGTCATTCATCGGGTGTGACGCAAAACCCTAAG
CTGTTTAGCACCTTCGTTGATACGGTCAAAATTGCGGAAGACAAAGGC
GGTCCGGGCCACAGCTCTGGTGTTACCCAAAACCCTAAACTGTTTAGC
ACGTTTGTGGATACGGTTAAAATCGCCGAAGATAAAGGCGGTGGCCAT
AGTTCCGGCGTCACGCAGAACCCTAAGCTGTTTTCAACGTTTGTCGAT
ACGGTGAAAATTGCCGAAGATAAAGGTGGCCACAGCAGCGGCGTTACC
CAAAACCCGAAACTGTTTTCGACGTTTGTTGATACGGTCAAAATCGCC
GAAGACAAAGGCCCGGGTGGCCATTCTAGCGGCGTGACGCAAAACCCT
AAACTGTTTAGTACCTTTGTTGACACGGTTAAAATTGCGGAAGATAAA
GGTGGCGGTCATAGTTCCGGCGTGACGCAGAATCCGAAACTGTTCAGC
ACCTTTGTGGACACCGTTAAAATCGCAGAAGATAAA.

In some embodiments, the chimeric P20C polypeptide may also comprise at its N-terminus, a tag from pEV-L8: His8-TEV-LIC vector (from Purdue University, IN). The tag from pEV-L8: His8-TEV-LIC vector has the amino acid sequence MHHHHHHHHGVDLGTENLYFQSNA (SEQ ID NO:31). In case the tag from pEV-L8: His8-TEV-LIC vector is cleaved, the chimeric P20C polypeptide will have the remaining 3 (SNA) amino acids at the N-terminus. The tag from pEV-L8: His8-TEV-LIC vector can be encoded by any suitable polynucleotide sequence, e.g., the DNA sequence, atgcaccatcatcatcatcatcatcatggtgttgatctgggtaccgagaacctgtacttccaatccaatgcc (SEQ ID NO:30).

The chimeric P20C polypeptide can be used in any suitable assay format. In some embodiments, the chimeric P20C polypeptide is immobilized on a substrate (e.g., a solid surface such as a silicon disk, a microtiterplate or a nitrocellulose membrane). In use, a sample, e.g., a canine blood sample, is applied to the substrate with immobilized chimeric P20C polypeptide on it. If the blood sample has canine antibodies to *A. phagocytophilum* antigen containing P20C epitope, the antibodies will bind to the immobilized chimeric P20C polypeptide. Subsequently, a signal moiety, e.g., a protein A or G conjugated to a detectable label, is applied and bound to the canine anti-*A. phagocytophilum* antibodies. The detection of the bound label indicates that the canine blood sample is positive for canine antibodies to *A. phagocytophilum* antigen.

The invention claimed is:

1. A method for detecting multiple disease antigens and/or antibodies in a sample, which method comprises a) contacting said sample with a composition which composition comprises an *Anaplasma phagocytophilum* p44 polypeptide comprising the amino acid sequence set forth in SEQ ID NO:6 and at least one of the following reagents:

(1) an antibody against a heartworm (*Dirofilaria immitis*) antigen, (2) an *Ehrlichia canis* gp36 polypeptide, and (3) an antigenic composition comprising a *Borrelia burgdorferi* polypeptide selected from the group consisting of OspA, OspC, OspF, p39 and a fusion peptide of p41 and VlsE; and b) detecting a polypeptide-antibody complex formed by a sandwich assay format wherein said *Anaplasma phagocytophilum* p44 polypeptide, said antibody against a heartworm (*Dirofilaria immitis*) antigen, said *Ehrlichia canis* gp36 polypeptide, and said *Borrelia burgdorferi* polypeptide function as capture binders or antibody, and a second labeled binder or antibody is used for generating a detectable signal.

2. The method of claim 1, wherein the composition in step a) comprises all four of the reagents.

3. The method of claim 1, wherein the reagent a)(1) is a chicken polyclonal antibody.

4. The method of claim 3, wherein the chicken polyclonal antibody is produced by immunizing chickens with a canine heartworm antigen.

5. The method of claim 1, wherein the reagent a)(2) comprises a polypeptide comprising the amino acid sequence set forth in SEQ ID NO:26.

6. The method of claim 5, wherein the polypeptide comprising the amino acid sequence set forth in SEQ ID NO:26 further comprises a tag sequence.

7. The method of claim 1, wherein the reagent a)(3) comprises at least two *Borrelia burgdorferi* polypeptides selected from the group consisting of:

5) an OspA polypeptide, 6) an OspC polypeptide, 7) an OspF polypeptide, 8) a p39 polypeptide, and 9) a fusion peptide of p41 and VlsE, wherein said antigenic composition does not consist of 5) and 6).

8. The method of claim 7, wherein the reagent a)(3) comprises at least 3, 4, or all 5 of the *Borrelia burgdorferi* polypeptides.

9. The method of claim 7, wherein the OspC polypeptide comprises the amino acid sequence set forth in SEQ ID NO:15.

10. The method of claim 7, wherein the OspF polypeptide comprises the amino acid sequence set forth in SEQ ID NO:18.

11. The method of claim 7, wherein the p39 polypeptide comprises the amino acid sequence set forth in SEQ ID NO:21.

12. The method of claim 7, wherein the fusion peptide of p41 and VlsE comprises the amino acid sequence set forth in SEQ ID NO:24.

13. The method of claim 12, wherein the fusion peptide of p41 and VlsE further comprises a tag sequence.

14. The method of claim 7, wherein the method is used for diagnosis, prognosis, stratification, risk assessment, or treatment monitoring of a disease.

15. The method of claim 14, wherein the disease is selected from the group consisting of a heartworm disease, ehrlichiosis, granulocytic anaplasmosis, and Lyme disease, and an antibody against a heartworm (*Dirofilaria immitis*) antigen is used for diagnosis, prognosis, stratification, risk assessment, or treatment monitoring of the heartworm disease, an *Ehrlichia canis* gp36 polypeptide is used for diagnosis, prognosis, stratification, risk assessment, or treatment monitoring of the ehrlichiosis, an *Anaplasma phagocytophilum* p44 polypeptide comprising the amino acid sequence set forth in SEQ ID NO:6 is used for diagnosis, prognosis, stratification, risk assessment, or treatment monitoring of the granulocytic anaplasmosis, and at least two *Borrelia burgdorferi* polypeptides selected from the group consisting of an OspA polypeptide, an OspC polypeptide, an OspF polypeptide, a p39 polypeptide and a fusion peptide of p41 and VlsE are used for diagnosis, prognosis, stratification, risk assessment, or treatment monitoring of the Lyme disease.

16. The method of claim 7, wherein the sample is selected from the group consisting of a serum, a plasma and a blood sample.

17. The method of claim 7, wherein the sample is a clinical sample.

18. The method of claim 7, wherein the polypeptide-antibody complex is assessed by a sandwich or competitive assay format, optionally with a binder or antibody.

19. The method of claim 18, wherein the binder or antibody is attached to a surface and functions as a capture binder or antibody.

20. The method of claim 19, wherein the capture binder or antibody is attached to the surface directly or indirectly.

21. The method of claim 20, wherein the capture binder or antibody is attached to the surface via a biotin-avidin (or streptavidin) linking pair.

22. The method of claim 18, wherein at least one of the binders or antibodies is labeled.

23. The method of claim 7, wherein the polypeptide-antibody complex is assessed by a sandwich assay format selected from the group consisting of an enzyme-linked immunosorbent assay (ELISA), immunoblotting, immunoprecipitation, radioimmunoassay (MA), immunostaining, chemiluminescence assay, and lateral flow immunoassay.

24. The method of claim 7, wherein the polypeptide-antibody complex is assessed in a homogeneous assay format.

25. The method of claim 7, wherein the polypeptide-antibody complex is assessed in a heterogeneous assay format.

26. The method of claim 1, wherein the *Anaplasma phagocytophilum* p44 polypeptide comprises an amino acid sequence set forth in SEQ ID NO:7.

* * * * *